(12) United States Patent
Silver

(10) Patent No.: US 9,044,182 B2
(45) Date of Patent: Jun. 2, 2015

(54) SENSORS FOR DETECTING SUBSTANCES IN BODILY FLUIDS

(71) Applicant: James H. Silver, Palo Alto, CA (US)

(72) Inventor: James H. Silver, Palo Alto, CA (US)

(*) Notice: Subject to any disclaimer, the term of this patent is extended or adjusted under 35 U.S.C. 154(b) by 64 days.

(21) Appl. No.: 13/804,184

(22) Filed: Mar. 14, 2013

(65) Prior Publication Data

US 2013/0202721 A1 Aug. 8, 2013

Related U.S. Application Data

(63) Continuation of application No. 13/359,313, filed on Jan. 26, 2012, now Pat. No. 8,609,426, which is a continuation of application No. 12/015,347, filed on Jan. 16, 2008, now Pat. No. 8,133,698, which is a continuation-in-part of application No. 11/280,680, filed on Nov. 16, 2005, now Pat. No. 7,769,420.

(51) Int. Cl.
*A61B 5/1473* (2006.01)
*A61B 5/00* (2006.01)
*A61B 5/0215* (2006.01)
*A61B 5/145* (2006.01)
(Continued)

(52) U.S. Cl.
CPC ... *A61B 5/14735* (2013.01); *Y10T 436/177692* (2015.01); *A61B 5/0031* (2013.01); *A61B 5/0215* (2013.01); *A61B 5/14528* (2013.01); *A61B 5/14532* (2013.01); *A61B 5/14539* (2013.01); *A61B 5/14546* (2013.01); *A61B 5/14557* (2013.01); *A61B 5/1459* (2013.01); *A61B 5/14865* (2013.01); *A61B 5/412* (2013.01); *A61B 5/686* (2013.01); *A61B 5/6862* (2013.01); *A61B 5/6876* (2013.01); *A61B 5/6882* (2013.01); *A61B 2560/0219* (2013.01); *A61F 2/82* (2013.01); *A61F 2250/0001* (2013.01); *G01N 33/84* (2013.01); *A61B 5/4839* (2013.01)

(58) Field of Classification Search
None
See application file for complete search history.

(56) References Cited

U.S. PATENT DOCUMENTS

| 4,580,568 A | 4/1986 | Gianturco |
| 4,655,771 A | 4/1987 | Wallsten |

(Continued)

FOREIGN PATENT DOCUMENTS

| WO | WO 99/26530 | 3/1999 |
| WO | WO 99/26530 | 6/1999 |

(Continued)

OTHER PUBLICATIONS

"Measurement of Acetylcholine-induced Endothelium-derived Nitric Oxide in Aorta Using a Newly Developed Catheter-type Nitric Oxide Sensor", Science Direct (www.sciencedirect.com), May 14, 2003.

(Continued)

*Primary Examiner* — Shanon A Foley
(74) *Attorney, Agent, or Firm* — Knobbe Martens Olson & Bear LLP

(57) ABSTRACT

A system is disclosed that extracts bodily fluid to a reaction chamber for monitoring a substance or property of the patient fluid. In one embodiment, a pump is used to advance the sample of bodily fluid through a filter to produce a filtrate. Another pump advances filtrate into the reaction chamber, while another pump advances reactant into the reaction chamber. A sensor in communication with the reaction chamber determines a concentration of nitric oxide or one of its metabolic products. Methods are also disclosed.

20 Claims, 53 Drawing Sheets

(51) Int. Cl.
| | |
|---|---|
| *A61B 5/1455* | (2006.01) |
| *A61B 5/1459* | (2006.01) |
| *A61B 5/1486* | (2006.01) |
| *G01N 33/84* | (2006.01) |
| *A61F 2/82* | (2013.01) |

(56) References Cited

U.S. PATENT DOCUMENTS

| | | | |
|---|---|---|---|
| 4,739,762 A | 4/1988 | Palmaz | |
| 4,765,961 A | 8/1988 | Schiff et al. | |
| 4,886,062 A | 12/1989 | Wiktor | |
| 4,890,620 A | 1/1990 | Gough | |
| 5,102,417 A | 4/1992 | Palmaz | |
| 5,183,740 A | 2/1993 | Ligler et al. | |
| 5,195,984 A | 3/1993 | Schatz | |
| 5,284,138 A | 2/1994 | Kujawski | |
| 5,411,551 A | 5/1995 | Winston et al. | |
| 5,421,955 A | 6/1995 | Lau et al. | |
| 5,431,160 A | 7/1995 | Wilkins | |
| 5,433,197 A | 7/1995 | Stark | |
| 5,443,500 A | 8/1995 | Sigwart | |
| 5,514,594 A | 5/1996 | Termin | |
| 5,582,170 A | 12/1996 | Soller | |
| 5,591,457 A * | 1/1997 | Bolton | 424/613 |
| 5,603,820 A * | 2/1997 | Malinski et al. | 205/781 |
| 5,789,447 A * | 8/1998 | Wink et al. | 514/611 |
| 5,873,906 A | 2/1999 | Lau et al. | |
| 5,876,432 A | 3/1999 | Lau et al. | |
| 5,885,842 A | 3/1999 | Lai | |
| 5,945,676 A | 8/1999 | Khalil et al. | |
| 6,015,387 A | 1/2000 | Schwartz et al. | |
| 6,024,763 A | 2/2000 | Lenker et al. | |
| 6,053,873 A | 4/2000 | Govari et al. | |
| 6,119,028 A | 9/2000 | Schulman et al. | |
| 6,206,835 B1 | 3/2001 | Spillman, Jr. et al. | |
| 6,212,416 B1 | 4/2001 | Ward et al. | |
| 6,231,516 B1 | 5/2001 | Keilman et al. | |
| 6,245,296 B1 | 6/2001 | Ligler et al. | |
| 6,258,026 B1 | 7/2001 | Ravenscroft et al. | |
| 6,280,604 B1 | 8/2001 | Allen et al. | |
| 6,285,897 B1 | 9/2001 | Kilcoyne et al. | |
| 6,331,163 B1 | 12/2001 | Kaplan | |
| 6,442,413 B1 | 8/2002 | Silver | |
| 6,475,235 B1 | 11/2002 | Jayaraman | |
| 6,477,395 B2 | 11/2002 | Schulman et al. | |
| 6,516,808 B2 | 2/2003 | Schulman | |
| 6,638,231 B2 | 10/2003 | Govari et al. | |
| 6,741,877 B1 | 5/2004 | Shults et al. | |
| 6,861,262 B2 | 3/2005 | Novinkski et al. | |
| 6,895,265 B2 | 5/2005 | Silver | |
| 6,915,147 B2 | 7/2005 | Lebel et al. | |
| 7,006,858 B2 | 2/2006 | Silver et al. | |
| 7,025,869 B2 | 4/2006 | Fine et al. | |
| 7,033,322 B2 | 4/2006 | Silver | |
| 7,181,261 B2 | 2/2007 | Silver et al. | |
| 7,769,420 B2 | 8/2010 | Silver et al. | |
| 8,114,350 B1 | 2/2012 | Silver et al. | |
| 8,133,698 B2 | 3/2012 | Silver | |
| 8,609,426 B2 | 12/2013 | Silver | |
| 2002/0042562 A1 | 4/2002 | Meron et al. | |
| 2002/0082490 A1 | 6/2002 | Roeper et al. | |
| 2002/0103424 A1 | 8/2002 | Swoyer et al. | |
| 2004/0127813 A1 | 7/2004 | Schwamm | |
| 2004/0176672 A1 | 9/2004 | Silver et al. | |
| 2004/0210298 A1 | 10/2004 | Rabkin et al. | |
| 2004/0224868 A1 * | 11/2004 | Meyerhoff et al. | 510/320 |
| 2004/0236201 A1 | 11/2004 | Label et al. | |
| 2005/0101841 A9 | 5/2005 | Kaylor et al. | |
| 2006/0079740 A1 | 4/2006 | Silver et al. | |
| 2007/0154569 A1 * | 7/2007 | Gladwin et al. | 424/718 |

FOREIGN PATENT DOCUMENTS

| | | |
|---|---|---|
| WO | WO 99/34731 | 7/1999 |
| WO | WO 00/74557 A1 | 12/2000 |

OTHER PUBLICATIONS

"New Methods to Evaluate Endothelial Function: A Search for a Marker of Nitric Oxide (NO) In Vivo: Re-evaluation of $NO_x$ in Plasma and Red Blood Cells and a Trial to Detect Nitrosothiols", Journal of Pharmacological Sciences, 2003, pp. 409-416, Japan.

Pan, M., et al., "Simple and Complex Stent Strategies for Bifurcated Coronary Arterial Stenosis Involving the Side Branch Origin," Am. J. Cardiol., 83: 1320-25 (1999).

Armour, J. et al., "Application of Chronic Intravascular Blood Glucose Sensor in Dogs," Diabetes 39:1519-26 (1990).

Bates, J. B. et al., "Thin Film Rechargeable Lithium Batteries for Implantable Devices," ASAIO J., 43:M644-M647 (1997).

Bindra, D. S. et al., "Design and in vitro studies of a needle type glucose sensor for subcutaneous monitoring," Anal. Chem., 63: 1692-6 (1991).

Charles, P., et al., "Synthesis of a Fluorescent Analog of Polychlorinated Biphenyls for Use in a Continuous Flow Immunosensor Assay," Bioconjugate Chem., vol. 6 (No. 6): 691-694 (1995).

Clark, L.C. et al., "Electrode Systems for Continuous Monitoring in Cardiovascular," Ann. NY Acad. Sci., 102: 29-45 (1962).

Colombo, A. et al., "Intracoronary Stenting Without Anticoagulation Accomplished with Intravascular Ultrasound Guidance," Circulation 91: 1676-88 (1995).

Davies, M.L., et al., "Polymer membranes in clinical sensor application, Part 1: an overview of membrane function," Biomaterials, 13: 971-89 (1992).

Erickson, K. A. et al., "Evaluation of a Novel Point-of-care System, the I-Stat Portable Clinical Analyzer," Clin. Chem. 39(2): 283-287 (1993).

Gauger, P. et al., "Explosives Detection In Soil Using a Field-Portable Continuous Flow Immunosensor," Journal of Hazardous Materials, 83: 51-63 (2001).

Goldberg, S. et al., "Benefit of Intracoronary Ultrasound in the Deployment of Palmaz-Schatz Stents", J. Am. Coll. Card. 24: 996-1003 (1994).

Hall, E., "Biosensors," Prentice-Hall, Englewood, NJ ((1991).

Hanbury, C.M. et al., "Antibody Characteristics for a Continuous Response Fiber Optic Immunosensor for Theophylline," Biosensors & Bioelectronics, vol. II (Issue 11): 1129-1138 (1996).

International Search Report PCT/US 08/51225—Dated Aug. 1, 2008.

Irsigler, K. et al., "Controlled Drug Delivery in the Treatment of Diabetes Mellitus," Crit. Rev. Ther. Drug Carrier Syst., 1(3): 189-280 (1985).

Jaffari, S.A et al., "Recent Advances in Amperometric Glucose Biosensors for in vivo Monitoring," Physiol. Meas. 16: 1-15 (1995).

Jaremko, J. et al., "Advances Towards the Implantable Artificial Pancreas for Treatment of Diabetes," Diabetes care, 21(3): 444-450 (1998).

Jiang, W. et al., "Stabilization and Controlled Release of Bovine Serum Albumin Encapsulated in Poly (D, L-lactide) and Poly(ethylene glycol) Microsphere Blends," Pharmaceutical Research, vol. 18 (No. 6): 878-885 (2001).

Jonsson, B., "The Economic Impact of Diabetes," Diabetes Care 21 (Suppl. 3): C7-C10 (1998).

Kerner, W. et al., "A Potentially Implantable Enzyme Electrode for Amperometric Measurement of Glucose," Horm. Metab. Res. Suppl. Ser. 20: 8-13 (1988).

Kusterbeck, A.W. et al., "A Continuous Flow Immunoassay for Rapid and Sensitive Detection of Small Molecules," Journal of Immunological Methods, 135: 191-197 (1990).

Ma, J. et al., "Antitumor Effect of the Idiotypic Cascade Induced by an Antibody Encapsulated in Poly(d,l-lactide-co-glycolide) Microspheres," Jpn. J. Cancer Res., 92: 1110-1115 (2001).

(56) References Cited

OTHER PUBLICATIONS

Measurement of Acetylcholine-induced Endothelium-derived Nitric Oxide in Aorta Using a Newly Developed Catheter-type Nitric Oxide Sensor, Science Direct (www.sciencedirect.com), May 14, 2003.

Millward, S. et al., "*Gunther Tulip Retrievable Vena Cava Filter: Results from the Registry of the Canadian Interventional Radiology Association*," J Vasc Interv Radiol, 12:1053-1058 (2001).

Mordenti, J. et al., "*Intraocular Pharmacokinetics and Safety of a Humanized Monoclonal Antibody in Rabbits after Intravitreal Administration of a Solution or a PLGA Microsphere Formulation*," Toxicological Sciences, 52: 101-106 (1999).

Moussy, F. et al., "*Performance of Subcutaneously Implanted needle-type glucose sensors employing a novel trilayer coating*," Anal. Chem., 65: 2072-7 (1993).

Narang, U. et al., "*Multianalyte Detection Using a Capillary-Based Flow Immunosensor*," Analytical Biochemistry, 255: 13-19 (1998).

Neuerburg, J. et al., "*New Retrievable Percutaneous Vena Cava Filter: Experimental In Vitro and In Vivo Evaluation*," Cardiovasc Intervent Radiol, 16:224-229 (1993).

Neuerburg, J. et al., "*Results of a Multicenter Study of the Retrievable Tulip Vena Cava Filter: Early Clinical Experience*," Cardiovasc Intervent Radiol, 20:10-16 (1997).

*New Methods to Evaluate Endothelial Function: A Search for a Marker of Nitric Oxide (NO) In Vivo: Re-evaluation of $NO_x$ in Plasma and Red Blood Cells and a Trial to Detect Nitrosothiols*, Journal of Pharmacological Sciences, 2003, pp. 409-416, Japan.

Olukoga, A. et al., "*An Overview of Biochemical Markers in Acute Coronary Syndromes*," The Journal of The Royal Society for the Promotion of Health, vol. 121 (2): 102-106 (2001).

Pan, M., et al. "*Simple and Complex Stent Strategies for Bifurcated Coronary Arterial Stenosis Involving the Side Branch Origin*," Am. J. Cardiol., 83: 1320-25 (1999).

Rabbany, S.Y. et al., "*Optical Immunosensors*," Critical Reviews in Biomedical Engineering, 22(5/6):307-346 (1994).

Scavani, M. et al., "*Long-Term Implantation of a New Programmable Implantable Insulin Pump*," Artif. Organs, 16: 518-22 (1992).

Stefan, R.I. et al., "*Immunosensors in Clinical Analysis*," Fresenius J Anal Chem 366: 659-668 (2000).

Torche, A. et al., "*PLGA Microspheres Phagocytosis by Pig Alveolar Macrophages: Influence of Poly (vinyl alcohol) Concentration, Nature of Loaded-Protein and Copolymer Nature*," Journal of Drug Targeting, vol. 7 (No. %): 343-354 (2000).

"*The Effect of Intensive Treatment of Diabetes on the Development and Progression of Long-Germ Complications in Insulin-Dependent Diabetes Mellitus*," The Diabetes Control and Complications Trial Research Group, New Eng. J. Med. 329: 977-86 (1993).

Updike, S.J. et al., "*Enzymatic Glucose Sensors: Improved Long-Term Performance in Vitro and In Vivo*," ASAIO j., 40: 157-163 (1994).

Updike, S.J. et al., "*The Enzyme Electrode*," Nature, 214: 986-8 (1967).

Vianello, F. et al., "*Continuous Flow Immunosensor for Atrazine Detection*," Biosensors & Bioelectronics, vol. I3 (Issue 1): 45-53 (1998).

Virmani, R. et al., "*Histopathologic Evaluation of an Expanded Polytetrafluoroethylene Nitinol Stent Endoprosthesis in Canine Iliofemoral Arteries*," JVIR, 10: 445-456 (1999).

Waxman, K. et al., "*Implantable Programmable Insulin Pumps for the Treatment of Diabetes*," Arch. Surg., 127: 1032-37 (1992).

Wilkins, E., et al. "*Glucose Monitoring: State of the Art and Future Possibilities*," Med. Engl.Phys., 18(4):273-88 (1996).

Wilson, G.S. et al., "*Progress Towards the Developments of an Implantable Sensor for Glucose*," Clin. Chem. 1992 38:1613-7.

Zhu, G. et al., "*Stabilization of Proteins Encapsulated in Sylindrical Poly(lactide-co-glycolide) Implants: Mechanism of Stabilization in Basic Additives*," Pharmaceutical Research, vol. 17 (No. 3): 351-357 (2000).

* cited by examiner

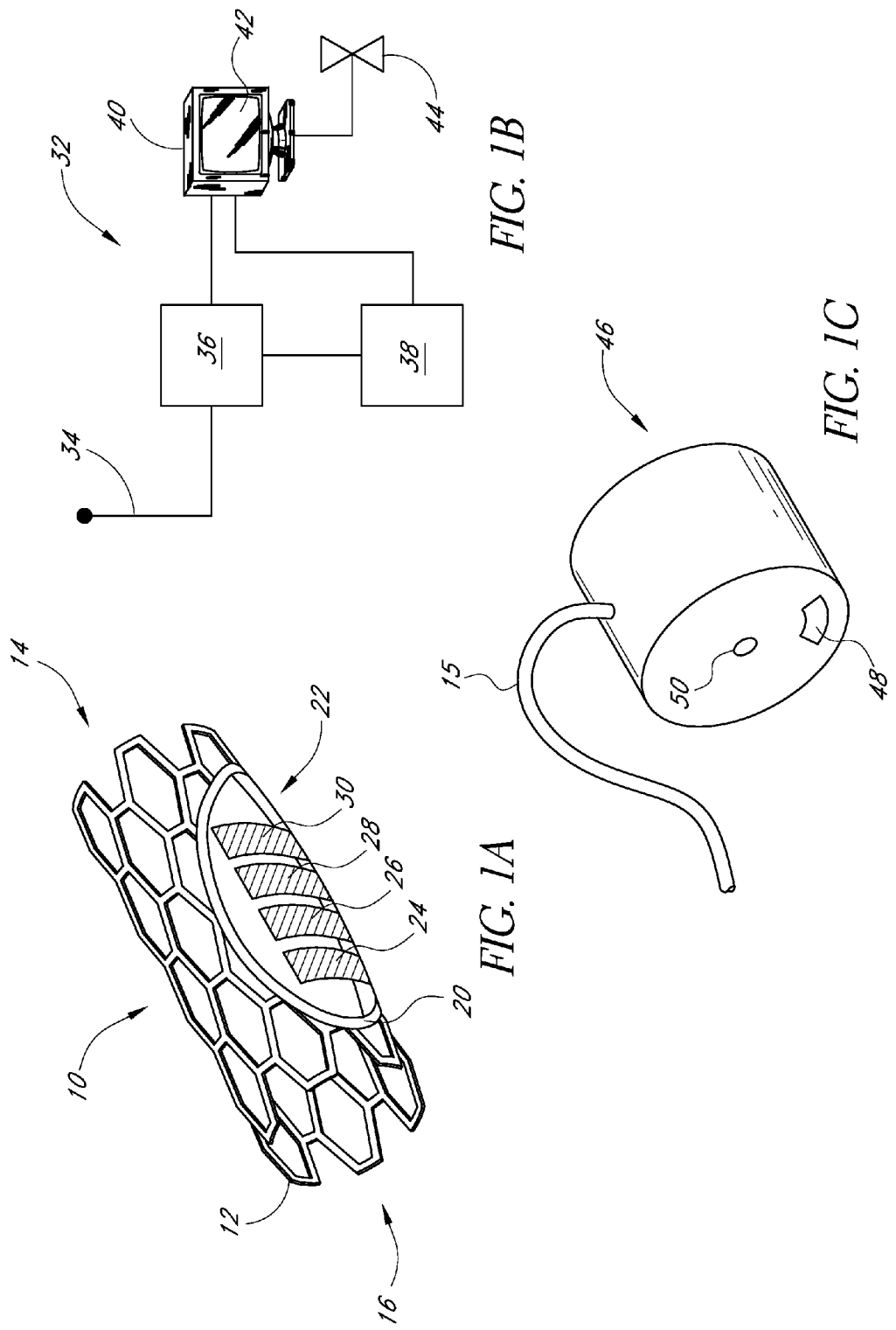

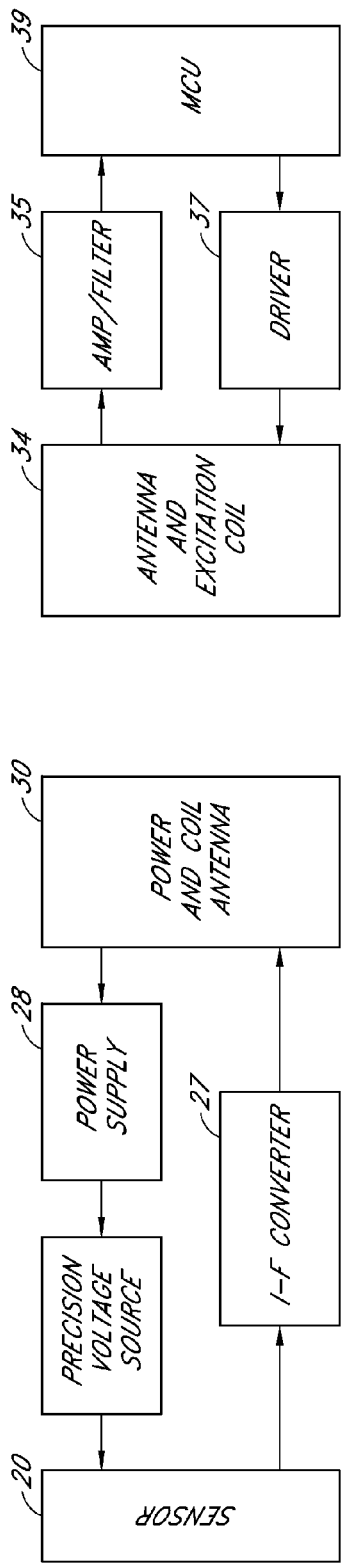
FIG. 1D
FIG. 1E
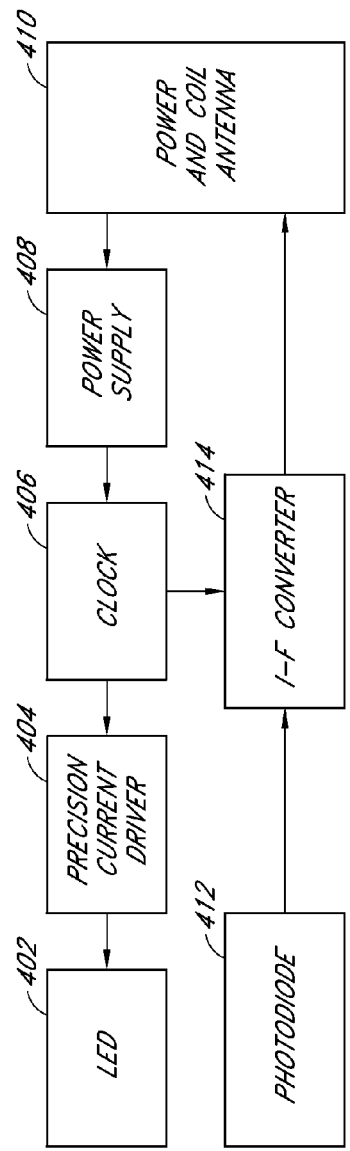
FIG. 13

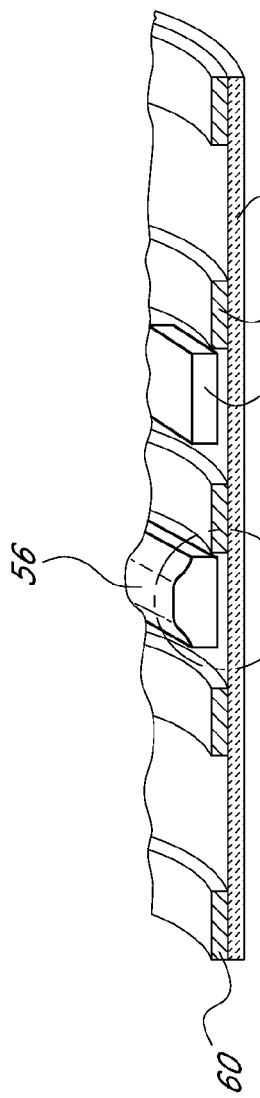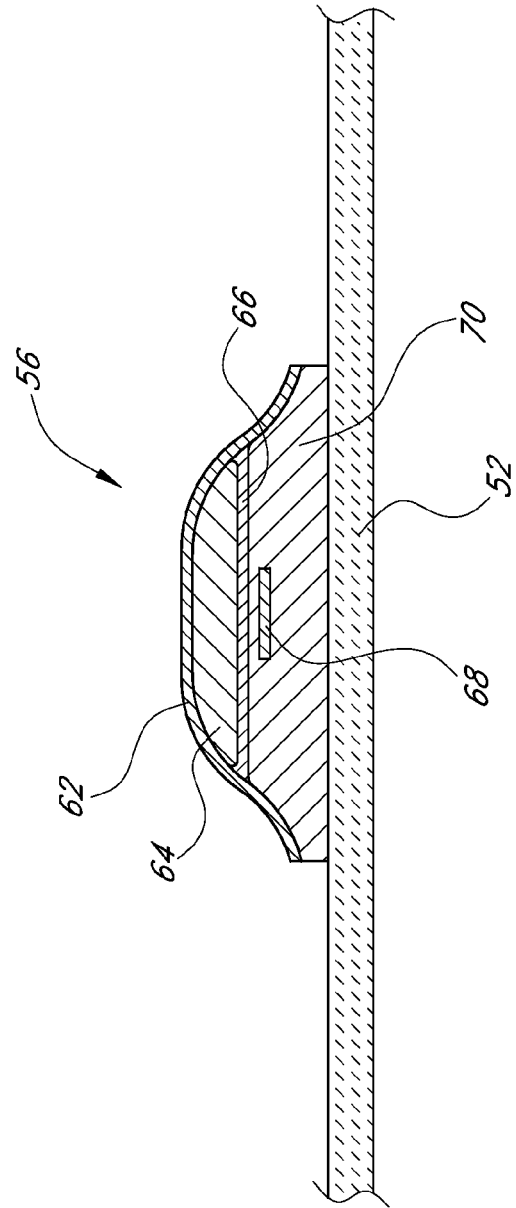

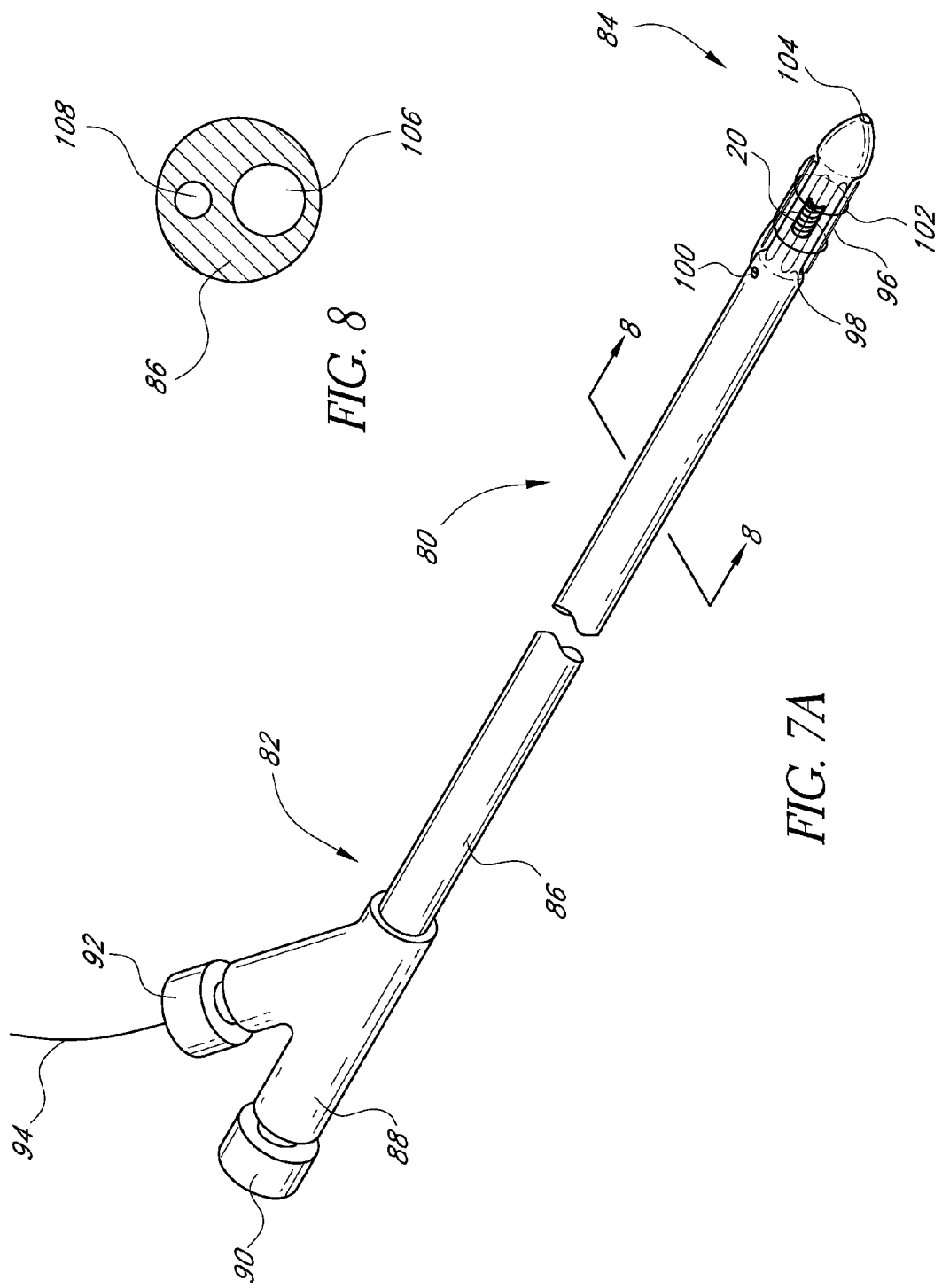

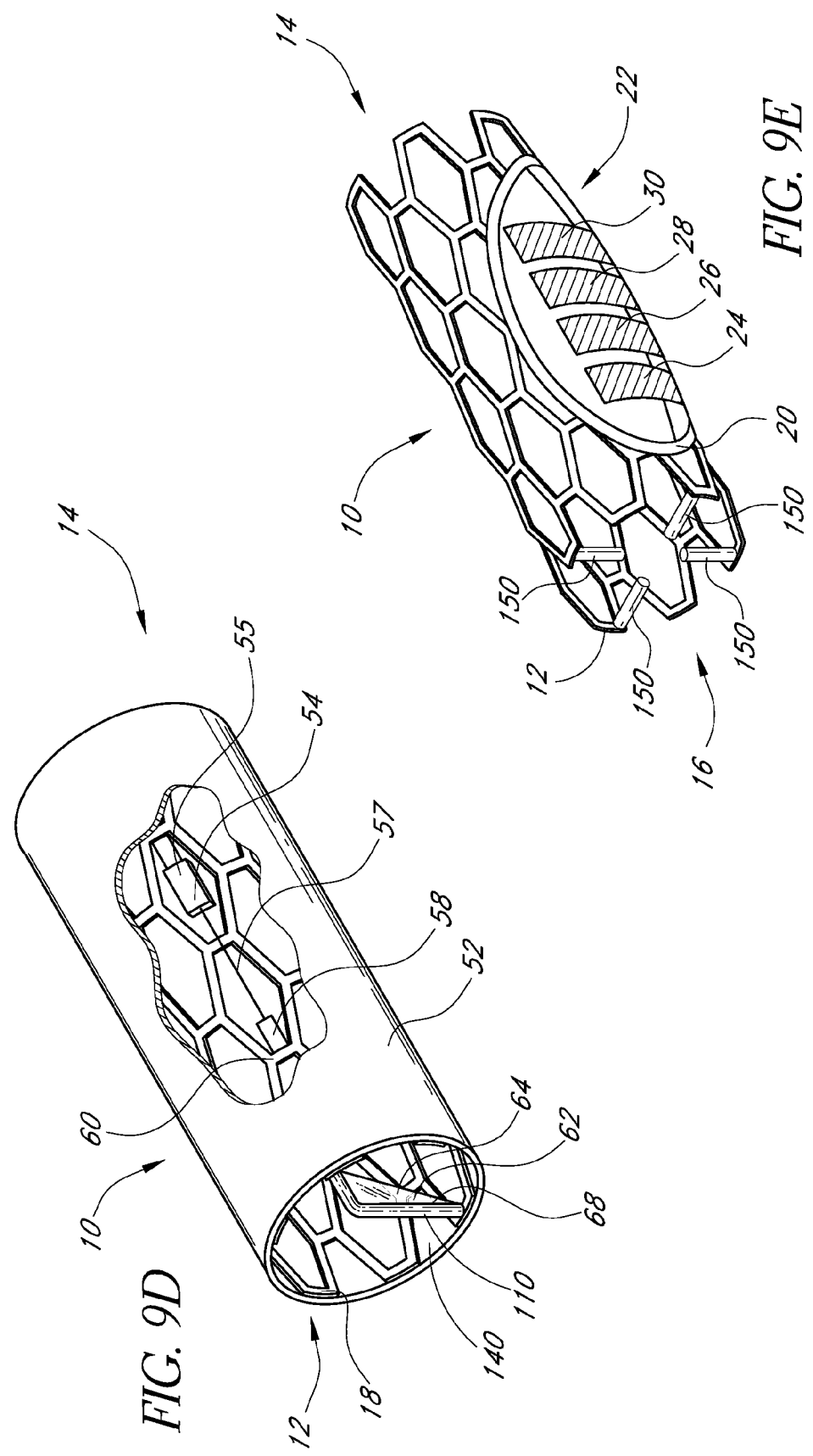

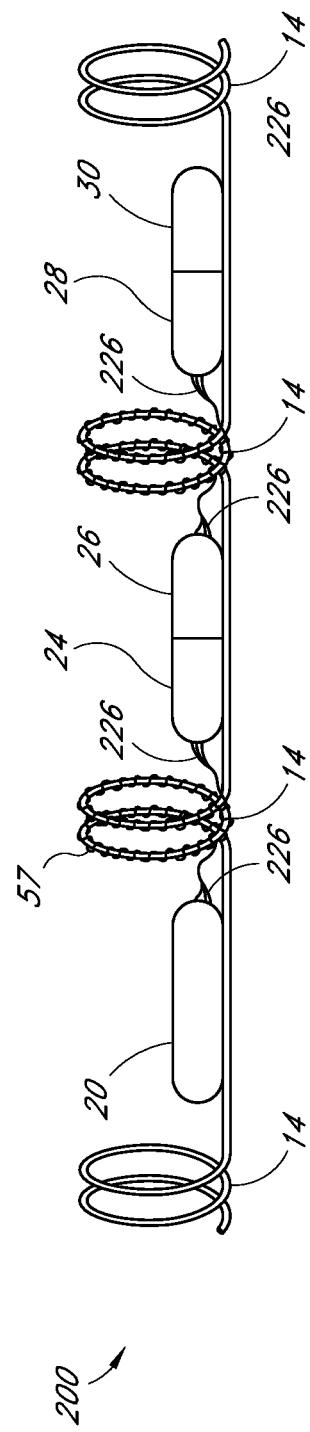

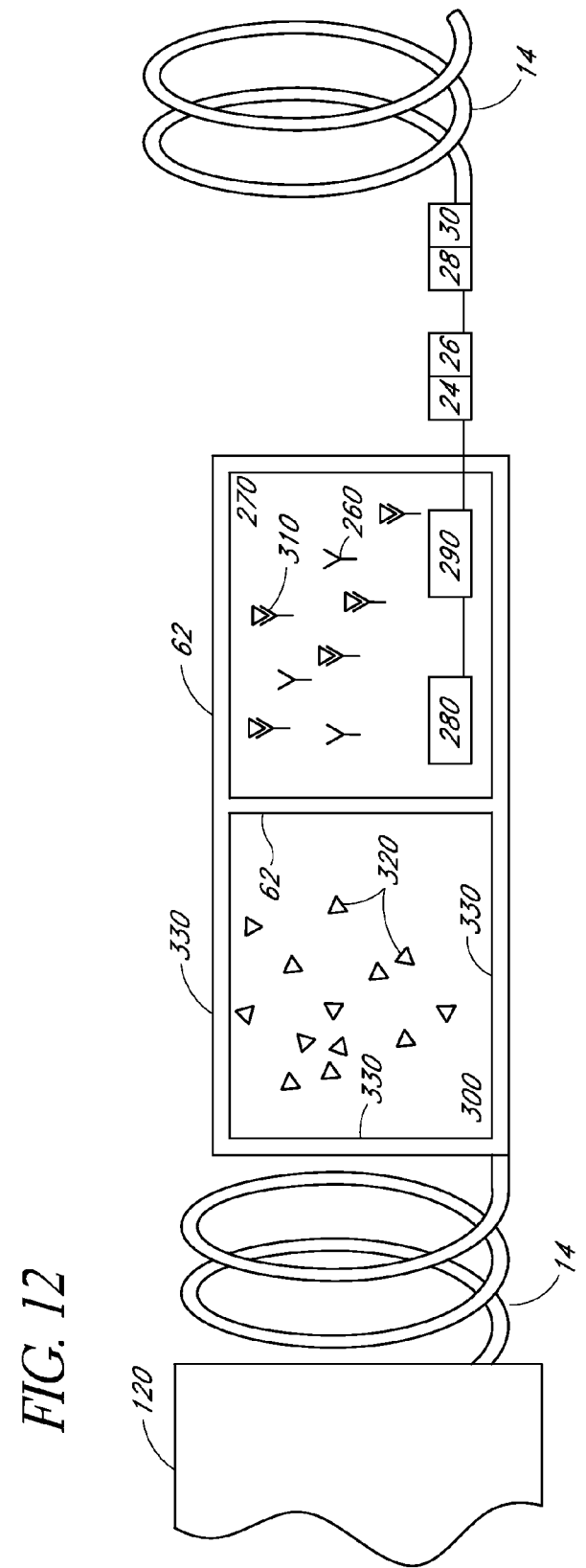

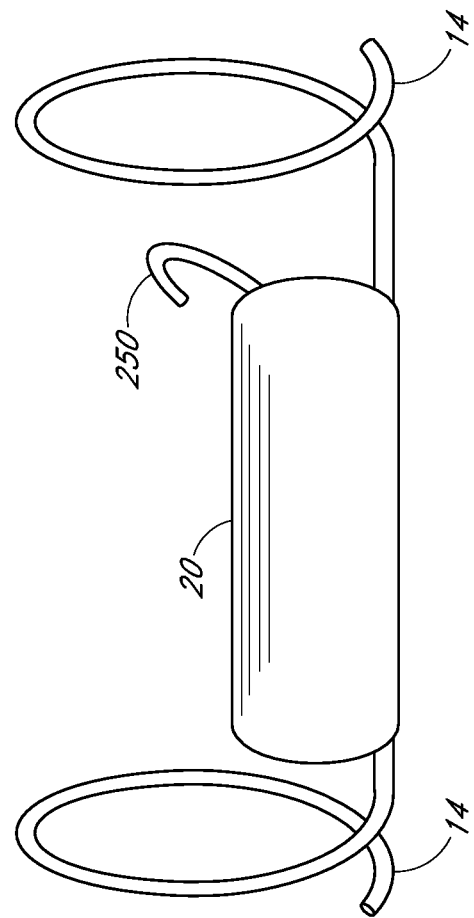

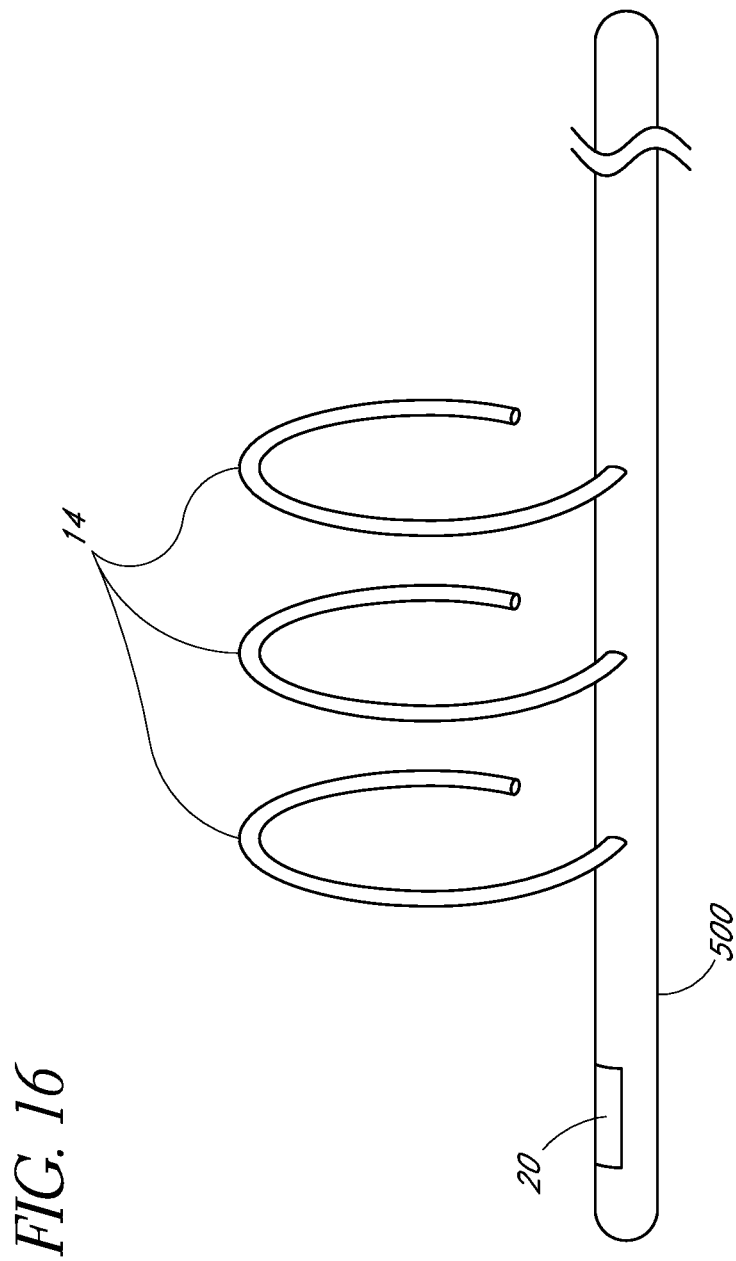

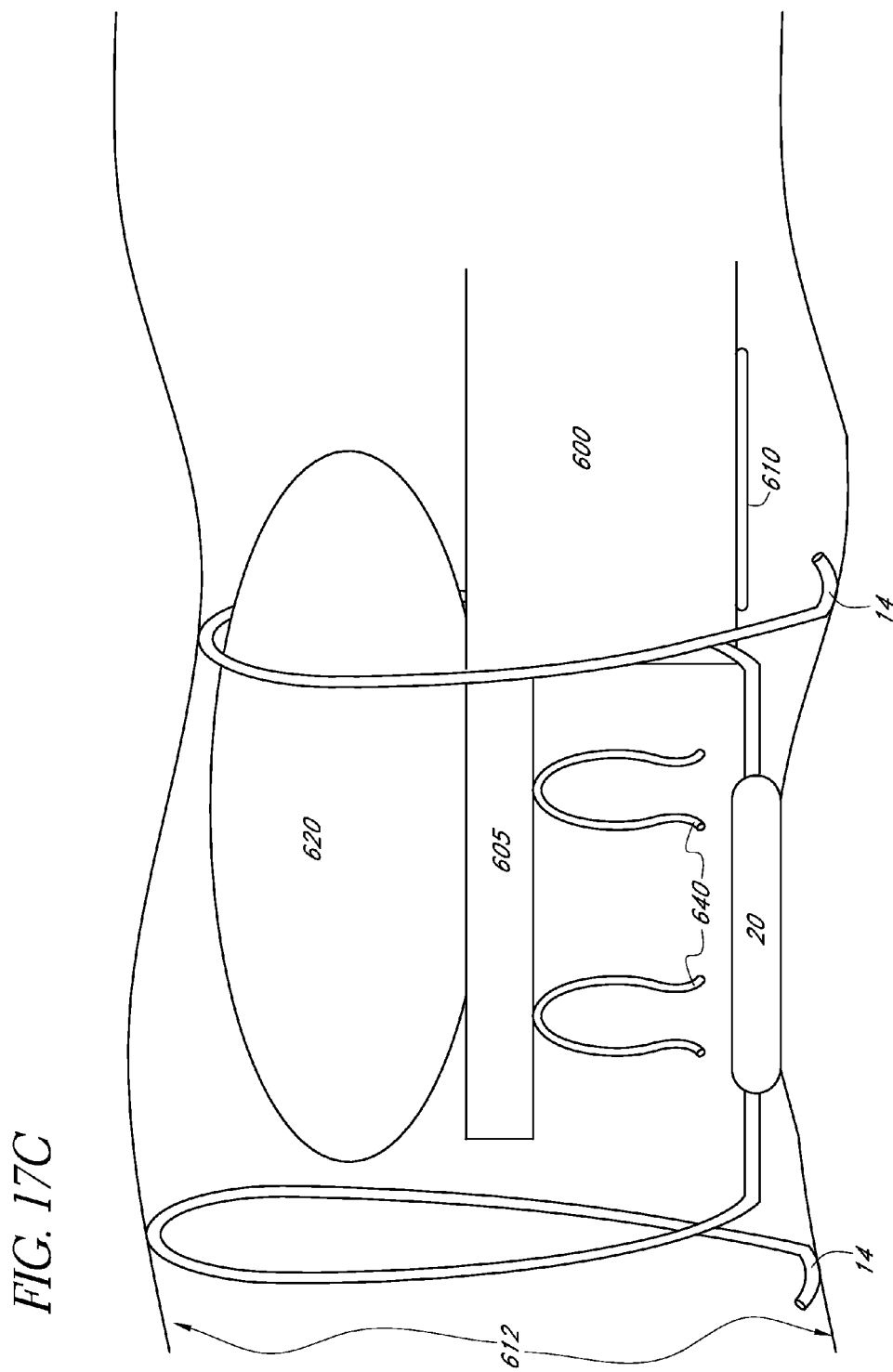

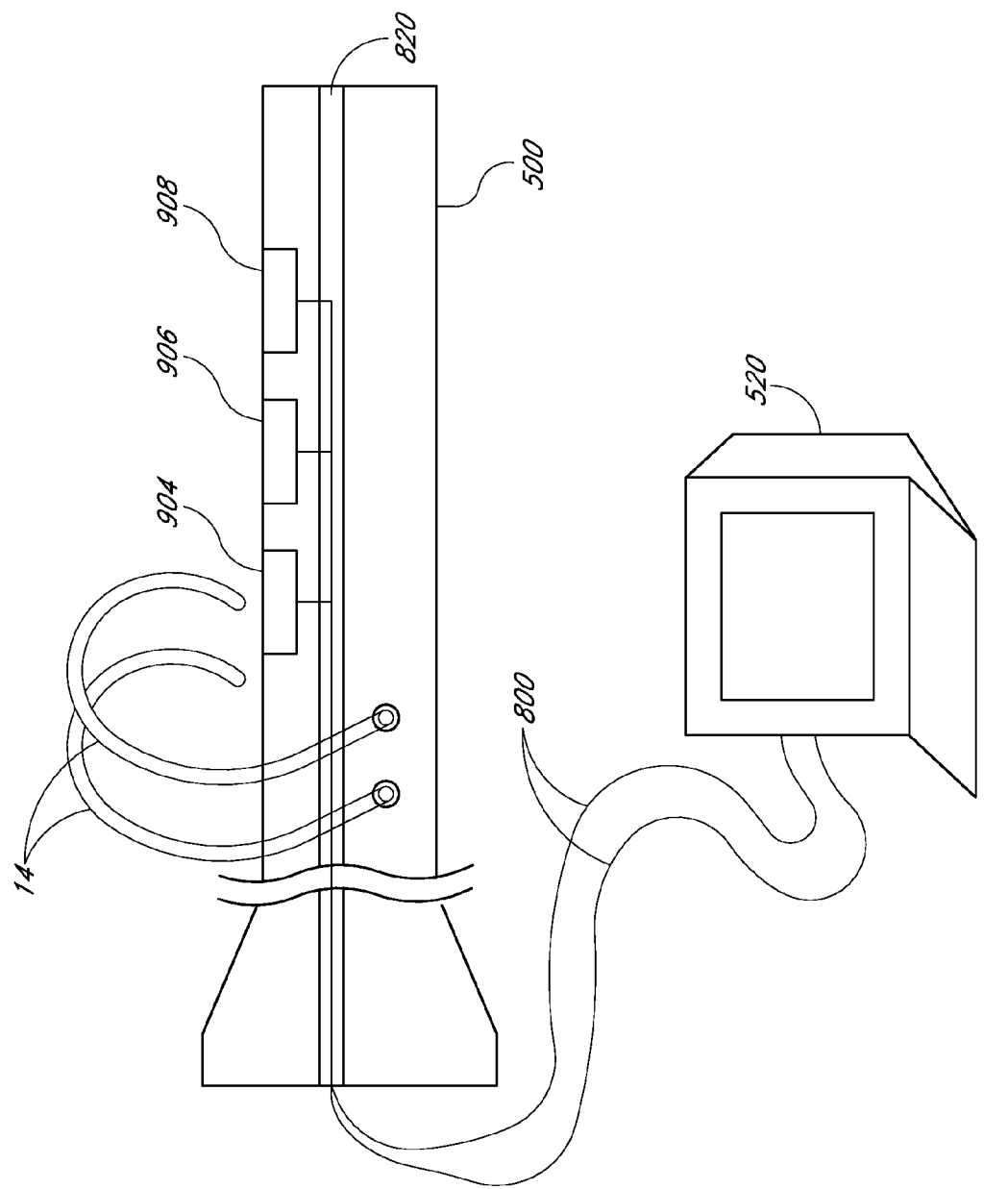

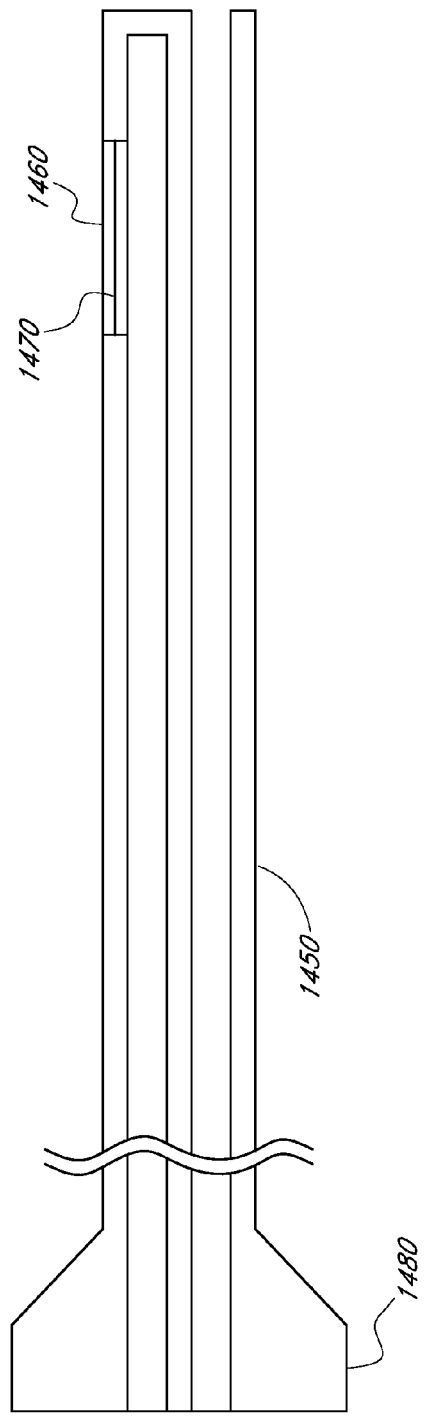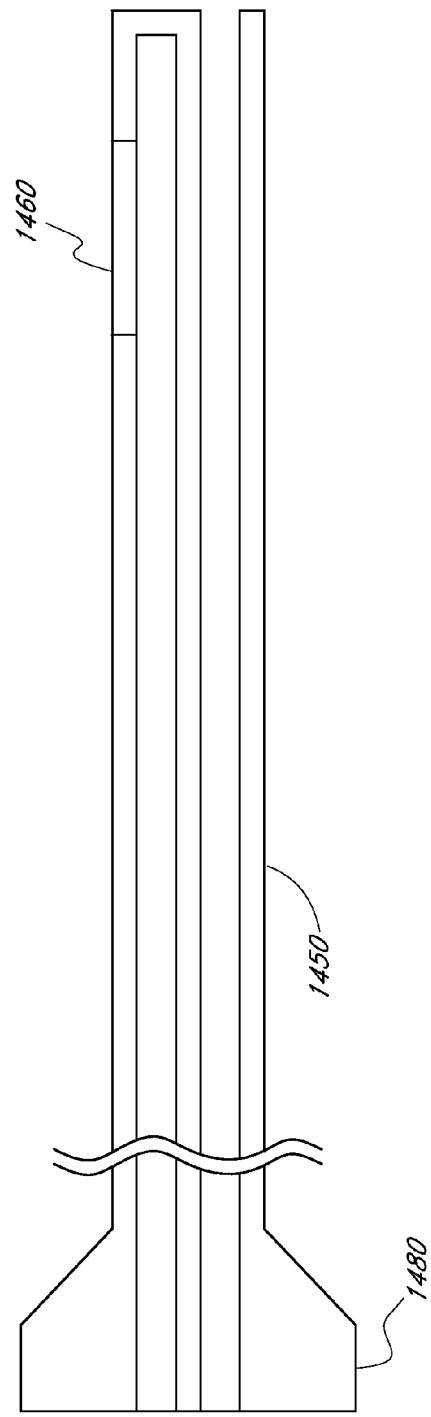

SENSORS FOR DETECTING SUBSTANCES IN BODILY FLUIDS

CROSS-REFERENCE TO RELATED APPLICATIONS

This application is a continuation of U.S. patent application Ser. No. 13/359,313, filed Jan. 26, 2012, which is a continuation of U.S. patent application Ser. No. 12/015,347, filed Jan. 16, 2008, which is a continuation-in-part of U.S. patent application Ser. No. 11/280,680, filed Nov. 16, 2005 (now U.S. Pat. No. 7,769,420). The full disclosures of these above-referenced applications are hereby incorporated by reference.

BACKGROUND OF THE INVENTION

1. Field of the Invention

The present invention generally relates to the use of sensors to monitor the concentration of a chemical species in bodily fluids.

2. Description of the Related Art

There exist numerous medical conditions which require monitoring of a chemical species within bodily fluids of a patient. For example, diabetes mellitus is a serious medical condition affecting approximately 10.5 million Americans, in which the patient is not able to maintain blood glucose levels within the normal range (normoglycemia). Approximately 10% of these patients have insulin-dependent diabetes mellitus (Type I diabetes, IDDM), and the remaining 90% have non-insulin-dependent diabetes mellitus (Type II diabetes, NIDDM). The long-term consequences of diabetes include increased risk of heart disease, blindness, end-stage renal disease, and non-healing ulcers in the extremities. The economic impact of diabetes to society has been estimated by the American Diabetes Association at approximately $45.2 billion annually (Jonsson, B., *The Economic Impact of Diabetes*, Diabetes Care 21(Suppl 3): C7-C10, (1998)).

A major long-term clinical study, the Diabetes Control and Complications Trial, involving 1,441 patients with insulin-dependent diabetes mellitus (Type I diabetes) over a 10-year period from 1984-1993, demonstrated that by intensive therapy (frequent administration of either short- or long-acting insulin), these long-term consequences (retinopathy, nephropathy, and neuropathy) could be reduced ("*The Effect of Intensive Treatment of Diabetes on the Development and Progression of Long-Term Complications in Insulin-Dependent Diabetes Mellitus*," The Diabetes Control and Complications Trial Research Group, New Eng. J. Med., 329: 977-86 (1993)). Unfortunately, a major difficulty encountered during the trial was that intensive treatment also resulted in a higher incidence of low blood glucose levels (hypoglycemia), which was severe enough to result in coma or death, as compared to patients under conventional medical management.

Currently, diabetics must monitor their condition by repeatedly pricking their fingers in order to obtain blood samples for evaluation. The major drawback to self-monitoring of glucose is that it is discontinuous and therefore the number of glucose measurements performed is dependent on the motivation of the patient.

Existing analytical techniques and devices for in vitro glucose measurements have a high level of accuracy (the error can be <1%). Many of these routine methods are accepted as standards of comparison with new devices. Management of diabetes currently relies on these methods to control the disease and minimize complications.

There are two main disadvantages to these existing options. First, sampling even a minimal amount of blood multiple times per day is associated with risks of infection, nerve and tissue damage, and discomfort to the patients. Second, in the case of dynamic changes in glucose concentration, very frequent or even continuous measurements of blood glucose levels are required (Wilkins, E., et al., "*Glucose Monitoring: State of the Art and Future Possibilities*", Med. Eng. Phys. 18(4):273-88, (1996)).

There are two main approaches to the development of a continuous blood glucose monitor. The first category is non-invasive sensors, which obtain information from physico-chemical characteristics of glucose (spectral, optical, thermal, electromagnetic, or other). The second category is invasive sensors. In this group, there is intimate mechanical contact of the sensor with biological tissues or fluids, because the device is placed within the body. (Wilkins, 1996).

Non-invasive sensor technology has focused on the absorption of the near-infrared (NIR) spectra by the analyte, in this case, glucose (See U.S. Pat. No. 5,945,676 to Khalil, et al., and U.S. Pat. No. 5,433,197 to Stark). Absorptions which occur in the NIR region are most often associated with overtone and combination bands of the fundamental vibrations of —OH, —NH, and —CH functional groups. As a result, most biochemical species will exhibit some absorption in the region of interest. Glucose measurements are usually performed in the spectra region from 4250 to 660 $cm^{-1}$. These highly overlapping, weakly absorbing bands were initially thought to be too complex for interpretation and too weak for practical application. Improvements in instrumentation and advances in multivariate chemometric data analysis techniques may allow meaningful results to be obtained from these complex spectra.

However, to date these devices are not particularly accurate even in the normal physiological range. A subject-dependent concentration bias has been reported. The temperature sensitivity of water absorption bands in the glucose-measuring region can be a significant source of error in clinical assays. In addition, the devices can also be affected by individual variations between patients at the measurement site. Skin location, temperature and tissue structure may affect the results, and decrease the accuracy of the reading.

Other investigators have looked into measurement of glucose from body fluids other than blood, such as sweat, saliva, urine, or tears. However, factors relating to diet and exercise can affect glucose levels in these fluids. In general, there is no strong correlation established between glucose concentration in the blood and in excreted fluids. The lag time between blood and excreted fluid glucose concentrations can be large enough to render such measurements inaccurate.

The continuous in vivo monitoring of glucose in diabetic subjects should greatly improve the treatment and management of diabetes by reducing the onus on the patient to perform frequent glucose measurements. Implanted glucose sensors could be used to provide information on continuously changing glucose levels in the patient, enabling swift and appropriate action to be taken. In addition, daily glucose concentration measurements could be evaluated by a physician. An implantable sensor could also provide an alarm for hypoglycemia, for example, overnight, which is a particular need for diabetics. Failure to respond can result in loss of consciousness and in extreme cases convulsive seizures. Similarly, a hyperglycemic alarm would provide an early warning of elevated blood glucose levels, thus allowing the patient to check blood or urine for ketone bodies, and to avert further metabolic complications. (Jaffari, S. A. et al., "Recent Advances In Amperometric Glucose Biosensors For In Vivo Monitoring", Physiol. Meas. 16:1-15 (1995)).

Invasive glucose sensors may be categorized based on the physical principle of the transducer being incorporated. Current transducer technology includes electrochemical, piezoelectric, thermoelectric, acoustic, and optical transducers.

In piezoelectric, thermoelectric, and acoustic (surface acoustic wave, SAW) sensors used for glucose measurement, an enzyme-catalyzed reaction is used to create a measurable change in a physical parameter detected by the transducer. The development of these sensors is at an early laboratory stage (Hall, E., *Biosensors*, Oxford University Press. Oxford, 1990). Optical sensors are based on changes in some optical parameter due to enzyme reactions or antibody-antigen reactions at the transducer interface. Based on the nature of the monitoring process, they are densitometric, refractometric, or colorimetric devices. At present, none of them meets the selectivity requirements to sense and accurately measure glucose in real physiological fluids.

There is a significant body of literature regarding the development of electrochemical glucose sensors. These generally incorporate an enzyme, which selectively reacts with glucose. Examples of enzymes, which selectively react with glucose, are glucose oxidase (GOD), hexokinase, glucose-6-phosphate dehydrogenase (G-6-PD), or glucose dehydrogenase. Hexokinase is an enzyme that catalyzes the phosphorylation of glucose by ATP to form glucose-6-phosphate and ADP.

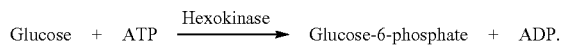

Monitoring the reaction requires a second enzyme, glucose-6-phosphate dehydrogenase, in the following reaction:

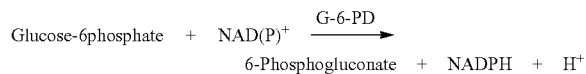

The formation of NADPH may be measured by absorbance at 340 nm or by fluorescence at 456 nm (Jaffari, 1995).

Glucose dehydrogenase is another enzyme, which may be used for monitoring glucose in the following reaction:

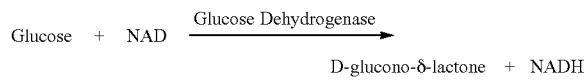

The NADH generated is proportional to the glucose concentration.

Glucose oxidase is the most commonly used enzyme reported in the literature. Its reaction is relatively simple, inexpensive, and may be monitored using a variety of techniques.

These advantages have led to the extensive use of this enzyme in clinical analysis as well as its incorporation in the majority of prototype biosensor configurations. The reaction of glucose with this enzyme is a two-stage reaction:

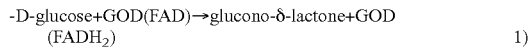   1)

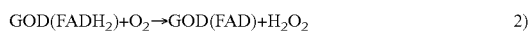   2)

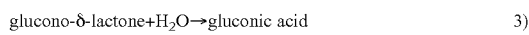   3)

The overall reaction is usually expressed as:

$\beta$-D-glucose+$O_2$+$H_2O$ gluconic→acid+$H_2O_2$   4)

The reaction can therefore be monitored by the consumption of oxygen, the production of hydrogen peroxide, or the change in acidity due to the increase of gluconic acid.

One of the key reasons for using these types of sensor in an intravascular environment, rather than subcutaneously or in other bodily environments, is the need to provide closed-loop control for diabetic patients. This would provide insulin delivery based on the patient's actual glucose measurements, as opposed to providing insulin based on some inexact approximation of the patient's glucose levels. This would of great benefit to diabetic patients. There is a widely recognized time delay between glucose changes in venous blood, and subcutaneous glucose changes. This time delay can range from just a few minutes, to up to 30 min. However, the mathematical algorithm used to couple the glucose signal to the insulin delivery system cannot tolerate a very long time delay. In fact, two authors have presented data which suggested that 10 minutes is the maximum delay which can be tolerated in closed-loop insulin delivery systems (Parker R S, Doyle F, et al., "A Model-Based Algorithm for Blood Glucose Control in Type I Diabetic Patients" IEEE Trans. Biomed. Engr. 46(2):148-157 (1999), and Gough D et al, "Frequency Characterization of Blood Glucose Dynamics" Ann Biomed Engr 31:91-97 (2003).) Longer time delays can cause the controller to become unstable, potentially creating life-threatening issues for the patient, such as delivery of extra insulin when blood glucose levels are falling rapidly.

Despite the foregoing and other efforts in the art, a suitable continuous in dwelling glucose sensor has not yet been developed.

A critical factor in the design of an implanted sensor is the anatomical site in which it is implanted. A few investigators have developed monitoring systems, which can be placed within the vascular system. Armour et al. ("*Application of Chronic Intravascular Blood Glucose Sensor in Dogs*", Diabetes 39:1519-26 (1990)) implanted a sensor into the superior vena cava of six dogs for a period of up to 15 weeks with relative success. However, due to the risks of thrombosis and embolization, the majority of investigators have focused on subcutaneous implantation.

A major drawback to subcutaneous implantation is the body's defense against foreign objects: the "foreign-body response". In this host response, if an object cannot be removed by the inflammatory response, foreign-body giant cells will form a "wall" around the object, which is subsequently followed by the formation of a fibrous capsule. If the object is a blood glucose sensor, it will no longer be in intimate contact with body fluids, and the signal will drift and stability will be lost. There are numerous reports of sensor stability being lost in about a week (Wilson, G. S., et al., "*Progress Towards The Development Of An Implantable Sensor For Glucose*", Clin. Chem. 1992 38:1613-7, and Kerner, et al., "*A Potentially Implantable Enzyme Electrode For Amperometric Measurement Of Glucose*", Horm. Metab. Res. Suppl. Ser. 20: 8-13 (1988)). Updike et al. (Updike, Stuart J., et al., "*Enzymatic Glucose Sensors: Improved Long-Term Performance In Vitro And In Vivo*", ASAIO J., 40: 157-163 (1994)) reported on the subcutaneous implantation of a sensor which was stable for up to 12 weeks, however, this evaluation was only performed in three animals.

Recent clinical studies have also demonstrated that implantable insulin pumps are feasible for implantation for over one year (Jaremko, J. et al., "*Advances Towards the Implantable Artificial Pancreas for Treatment of Diabetes,*"

Diabetes Care, 21(3): 444-450 (1998)). The research was inspired by the goal of the development of the artificial pancreas, and promising initial clinical trials using implantable insulin pumps. At this point in time, development of implantable insulin pumps is at a very advanced stage, with units being implanted for over 2 years in canines (Scavani et al., "*Long-Term Implantation Of A New Programmable Implantable Insulin Pump,*" Artif. Organs, 16: 518-22 (1992)) and in 25 patients for up to 3 years (Waxman, et al., "*Implantable Programmable Insulin Pumps For The Treatment Of Diabetes*", Arch. Surg., 127: 1032-37 (1992)).

A number of wearable insulin pumps are described by Irsigler et al. ("*Controlled Drug Delivery In The Treatment Of Diabetes Mellitus,*" Crit. Rev. Ther. Drug Carrier Syst., 1(3): 189-280 (1985)). Thus, it should be relatively straightforward to couple a long-term implantable glucose sensor as described in this disclosure, to an insulin pump to optimize glycemic control for the patient.

In another aspect of this invention, it is possible to apply the principles discussed above to the direct, continuous monitoring of arterial blood gases (ABG). Arterial blood gas values such as $pO_2$, $pCO_2$, and pH are the most frequently ordered laboratory examinations in the intensive care setting and the operating room (C. K. Mahutte, "Continuous intra-arterial blood gas monitoring," Intensive Care Med (1994) 20:85-86). In the intensive care unit (ICU), ABG is typically monitored once a day, and additional measurements are only made once the patient has experienced a deleterious event. Limited additional sampling is performed at the discretion of a physician or nurse. There can be a significant time delay between the time the tests are ordered, and the results are returned (E. E. Roupie, "Equipment Review: Continuous assessment of arterial blood gases," Crit. Care 1997 1(1):11-14).

In the case of continuous monitoring, significant changes in ABG values or trends would cause a rapid, therapeutic response on the part of the physician, so potentially catastrophic events could be avoided. Continuous, non-invasive monitoring techniques such as pulse oximetry and continuous capnography have been introduced for this reason. Unfortunately, these devices are not always accurate in cases such as shock, hypothermia, or during the use of vasopressors. Further, pulse-oximetry does not measure oxygen tension.

A number of attempts have been made to develop improved arterial blood gas monitors. There are two basic types of arterial blood gas monitors. In the first type, termed extra-arterial blood gas (EABG) monitors, the patient's blood gas values are measured from a sample in the arterial catheter. This can significantly reduce the time delay in obtaining results, as compared to sending the sample to a laboratory. However, it is an on-demand system, not a continuous one, so the frequency of sampling is once again dependent upon the physician or nurse.

The second type of device, known as an intra-arterial blood gas (IABG) monitor, is inserted directly into the arterial blood. However, the consistency and reliability of these IABG monitors have not been clinically acceptable because of problems associated with the intra-arterial environment. (C. K. Mahutte, "On-line Arterial Blood Gas Analysis with Optodes: Current Status," Clin. Biochem 1998; 31:119-130).

In another aspect of this invention, implantable sensors capable of monitoring hemodynamic conditions over extended periods of time may be useful in patients with heart failure. Such measurements have traditionally been restricted to cardiac catheterization laboratories and intensive care units (ICU's). Measurements cannot be made easily in an ambulatory setting, or under conditions of cardiac loading, such as exercise. Ohlsson et al (Ohlsson A, et al., "Continuous ambulatory monitoring of absolute right ventricular pressure and mixed venous oxygen saturation in patients with heart failure using an implantable hemodynamic monitor: Results of a one year multicentre feasibility study," Eur Heart J 22:942-954 (2001)) describe implantation of a pressure sensor and an oxygen sensor, the IHM-1, Model 10040 (Medtronic, Inc.). However, in this study, 12 out of 21 oxygen sensors failed within the first 6 months of implantation. A fibrinous coating covered one of the sensors, and it was believed that this was responsible for sensor failure. In addition, surgical implantation of this pacemaker-style device requires a 2-3 hour procedure in the operating room, which is more costly than a catheterization procedure to insert a pressure sensor. Data from this study, however, points to the importance of long-term, continuous pressure monitoring, as opposed to one-time measurements using standard cardiac catheterization techniques.

In another aspect of this invention, the sensor may be used for measuring flow rates within a vessel. Congestive heart failure affects more than 5 million persons in the United States, and the rate is increasing as people age and more of them survive heart attacks. Finding the right treatment often involves a trial-and-error process, with the physician trying different combinations of drugs and different dosages to produce the best results. That means repeated blood pressure and flow measurements and invasive cardiac catheterization procedures to measure the effects on the heart.

In U.S. Pat. No. 6,053,873 issued Apr. 25, 2000 to Govari et al, a method of monitoring flow rates within a stent is described. In particular, the use of ultrasonic sensors to monitor blood flowrates is described. However, due to the change in composition and thickness of the biological material present on the sensor surface, the boundary conditions at the sensor may change over time. Initially, the sensor surface, which may be calibrated against blood, may become covered with a layer of thrombus over time. Subsequently, the thrombus will transform into fibrous tissue, affecting the absorption of the ultrasound signal. Blood may have an ultrasound absorption level similar to water, of around 0.002 dB/MHz cm, while the fibrous tissue layer may have an absorption level similar to muscle, of around 2 dB/MHz cm. Thus, such a sensor may require periodic re-calibration. Unfortunately, the re-calibration process requires an invasive cardiac catheterization procedure, in which flow rates are determined using ultrasound, thermodilution, or the Fick method. In order to avoid additional interventional procedures, the fouling-resistant approach described herein may be valuable.

In U.S. Pat. No. 6,309,350 to VanTassel, et al., issued Oct. 30, 2001, a sensor is described which is anchored in the wall of the heart, or in a blood vessel. However, no mention is made of the difficulty with sensor fouling due to thrombus formation, or how to compensate for that. Pressure sensors would require recalibration as the softer thrombus transforms into neointimal tissue, or as the thickness of the encapsulating tissue layer changes. While the device could be initially calibrated during implantation, it would need to be recalibrated over time. Because recalibration requires an invasive cardiac catheterization procedure, it would be desirable to avoid this if at all possible.

In addition, VanTassel et al. suggest the use of standard thermodilution methods to determine flow rates. Thermodilution is normally performed by injection of either room temperature or iced saline through a catheter. However, it is desirable to avoid re-interventions if possible. Therefore, standard thermodilution methods are less desirable than the current invention. In addition, it is impractical to use the sensor in the standard method, i.e., by locally cooling the blood, because chilling units are impractically large for implantation as a sensor. Further, thermodilution methods would be inaccurate if the thermocouple or sensing element was covered by a relatively thick layer of cells. This would be especially true if only a small temperature rise were introduced into a large volume of flowing blood, such as in the pulmonary artery. Larger temperature rises (>2.5° C.) would cause local tissue damage.

Stroke, also known as cerebral infarction, is the third most common cause of death in the US and Europe. There are approximately 1 million acute ischemic strokes in Europe annually. Stroke survivors are often significantly disabled, and must undergo extensive rehabilitation. The estimated short term costs of a stroke are $13,649 per patient, and the long term costs are $45,893 for a minor stroke and $124,564 for a major stroke (Caro, J J, et al., "Stroke Treatment Economic Model (STEM): Predicting Long-term Costs from Functional Status", Stroke 1999; 30:2574-2579). The direct and indirect economic impact of stroke in the US is estimated to be $43.3 billion (US). According to the National Institutes of Health recombinant tissue-type plasminogen activator trial, if stroke could be treated in the first hours after the stroke occurs, the damage can be minimized (National Institute of Neurological Disorders and Stroke. rt-PA Stroke Study Group. "Tissue Plasminogen Activator for acute ischemic stroke." N Engl J Med 1995; 333:1581-1587). However, if treatment is delayed, then the damage becomes worse. Unfortunately, symptoms of stroke are not widely recognized, and significant delays in treatment are introduced by the failure to recognize the problem.

Risk factors such as high blood pressure, cholesterol, smoking, obesity, and diabetes increase the chances that an individual will suffer a stroke. Patients with significantly increased risks of stroke include patients with atrial fibrillation, coronary heart disease, asymptomatic carotid stenosis, previous stroke, or transient ischemic attack (TIA). In the latter subsets, approximately 25% of stroke survivors experience a recurrent stroke within five years, and among patients with TIA, the risk for stroke is 5% within 48 hours, 12% within 1 year, and up to 30% within 5 years.

In addition, each year, a significant number of surgical procedures are performed in which the patient is exposed to the risk of stroke in a hospital setting. For example, according to the American Heart Association, there are approximately 500,000 coronary artery bypass grafting (CABG) procedures performed annually. The risk of stroke during or shortly after these procedures is about 5%. Carotid endarterectomy is another common surgical procedure which is intended to reduce the long-term risk of stroke, but still carries significant short-term stroke risk of about 5-10%. In-hospital monitoring would be suitable for patients undergoing cardiac surgery, large vessel surgery, intra-cranial surgery, or other procedures that may place them at substantially increased risk of stroke either during the procedure, or during the post-operative recovery period.

The risk of stroke either during or following surgery is significantly increased for a period of approximately one month (David J. Blacker, Kelly D. Flemming, Michael J. Link, Robert D. Brown, Jr. "The Preoperative Cerebrovascular Consultation: Common Cerebrovascular Questions Before General or Cardiac Surgery" Mayo Clin Proc. 2004; 79:223-229, and PCA Kam, R M Calcroft, "Perioperative stroke in General Surgical Patients," Anesthesia 1997; 52:879-883). Strokes which occur in-hospital often go untreated for significant periods of time, for a variety of reasons including misdiagnosis, misinterpretation of stroke symptoms as due to other factors, and the referring team not being familiar with acute stroke assessment (David J Blacker, "In-hospital stroke" Lancet Neurol 2003; 2: 741-46). Since the cost of stroke is so significant both in financial terms and in the loss of quality of life, it would be desirable to alert the physician to the occurrence of stroke as quickly as possible, so that permanent damage may be prevented or reduced. Therefore, it would be desirable to have a stroke-monitoring device that can be used for this period of time. Further, it would be desirable to have a portable monitoring system, which the patient can use whether in the hospital, or following discharge.

Current stroke monitoring methods provide responses that are generally too slow to allow tissue rescue to be performed by the physician. Currently, one method of perioperative stroke monitoring, somatostatic excitatory potentials (SSEP) is rather slow, and often does not provide physicians with sufficient warning to alter patient outcomes. In instances where the motor pathways and sensory pathways are not in close proximity, significant loss of motor function can occur without detection by SSEP. Another method, which may be statistically correlated with stroke, is transcranial Doppler (TCD). Using this method, both reduced flow rates and emboli may be detected. However, this does not detect stroke directly. Since there are usually a number of embolic events during a surgical procedure, it would be desirable to alert the physician only when these emboli cause a stroke.

In the acute phase of stroke, or cerebral infarction, a great deal of experimental data suggests that free radicals, including superoxide, hydroxy radical, and nitric oxide (NO) are one of the most important factors causing brain damage. J. Rodrigo, D, et al (Histol. Histopathol. 17, 973-1003 (2002)) have observed that most of the morphological and molecular changes associated with ischemic damage were prevented by treatment with inhibitors of NO production. In addition, there is a significant increase in the concentration of NO following cerebral ischemia. There is also significant NO release in hemorrhagic stroke. (Chen H H, et al, "Low cholesterol in erythrocyte membranes and high lipoperoxides in erythrocytes are the potential risk factors for cerebral hemorrhagic stroke in human" Biomed Environ Sci. 2001 September; 14(3):189-98). Therefore, the detection of NO in the acute phase of ischemic or hemorrhagic stroke would provide an early detection method for stroke, allowing treatment to be performed as promptly as possible by the physician or healthcare provider.

Animal studies have demonstrated an increase in nitric oxide in brain tissue shortly after ligation of the middle cerebral artery (Lin, S Z, et al., "Ketamine Antagonizes Nitric Oxide Release From Cerebral Cortex after Middle Cerebral Artery Ligation in Rats", Stroke 1996; 27:747-752). It has further been demonstrated that there is a significant increase in levels of nitrite and nitrate ions in the jugular vein of a rat, immediately following induction of ischemic stroke (Suzuki, M, et al., Brain Research 951 (2002) 113-120). It has also been demonstrated that the level of these metabolites are significantly higher in cerebrospinal fluid (CSF) at the time stroke patients are admitted to the hospital, which is often many hours after the stroke (Castillo, J. et al., "Nitric Oxide-Related Brain Damage in Acute Ischemic Stroke", Stroke 2000; 31:852-857). Increased nitrate and nitrite levels correlate with increased infarct volume and poorer neurological outcomes.

Nitric oxide sensors have been coupled with catheters and used in vivo in a canine aorta in order to monitor sub-nanomolar changes in NO release in response to acetylcholine stimuli (Seiichi Mochizuki, Takehiro Miyasaka, Masami Goto, Yasuo Ogasawara, Toyotaka Yada, Maki Akiyama, Yoji Neishi, Tomohiko Toyoda, Junko Tomita, Yuji Koyama, Katsuhiko Tsujioka, Fumihiko Kajiya, Takashi Akasaka, and Kiyoshi Yoshida "Measurement of acetylcholine-induced endothelium-derived nitric oxide in aorta using a newly developed catheter-type nitric oxide sensor" Biochem Biophys Res Comm 306 (2003) 505-508). Unfortunately, there are a number of problems associated with simple catheter-sensor combinations, as discussed for the intra-arterial blood gas sensors that have been investigated clinically (C. K. Mahutte, "On-line Arterial Blood Gas Analysis with Optodes: Current Status," Clin. Biochem 1998; 31:119-130). These problems include thrombus formation at the tip, measurement of analyte concentrations in the vascular wall instead of the blood stream, vessel compression due to patient movement, and vasospasm. In addition, signal variation due to catheter movement is also a potential problem. All of these issues are addressed in the present invention.

Other challenges with the measurement of nitric oxide in vivo include its low concentration (in the nanomolar range), and its short half-life (3-5 sec). (DS Bredt, "Endogenous Nitric Oxide Synthesis: Biological Functions and Pathophysiology", Free Rad. Res. 31(6):577-596 (1999).) Nitric oxide electrodes are also sensitive to variations in flow rate and temperature, further complicating the measurement of NO in blood.

A potential solution to this challenge is to monitor the metabolic products of NO, which include nitrite and nitrate. However, nitrite ($NO_2$), one of the metabolic products of nitric oxide, also has a relatively short half-life of about 10 minutes in blood. Therefore, even analysis of nitrite levels in blood using HPLC requires that chemical stabilizers be added to prevent the decomposition of nitrite prior to analysis. The available methods for measurement of nitrite levels in blood and plasma based on mass spectroscopy and chemiluminescence require several chemical and physical preparatory steps and the use of standard curves. The samples have to be grouped for a proper assessment and the nitrite levels needs to be determined in a delayed fashion, with the most reliable results reported after finishing the entire sample collection and analysis. Nitrite and nitrate have widely varying background levels, which are influenced by a number of factors including diet. There are currently no commercially available $NO_2$ sensors that can directly measure $NO_2$ in the physiological concentration range in blood or in electrolyte solutions (such as ultrafiltrate solutions) obtained from blood (0.5 to 2 $\mu M$ $NO_2$).

Variable background contamination of water and laboratory supplies are known to be issues in the measurement of nitrites and nitrates. "Considering the frequent need to measure NO in the nanomolar range when dealing with biological samples, the nitrite contamination found in tap water is highly problematic. Further, because of the ubiquitous nature of nitrite, the use of substantially nitrite-free water is imperative not only when diluting standards and samples, but also when rinsing glassware and syringes. The importance of using fresh filtered or glass-bottled water is underscored by the fact that NO from the air can react with oxygen in water to form nitrite. The use of substantially nitrite-free water in solutions such as the preservation solution and to dissolve EDTA is also important in order to eliminate nitrite contamination in these solutions." (Peter H. MacArthur, Sruti Shiva, Mark T. Gladwin, "Measurement of circulating nitrite and S-nitrosothiols by reductive chemiluminescence", Journal of Chromatography B, 851 (2007) 93-105.) "Nitrite, the oxidative breakdown product of NO and a ubiquitous trace contaminant of chemicals and laboratory glassware, is a well-known nuisance in NO analytical chemistry." (Xunde Wang, Nathan S. Bryan, Peter H. MacArthur, Juan Rodriguez, Mark T. Gladwin, and Martin Feelisch, "Measurement of Nitric Oxide Levels in the Red Cell Validation Of Tri-Iodide-Based Chemiluminescence With Acid-Sulfanilamide Pretreatment" J Biological Chemistry Vol. 281, No. 37, pp. 26994-27002 (2006).)

In particular, ultrafiltration membranes can be a source of nitrite and nitrate contamination, and therefore their use is challenging. "Use of ultrafiltration units to remove protein from plasma is a cause of heavy contamination that persists to a certain degree even after several washes with pure water." (Takaharu Ishibashi, Junko Yoshida, and Matomo Nishio, "New Methods to Evaluate Endothelial Function: A Search for a Marker of Nitric Oxide (NO) In Vivo: Re-evaluation of NOx in Plasma and Red Blood Cells and a Trial to Detect Nitrosothiols" J Pharmacol Sci 93, 409-416 (2003).) In addition, the time delay imposed by ultrafiltration of samples means that measurement of nitric oxide itself from a sample is unlikely.

In addition to monitoring for cerebral ischemia, monitoring $NO_2$ concentrations may also have applications in ischemia in general, including cardiac ischemia, in septic shock (660,000 patients/year) (Kuhl S J, Rosen H. "Nitric oxide and septic shock—from bench to bedside." West J Med 1998; 168:1 76-181; and Greg S. Martin, M.D., David M. Mannino, M.D., Stephanie Eaton, M.D., and Marc Moss, M.D. "The Epidemiology of Sepsis in the United States from 1979 through 2000", NEJM 348:1546-1554 (2003).), traumatic brain injury (280,000 patients/year) (Hlatky, R et al, Role of Nitric Oxide in Cerebral Blood Flow Abnormalities After Traumatic Brain Injury, J Cereb Blood Flow Metab 23:582-88 (2003).) subarachnoid hemorrhage (SAH) (21,000 patients/year) (R Loch Macdonald, Ryszard M Pluta and John H Zhang, Nature Clinical Practice Neurology May 2007 3(5) 256-63; and Writing Group Members, Thomas Thom, et al., "Heart Disease and Stroke Statistics—2006 Update. A Report From the American Heart Association Statistics Committee and Stroke Statistics Subcommittee", Circulation February 2006; 113:e85-e151) asthma, and pain management (A. Koch, K. Zacharowski, O. Boehm, M. Stevens, P. Lipfert, H-J. von Giesen, A. Wolf and R. Freynhagen, "Nitric oxide and pro-inflammatory cytokines correlate with pain intensity in chronic pain patients" Inflamm. res. 56 (2007) 32-37), erectile dysfunction, pulmonary hypertension, and other pathologic conditions as known to one of skill in the art.

Notwithstanding the efforts in the prior art, however, there remains a need for intravascular sensors for implantation or insertion in a blood vessel, which can provide useful blood glucose or other physico-chemical readings for an extended period of time, without material interference from thrombus formation, embolization, or other foreign body response. Preferably, the sensor is capable of continuous or near continuous monitoring, and driving an implantable insulin pump and/or making blood glucose or other data available to the patient or medical personnel.

SUMMARY OF THE INVENTION

The present invention generally relates to the use of sensors to monitor the concentration of a chemical species in bodily fluids, and more specifically, to a novel sensor configuration to monitor glucose levels in a body vessel. The device is an implantable sensor, which is delivered to the patient's vascular system preferably transluminally via a catheter, using a stent or stent-graft as a platform. One feature of the device is that the sensor surface is placed at the apex of the luminal surface of a streamlined housing, so that the shear rate at the sensor/blood interface is sufficient to minimize the thickness of the formed thrombus layer. In this manner, significant tissue deposition or encapsulation due to potential fibrotic reactions is minimized, and transport of glucose to the sensor is not altered over time.

Thus, there is provided in accordance with one aspect of the present invention a blood glucose detector for implantation within a blood vessel. The blood glucose detector comprises a support, having a first side for contacting the wall of the vessel and a second side for facing radially inwardly towards the center of the vessel. A sensor is carried by the support, and the sensor has a sensing surface thereon. The sensing surface is spaced radially inwardly from the first side by a distance of at least about 0.2 to 2.5 mm, such that the velocity of blood in the vessel inhibits obstruction of the sensing surface. Preferably, the distance is at least about 0.5 mm. The blood glucose detector further comprises a transmitter on the support, for transmitting information from the sensor to an external receiver. In one embodiment, the support comprises an expandable tubular body. The tubular body may be either a balloon expandable or a self-expandable component such as a stent. The tubular body may be further provided with a tubular sheath on the radially inwardly directed surface and/or the radially outwardly directed surface. In one embodiment, the sensor comprises an analyte permeable membrane and an enzyme gel layer.

In accordance with another aspect of the present invention, there is provided a method of prolonging the useful life of a sensor in a blood vessel. The method comprises the steps of providing a sensor having an analyte sensing surface thereon, and positioning the sensor at a site in a blood vessel such that the sensing surface is positioned radially inwardly from the vessel wall by a sufficient distance that the blood flow shear rate at the sensing surface substantially delays obstruction of the sensing surface. Preferably, the positioning step comprises carrying the sensor on a catheter and transluminally advancing the catheter to the site.

In accordance with a further aspect of the present invention, there is provided an implantable sensor for sensing the presence of an analyte in a vessel. The sensor comprises a tubular support structure for anchoring the sensor in a vessel. The support has a sidewall with a luminal side facing towards the center of the vessel and an abluminal side facing towards the wall of the vessel. A sensor housing is carried by the support structure, the housing having a streamlined exterior configuration to minimize blood flow turbulence. A power supply and electrical circuitry are provided in the housing, and a sensing surface carried by the housing is exposed to the exterior of the housing. The sensing surface is positioned on the radially inwardly most portion of the luminal side of the housing.

In accordance with a further aspect of the present invention, there is provided an implantable sensor for sensing the presence of an analyte in a vessel that can be retrieved. The sensor comprises a support structure for anchoring the sensor in a vessel. The sensor further comprises a snareable member connected to the sensor that allows allow for removal of the sensor in a catherization procedure. In one embodiment, the snareable member is a hook.

In accordance with a further aspect of the present invention, a method for retrieving an implanted sensor is provided. Under fluoroscopic guidance, a guiding catheter of sufficient diameter so as to be able to accommodate the retrieved sensor and its anchoring platform is inserted. A snare is inserted through the guiding catheter and is guided to a sensor hook. The snare grasps the sensor hook and the sensor collapses into a retrieval catheter. The sensor and guiding catheter are simultaneously withdrawn from the patient's body.

In accordance with a further aspect of the present invention, another method for retrieving an implantable sensor on a support is provided. Under fluoroscopic guidance, a catheter with a clip is positioned so that the clip is adjacent to an sensor attached to a stent. A balloon attached to the catheter is inflated so that the clip is forced around the sensor. After deflating that balloon, another balloon is inflated so that the clip pulls the sensor away from the stent, thus separating the sensor therefrom.

In accordance with a further aspect of the present invention, another method for retrieving an implantable sensor on a support is provided. In this case, the sensor housing or sensor anchors are connected to a tether, which is used for removing the sensor at the end of its useful life.

In accordance with a further aspect of the present invention, there is provided an implantable immunosensor. The immunosensor comprises a support structure. The immunosensor produces an electrical signal representative of a reaction between an analyte and an antigen.

In another aspect of this invention, the sensor may be an infrared sensor placed either intraluminally or extraluminally in a blood vessel. The infrared sensor produces an electrical signal indicative of the concentration of chemical compounds in blood.

In accordance with a further aspect of the present invention, there is provided an implantable blood gas monitor. The blood gas monitor produces an electrical signal indicative of the partial pressure of dissolved blood gases or pH.

In accordance with a further aspect of the present invention, there is provided an implantable ion-selective electrode. The ion selective electrode produces an electrical signal indicative of the concentration of electrolytes in blood.

In accordance with a further aspect of the present invention, there is provided an implantable pressure sensor. The pressure sensor produces an electrical signal indicative of the pressure in the vessel.

In accordance with a further aspect of the present invention, there is provided an implantable flow sensor. The flow sensor produces an electrical signal indicative of the flowrate in the vessel.

In accordance with a further aspect of the present invention, there is provided a sensor for insertion or implantation within a blood vessel that minimizes the formation of thrombus. The sensor comprises a support, having a first side for contacting the wall of the vessel and a second side for facing radially inwardly toward the center of the vessel and a sensor carried by the support and having a sensing surface thereon. The sensing surface of the sensor is spaced radially inwardly from the first side and includes a layer that minimizes the formation of thrombus. The sensor can include a transmitter on the support, for transmitting information from the sensor to an external receiver. The layer can be an anticoagulant (such as heparin or hirudin), a thromboresistant material such as phosphoryl choline, a hydrogel (such as poly (ethylene glycol), poly(N-vinyl pyrrolidone), poly(hydroxyethylmethacrylate), polyacrylamide, polyacrylic acid, cross-linked collagen, sulfonated polyurethane or other sulfonated polymer, or other thromboresistant materials as are known in the art, or can release a pharmacological agent that inhibits cell proliferation or migration.

In accordance with a further aspect of the present invention, there is provided an intravascular sensor for sensing the presence of nitric oxide or a nitric oxide metabolite or glutamate or aspartate or calcium or potassium in a vessel. The sensor comprises a support structure, a sensor housing carried by the support structure, and a sensing surface exposed to the surrounding environment. The sensor can detect nitric oxide or a nitric oxide metabolite or glutamate and can be used in an intravascular environment. The support structure can be a stent or a catheter.

In accordance with a further aspect of the present invention, there is provided an implantable sensor that monitors NO and/or its metabolites (nitrites, nitrates) and provides an indication such as an audio or visual alarm if the concentration of NO and/or its metabolites meets predetermined criteria.

In accordance with a further aspect of the present invention, there is provided an implantable sensor with an enzyme electrode for monitoring glutamate, aspartate, arginine, citrulline, or acetylcholine.

In accordance with a further aspect of the present invention, there is provided an implantable sensor with an electrode for monitoring calcium, potassium or dopamine in order to monitor for stroke or ischemia.

In accordance with a further aspect of the present invention, there is provided an implantable sensor with an enzyme electrode for glutamate for which is configured to monitor the consumption of oxygen.

In accordance with a further aspect of the present invention, there is provided an implantable sensor with an electrode for monitoring the rate of change of NO or its metabolites (nitrites, nitrates), and/or aspartate, arginine, citrulline, acetylcholine, calcium, potassium or dopamine.

In accordance with a further aspect of the present invention, there is provided an implantable sensor with an electrode for monitoring NO or its metabolites, or another analyte or substance of interest, or the rate of change of the concentration of the subject analyte.

In accordance with a further aspect of the present invention, there is provided an implantable sensor coated with an antithrombotic layer, such as an anticoagulant (such as heparin or hirudin), a hydrogel (such as poly(ethylene glycol), poly(N-vinyl pyrrolidone), poly(hydroxyethylmethacrylate), polyacrylamide, polyacrylic acid, cross-linked collagen, sulfonated polyurethane or other sulfonated polymer, or other hydrogels, or phosphoryl choline), or is coated with a substance that can release a pharmacological agent that inhibits cell proliferation or migration.

In accordance with a further aspect of the present invention, there is provided an implantable sensor with sensor circuitry for measuring the concentration of an analyte, when the analyte generates a low current signal.

In accordance with a further aspect of the present invention, there is provided an implantable sensor with an activatable retrieval mechanism, such as a hook, and electrical circuitry for activating the retrieval mechanism.

In accordance with a further aspect of the present invention, there is provided an implantable sensor attached to a tether, for retrieval purposes, that is attached to a monitor.

In accordance with a further aspect of the present invention, there is provided a catheter including one or more sensors and an anchoring platform that stabilizes the catheter near the side of a lumen.

In accordance with a further aspect of the present invention, there is provided a catheter including one or more sensors and side holes within the catheter wall for the purpose of flushing the sensor surface.

In accordance with a further aspect of the present invention, there is provided a catheter including a sensor and an anchoring platform that stabilizes the sensor in the middle of a lumen.

In accordance with a further aspect of the present invention, there is provided a microdialysis catheter including a sensing surface with a substance-selective membrane. A perfusate is pumped past the membrane though a lumen in the catheter allowing the substance of interest to diffuse across the membrane. Then, the perfusate and the substance of interest are pumped through a return lumen in the catheter to an external reaction chamber for analysis.

In accordance with a further aspect of the present invention, there is provided an ultrafiltration or microfiltration system, including a catheter with a semi-permeable membrane. An ultrafiltrate is pumped across the membrane though a lumen in the catheter. Then, the ultrafiltrate containing the substance of interest is pumped through a return lumen in the catheter to an external reaction chamber for analysis.

In accordance with a further aspect of the present invention, there is provided an ultrafiltration system with a size-selective membrane. An ultrafiltrate is pumped past the ultrafiltration membrane to an external reaction chamber for analysis.

In accordance with a further aspect of the present invention, there is provided sensor circuitry for evaluating the signals from multiple sensors, and activating an alarm system in response thereto.

In accordance with a further aspect of the present invention, there is provided an implantable sensor system that includes multiple sensors of the same type to provide redundancy.

In accordance with a further aspect of the present invention, there is an implantable sensor system including sensors of more than one type that simultaneously measure multiple analyte concentrations, or their rates of change, in vivo.

In accordance with a further aspect of the present invention, there is provided an implantable sensor system and method where the sensor's output signal is analyzed in combination with the output signal from an external monitor, such as Transcranial Doppler (TCD) or somatosensory evoked potentials (SSEP).

In accordance with a further aspect of the present invention, there is provided an implantable sensor including electrical leads that are connected to an external monitoring device so that the sensor's electrical signals are transmitted out of the body using the electrical leads.

In accordance with a further aspect of the present invention, there is provided an implantable sensor including electrical leads that are connected to an implanted device, such as a subdermal device like a pacemaker, and that allows for the sensor's electrical signals to be sent to the implanted device and then outside the body through the implanted device.

In accordance with a further aspect of the present invention, there is provided a sensing system having antimicrobial coatings on any part of the system. The coatings may extend from the inside to the outside of the body in a system having a percutaneous catheter or wire.

In accordance with a further aspect of the present invention, there is provided an implantable sensor including an anti-fouling surface and a bioprotective layer of ePTFE underneath the anti-fouling surface.

In accordance with a further aspect of the present invention, there is provided an implantable sensor that may be surgically placed in the cerebral ventricles, in order to monitor analyte concentrations in cerebrospinal fluid (CSF) which are indicative of stroke, such as NO, its metabolites, or another analyte or substance of interest.

In accordance with a further aspect of the present invention, there is provided a system and method in which multiple implantable sensors are implanted at different locations within the body of the patient.

In accordance with a further aspect of the present invention, there is provided an implantable sensor and related circuitry for performing fast-scan cyclic voltammetry, for example, for monitoring dopamine.

In accordance with a further aspect of the present invention, there is provided an implantable sensor coupled with a thermocouple.

In accordance with a further aspect of the present invention, there is provided an implantable nitrite sensor prepared by coating an NO sensor with an acidic polymer, and an iodide gel layer and iodide-containing matrix in order to convert nitrite into NO for direct measurement.

In accordance with a further aspect of the present invention, there is provided a catheter that extracts patient fluid by circulating saline solution past a surface of the catheter. The extracted fluid can be monitored for NO or its metabolites, or other substances or analytes of interest.

In accordance with a further aspect of the present invention, there is provided a guidewire that includes a sensor. The sensor is attached to or positions coaxially within the guidewire. The sensor includes a sensing surface exposed to the exterior of the sensor. The sensor is configured to detect a concentration of a substance.

A catheter is disclosed that includes an ultrafiltration or microfiltration membrane. A pump extracts fluids from the body via the catheter and membrane. A sensor analyzes the fluid.

A system is disclosed for measuring nitric oxide or one of its metabolic products. The system includes a fluid flow path extending between an end adapted for receiving a sample of bodily fluid and a reaction chamber. A filter is located in the flow path. A first pump advances the sample through the filter to produce a filtrate. A second pump advances filtrate into the reaction chamber. A third pump advances reactant into the reaction chamber. A sensor in communication with the reaction chamber determines a concentration of nitric oxide or one of its metabolic products. Metabolic products can include $NO_2$ and $NO_3$.

In accordance with an embodiment of the present invention, the system includes a catheter.

In accordance with an embodiment of the present invention, the pumps may be vacuum pumps.

In accordance with another embodiment of the present invention, two reactant reservoirs are in communication with the reaction chamber. A pump advances a mixture from the first and second reactant reservoirs and the filtrate into the reaction chamber.

A method for measuring a level of nitric oxide or one of its metabolic products in bodily fluid is disclosed. A stream of bodily fluid is directed through a filter to produce a filtrate. The filtrate is then directed into a reaction chamber. A reactant is provided that is directed into the reaction chamber to react with the filtrate to produce a reaction product. The concentration of nitric oxide or one of its metabolic products in the reaction product is measured.

In accordance with an embodiment of the present invention, the stream of bodily fluid is directed by use of a first pump.

In accordance with an embodiment of the present invention, the reactant is directed by use of a second pump.

In accordance with an embodiment of the present invention, the filtrate is directed by use of a third pump.

In accordance with an embodiment of the present invention, the bodily fluid is blood or interstitial fluid or cerebrospinal fluid.

In accordance with another embodiment of the present invention, acid and iodide are mixed to produce the reactant. The reactant can also be a solid, such as $Cr_2O_3$.

An apparatus for measuring nitrite in blood of a human or animal subject is disclosed. The apparatus comprises a housing, at least a portion of which is configured for placement in a blood vessel of the subject and a size-exclusion filter configured to allow nitrite ions to pass through the filter and impede passage of particles having a molecular weight greater than about 60 kD through the filter. The apparatus comprises a nitrite reduction agent within the housing, configured to reduce nitrite ions to nitric oxide, and a nitric oxide electrode within the housing for measuring nitric oxide.

In accordance with another embodiment, the housing comprises a needle configured for advancement into a blood vessel of the subject.

In accordance with another embodiment, the filter is configured to allow nitrite molecules to pass through the filter.

In accordance with another embodiment, the filter is configured to exclude hemoglobin and erythrocytes.

In accordance with another embodiment, the apparatus further comprises a vacuum source coupled with the housing, configured to improve flux through the filter.

In accordance with another embodiment, the filter comprises a membrane comprising a material selected from the group consisting of polycarbonate, polysulfone, polyethersulfone, polyarylethersulfone, polyurethane, polyacrylonitrile, regenerated cellulose, mixed cellulose ester, polyester, Nylon, poly(vinylidene fluoride) (PVDF), polypropylene, and polytetrafluoroethylene.

In accordance with another embodiment, the filter comprises a thromboresistant coating.

In accordance with another embodiment, the nitrite reduction agent comprises a constant voltage electrode. The apparatus may further comprise a constant voltage source configured to be coupled to the constant voltage electrode. In accordance with another embodiment, the constant voltage source and the constant voltage electrode are configured to apply a voltage of about 1.2 V referenced to a normal hydrogen electrode (NHE).

In accordance with another embodiment, the nitrite reduction agent comprises an anion-exchange membrane within the size-exclusion filter, configured to allow nitrite ions to pass through the membrane and impede passage of cations; and a dilute acid within the anion-exchange membrane. The dilute acid may comprise less than about 1 ml of a dilute acid. The dilute acid may comprise carbonic acid. The apparatus may further comprise an anode positioned between the size-exclusion filter and the anion-exchange membrane; and a cathode positioned within the anion-exchange membrane, wherein the anode and cathode are in electrical communication with a voltage source.

A method of measuring nitrite in blood of a human or animal subject is disclosed. The method comprises inserting a sensor within blood of a patient; excluding particles with a molecular weight greater than 60 kD from a vicinity around the sensor using a size-exclusion filter; converting nitrite ions included in the vicinity around the sensor to nitric oxide; and measuring a concentration of nitric oxide using a sensor.

In accordance with another embodiment, excluding particles with a molecular weight greater than 60 kD from a vicinity around the sensor comprises excluding cells and proteins from a vicinity around the sensor.

In accordance with another embodiment, converting nitrite included in the vicinity to nitric oxide includes applying a constant voltage to the vicinity. Converting nitrite included in the vicinity to nitric oxide may include applying a voltage of about 1.2 V, referenced to a normal hydrogen electrode, to the vicinity.

In accordance with another embodiment, converting nitrite included in the vicinity to nitric oxide includes reacting nitrite with dilute acid, reducing the nitrite to nitric oxide. The method may further comprise containing the dilute acid within an area around the electrode sensor. Containing the dilute acid within an area around the electrode sensor may comprise using an anion-exchange membrane. The method may further comprise providing an electromotive force to increase a rate of nitrite particles diffusing across the anion-exchange membrane. Providing the electromotive force may comprise positioning an anode between the anion-exchange member and the size-exclusion filter and positioning a cathode within the anion-exchange member and applying a voltage to the anode and cathode. A constant or varying voltage may be applied to the anode and the cathode.

In accordance with another embodiment, the method further comprises determining a level of nitrite within the blood based on the concentration of nitric oxide.

In accordance with another embodiment, the method further comprises triggering an alarm if a concentration of nitric oxide is outside a particular range.

In accordance with another embodiment, the method further comprises triggering an alarm if a rate of change of nitric oxide concentration exceeds a particular rate.

A method of treating a patient with nitrite is disclosed. The method comprises administering nitrite or nitric oxide to the patient and monitoring a level of nitrite within blood of the patient. Monitoring a level of nitrite within blood of the patient comprises inserting a sensor within the blood of a patient; excluding particles with a molecular weight greater than 60 kD from a vicinity around the electrode sensor using a size-exclusion filter; converting nitrite ions included in the vicinity around the sensor to nitric oxide; and measuring a concentration of nitric oxide using sensor.

In accordance with another embodiment, the method further comprises using the concentration of nitric oxide to determination a level of nitrite within the blood of the patient.

In accordance with another embodiment, the method further comprises modifying an amount of nitrite or nitric oxide administered to the patient based on the concentration of nitric oxide measured. The method may further comprise modifying an amount of nitrite or nitric oxide administered to the patient based on the level of nitrite within the blood of the patient.

Further features and advantages of the present invention will become apparent to those of skill in the art in view of the detailed description of preferred embodiments which follows, when considered together with the attached drawings and claims.

BRIEF DESCRIPTION OF THE DRAWINGS

FIG. 1A is a perspective view of an expanded stent with an embedded sensor housing on its abluminal side.

FIG. 1B is a block diagram of remote circuitry for an external monitoring device.

FIG. 1C is a diagram of a wearable or implantable insulin pump.

FIG. 1D is a block diagram of the sensor circuitry for measuring analyte concentration.

FIG. 1E is a block diagram of the remote measurement unit.

FIG. 3 is a cross-section taken along the line 3-3 in FIG. 2.

FIG. 4 is an enlarged cross-sectional view through the sensor element of FIG. 3.

FIG. 7A is a side elevational view of the distal end of a catheter-based delivery system for a stent sensor device.

FIG. 8 is a cross-sectional view of the catheter-based delivery system taken along the 8-8 line of FIG. 7A.

FIG. 9D is a perspective partial cut away view of a stent sensor device surrounded by a sheath with a transducer partially across the cross-section of the stent.

FIG. 9E is a perspective view of an expanded stent with an embedded sensor housing on its abluminal side and four perpendicular transducers placed partially across the cross-section of the stent.

FIG. 10 is a side elevational view of a sensor and transmitter, with expanded anchoring stents at the proximal end of the sensor, intermediate between the sensor and transmitter, and at the distal end of the transmitter.

FIG. 12 is a diagram of a constrained anchoring platform or stent with a sensor housing containing a reservoir for delivery of labeled target molecules, and a sensing compartment containing a signal source, a receiver and antibodies with and without labeled target molecules, signal processing circuitry, and a radiotransmitter.

FIG. 13 is a block diagram of the fluorescence based sensor electronics of the sensor of FIG. 12.

FIG. 14B is a diagram of an expanded anchoring platform or stent with an embedded sensor housing on its luminal side, and containing a hook on the sensor housing with which the device can be retrieved.

FIG. 16 is a side view diagram of a catheter containing a sensor near its distal end, with self-expanding split-ring anchors.

FIG. 17C is a side view of a retrieval catheter in a blood vessel.

FIG. 22A is a diagram of a catheter with multiple sensors and an anchoring platform which stabilizes the sensor near the side of a lumen, and an external monitoring system.

FIG. 32A is a side elevational view of a catheter containing a ultrafiltration or microfiltration membrane near its distal tip.

FIG. 32B is a side elevational view of a catheter containing an ultrafiltration or microfiltration membrane within a window near its distal tip.

DETAILED DESCRIPTION OF THE PREFERRED EMBODIMENT

Glucose Sensor

Figure 2:
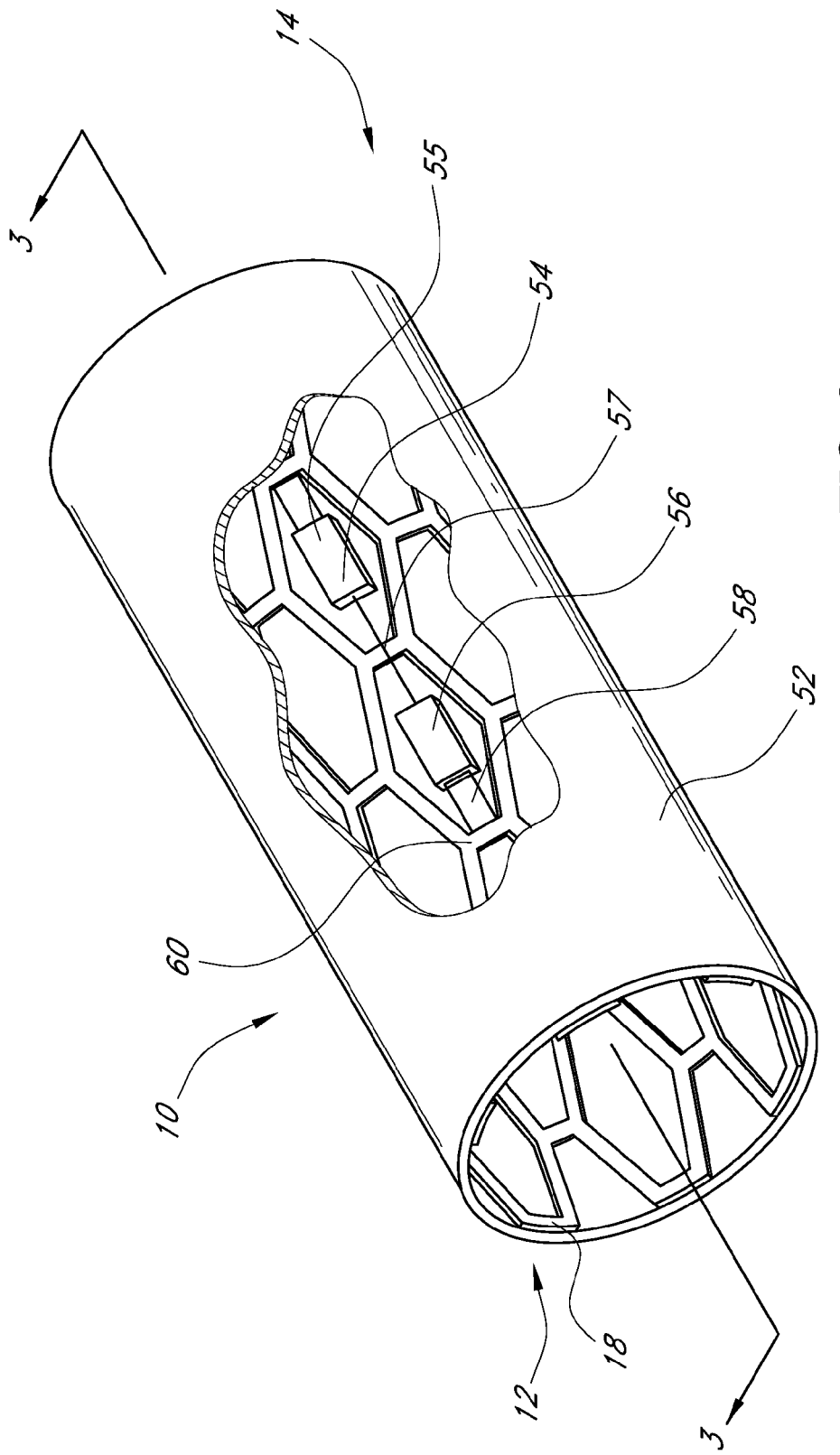
FIG. 2 is a perspective partial cut away view of a stent sensor device surrounded by a sheath.

In accordance with the present invention, an intraluminal blood glucose sensor is provided on a support structure such as a modified stent of the type implanted following percutaneous transluminal coronary angioplasty (PTCA) for the treatment of atherosclerosis. Atherosclerosis is the build-up of fatty deposits or plaque on the inner walls of a patient's arteries. These lesions decrease the effective size of the artery lumen and limit blood flow through the artery, prospectively causing a myocardial infarction or heart attack if the lesions occur in coronary arteries that supply oxygenated blood to the heart muscles. In the angioplasty procedure, a guide wire is inserted into the femoral artery and is passed through the aorta into the diseased coronary artery. A catheter having a balloon attached to its distal end is advanced along the guide wire to a point where the stenotic lesions limit blood flow through the coronary artery. The balloon is then inflated, compressing the lesions radially outward against the wall of the artery and substantially increasing the size of the arterial lumen, to improve blood circulation.

Increasingly, stents are being used in place of or in addition to PTCA for treatment of atherosclerosis, with the intent of minimizing the need to repeatedly open a stenosed artery. Although a number of different designs for stents exist in the prior art, all are generally configured as elongate cylindrical structures that can assume two different states, one having a substantially greater diameter than the other. A stent is implanted in a patient's vascular system using an appropriate delivery system. There are two basic types of stents. The first type is termed "balloon expandable", and refers to stents that are expanded radially outward due to the force from an inflated angioplasty balloon, such as the Palmaz-Schatz stent, the Gianturco-Roubin stent, and the Strecker stent. The second type is termed "self-expandable", and refers to and those that are self-expanding, such as the Hemobahn™ and SMART Stent™ (made of nickel titanium memory alloy), and the Wallstent (made of Elgiloy).

Typically, a stent carried by a delivery catheter is advanced through a guide catheter to a site within the patient's artery. For the balloon expanded type, after the introducer sheath is retracted, a balloon disposed inside the stent is inflated to a pressure ranging from about six to ten atmospheres. The force produced by the inflated balloon expands the stent radially outward beyond its elastic limit, stretching the vessel and compressing the lesion to the inner wall of the vessel. A self-expanding stent expands due to spring force following its positioning within the artery, after a restraining sheath is retracted from the compressed stent. Following the expansion process, if the balloon expandable type is used, the balloon is deflated and removed from inside the stent and the catheter and other delivery apparatus is withdrawn. The lumen through the vessel should be substantially increased, improving blood flow.

After a stent or other endoluminal device is implanted, a clinical examination and either an angiographic or ultrasonographic morphological procedure is performed to evaluate the success of the procedure in opening the diseased artery or vessel. These tests are typically repeated periodically, e.g., at six-month intervals, because restenosis of the artery may occur.

Although the sensor of the present invention may be carried by any of a wide variety of intraluminal support structures, balloon expandable or self-expandable stents are preferred by the present inventor. In general, the stent may be modified from those intended for supporting a treatment site following angioplasty, in view of the preferred placement in a healthy section of the vessel as is discussed in greater detail below. In addition, the wall of the stent may be modified to support the sensor, as is also discussed in greater detail below. As well as providing a useful support structure with known deployment characteristics, a stent provides a useful platform for a variety of additional reasons. For example, it is impractical to pass an electronic conductor through the wall of an artery or vessel to monitor the condition of an implanted sensor for long periods of time. Also, any active glucose sensor would likely be energized with electrical power. Again, it is less practical to supply power to such a sensor through any conductor that perforates the vessel wall or that passes outside the patient's body.

In addition to stents, the generic term endoluminal implant encompasses stent-grafts, which are also sometime referred to as "covered stents." A stent-graft is a combination of one or more stents and a synthetic graft that is typically implanted at a desired point in a vessel using an endoscopic approach. The stent is attached either to the ends or throughout the body of the synthetic graft, and is used to hold the graft in position. Sometimes, hooks are provided on the stent to ensure that the graft remains in the desired position within the vessel. Clearly, it would also be desirable to monitor the status of glucose and other parameters through a stent graft, just as noted above in regard to a stent.

Endoluminal implants are used in other body passages in addition to blood vessels. For example, they are sometimes used to maintain an open lumen through the urethra, or through the cervix. A stent placed adjacent to an enlarged prostate gland can prevent the prostate from blocking the flow of urine through the urinary tract. Tracheal and esophageal implants are further examples of endoluminal implants. In these and other uses of an endoluminal implant, provision for monitoring parameters related to the status of flow and other conditions in the patient's body would be desirable. Information provided by monitoring such parameters can enable more effective medical treatment of a patient.

A number of factors will affect the function of a glucose sensor implanted within a blood vessel. As with stents, the device should be designed to minimize the risk of thrombosis and embolization. Thus, slowing or stoppage of blood flow at any point within the lumen should be minimized. Colombo et al. ("*Intracoronary Stenting Without Anticoagulation Accomplished With Intravascular Ultrasound Guidance,*" Circulation 91:1676-88, (1995)) and Goldberg et al. ("*Benefit Of Intracoronary Ultrasound In The Deployment Of Palmaz-Schatz Stents*", J. Am. Coll. Card. 24: 996-1003, (1994)) demonstrated that a factor resulting in subacute stent thrombosis in coronary arteries was inadequate expansion of the stent. This was done using intravascular ultrasonography (IVUS). Another factor, and related, is that the stents should be placed in close apposition to the vessel wall, so that the only flow obstructions are at the luminal surface of the stent struts. They later demonstrated that by using non-compliant balloons at high pressure (18 atm), that even the final assessment using IVUS is not required; an important consideration for centers lacking such equipment. Thus, it is preferable to minimize flow disturbances which may be created by stent implantation. This is more preferable in the smaller coronary arteries, which range from about 2.5-4 mm in diameter, than it is in other, larger arteries, where small amount of mural thrombus will have less effect on the volumetric flowrate.

Another factor is that the stent platform is not a solid piece of impermeable material, such as a rolled sheet, or a "jelly-roll", as described by Winston et al. (U.S. Pat. No. 5,411,551 issued May 2, 1995). In in vivo studies, Virmani, et al. ("*Histopathologic Evaluation Of An Expanded Polytetrafluoroethylene Nitinol Stent Endoprosthesis In Canine Iliofemoral Arteries,*" JVIR, 10:445-456 (1999)) demonstrated that when endovascular stent-grafts are covered with porous graft material, it is possible for the graft material, in this case ePTFE, to become covered with a nearly intact layer of endothelial cells. However, when the same graft material was rendered impermeable to the underlying host vessel by wrapping it in FEP, the graft material was instead covered with a thick layer of thrombus. This demonstrates the desirability of using porous stents as anchors for the sensor.

Usually, a layer of fibrin clot deposits on the luminal surface of the implanted stent. After 3-4 weeks, the fibrin layer is typically remodeled into fibro-collagenous tissue, with a layer of endothelial cells present on the flow surface. However, if a relatively thick layer of fibro-collagenous tissue forms on the surface of an endovascular sensor, it may experience the same loss of signal that has been reported for subcutaneously implanted sensors. That is, a modified type of "foreign-body response" may occur, and glucose may not be able to freely and rapidly diffuse to the sensor. Evaluation of an ePTFE (expanded polytetrafluoroethylene) covered stent graft (Virmani, et al., 1999) showed that in areas where the graft surface was further from the center of the flow channel, it became covered with a relatively thick layer of thrombus, which eventually converted to fibro-collagenous tissue. In areas where the graft surface was closer to the center of the flow channel, it became covered with a relatively thin layer of tissue, and in some cases remained uncovered for periods of up to one year in a canine. Thus, there is a balance between minimizing disruption of blood flow, and excessive thrombus deposition.

Unlike a stent or stent-graft, which is used in the treatment of occlusive or aneurysmal vascular disease, however, the stent-sensor combination of the present invention should be placed in a relatively healthy portion of the artery. If it is placed in a stenotic or calcified area, it may be difficult for the device to expand completely, so the device may be more narrowed than is intended, resulting in thrombotic fouling of the sensor, or distal embolization may occur. If the device is placed in an aneursymal vessel, it may expand more than intended, and again, fail to function as designed.

In addition, some types of sensors require that the actual sensing component be covered with a semi-permeable membrane in order to allow certain components such as glucose to pass through, while excluding cells, enzymes, or other factors which could damage the sensor. Thus, a stent-graft-sensor combination might be more suitable than a stent-sensor combination without the graft material. Further considerations will become apparent from the illustrated embodiments of the present invention which are discussed below.

FIG. 1A shows a perspective view of an expanded implantable sensor device 10 having a proximal end 12, a distal end 5 and a central lumen 16 extending therethrough. The expanded implantable sensor device 10 is comprised of a stent 14 and a sensor 20. Although the stent 14 illustrated in FIG. 1A resembles a Palmaz-Schatz stent, it is understood that any of a wide variety of stent configurations can be utilized such as those identified below. Whether the stent is a balloon expandable or self-expandable variety, the stent 14 comprises a tubular sidewall 18, which may be compressed to a relatively small diameter for delivery using a catheter, and which may be expandable to the approximate diameter of the vessel or to a diameter approximately 5-25% greater than the diameter of the vessel lumen.

In general, a self-expanding variety of stent or stent-graft such as the S.M.A.R.T. Stent (Cordis Corp., Miami, Fla.) or Hemobahn (W.L. Gore & Associates, Flagstaff, Ariz.) is preferred, because the presence of the sensor body may impede proper expansion of the stent platform using a balloon. The sensor housing can preferably be attached to the stent by use of adhesives, by tying (suturing) the two components together, or by use of thermal bonding, soldering, welding or brazing, or mechanical interfit or the like. The sensor and sensor housing should be attached to the stent along a single row of stent struts, so that the struts may fully expand without needing to stretch the sensor housing, or being constrained by the sensor housing.

An example of the type of stent which could be used in certain embodiments of the present invention is described by Lau et al. in U.S. Pat. No. 5,876,432, issued Mar. 2, 1999 which is herein incorporated by reference. Other stents which are suitable for use in the present invention are described by U.S. Pat. No. 4,739,762 to Palmaz, issued Apr. 26, 1988; U.S. Pat. No. 5,102,417 to Palmaz, issued Apr. 7, 1992; U.S. Pat. No. 5,421,955 to Lau et al., issued Jun. 6, 1995; U.S. Pat. No. 5,195,984 to Schatz, issued on Mar. 23, 1993; U.S. Pat. No. 4,886,062 to Wiktor, issued Dec. 12, 1989; U.S. Pat. No. 4,655,771 to Wallsten, issued Apr. 7, 1987; U.S. Pat. No. 5,443,500 to Sigwart, issued Aug. 22, 1995; and U.S. Pat. No. 4,580,568 to Gianturco, issued Apr. 8, 1986; which are all incorporated in their entireties herein by reference. The expanded inside diameter of the device may range from 3 to 20 mm, and the length of the device may range from 1 to 30 cm. The radially inwardly facing or radially outwardly facing sidewall of the stent may also be covered by a sheath as is known in the art. The sheath can be bonded to the surface of the stent so that the sheath remains in close apposition to the vessel wall.

Attached to the stent 14, a sensor 20 contains the sensing circuitry within its housing. Depending upon the stent 14 design and sensor 20 design, the attachment between the sensor 20 and the stent can take any of a variety of forms as will be apparent to those of skill in the art in view of the disclosure herein. For example, adjacent axially extending parallel struts of the stent design illustrated in FIG. 1A spread circumferentially apart upon expansion. Thus, the sensor 20 should be mounted to only colinear axial struts along the length of the stent unless the mounting is designed to accommodate circumferential separation of parallel struts. Alternatively, the sensor 20 may be positioned in an aperture which is cut in the sidewall of the stent 14, and attached to the strut portions adjacent to the edge of the aperture. Attachment may be accomplished in any of a variety of ways, such as by the use of adhesives, thermal bonding, soldering, welding or brazing, or mechanical interfit, depending upon the construction materials of the stent 14 and the sensor 20. Alternatively, the sensor 20 may be solvent bonded, adhesively bonded or otherwise attached to an expandable tubular sleeve which is positioned concentrically about the stent 14. Other attachment configurations can be devised by those of skill in the art in view of the disclosure herein.

In the illustrated embodiment, all or a portion of the sensor 20 is positioned on the radially outwardly facing surface of the tubular sidewall 18. Positioning the sensor 20 on the radially outwardly facing surface (sometimes referred to herein as the abluminal surface) may advantageously optimize blood flow through the central lumen 16 and/or reduce turbulence in the central lumen 16. Alternatively, the sensor 20 may be positioned on the radially inwardly facing surface (sometimes referred to herein as the luminal surface) of the stent. In addition, the stent struts or other elements which make up the sidewall 18 may be removed or modified at the portion of the sidewall corresponding to the sensor 20 such that the sensor 20 may be mounted within the resulting opening in the sidewall. Because the implantable sensor device 10, in accordance with the present invention, is preferably positioned within a healthy section of the vessel, the radial strength normally required for a stent in a post-angioplasty application is unnecessary. Thus, the present inventor believes that any reduction in radial support which may result from reasonably dimensioned apertures or other modifications to the sidewall to attach sensor 20 will not adversely affect the role of the stent as a sensor support structure in the context of the present invention. Additional details concerning the position of the sensor 20 with respect to the tubular wall 18 will be discussed below in connection with FIGS. 5A-5C.

The sensor circuitry 22 includes a sensing circuit 24, which is connected to a signal processing circuit 26, which is connected to a power source 28, a radio transmitter 30, and an antenna (not shown) to transmit signals about the glucose concentration to a remote device. The antenna (not shown) may be a thin wire wound around the stent 10, or preferably, may be wound around a small ferrite core, as commonly used for such applications. This provides certain advantages, such as increased signal strength or increased transmission distance for the same amount of power required. In Keilman et al. (U.S. Pat. No. 6,231,516, issued May 15, 2001), for example, the implied requirement to minimize protrusion of the sensor and transmitter into the vessel lumen requires that the stent be constructed using unwieldy manufacturing processes, and the signal strength is weakened by the inability to use a ferrite core.

The power source 28 may be inductively coupled to an external device, or it may be a thin film rechargeable battery, as in Bates, J. B. et al., *"Thin Film Rechargeable Lithium Batteries for Implantable Devices"*, ASAIO J., 1997 43:M644-M647, which is incorporated herein by reference. Alternatively, the power source may be a battery, such as lithium iodide, lithium silver vanadium oxide, lithium carbon monofluoride, or lithium ion rechargeable battery, as commercially available from Wilson Greatbatch Technologies, Inc. (Clarence, N.Y.).

The glucose sensor monitoring circuit and the remote measurement unit circuit are shown in FIGS. 1D and 1E. The glucose sensor monitoring circuit consists of a voltage source (25) to drive the sensor (20), and a current-to-frequency converter (27). The circuit is powered by an external field produced by the remote measurement device. In normal operation, the remote measurement device (FIG. 1E) is placed over the area where the sensor is implanted. This produces a voltage across the Power Coil and Antenna (30) that is then regulated by the power supply (28) to provide a source of power for the sensor electronics (voltage source and current-to-frequency converter). Once powered, the circuit will produce an output frequency that is directly proportional to the concentration of glucose.

FIG. 1E shows a block diagram of the electronics for the remote measuring unit. The remote monitoring unit provides the drive to power the sensor electronics and also receives and processes the signal from the V-F converter. A high current drive circuit (37), running at a frequency much lower than the V-F converter, is used to excite the antenna/excitation coil (34). Because the signal received from the sensor is much higher than the excitation signal, the former is filtered and amplified in amplifer/filter (35). The microcontroller (39) measures the frequency and then uses a calibrated look-up table to provide translation to the proper units and also to compensate for any non-linearities in the device response curves. The final result is displayed on an LCD (not shown) for the user.

The sensing circuit 24 is in electrical communication with a sensing surface (not illustrated in FIG. 1A) for sensing the analyte of interest in the fluid stream. In the embodiment illustrated in FIG. 1A, the sensor surface is preferably positioned radially inwardly from the radially inwardly facing surface of the tubular sidewall 18, to improve the useful life of the device as is discussed elsewhere herein. Thus, in an embodiment such as that illustrated in FIG. 1A in which the sensor 20 is positioned on the abluminal side of the tubular sidewall 18, the sensor surface is displaced radially inwardly such as by a radially inwardly extending portion of the housing or other support (not illustrated) to achieve the desired radial position of the sensor surface. Alternatively, in an embodiment in which the sensor 20 is positioned on the luminal side of the tubular side wall 18, or within or through an opening in the tubular sidewall 18, the sensor surface may be positioned directly on a radially inwardly-most extending portion of the sensor 20 as is discussed elsewhere herein.

The sensor surface is preferably covered by a semi-permeable membrane (not shown), which contacts passing blood when the stent 14 is placed in a blood vessel. The permeability of the membrane is selected to allow blood glucose, or the analyte of interest to freely contact the sensor, while restricting the passage of other blood components. The semi-permeable membrane may comprise ePTFE, Dacron®, polyurethane, silicone rubber, poly(lactide-co-glycolide) (PLGA), poly(caprolactone) (PCL), poly(ethylene glycol) (PEG), collagen, polypropylene, cellulose acetate, poly(vinylidene fluoride) (PVDF), nafion or other biocompatible material. These membrane materials may also be used for the tubular sheath which can be used to surround either the luminal or abluminal surfaces of the stent. The membrane of the sheath may be bonded to the stent by adhesives or by tying (suturing) the two components together or by use of thermal bonding, soldering, welding or brazing, or mechanical interfit. The pore size of the lumenal membrane may be large enough to allow cells to come through if it covers the sensor surface, but the sensor membrane should have a pore size (MW cutoff of about 1000) which will allow glucose to pass, while restricting the passage of larger molecules. The entire tube surface does not have to be composed of the same membrane material. The part of the device near the sensing element can be composed of a different material or have a different porosity than the material in the rest of the device.

Referring to FIG. 1B, a remote circuit 32 is equipped with an antenna 34 and a signal processing unit 36, which converts the electronic signal from the embedded sensor into a concentration level or other indicium of the analyte. Preferably, an alarm circuit 38 and a display 40 are also provided. Information regarding the level of the analyte of interest can be displayed on the display 40 such as a monitor 42. The signal processing unit 36 may be provided with a lookup table or other baseline of normal or expected values for the analyte of interest. If the concentration of the analyte goes outside of the prescribed range, or if an electronic failure is detected, a warning audible, visible, or tactile signal is preferably produced from the alarm system 38. A transmitter 44 may also be included in the remote circuitry 32 in order to transmit data about the level of the analyte of interest to an implantable infusion pump, or the like.

The remote circuitry 32 can be provided in any of a variety of physical forms, depending upon the intended use of the device. For example, in a hospital or other immobilized patient setting, the remote circuitry 32 can be provided in a desktop or bedside housing and coupled directly to a display 40 such as a monitor 42. Alternatively, ambulatory patient devices may be provided by deleting a permanent coupling to the monitor 42 and packaging the remaining components of remote circuit 32 in a wearable form, such as a compact self-contained unit adapted for attachment to the wearer's clothing or including straps so that it can be strapped to the patient's body. In an ambulatory device, the signal processing unit 36 includes sufficient memory to record the glucose values over a predetermined period of time. The patient can couple the wearable device to an external monitor 42 or other electronics periodically, such as one or more times per day. Analyte data may thereafter be displayed in readable form, such as on a monitor 42 in table form or in graph form with a time unit on the X axis and a glucose value or derivative data on the Y axis.

The wearable unit (not illustrated) may additionally be provided with a data export coupling, such as a telephone connector, for connecting the signal processing unit 36 via internal or external modem into the telephone system. In this manner, the patient can transmit condensed analyte data to the healthcare provider for further monitoring and/or analysis. The wearable unit may additionally be provided with one or more manual data inputting elements ranging from a simple push button to a keypad, to allow manual data entry relating to significant dietary or other events. For example, meal times, significant fluid intake, manual insulin injection or other administration, or any of a variety of other significant events can be marked in the data, so that the patient or reviewing medical personnel can correlate the event with the blood glucose data.

Referring to FIG. 1C, there is schematically illustrated an implantable or externally wearable infusion pump 46. The infusion pump 46 may be controlled by the remote circuit 32 via a receiver 48 in the pump, or may be manually controlled using sensor information only as a guideline. The infusion pump 46 may be refilled through an appropriately designed port 50 such as a pierceable septum using a hypodermic needle or other appropriate delivery system. The infusion pump 46 may be implantable, as described by Irsigler et al., ("*Controlled Drug Delivery in the Treatment of Diabetes Mellitus*", Crit. Rev. Ther. Drug Carrier Syst. 1(3): 189-280 (1985)), which is incorporated herein by reference. Alternatively, it may be worn externally by the patient, and infuse insulin or other drugs as appropriate through a catheter 15 which is inserted into the patient's body. External insulin infusion pumps are currently marketed by suppliers like Medtronic, or Siemens. However, these pumps are not designed to receive a continuous signal from an implanted sensor, but instead are pre-programmed to approximate the patient's baseline insulin requirements. Such pumps can be modified with an appropriate circuitry to receive and respond to output from the glucose sensor by those of skill in the art in view of the disclosure herein.

Now referring to FIG. 2, a covered implantable sensor device 10 is shown. The sensor 10 comprises a cylindrical stent wall 18 surrounded by a sheath 52. An antenna (not shown) may be wound around the body of the sensor 10 and connected to the power source or the transmitter. All relevant electronics are schematically illustrated as in electronics housing 54 which is electrically coupled to a sensor 56 by one or more conductors 57. All such junctions of dissimilar metals are coated with polymers which are impermeable to bodily fluids in order to reduce galvanic corrosion. The analyte sensing element 56 is covered with a membrane 62 (FIG. 4) which is permeable to the analyte of interest. The analyte sensing element 56 extends radially inwardly within the sensor 10 where blood flow conditions are optimal.

Now referring to FIGS. 2, 4 and 5, the illustrated analyte sensing element 56 contains an enzyme gel layer 64, which is placed adjacent to the outer permeable membrane 62. The analyte diffuses through the membrane 62 to the gel enzyme layer 64. The reaction between the analyte and the enzyme occur in the gel enzyme layer 64. The reaction products then pass through an inner membrane 66 and react at the surface of a noble metal electrode 68, producing a current. An appropriate potential is applied to the electrode 68 from the power source contained in electronics housing 54 resulting in a signal, which is sent to the signal processing unit. The signal is then passed through the transmitter which transmits the information regarding the analyte of interest to an external monitor and/or implantable pump as has been discussed. The power source, the signal processing unit, and the transmitter are completely encapsulated in a housing 55 which is impermeable to biological fluids. The same housing 55 or a separate housing 70 also encapsulate the analyte sensor except for the membrane 62.

The sensor(s) to be incorporated into the device may be either electrochemical, piezoelectric, thermoelectric, acoustic, or optical. As known to those skilled in the art, there is a significant body of literature regarding the development of electrochemical glucose sensors. These generally incorporate an enzyme, which selectively reacts with glucose.

Electrochemical biosensors may be categorized as amperometric, conductometric, or potentiometric. Amperometric measurements are based on the oxidation or reduction or electrochemically active substances involved in the oxidation of glucose via glucose oxidase. Another method is measurement of changes in local pH due to the gluconic acid produced using a potentiometric sensor, usually a coated-wire pH selective electrode and/or ion-selective field effect transistor (ISFET). Conductometric sensors are based on the principle of electrical resistance changes during the reaction.

Potentiometric and conductometric sensors are currently limited due to the presence of numerous interfering chemicals in the environment. The main disadvantage of these sensors is their low sensitivity. The response of the potentiometric sensor depends on logarithmic changes in analyte concentration.

Microelectronics using ion selective field effect transistors (ISFET's) have been used for measurements of different analytes in body fluids (Erickson, K. A., et al., "Evaluation of a Novel Point-of-care System, the I-Stat Portable Clinical Analyzer", Clin. Chem. 39(2):283-287 (1993) which is herein incorporated). This allows miniaturization and integration of the transducer with associated electronic circuitry into a single chip. However, corrosion of the semiconductor material surface in saline and in physiological fluids is presently a problem for in vivo use. This problem may be corrected by surface coating or passivation of the ISFET. These types of sensors also belong to the class of potentiometric sensors, as described above.

Amperometric sensors respond linearly to the analyte concentration. If the limiting processes in signal generation are the enzymatic reactions, the dependence of the signal on glucose concentration is non-linear according to Michaelis-Menton kinetics. When the sensor operates in a glucose diffusion-limited mode, the signal is linearly proportional to the analyte concentration. Amperometric sensors are further subdivided into three classes:

1) Based on the production of hydrogen peroxide or consumption of oxygen.
2) Low molecular weight compounds used as mediators of the electron transfer process.
3) Direct electron transfer between the enzyme and the electrode.

Oxygen—Electrode Based Sensors:

An operational enzyme electrode was first reported by Updike and Hicks (Updike, J. W., and Hicks, J. P., "*The Enzyme Electrode,*" Nature, 214: 986-8, (1967)) based on a description by Clark and Lyons (Clark L. C., and Lyons, C., "*Electrode Systems for Continuous Monitoring in Cardiovascular,*" Ann. NY Acad. Sci., 102:29-45 (1962)). In this process, the oxygen consumed in the oxidation of glucose is measured. The Clark oxygen electrode employs a platinum cathode held at a potential of approximately (−)0.6 V versus the saturated calomel electrode (S.C.E.), a sufficiently negative potential to reduce oxygen as follows:

$$O_2 + 4H^+ + 4e^- \rightarrow 2H_2O$$

Because the species being measured in this reaction is a gas, interference from other species in the biological fluid is negligible. However, the signal is determined from reduction of the initial current, making glucose determinations at low concentrations difficult. Further, the system requires the use of a second electrode without any glucose oxidase, to determine the local oxygen tension for the glucose measurement. In addition, it is necessary to insure that there is excess oxygen in the catalytic layer so that the reaction rate is limited by the glucose. The ratio of blood glucose to oxygen can be as high as 10 to 1 in arterial blood, and 100 to 1 in venous blood. (Jaffari 1995) An oxygen electrode sensor has been described by Armour et al. (1990), which was implanted in the superior vena cava of six dogs for up to 15 weeks, with good agreement with standard in vitro assays.

Hydrogen Peroxide based sensors measure hydrogen peroxide production based on the oxidation of glucose at potentials above +600 mV vs. SCE. This signal is directly related to the concentration of glucose in the sample.

$$H_2O_2 \rightarrow O_2 + 2H^+ + 2e^-$$

Unfortunately, the high operating potential required can also result in the oxidation of other chemical species in the blood. This may be overcome by the use of membranes. Bindra et al. (Bindra, D. S. et al., "*Design and in vitro studies of a needle type glucose sensor for subcutaneous monitoring,*" Anal. Chem., 63: 1692-6 (1991)) reported glucose detection for up to 10 days in rats with a needle-type sensor, which consisted of GOD immobilized onto cellulose acetate as an inner membrane, and polyurethane as an outer membrane. Moussy et al. (Moussy, F. et al., "*Performance of subcutaneously implanted needle-type glucose sensors employing a novel trilayer coating,*" Anal. Chem., 65: 2072-7 (1993)) used a needle type sensor with a trilayer coating. Nafion was used as an outer membrane, and poly (o-phenylenediamine) as an inner membrane to reduce interference from small electroactive species. GOD was immobilized between these two layers. As with the oxygen electrodes, the reaction must be limited by glucose, not oxygen.

In amperometric sensors with mediated electron transfer, oxygen as an electron acceptor is substituted by an artificial mediator, to overcome the tissue oxygen dependence of amperometric biosensors. Ferrocene and its derivatives are the most commonly used, although hexacyanoferrate (III), tetrathiafuvalene, and ruthenium hexamine (Jaffari, 1995) have also been investigated. In these sensors, a process involving the mediator instead of oxygen takes place:

$$GOD(red) + Mediator(ox) \rightarrow GOD(ox) + mediator(red)$$

At the electrode:

$$Mediator(red) \rightarrow Mediator(ox)$$

The electrochemical oxidation of the reduced mediator occurs at a low potential, thus reducing the sensitivity of the sensor to interfering compounds.

Limitations to the in vivo use of the sensor involve leaching of the mediator, and the possible toxicity of the mediator. This has been addressed by approaches such as:

1) Binding of the mediator to high molecular weight compounds,
2) Entrapment of the mediator and enzyme in conducting polymer films,
3) Covalent attachment of the mediator to a polymer film,
4) Modification of the enzyme with mediator molecules, and
5) Use of polymeric mediators.

All of these approaches have been investigated to reduce mediator leaching, although none have been tested in vivo (Jaffari, 1995).

An advantage of this type of sensor, because oxygen is not involved in the signal generation process, is that the sensor signal becomes independent of the oxygen concentration (Wilkins, 1996).

Amperometric sensors with direct electron transfer are independent of the oxygen concentration and involve direct oxidation of glucose by GOD at an electrode constructed from conducting organic salts (charge-transfer organic complexes with electron conductivity). Sensors based on this principle have been tested in vivo in rats, but little is presently known about the biocompatibility of such materials.

Examples of sensors that would be suitable for use in this invention include electrochemical sensors described in U.S. Pat. No. 6,001,067, issued to Shults, et al., "Device and method for determining analyte levels", Dec. 14, 1999, and U.S. Pat. No. 6,212,416, issued to Ward et al, Apr. 3, 2001, "Device for monitoring changes in analyte concentration".

Other types of sensors suitable for practicing the present invention, and which also depend on continuous blood glucose transport to the sensor, are fluorescence based sensors described in patents issued to Colvin, including U.S. Pat. No. 5,517,313, (issued May 14, 1996), and further described in U.S. Pat. No. 5,894,351 issued Apr. 13, 1999, U.S. Pat. No. 5,910,661 issued Jun. 8, 1999, U.S. Pat. No. 5,917,605 issued Jun. 29, 1999, U.S. Pat. No. 6,304,766 issued Oct. 16, 2001, and the following patents issued to Colvin et al., including U.S. Pat. No. 6,330,464 issued Dec. 11, 2001, U.S. Pat. No. 6,344,360, issued Feb. 5, 2002.

Another type of sensor for which the present invention is well suited, are pressure-based sensors, in which glucose sensitive hydrogels exert pressures which are related to glucose concentrations, described by Han et al in U.S. Pat. No. 6,514,689, "Hydrogel Biosensor", issued Feb. 4, 2003.

The most commonly used membrane for implantable biosensors is polyurethane (Jaffari, 1995). Other membranes which have been investigated include cellulose acetate, polypropylene, silicone rubber, and Nafion. These membranes have shown promise in short term monitoring, but long-term monitoring has been more difficult. Davies et al.

(Davies, M. L., et al., "*Polymer membranes in clinical sensor application. Part 1: an overview of membrane function,*" Biomaterials, 13: 971-89, (1992)) have reviewed extensively the range of polymers used as membranes for biosensors. Updike reported that immobilization of glucose oxidase within a membrane allowed it to accurately measure glucose levels for well over one year.

In a preferred embodiment, an amperometric electrode is used. The characteristics of such an electrode, such as one available from Minimed, Inc. (Sylmar, Calif.), is related to the production of hydrogen peroxide in the conversion of glucose to gluconic acid by glucose oxidase. The noble metal electrode 68 may be connected to any of a variety of RF transceivers. To avoid the use of batteries, which may be too large for this application, the system may be powered by, and signal transmission occurs via an inductive link. This requires an inductive coil (not shown) to be placed both inside the external receiver and an inductive coil (not shown) within the implantable sensor device 10. An example of the type of transceiver to be used is employed in the Ventak Mini IV automatic implantable cardioverter defibrillator (Guidant Corp, Santa Clara, Calif.). The transceiver coil in the preferred embodiment is specifically adapted for use with a stent platform. The size of the coil, in addition to the number of turns around the implant limits the power and signal transmission distance between the implant and the external receiver/power supply. In order to maximize the diameter of the coil, the coil is wound around the outside of the implantable sensor device 10. The transceiver coil is made from an electrically conductive material, and is coated to prevent corrosion. The coil may be aligned with and bonded to the struts of the implantable sensor device 10, in order to minimize any impact on expansion of the implantable sensor device 10. Alternatively, the struts of the implantable sensor device 10 themselves may serve as the antenna coil. In addition, in order to maximize signal transmission, the internal and external coils should be aligned so that their major axes are parallel. The external receiver coil should contain a ferrite core to optimize power and signal transmission. The external receiver and power supply should be designed so that it can be worn on the patient's body, and can be oriented to maximize the signal from the implanted sensor. This can be done by custom-placed foam padding to orient the external receiver and power supply.

Figure 6A:
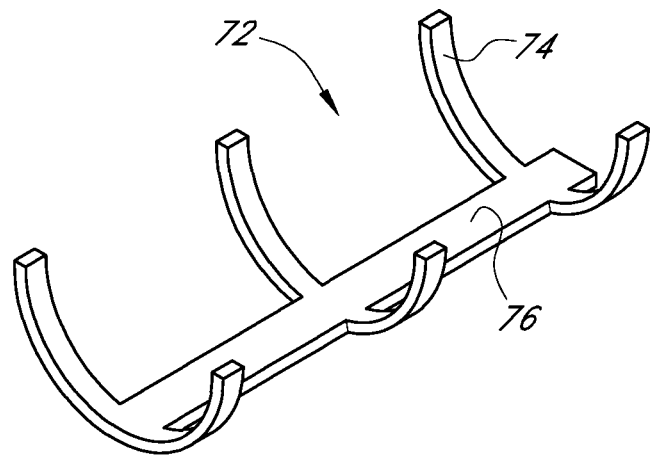
FIG. 6A is a perspective view of an alternate support structure in accordance with the present invention.
Figure 6B:
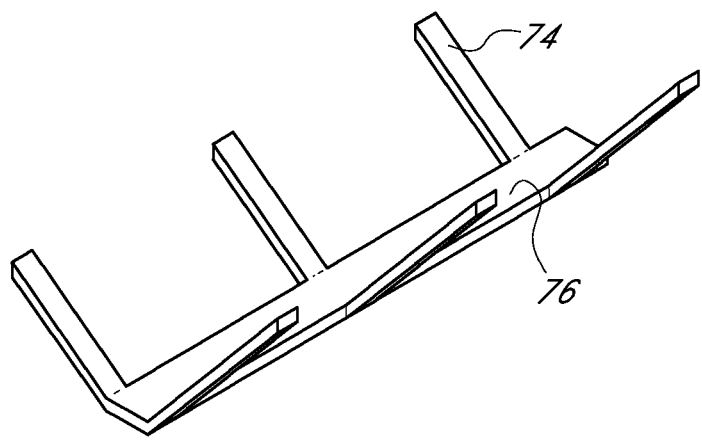
FIG. 6B is a perspective view of a further support structure in accordance with the present invention.
Figure 6C:
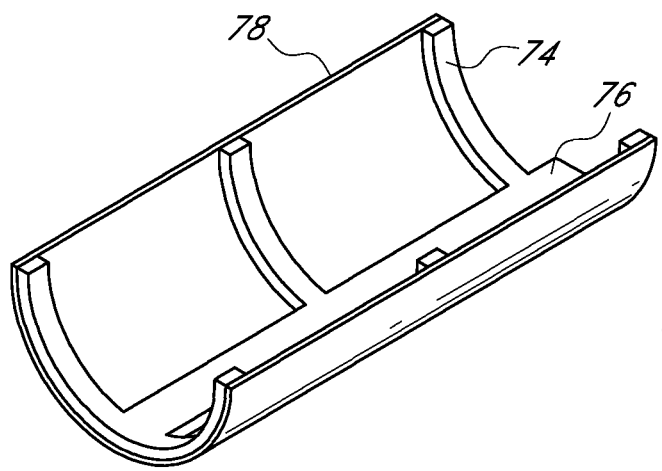
FIG. 6C is a perspective view of the support structure illustrated in FIG. 6A, provided with an outer fabric sheath.

Now referring to FIGS. 6A-6C, alternatively, the sensor device may be held in place within the vessel by any of a variety of anchoring systems other than a graft or stent. For example, any of a variety of anchoring structures may be provided with hooks or barbs to engage the vessel wall. Alternatively, semicircular cages or struts may be used, which only extend through a partial circumference of the vessel. FIG. 6A shows struts 74 that can be positioned securely against a blood vessel. An axially extending strut 76 connects the circumferential struts 74, and also could support a sensor. The support 72 can be manufactured in a variety of ways, such as by injection molding a suitable polymeric material or by laser cutting from stainless steel, Nitinol or other tube stock. FIG. 6B shows alternate struts 74 that can be secured against the vessel wall. Again, connecting struts 74 is one or more connecting struts 76. FIG. 6C shows a modification of the device shown in FIG. 6A, where the support 72 is provided with a sheath 180. In the case of Ward et al. (U.S. Pat. No. 6,212,416), they suggest the possible use of the sensor in an artery or vein, but provide no mechanism to secure the sensor within the vessel. If used as described, without such anchoring mechanism, the device would migrate within the vessel, causing significant injury to the patient, such as stroke, myocardial infarction, or pulmonary embolism, all of which are life threatening.

In order to implant an implantable sensor device within the vasculature of the patient, a catheter-based delivery system is used. All implantable sensor devices are formed to include a central lumen with a diameter in the reduced profile sufficient to allow passage of a guide wire and a catheter tip through it. The implantable sensor device is mounted onto a catheter tip, and then collapsed to as small a diameter as possible. The implantable sensor device may be deployed by removal of a deployment sheath, or other methods, which may be preferred for the specific type of stent platform being employed. These methods are well known in the art. After the implantable sensor device is deployed, the catheter and guidewire are removed from the (now enlarged) central lumen in the implantable sensor device. The implantable sensor device is placed such that neither the catheter nor the guidewire adversely affects the electronic circuitry.

Preferably, the implantable sensor device is implanted in a relatively large artery or vein (>5 mm) in order to minimize the risk that the implant may occlude the artery. In addition, a healthy artery or vein should be chosen, so that the device can open completely, and so that the flow patterns are normal.

Clinically, it is now accepted practice to place the stent in a parent vessel so that the stent struts cross the ostium of a side branch vessel. This is called "stent jail." (Pan, M., et al., "*Simple and Complex Stent Strategies for Bifurcated Coronary Arterial Stenosis Involving the Side Branch Origin,*" Am. J. Cardiol., 83: 1320-25 (1999)). In addition, for stent-grafts for aortic aneurysm repair, investigation is being carried out regarding stent struts which cross the renal artery ostia. An example of such a suprarenal device is the Talent Aortic Stent-Graft (Medtronic, Inc.). This suggests that it is possible to have a wire (or transducer) which is placed directly across an artery without thrombus formation or thrombo-embolization. Thus, in an alternative embodiment, the sensor or sensing element (i.e., the transducer) can be placed directly across the path of the flowing blood, on a surface with low cross-sectional area, such as a wire with a diameter of 0.003" to 0.025", or a ribbon, oriented with its narrow edge facing upstream. The transducer or sensor can be placed on either the proximal, distal, or lateral faces of the wire or ribbon.

As with sensors mounted on or near the wall of the vessel, it is important that the sensor be placed across a large vessel with high blood velocity. This will not result in significant thrombus deposition, and any emboli which may result will be of sufficiently small size that they will be readily lysed by the patient.

As with stents, there are a multitude of possible designs for a sensing element which is placed directly across the bloodstream, as will be appreciated by those skilled in the art. The transducer (or sensing element) could be placed along the surface of a single, straight wire. FIG. 9A shows a cross-sectional view through a stent 14, which includes a sensing element 120 consisting of a wire-like noble electrode 68, which in turn is covered by a gel-enzyme layer 64 and finally by an analyte-permeable membrane 62. The outside of the analyte-permeable membrane 62 is bound to a wire-like structure made of a shape memory material 110 such as nitinol, which is either part of or is bonded to the stent 14. The shape memory material allows the electrode 68 and sensing element 120 to be positioned directly across the lumen of the vessel, as described above. The electrode 68 is connected to the signal processing unit (not shown) through a conductor (not shown). The remainder of the implantable sensor 10, including the power source, signal processing unit, transmitter, and stent, are positioned to be flush against the vessel wall.

Figure 9B:
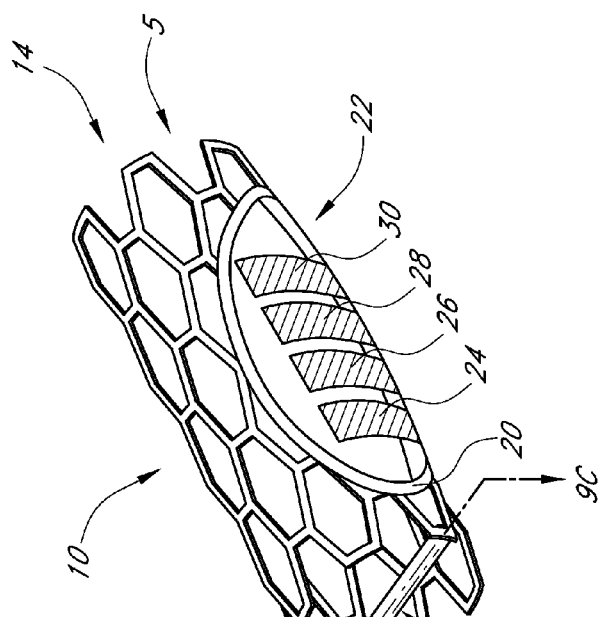
FIG. 9B is a perspective view of an expanded stent with an embedded sensor housing on its abluminal side and a transducer across the cross-section of the stent.
Figure 9C:
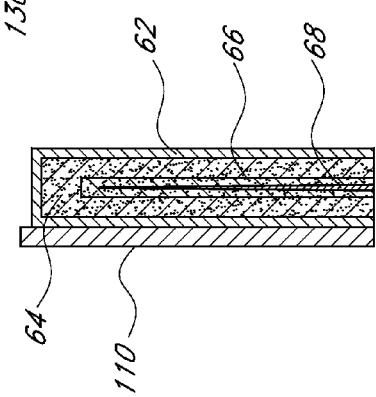
FIG. 9C is an enlarged cross-sectional view of the transducer of FIG. 9B, taken from the 9C-9C line.
Figure 9A:
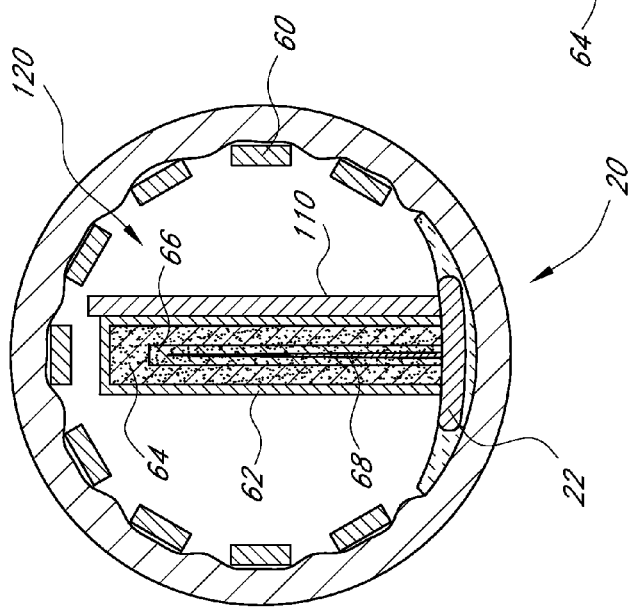
FIG. 9A is a cross-sectional view through a stent showing a transducer across the cross-section of the stent in accordance with the present invention.

FIG. 9B shows an implantable sensor device 10 with a sensing element 130 across the cross-section of the stent 14, with sensor circuitry 22. FIG. 9C shows an enlarged cross-sectional view of the sensing element 130 of FIG. 9B, taken along the 9C-9C line. The sensing element 130 consists of a wire-like noble electrode 68, which in turn is covered by a gel-enzyme layer 64 and finally by an analyte-permeable membrane 62. The outside of the analyte-permeable membrane 62 is bound to a wire-like structure made of a shape memory material 110 such as nitinol, which is bonded to the stent 14 on both ends. The sensing element 130 is connected to the sensing circuit 24 through a conductor (not shown).

FIG. 9D illustrates a transducer 140, consisting of a wire-like noble electrode 68, which in turn is covered by a gel-enzyme layer 64 and finally by an analyte-permeable membrane 62, which is bound to a wire-like structure made of a shape memory material 110 such as nitinol, which is bonded to the stent 14. The sensing element 140 is connected to the sensing circuit 24 through a conductor (not shown).

FIG. 9E shows another configuration with quadruple sensing elements 150, each at right angles to each other, attached to stent 14, with sensor circuitry 22. The sensing elements 150 are connected to the sensing circuit 24 through a conductor (not shown). Alternatively, multiple transducers could be positioned to form a wire mesh, provided the mesh size is sufficiently large to permit blood flow without significant thrombo-embolization. In other acceptable configurations, a very small sensor surface area impedes blood flow, compared to the blood vessel's cross-sectional area.

Referring to FIG. 7A, there is disclosed a deployment catheter 80 which may be utilized to deploy a self-expandable stent type sensor support in accordance with the present invention. The catheter 80 comprises a proximal end 82, a distal end 84 and an elongate flexible tubular body 86 extending therebetween. The length of the tubular body 86 will vary depending upon the intended access point and deployment site for the stent sensor. For example, lengths in the area of about 120 cm to about 140 cm are typical for use in a coronary artery implantation by way of a femoral artery percutaneous puncture site. Other lengths for different access sites and deployment sites will be apparent to those of skill in the art in view of the disclosure herein.

The tubular body 86 may be manufactured in accordance with any of a variety of known techniques, such as by extrusion of appropriate biocompatible polymeric materials. Known materials which are commonly used for this application include high density polyethylene, polytetrofluoroethylene, nylons, and a variety of others known in the art. Alternatively, at least a portion or all of the lengths of the tubular body 86 may comprise a spring coil, solid wall hypodermic needle tubing, or braided reinforced wall, depending upon the functional requirements of the catheter.

For most applications, the tubular body 86 will be provided with an approximately circular cross-sectional configuration having an external diameter within the range of from about 0.025 inches to about 0.065 inches. In accordance with one embodiment of the invention, the tubular body 86 comprises a multilumen extrusion having an external diameter of about 0.042 inches (3.2 f) throughout substantially all of its length. Alternatively, the tubular body 86 can have diameters as large as 12 Fr or higher. For percutaneous placement into larger vessels such as the iliac artery. Additional dimensions, materials and manufacturing techniques are well known in the angioplasty catheter art.

The proximal end 82 is provided with a manifold 88, having a variety of access ports depending upon the desired functionality of the catheter 80. In the illustrated embodiment, the manifold 88 is provided with a guidewire port 90 and a deployment wire port 94. Manifold 88 may be manufactured by injection molding, or other techniques known in the art.

The distal end 84 of deployment catheter 80 is provided with a collapsed support structure 96 having a sensor housing 20 thereon in accordance with the present invention. The support structure 96 is illustrated in its collapsed, low profile configuration, such as for transluminal advancement towards a placement site. The tubular body 86 may be provided with an annular recess 98 near the distal end 84, for receiving the support structure 96. In addition, the tubular body 86 may be provided with a recess for receiving the sensor housing 20, thereby reducing the collapsed profile of the loaded catheter 80.

The support structure 96 may be constrained in its reduced crossing profile configuration in any of a variety of ways as has been discussed. In this illustrated embodiment, the support structure 96 is restrained in its collapsed configuration by a deployment wire 94. Deployment wire 94 extends throughout the length of the tubular body 86 through a deployment wire lumen 108, such that a proximal end of the deployment wire 94 may be proximally retracted by the clinician. The distal end of the deployment wire 100 exits the tubular body 86 at a deployment wire port 100, and loops the support structure 96 in one or more loops or slip knots 102 to restrain the support structure 96 in its collapsed configuration. Loops or slip knots 102 are configured such that proximal retraction on deployment wire 94 causes the loops or slip knots 102 to become untied or otherwise disengaged, thereby releasing the support structure 96 so that it expands radially outwardly from its low profile introduction configuration to its radially enlarged implanted configuration. For applications in which the deployment site is removed from the percutaneous access site, the catheter 80 is preferably introduced over a guidewire as is known in the art. For this purpose, a distal guidewire opening 104 is in communication with the proximal guidewire port 90 by a guidewire lumen 106 extending therebetween.

An example of a similar delivery system is shown in U.S. Pat. No. 5,873,906 to Lau, et al. issued Feb. 23, 1999, which is herein incorporated by reference.

Figure 7B:
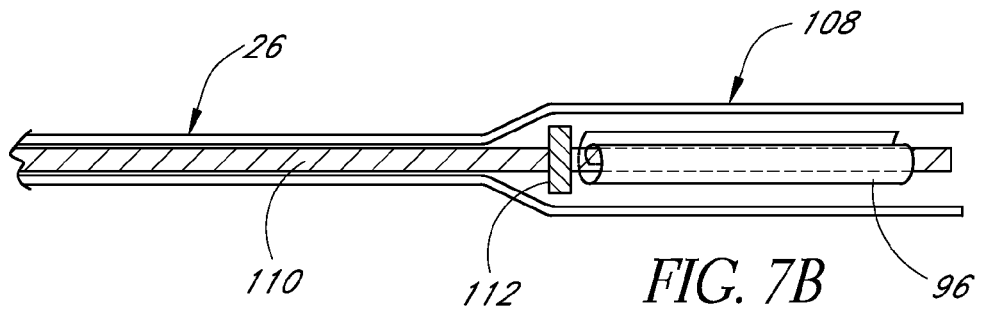
FIG. 7B is a cross-sectional view of a catheter-based delivery system for a rolled sheet type self-expanding stent with an embedded sensor.

Referring to FIG. 7B, the self-expanding implantable sensor device 96 can be deployed from a tubular restraining sheath 108 by pushing a rod 110 optionally attached to a disk 112, until the implantable sensor device 96 is pushed clear of the restraining sheath 108. An example of such a technique is described in U.S. Pat. No. 5,411,551 to Winston et al. (issued May 2, 1995).

Figure 7C:
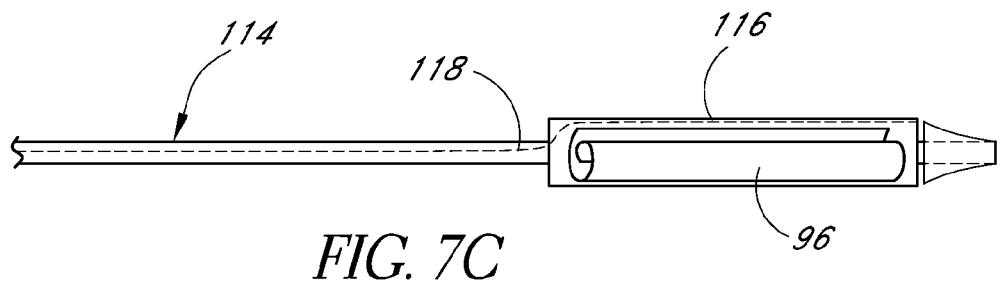
FIG. 7C is a cross-sectional view of a catheter-based delivery system, which uses a restraining sheath, for a self-expanding stent with an embedded sensor.

Referring to FIG. 7C, another deployment method for a self-expanding implantable sensor device 96 is shown. The implantable sensor device 96 is restrained onto the shaft of the catheter 114 by a sheath 116 and a tether line 118. The sheath 116 unfolds when the tether line 118 is pulled, allowing the implantable sensor device 96 to deploy.

Figure 7D:
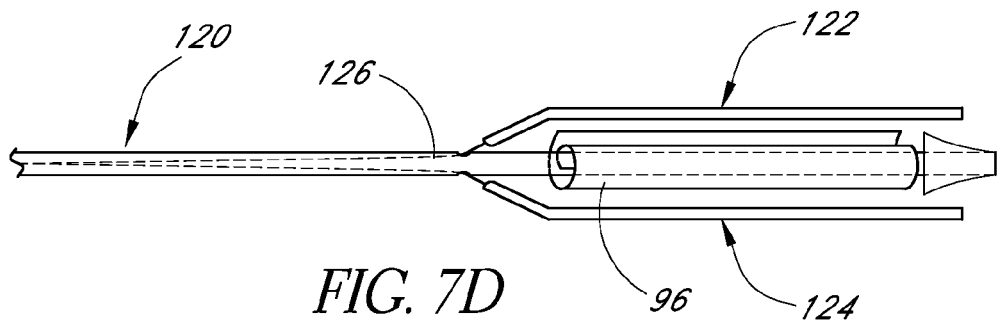
FIG. 7D is a cross-sectional view of a catheter-based delivery system, with a pull-away sheath, for a self-expanding stent with an embedded sensor.

Now referring to FIG. 7D, another deployment method for a self-expanding implantable sensor device 96 is shown. The implantable sensor device 96 is restrained onto the shaft of the catheter 120 by two or three or more restraining prongs 122, 124. The restraining prongs 122,124 are retracted when one or more deployment wires 126 are pulled, allowing the implantable sensor device 96 to expand. An example of this can be shown in U.S. Pat. No. 6,024,763 to Lenker et al. (issued Feb. 15, 2000), which is herein incorporated by reference. However, in this patent, the rails are only designed to minimize frictional forces between a deployment sheath and the device. They are not actually used as the deployment mechanism. In the present case, prongs can be used to minimize the delivery profile of the device. Because the sensor and electronic circuitry may not collapse to a profile as small or as circular as a stent or stent-graft, it may be more appropriate to position the electronic components on one side of the catheter, and layer the collapsed stent on the opposite side of the catheter. This could be achieved by use of delivery prongs, as described.

Figure 7E:
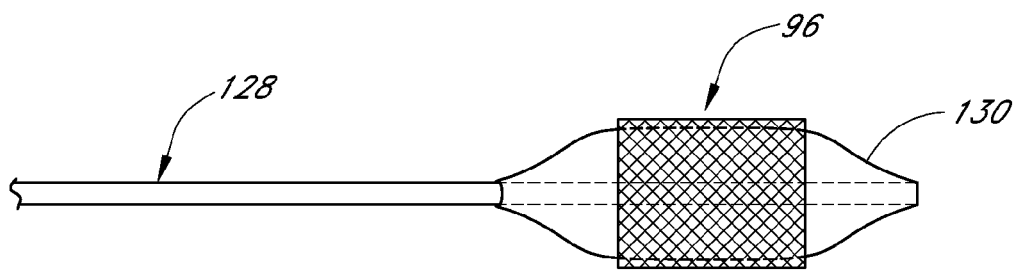
FIG. 7E is a cross-sectional view of a catheter-based delivery system for a balloon expandable stent with an embedded sensor.

Referring to FIG. 7E, the implantable sensor device 96 may be deployed by use of a suitable balloon catheter 128 if a balloon expandable stent platform is used. The balloon 130 is inflated at elevated pressures of 2 to 20 atmospheres, and after the implantable sensor device 96 is fully expanded, the balloon 130 is deflated and then the balloon catheter 128 is withdrawn. Use of such balloon catheters is well known in the art.

Figure 7F:
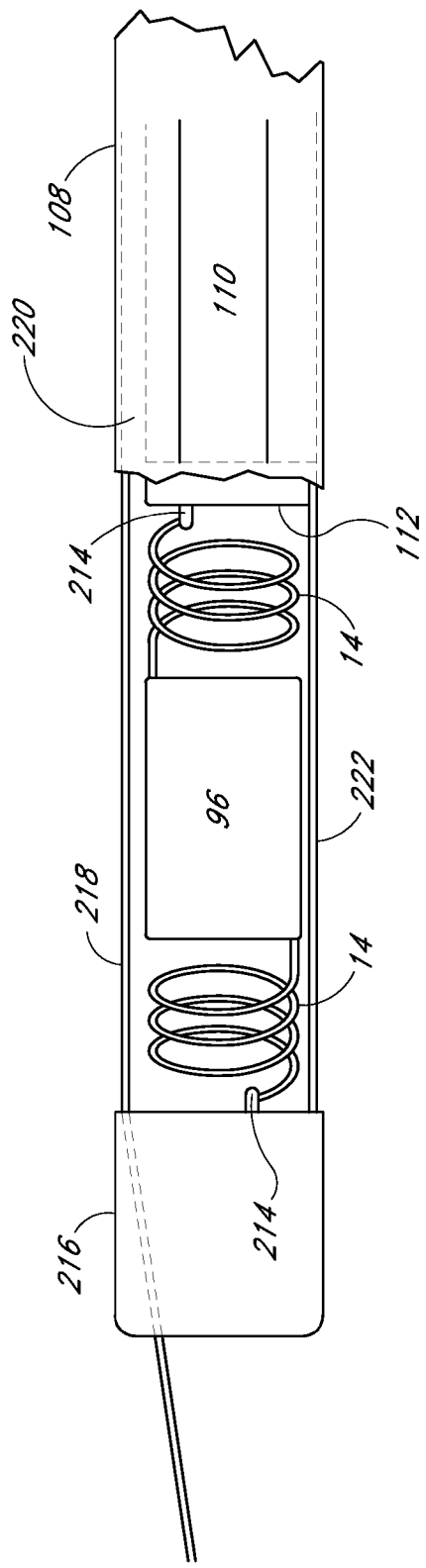
FIG. 7F is a cross-sectional view of a catheter-based delivery system for a self-expanding stent with an embedded sensor, in which the guidewire lumen passes on either side of the sensor.

Referring to FIG. 7F, the self-expanding implantable sensor device 96 can be deployed from a tubular restraining sheath 108 by proximally retracting the sheath 108 with respect to a push rod 110 optionally attached to a disk 112, until the implantable sensor device 96 is exposed clear of the restraining sheath 108. The constrained stent support structures 14 at either end of the sensor 96, may be held in place by a release mechanism, 214, which may be a simple knob or hook. Prior to deployment, the atraumatic catheter tip 216 is in direct apposition to tubular restraining sheath 108. As the sensor device is pushed clear of the restraining sheath, a small shaft 222 connects the push rod 110 or disk 112 to the catheter tip 216. A guidewire 218 passes through guidewire lumen 220, which may be located eccentrically with respect to the axis of the catheter. An example of a similar technique is described in U.S. Pat. No. 5,411,551 to Winston et al. (issued May 2, 1995) which is incorporated herein by reference. However, in Winston, the guidewire passes directly through the center of the catheter, whereas in the present disclosure the guidewire passes eccentrically through the delivery catheter. Allowing the guidewire to pass eccentrically through the catheter allows the sensor to be hermetically sealed, and permits a less complex sensor geometry. Additionally, the eccentric guidewire lumen provides a smaller delivery profile for the sensor and its delivery system.

Figure 5C:
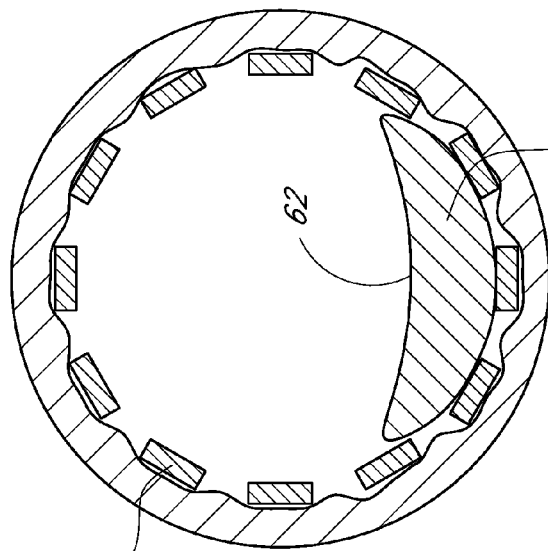
FIG. 5C is a cross-sectional view as in FIG. 5A of a stent with an embedded sensor mounted completely on the luminal side of the stent.
Figure 5B:
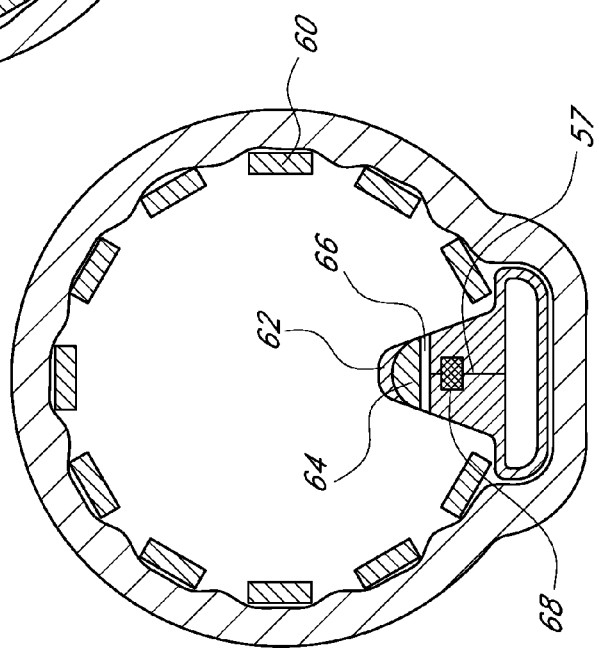
FIG. 5B is a cross-sectional view as in FIG. 5A of a stent with an alternate configuration for the embedded sensor.
Figure 5A:
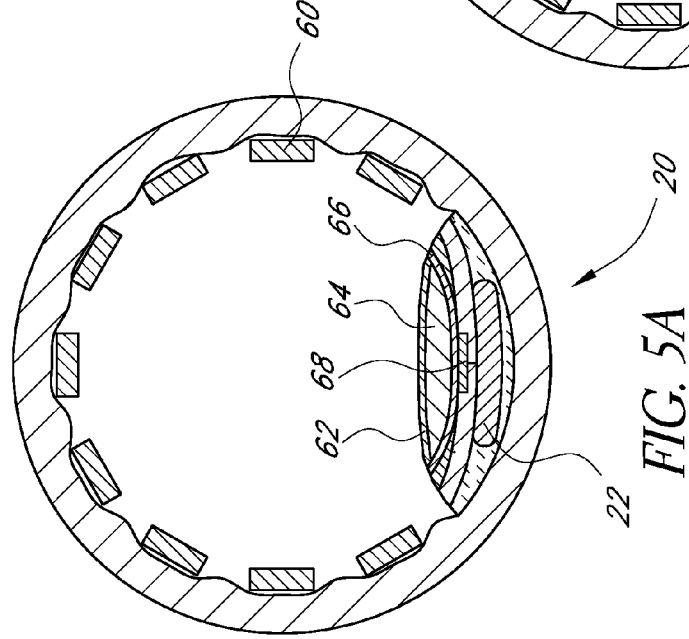
FIG. 5A is a cross-sectional view through a stent showing one mounting configuration of an embedded sensor in accordance with one embodiment of the present invention.

Now referring generally to FIGS. 5A-C, as the blood passes over the sensor 20, glucose diffuses through the semi-permeable membrane 62. The housing design should keep the blood shear rate at the apex of the housing sufficiently high that there is minimal thrombosis on this surface and any formed thrombus will be of minimal thickness. Thus, diffusion of glucose through the semi-permeable membrane 62 should be the rate-limiting step, and surface of the device should not become covered in a fibrous capsule, as in the case of subcutaneous sensors. The glucose reacts with the glucose oxidase to produce hydrogen peroxide, which further reacts to produce an amperometric signal. The amperometric signal is converted by an appropriately designed electronic circuit so that it may be transmitted using the RF transceiver.

In general, the surface of the sensor 20 should be placed on the luminal side of the stent. With the exception of the glucose permeable membrane, which is part of the sensor, the electronic components of the sensor should be encapsulated in a conformal coating such as a fluoropolymer or a polyamide, and injection-molded or dip-coated in a silicon rubber, polyurethane, or other biocompatible housing material.

The sensor housing should be given a streamlined shape, with gradually sloped transitions at both its proximal and distal ends, in order to minimize flow disturbances. The housing should be as wide or wider at its base than at its apex. The apex of the housing should not protrude higher than 5-50% of the diameter of the fully deployed device. The glucose permeable membrane 62 should be placed at the apex of the housing, should not be encapsulated in the housing material, and should face the bloodstream. The glucose permeable membrane 62 should occupy the majority of the area of the housing apex.

Alternatively, if the device includes a graft on the luminal surface of the stent, the sensor may be placed on either the luminal or abluminal surface of a graft material. If the graft is place on the abluminal surface of the stent, the sensor should be placed on the luminal surface of the graft. The graft material is preferably a fluoropolymer, such as ePTFE. If the housing is placed on the luminal surface of the graft, it is bonded by partially dissolving the housing material thermally or using an appropriate solvent so that the housing becomes physically interpenetrated with the graft or with an appropriate adhesive, such as melt-processed poly(tetrafluoroethylene-co-hexafluoropropylene) (FEP). If the sensor is placed between the stent structure and the graft, it should be bonded to both the stent and the graft, to prevent graft movements from causing thrombosis.

Generally, the height of the sensor is estimated to be 2 to 3 times the thickness of a stent strut, based on some observations of a limited number of stent designs (Virmani, 1999). This estimate represents the approximate thickness of the fibrous tissue layer above the stent surface. Thus, the sensor height above the stent luminal surface should be 1-2 times the thickness of a stent strut. The strut thickness varies with design, but is roughly 0.005" to 0.010" (0.13 to 0.26 mm). Thus, by using this approach, the housing should protrude about 0.2 to 0.5 mm above the stent luminal surface.

The effect that this will have on the target vessel is a function of the diameter of the vessel, as given in the following table:

| Vessel Diameter (mm) | Sensor Height above struts (mm) | Loss in Diameter (%) | Loss in Area (%) |
|---|---|---|---|
| 10 | 0.5 | 5.0 | 9.8 |
| 10 | 0.2 | 2.0 | 4.0 |
| 9 | 0.5 | 5.6 | 10.8 |
| 9 | 0.2 | 2.2 | 4.4 |
| 8 | 0.5 | 6.3 | 12.1 |
| 8 | 0.2 | 2.5 | 4.9 |
| 7 | 0.5 | 7.1 | 13.8 |
| 7 | 0.2 | 2.9 | 5.6 |
| 6 | 0.5 | 8.3 | 16.0 |
| 6 | 0.2 | 3.3 | 6.6 |
| 5 | 0.5 | 10.0 | 19.0 |
| 5 | 0.2 | 4.0 | 7.8 |

As is evident from the table, the smaller the vessel and the greater the sensor height, the greater the obstruction which is created. Design requirements will vary and require investigation for each application as is well known in the art.

This table also provides insights into the intrusion of the sensor as a percentage of post-deployment vessel diameter. A native vessel with greater than 50% diameter stenosis is clinically defined to be a restenotic vessel, and typically requires re-intervention. It is estimated that the sensor should not obstruct more than about 25% of the vessel diameter. Alternatively, the percent area loss of a vessel, along with a sensor height, can be examined and examples are tabulated below:

| Vessel Diameter (mm) | Sensor Height above struts (mm) | Loss in Diameter (%) | Loss in Area (%) |
|---|---|---|---|
| 10 | 0.5 | 5.0 | 9.8% |
| 10 | 2.5 | 25.0 | 43.8% |
| 9 | 0.5 | 5.0 | 9.8% |
| 9 | 2.3 | 25.0 | 43.8% |
| 8 | 0.4 | 5.0 | 9.8% |
| 8 | 2.0 | 25.0 | 43.8% |
| 7 | 0.4 | 5.0 | 9.8% |
| 7 | 1.8 | 25.0 | 43.8% |
| 6 | 0.3 | 5.0 | 9.8% |
| 6 | 1.5 | 25.0 | 43.8% |
| 5 | 0.3 | 5.0 | 9.8% |
| 5 | 1.3 | 25.0 | 43.8% |

Using this approach, the sensor height can range from about 0.3 to 2.5 mm in height above the stent luminal surface.

With regard to flow velocity, flow measurements in piping systems are commonly obtained from the pressure drop across a restriction, such as a Venturi meter. As is discussed above, the restriction should not be greater than about 25% of the vessel diameter. Because the volumetric flowrate, Q, must be the same both proximal to and within the restriction, the velocity within the restriction is related to the upstream velocity by:

$$v_2 = v_1(A_1/A_2)$$

Therefore, for an approximately 25% restriction in diameter, the restriction in area is about 43.8%, and the velocity within the restriction is about 178% of the upstream velocity, and for an approximately 5% restriction in diameter, the velocity within the restriction is approximately 111% of the upstream velocity.

The above analysis is true for situations where the velocity profile is almost flat, e.g., in turbulent flow in a pipe. For laminar flow, there will be a parabolic velocity distribution, with zero velocity at the wall, and maximum velocity occurring in the middle. This distribution may be somewhat impractical to measure, so the exact position where 178% of the proximal velocity occurs may be hard to establish. Thus, another approach to determining the proper height of the sensor is to find the sensor height where the blood velocity is approximately 125-200% of its proximal velocity. This can be determined using duplex ultrasound, or hot-wire anemometry, or other flow-measuring techniques. Using this approach, the sensor may be flush mounted against the wall of the vessel, with a flow impedance device mounted at the same axial position within the vessel, in order to increase the velocity within the sensor/impedance device to about 125-200% of the proximal flow velocity. The location where the estimate of the proximal flow velocity is approximately 200% is preferred. This would allow for the possibility of flush mounted sensors.

One key problem with most implanted sensors is fibrous tissue encapsulation. While proper positioning of the sensor within the vessel can minimize the thickness of a fibrous tissue layer, it may not be possible to avoid endothelialization of the sensor surface. Thus, the sensor design of the current invention may not actually project completely beyond the tissue growth, but the thickness of the tissue layer would ideally be only a single layer of endothelial cells.

Prior to implantation, the sensor may be checked for a reproducible response to glucose concentration. This may be done in the operating theater using sterile technique immediately prior to implantation, or may be done in a batch-wise manner during the manufacturing process. Following implantation, the sensor may then be calibrated by comparison of the output signal with an accepted standard. Typically, this may be done by comparing the signal with the value obtained from a laboratory glucose sensor, such as made by Yellow Springs Instruments (Yellow Springs, Ohio). Preferably, the calibration curve should be stable over time and for wide range of glucose values. For example, the slope of the calibration curve should be sufficiently stable to give an error of less than ten percent. Weekly calibrations should be sufficient to insure stable and accurate readings, however calibration can be performed as frequently as required. For example, there may be a change in sensitivity over the first month or so, if the transducer becomes endothelialized. However, after that point, the system should be stable. Thus, calibrations could be required as often as every other day at first, and taper off to no more than about once per week.

Once calibrated, if the external signal produced by the sensor indicates that the glucose level is outside of the normal physiological range, there are several possible outcomes.

1. An audible, visible or tactile alarm may sound, so that the patient or physician may check the sensor with a home glucose monitoring kit (e.g., One Touch, LifeScan, Johnson & Johnson), and then take appropriate action such as administration of insulin or glucose.
2. The signal may be transmitted directly to an implantable insulin pump, which may administer insulin directly without requiring a response by the patient.

FIGS. 5A-C show various embodiments in which the sensor and transmitter are on either the luminal or abluminal surface of the stent. Now referring to FIG. 5A, an implanted sensor 20 is shown in a transverse cross-sectional view through the vessel. The struts 60 of the implantable sensor device may be surrounded by an inner tubular sheath (not illustrated for simplicity), which would contact the blood vessel wall when deployed. The sensor housing 20 sits between a pair of struts 60. The membrane 62 is exposed to the blood flow. The analyte sensor 56 will normally have a larger cross-sectional area than the stent struts 60. The outer sheath allows for enhanced uniform radial expansion (beyond that of self-expanding struts), especially if the sheath is bonded to each of the struts 60 of the stent, and is bonded through the length of the stent, not just at the ends. This would link each of the struts 60 to its neighbors, preventing uneven expansion. It would also be advantageous to make the sheath out of a material which could be stretched slightly to obtain its final diameter, so that irregularities in the flow surface are minimized, except in the region of the sensor.

When a non-sheath implantable sensor device is either balloon expanded (or in the case of self-expanding stents, following balloon touch-up), the stent struts 60 can be embedded more deeply into the vessel wall than the sensor housing 20. If the struts 60 were positioned between the flowing blood and the sensor surface, they would cause flow stagnation, and therefore thrombosis on the membrane 62 of the sensor. If the sensor is placed instead on the luminal surface of the stent, the sensor will again be embedded less deeply in the vessel wall, although without struts 60 on its luminal surface, there will be minimal hemostasis and thrombus formation on the transducer surface.

As it can be seen, the sensor could be placed either between the stent struts and the inner sheath, or on the luminal surface of the inner sheath. In both cases, a semi-permeable membrane might still be necessary to insure that only the analyte of interest reaches the surface of the sensor. In either case, the sensor should be designed with a streamlined profile at both its proximal and distal ends, to minimize regions of hemostasis.

In accordance with another aspect of the invention, the sensor and its associated circuitry are connected between two or more stent segments, with or without the presence of a stent or supporting member at the location of the sensor. This provides a number of advantages, including a decrease in the delivery profile, and an increase in flexibility. This allows easier access to sites with tortuous vascular anatomy, but will still allow the sensor to maintain its same relative position in the blood vessel.

FIG. 10 shows a side elevational view of a sensor 20, a sensing circuit 24 and signal processing unit 26, a power source 28 and a radio-transmitter 30, with expanded anchoring stents 14 at the proximal end 200 of the sensor 20, intermediate between the sensor 20 and the sensing circuit 24 and signal processing circuits 26, also intermediate between the sensing circuit 24 and signal processing circuits 26 and the power source 28 and radio-transmitter 30, and at the distal end 210 of the power source 28 and radio-transmitter 30. Each segment of the implantable sensor device is connected to its neighboring segment by the use of electrical connectors 57, with strain relief elements 226. The electrical connectors 57 are hermetically sealed. Additionally, the electrical connectors 57 are of sufficient length, and have redundancies so that they can connect the various segments allowing flexibility of positioning between each segment of the implantable sensor while minimizing the strain imparted on the connectors. It is important to note that the relative position of each of these components between the anchoring stents is somewhat arbitrary. The device could be designed with these components in any order, and still function equally well, as will be apparent to those skilled in the art.

Figure 11:
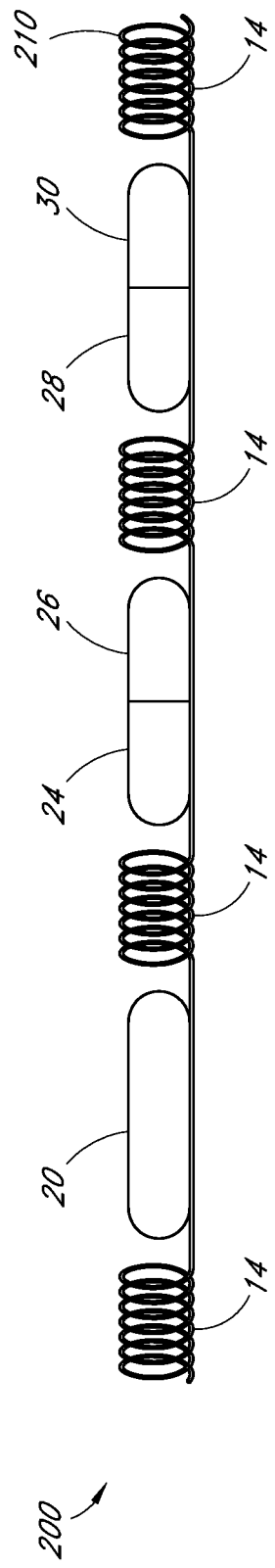
FIG. 11 is a side elevational view of a sensor and transmitter, with anchoring stents in the compressed state at the proximal end of the sensor, intermediate between the sensor and transmitter, and at the distal end of the transmitter.

FIG. 11 shows a side elevational view of a sensor 20, a sensing circuit 24 and signal processing unit 26, a power source 28 and a radio-transmitter 30, with anchoring stents 14 in the compressed state such as within a tubular deployment catheter at the proximal end 200 of the sensor 20, intermediate between the sensor 20 and the sensing circuit 24 and signal processing circuits 26, also intermediate between the sensing circuit 24 and signal processing circuits 26 and the power source 28 and radio-transmitter 30, and at the distal end 210 of the power source 28 and radio-transmitter 30. The advantages of this segmented embodiment of the invention are that the overall delivery profile of the device is reduced, and the device becomes more flexible for delivery through tortuous vessels.

Thus, the present invention provides at least one electrical component, having at least a first support on a proximal end and a second support on a distal end, for supporting the component in a body lumen. As disclosed herein, the electrical circuitry may desirably be divided into at least two or three discrete physical components spaced axially apart and in electrical communication with each other to minimize the implanted profile and enhance deliverability. Each of the components may be provided with a proximal and a distal support, as illustrated in FIGS. 10 and 11. The two or three or four or more supports may be connected together independently of the intervening electrical component, or may be connected only through the housing of the intervening electrical component. The supports may comprise any of a variety of self-expandable coils or other structures well known in the self expandable stent and graft (e.g., abdominal aortic aneurysm graft) arts. Alternatively, balloon expandable or mechanically expandable anchor structures may be used. In an alternate configuration, the support may comprise an elongated ribbon or wire such as Nitinol which is based into a spiral, having the electrical components spaced axially apart therealong.

Monitoring of Other Substances

In another aspect of this invention, it is possible to monitor substances other than glucose by using different enzymes, as listed in the table below:

| ANALYTE | ENZYME |
| --- | --- |
| glucose | glucose oxidase |
| glucose | glucose dehydrogenase |
| lactate | lactate oxidase |
| l-methionine | l-amino acid oxidase |
| l-phenylalanine | l-amino acid oxidase |
| d-aspartate | d-amino acid oxidase |
| d-glutamate | d-amino acid oxidase |
| urate | urate oxidase |
| ethyl alcohol | alcohol oxidase |
| methyl alcohol | alcohol oxidase |
| cholesterol | cholesterol oxidase |
| ascorbic acid | ascorbate oxidase |

In still another aspect of the invention, a different class of sensors is used to detect the presence of chemical analytes in blood. These sensors, termed "immunosensors", rely on the interaction between an antibody and its antigen, which are very specific, and typically there is a very strong interaction between antibody and antigen. This type of detection system may have broader applicability for detecting molecules in blood as compared with enzymatic sensors (Rabbany S Y, Donner B L, Ligler F S, "Optical Immuno sensors" Crit. Rev Biomed Eng 1994; 22(5-6):307-46; and Stefan R I, van Staden J F, Aboul-Enein HY, "Immunosensors In Clinical Analysis" Fresenius J Anal Chem 2000 March-April; 366(6-7):659-68). Antibodies can be produced which can recognize almost any biomolecule, and therefore the number of possible target analytes could be substantially increased using this method. As Stefan et al. (2000) state, "The main problem of [immunosensor] utilization is the interference or loss of affinity when real biological fluids (e.g., blood, serum, plasma, urine, saliva) have to be analyzed." They continue, "For in vivo tests with immunosensors, highly biocompatible materials have to be found for electrode construction" (emphasis added). The present invention provides an excellent method for solving the key issue of immunosensor fouling.

There are a number of potential applications of this technology, including detection of infectious disease, cardiac disorders, and cancer, as well as clinical drug monitoring. (Rabbany 1994). Other potential applications include illicit drug monitoring, and research applications focused on drug development and pharmacokinetics studies. For instance, Hanbury et al. (Hanbury C M, Miller W G, Harris R B, "Antibody Characteristics For A Continuous Response Fiber Optic Immunosensor For Theophylline" Biosens Bioelectron 1996; 11(11):1129-38) describe a continuous immunosensor for monitoring theophylline, a vasodilator with a narrow therapeutic range (55-110 µM), and which requires frequent monitoring to assure therapeutic efficacy and prevent toxicity.

Another important application would be in the area of crisis-oriented diagnostics. For example, heart patients presenting with chest pain, or those at risk for recurrent acute myocardial infarction (AMI), could be quickly diagnosed with AMI by using the present invention to monitor for biochemical markers such as creatine kinase (CK-MB), serum cardiac troponins (cTnT or cTnI), aspartate aminotransferase (AST), lactate dehydrogenase (LDH), beta-hydroxybutyrate dehydrogenase (HBD), serum myoglobin, glycogen phosphorylase isoenzyme BB (GPBB), fatty acid binding protein (FABP), phosphoglyceric acid mutase isoenzyme MB, enolase isoenzyme alpha beta, S100a0, and annexin V (Olukoga A, Donaldson D, "An Overview Of Biochemical Markers In Acute Coronary Syndromes", J Royal Soc Promot Health 121(2):102-106 (2001).) Of potentially greater value is use the present invention to monitor for biochemical markers which may precede AMI, such as C-reactive protein (CRP) (Rabbany 1994), serum TnT, and inflammatory markers such as V-CAM, I-CAM, or interleukin-6 for the prognosis of myocardial infarction. For such applications, speed and accuracy of monitoring are essential.

Other potential uses of this type of immunosensor include monitoring anticoagulation levels, which might include monitoring for thrombin, prothrombin fragment 1+2 (F1+2), fibrinopeptides A or B, Factor Xa, thrombin-antithrombin III complex, or platelet release products such as thromboxane A2, PDGF, or markers of fibrin degradation such as D-dimer, other markers which could potentially serve as an index for a patient's level of anticoagulation. Finally, the prospect of continuous, ambulatory monitoring provides improved therapeutic efficacy, cost containment, convenience, and patient peace of mind.

Continuous immunosensors have been previously demonstrated (Ligler, et al., U.S. Pat. No. 5,183,740 "Flow Immunosensor Method And Apparatus," Feb. 2, 1993; and Ligler, et al., U.S. Pat. No. 6,245,296 "Flow Immunosensor Apparatus," issued Jun. 12, 2001) for the detection of explosives in soil samples, among other applications (Gauger P R, Holt D B, Patterson C H Jr, Charles P T, Shriver-Lake L, Kusterbeck A W, "Explosives Detection In Soil Using A Field-Portable Continuous Flow Immunosensor," J Hazard Mater 2001 May 7; 83(1-2):51-63; Vianello F, Signor L, Pizzariello A, Di Paolo M L, Scarpa M, Hock B, Giersch T, Rigo A., "Continuous Flow Immunosensor For Atrazine Detection," Biosens Bioelectron 1998 Jan. 1; 13(1):45-53; Narang U, Gauger P R, Kusterbeck A W, Ligler F S, "Multianalyte Detection Using A Capillary-Based Flow Immunosensor," Anal Biochem 1998 Jan. 1; 255(1):13-19; Kusterbeck A W, Wemhoff G A, Charles P T, Yeager D A, Bredehorst R, Vogel C W, Ligler F S, "A Continuous Flow Immunoassay For Rapid And Sensitive Detection Of Small Molecules," J Immunol Methods 1990 Dec. 31; 135(1-2):191-7; and Charles P T, Conrad D W, Jacobs M S, Bart J C, Kusterbeck A W, "Synthesis Of A Fluorescent Analog Of Polychlorinated Biphenyls For Use In A Continuous Flow Immunosensor Assay," Bioconjug Chem 1995 November-December; 6(6):691-4.) and sample analysis is very rapid (<5 minutes). However, the continuous immunosensors described are not readily translated to the clinical need for ambulatory monitoring. For instance, Ligler (1993) teaches that the level of the target molecule in the system should be measured by determining the amount of label that is released from the apparatus, not the amount of antibody-antigen complex remaining in region of the apparatus. Measuring the amount of the labeled target molecule released into the bloodstream would require that samples be taken from the patient on a frequent basis. This would not provide any benefit over using a standard enzyme-linked immunosorbent assay (ELISA) or radioimmunoassay (RIA) to look for this same unlabeled analyte of interest.

As described in FIGS. 1-5 and 9-11, above, the sensor 20 may in a preferred alternative embodiment, be an immunosensor. The anchoring platform for this embodiment of the invention is similar to that which was previously described in the context of electrochemical glucose sensors, as is the positioning of the sensor 20 and radiotransmitter 30 with respect to the anchoring platform 14, and the radiotransmitter 30 for sending the signal to the external device. A power source 28, sensing circuit 24, and a signal processing circuit 26 are also included with the immunosensor. The external device provides a read-out of the data regarding the concentration of analyte in the patient's blood at any time, and appropriate audible, visual, vibratory, or other signals are given to notify the user of an important change in condition.

As with enzymatic glucose sensors, there are a multiplicity of ways in which the molecular recognition event (i.e., the antibody-antigen reaction) can be translated into an electrical signal. These include amperometric, potentiometric, piezoelectric, surface plasmon resonance (SPR), scintillation, acoustic, fluorescent and chemiluminescent immunosensors (Stefan 2000). These types of sensors have been previously described in the literature (Stefan 2000).

Amperometric sensors typically use enzymes (Rabbany 1994) such as alkaline phosphatase or horse-radish peroxidase to label antigens or antibodies, so that the reaction products produced by the enzyme (rather than the antibody or antigen) provide the actual signal to be detected (Stefan 2000). This adds a level of complexity for an implantable device, because a third component is now required, in addition to the antibody and antigen. For this type of immunosensor, not only are the antigen of interest and an enzyme-labeled antibody required, but an appropriate substrate for the enzyme label is also required. This enzyme substrate can be delivered under conditions to insure that the signal being produced is determined by the amount of enzyme-labeled antibody present, rather than the amount of substrate for the enzyme.

Potentiometric sensors have excellent reproducibility, although according to Stefan (2000), "in most cases, potentiometric transducers cannot provide the necessary sensitivity for the antigen-antibody reaction." This is because the resulting signal is proportional to the logarithm of the analyte concentration.

Piezoelectric sensors, such as those based on the quartz-crystal microbalance (QCM) may not be well suited to this application, due to the high background response from non-specific adsorption (Stefan 2000). Surface plasmon resonance detection is also less well suited to the present application, due to interference from non-specific binding (Rabbany 1994, Stefan 2000).

In principal, detection could be performed by the use of antigens labeled with radionuclides. In that case, a scintillation detector such as a NaI crystal coupled with a photodiode or photomultiplier tube could be used. The detector for this type of sensor is otherwise similar to that described below for the fluorescence detectors. However, the use of radionuclides as labeling agents is less attractive, due to problems with handling, and exposure of the patient and physician to radiation.

Optical immunosensors include fluorescent or chemiluminescence-based sensors. A fluorescence-based sensor is shown in FIG. 12, and is supported by a stent structure 14 which is in the compressed state for delivery from a catheter 120. In this sensor, the labeled target molecule 260 has a fluorescent label, such as fluorescein, tetramethylrhodamine, or Texas Red. If a fluorescent label is used, the sensor will consist of both a light source 280 such as a light-emitting diode (LED), and a photosensitive detector such as a photomultiplier tube or photodiode 290, such as that supplied by Silicon Sensors (Madison, Wis.). The light source 280 with a filter (not shown) produces light at the excitation wavelength $\lambda_1$, and the photodiode 290 with a filter (not shown) detects the light at wavelength $\lambda_2$ emitted by the fluorescence of the label. In the case of fluorescein, the wavelength of light that is absorbed by the label is in the range of 470 nm, and the wavelength of fluorescent light is in the range of 540 nm. The sensing circuit 24 and radiotransmitter 30 are also included.

The intensity of light detected by the photodiode provides an electrical signal, which is dependent upon the intensity of the detected fluorescence. A change in signal level will indicate a change in the concentration or presence of the antigen of interest.

FIG. 12 also shows a sensor 20 containing a reservoir 300 of labeled antigen 320 which is included as part of the sensor. The reservoir is encapsulated on all but one side by a membrane 330 that is impermeable to the analyte of interest. The impermeable membrane may be a poly(carbonate urethane), silicone rubber, Parylene, Teflon, or water-impermeable polymer. A semi-permeable membrane 62 is included on the final side of the reservoir, which adjoins the sensor compartment as a semi-permeable barrier to control the rate at which the labeled antigen diffuses from the reservoir to the sensing compartment. The semi-permeable membrane 62 is preferably a hydrogel, such as poly(ethylene glycol) (PEG), poly(vinyl alcohol) (PVA), poly(N-vinyl pyrrolidone) (PVP), polyacrylamide, poly(acrylic acid) (PAA), poly(hydroxyethyl methacrylate) (PHEMA), or other. The thickness, chemical nature, and cross-link density of the hydrogel can be controlled as is known by those skilled in the art in order to obtain an appropriate rate of diffusion of labeled antigen out of the reservoir, and into the sensor compartment. Further, this semi-permeable membrane 62 may contain multiple layers, such as a hydrogel bonded to a dialysis membrane, polyurethane, poly(vinylidene fluoride) (PVDF), ePTFE, Nafion, or other second membrane layer. The reservoir provides a flux of labeled target molecule which allows the sensor to be replenished over time, and allows the measurement of both decreases and increases in analyte concentration in the blood. The reservoir provides the added benefit of extending the lifetime of the sensor.

The sensor for this embodiment detects the presence of the target molecule as follows. First, an antibody 260, which hereafter refers to any of combination of polyclonal antibodies, monoclonal antibodies, or the Fab fragment of an antibody, is immobilized on or near the sensor light source 280 and photodetector 290. The antibodies may be from human, mammalian, or non-mammalian origins, provided that adequate cross-reactivity between the antibody and antigen can be established. The antibodies may be immobilized within or upon films (not shown) or membranes (not shown) that may be present on the surface of the light source 280 or photodetector 290. In addition, the antibodies may be immobilized onto particulate supports near the sensor component, such as Sepharose (Pharmacia). The immobilization may be performed by covalently bonding the antibody to the substrate with bi-functional molecules such as glutaraldehyde, carbodiimides, biotin-avidin, and other molecules with one or more functional groups on each of at least two ends as are well known to those skilled in the art. Additionally, bi-functional spacer molecules such as N-hydroxysuccinimide derivatized polyethylene glycols may be used to bind the antibody within the sensor compartment. Because immobilization of antibodies can significantly change their reactivity, methods for improved orientation of the antibodies have been described (Stefan, 2000). During the manufacture or final preparation of the device, prior to implantation in the patient, the antibody is saturated with a large excess of labeled antigen, beyond the stoichiometric excess needed to fully occupy all the available sites on the antibodies.

In comparison with enzymatic electrochemical sensors, immunosensors may preferably be modified so that the luminal sensor surface is positioned even closer to the center of the blood vessel in order to further reduce endothelial coverage, because not all antigens are capable of passing through an endothelial layer. The outer membrane 62 covering the luminal surface of the sensor is preferentially a hydrogel, such as poly(ethylene glycol) (PEG), poly(vinyl alcohol) (PVA), poly(N-vinyl pyrrolidone) (PVP), poly(hydroxy ethylmethacrylate) (PHEMA), or other, in order to further reduce the probability of cell adhesion to the surface. It may also come from the group consisting of ePTFE, polyurethane, silicone rubber, cross-linked collagen, polypropylene, cellulose acetate, poly(vinylidene fluoride) (PVDF), Nafion or other biocompatible material. The outer membrane must also be permeable to the analyte of interest. The permeability of the membrane is selected to allow the analyte of interest to freely contact the sensor, while restricting the passage of other blood components. The permeability of this membrane 62 can be controlled by varying the porosity of the hydrogel or polymer, which can be controlled by varying the cross-link density and the molecular weight of the polymer between cross-links. Additionally, the thickness of the outer membrane can be controlled, allowing control of the transport rate of the target analyte. Finally, the outermost membrane may be bonded to a second, inner membrane layer which may be made from either ePTFE, polyurethane, silicone rubber, cross-linked collagen, polypropylene, cellulose acetate, poly(vinylidene fluoride) (PVDF), Nafion, or other biocompatible membrane material with controlled porosity to further control the transport of the target molecule to the sensor.

As the sensor is exposed to flowing blood containing the antigen of interest, there will be a competition for the antibody binding sites on the sensor between the labeled antigen (both that originally implanted in the sensor compartment 270 and that contained in an additional reservoir 300 of labeled target molecules) and the antigen in the bloodstream. Over time, there will be a displacement of the labeled antigen originally supplied in the sensor by the non-labeled antigen, which is present in the bloodstream. Rabbany (1994) reports that the antibody-antigen reaction is seen as nearly irreversible except in the case of continuous-flow immunosensors. Because of this, only when unlabeled antigen is present in the continuously flowing blood is the labeled antigen displaced. Thus, if no antigen is present in the blood, the sensor will remain undepleted. The amount of antigen-antibody complex 310 can be measured on a very frequent (nearly continuous) basis. To do this, the LED emits a pulse of light, and the resulting fluorescence intensity is measured by the photodiode.

Now referring to FIG. 13, the light emitting diode sensor circuit consists of a constant-current LED drive circuit 404 that ensures consistent brightness over a range of input voltages. The LED 402 is controlled by a square wave clock circuit 406 that gates the LED 402 on and off at rate that can be set for the particular application. This type of sensor is powered by the power supply 408 via the power coil/antenna 410.

The light detector circuit consists of a photodiode 412 and a current-to-frequency converter 414. The I-F converter output is gated by the clock 180 degrees out of phase with respect to the signal used to drive the LED. This ensures that there is no output from the converter when the LED is being driven.

In an alternate embodiment, the reservoir can instead be fabricated from a degradable material such as poly(lactide-co-glycolide) (PLGA), polycaprolactone (PCL), or other controllably degradable material. The labeled target molecule is incorporated into such a matrix by mixing the target molecule directly into a solution of PLGA, and precipitating the PLGA. Alternatively, the reservoir is loaded with microspheres containing either the antibody or antigen of interest (Ma J, Luo D, Qi W, Cao L, "Antitumor Effect Of The Idiotypic Cascade Induced By An Antibody Encapsulated In Poly (D,L-Lactide-Co-Glycolide) Microspheres," Jpn J Cancer Res 92(10); 1110-15, (2001); Torche A M, Le Corre P, Albina E, Jestin A, Le Verge R, "PLGA Microspheres Phagocytosis By Pig Alveolar Macrophages: Influence Of Poly(Vinyl Alcohol) Concentration, Nature Of Loaded-Protein And Copolymer Nature," J Drug Target 7(5):343-54 (2000); Mordenti J, Thomsen K, Licko V, Berleau L, Kahn J W, Cuthbertson R A, Duenas E T, Ryan A M, Schofield C, Berger T W, Meng Y G, Cleland J, "Intraocular Pharmacokinetics And Safety Of A Humanized Monoclonal Antibody In Rabbits After Intravitreal Administration Of A Solution Or A PLGA Microsphere Formulation," Toxicol Sci 52(1):101-6, (1999)). These microspheres may be prepared by emulsion polymerization, as is known in the art. It is possible to control the release rate of labeled target molecule from these degradable microspheres by varying the co-polymer composition and particle size. For example, a 50:50 ratio of lactide to glycolide monomers is known to degrade more rapidly than homopolymers of either poly(lactide) or poly(glycolide).

One difficulty with these types of systems is that as the matrix degrades, its by-products can affect the pH of the local micro-environment. This may have an effect on the stability and solubility of the labeled antigen. A solution to this may be found by incorporating basic salts, such as magnesium hydroxide, calcium hydroxide, calcium phosphate, or zinc sulfate, in order to maintain a pH neutral environment, as described by Zhu et al (Zhu G, and Schwendeman SP, "Stabilization of Proteins Encapsulated in Cylindrical Poly(lactide-co-glycolide) Implants: Mechanism of Stabilization by Basic Additives", Pharm Res 17(3):351-7 (2000)). Another approach by Jiang (Jiang W, and Schwendeman S P, "Stabilization and Controlled Release of Bovine Serum Albumin Encapsulated in Poly(D,L-lactide) and Poly(ethylene glycol) Microsphere Blends", Pharm Res 18(6): 878-885 (2001)) is to blend a highly water-soluble polymer such as poly(ethylene glycol) (PEG), poly(N-vinyl pyrrolidone) (PVP), or poly (vinyl alcohol) (PVA), with a more slowly degrading homopolymer, such as poly(lactide) (PLA) or poly(glycolide) (PGA). However, the only requirement for the present invention is that the microsphere delivery system is able to maintain antigenic recognition of the labeled target molecule. It is not necessary that the activity of the target molecule be maintained.

One of the difficulties with measuring the amount of labeled antigen-antibody complex still present near the sensor, however, is that of sensor response time. That is, if the amount of label bound to the sensor is relatively large compared to the amount which is displaced, it will be difficult to accurately determine the concentration of the analyte. This is because the difference between two large and uncertain numbers also has a high degree of uncertainty. Thus, the current approach will have a somewhat longer sensor response time, or require a larger change from baseline, and hence have a somewhat lower sensitivity, as compared to the approach described by Ligler (1993), in order to establish a measurable change in antigen level. Sensor response times are dependent on the concentration of antigen in the bloodstream, the rate at which the antigen is transported across the semi-permeable membrane, the reaction rate between antigen and antibody, and the rate at which the displaced, labeled antigen is transported out of the sensor compartment, into the bloodstream. In addition, the relative concentrations of labeled antigen from the reservoir and unlabeled antigen from the bloodstream, which are present in the sensor compartment, will also play an important role. Similarly, the lifetime of the sensor will be dependent on the factors listed above, as well as the amount of labeled target molecule incorporated in the reservoir. If the sensor lifetime were limited by the amount of labeled target molecule incorporated in the reservoir, it may be possible to extend the sensor lifetime, for example, by re-loading the sensor with controlled-release microspheres in a secondary catheterization procedure, or by direct injection with a syringe and needle.

In an alternative embodiment, it is possible to immobilize the antigen, and label the target antibody, in order to monitor the presence of antibodies in the bloodstream. This is done by reversing the immobilization of the antigen near the sensor, and providing a reservoir of labeled antibody as described above for FIG. 12. This may be useful for monitoring patients with conditions such as HIV or AIDS.

For the various conditions requiring continuous monitoring, as described herein, the sensors are not expected to have an indefinite service lifetime. Therefore, it may be desirable to remove an implanted sensor at the end of its functional life. Since it is expected that a sensor for long-term use may become embedded in neointimal tissue, special consideration must be given to the design of the sensor platform in order to allow retrievability.

Certain medical devices, such as inferior vena cava filters like the Gunther-Tulip Filter (Cook, Inc.) or the OptEase Filter (Cordis, Inc.) are designed to be retrievable within a certain period of time. Both of these devices use hooks, which can be engaged by retrieval systems, such as the Amplatz GooseNeck Snare (eV3, Inc.) These hooks are positioned in the center of the flowstream, and thus are designed to not become incorporated into the wall of the vessel. In certain cases, the Gunther Tulip filter has been reported to tilt, such that its retrieval hook contacts the wall and becomes incorporated, making retrieval impossible (Millward, S F, et al., JVIR 2001, 12:1053-1058).

An implantable sensor of an embodiment of the present invention can also be designed to be retrievable. Recent work has shown that vena cava filters can be removed from a blood vessel following implantation. (Neuerburg, J, Gunther, R W, Rassmussen, E, Vorwerk D, Tonn K, Handt S, Kupper W, Hansen J V, "New Retrievable Percutaneous Vena Cava Filter Experimental In Vitro And In Vivo Evaluation," Cardiovasc Intervent Radiol 16(4): 224-9 (1993); Neuerburg, J M, Gunther, R W, Vorwerk D, Dondelinger R F, Jager H, Lackner K J, Schild H H, Plant G R, Joffre F G, Schneider P A, Janssen J H, "Results Of A Multicenter Study Of The Retrievable Tulip Vena Cava Filter: Early Clinical Experience," Cardiovasc Intervent Radiol 16(4): 224-9 (1993); and Millward S F, Oliva V L, Bell S D, Valenti D A, Rasuli P, Asch M, Hadziomerovic A, Kachura J R, "Gunther Tulip Retrievable Vena Cava Filter: Results From The Registry Of The Canadian Interventional Radiology Association," J Vasc Intery Radiol 12(9): 1053-8 (2001).) At any point up to a biologically determined retrieval limit, it is possible to remove both the sensor and its anchoring platform, using a device such as the GooseNeck Snare (Microvena Corp.) in a follow-up catheterization procedure.

Figure 14A:
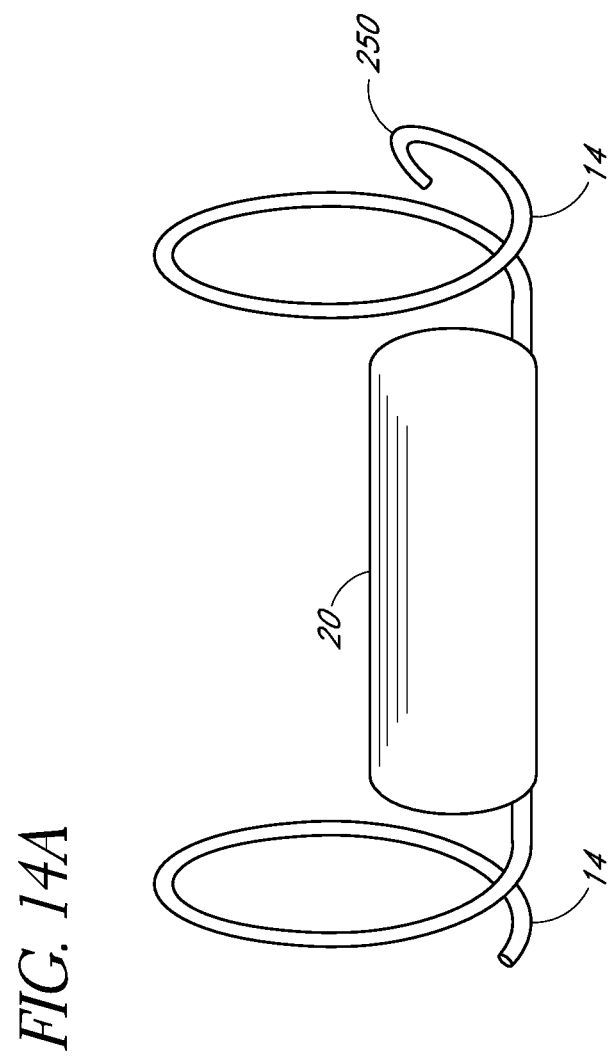
FIG. 14A is a diagram of an expanded anchoring platform or stent with an embedded sensor housing on its luminal side, and containing a hook with which the device can be retrieved.

As shown in FIG. 14A, the anchoring platform 14 can be designed with a hook, loop, eye, or other easily snareable feature 250 such as at the downstream end, so that it can be removed up to a certain period of time without the necessity of leaving the device permanently implanted in the patient. In this example, the hook is preferably made of the same material as the anchoring platform, such as 316L stainless steel, nitinol, Phynox, Elgiloy, or other similar material, and may either be laser-cut from the same tubing stock as the anchoring platform, or may be laser-welded onto the anchoring platform. The hook may preferably have a diameter greater than that of the retrieval snare wire, typically 0.020-0.030" in diameter, so that the retrieval snare can easily rest in the hook. The hook may be made from a wire with a diameter ranging from about 0.001" to 0.040", and may have a radius of curvature from about 0.001" to about 0.040", and a length of about 0.5 to 10 mm. The hook may be formed by thermal and or mechanical process, such as a hot die, and may be reduced to its final dimension by electropolishing or chemical etching. As an alternative to a hook, a feature such as a ball with a diameter of about 0.75 to 2 mm may be formed at the end of straight segment of wire with a diameter of about 0.5 mm. The hook may also be shaped like a closed loop, or like an anchor, with each arm of the anchor having a length of about 0.5 to 1 mm.

In FIG. 14A, the snareable feature 250 on the anchoring platform protrudes slightly into the lumen of the vessel, so that it does not become completely encapsulated in tissue. In an alternative embodiment, as shown in FIG. 14B, the snareable feature 250 is mounted to the distal end of the sensor housing 20. Typically in order to prevent corrosion, the sensor electronics will be hermetically sealed using either a glass, ceramic, epoxy, or metal housing. In this case, the snareable feature may be either laser-welded to the metal housing, or embedded in the glass, ceramic or epoxy at the time the hermetic seal is formed.

The sensor housing may be coupled to the anchoring platform using mechanical clips designed to release under the appropriate applied force, or using degradable materials such as PLGA or PLA. Because the luminal surface of the sensor housing is designed so that it does not become encapsulated with fibrous tissue, it is possible to retrieve the sensor component at any time following implantation. However, with degradable materials, the implant must remain in place long enough for these degradable anchors to lose their strength and give way during retrieval. The anchoring platform is left behind. In these embodiments of the invention, the snareable feature makes the device suitable for continuous monitoring of a temporary patient condition. It is also suitable for short-term monitoring of drugs, such as those with a narrow window between efficacy and toxicity. In addition, it is possible to remove a sensor that may no longer be functional.

Figure 15A:
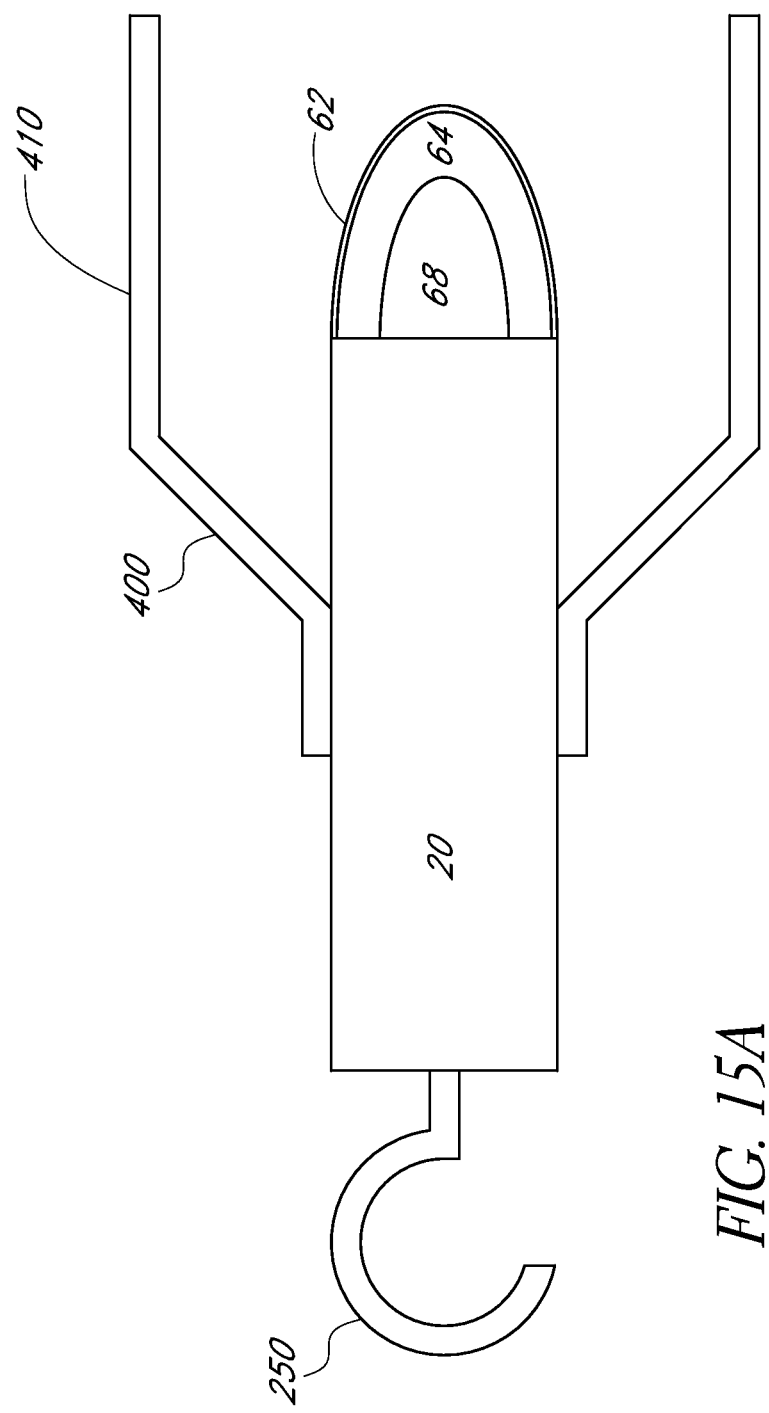
FIG. 15A is a side view diagram of an expanded anchoring platform with an embedded sensor, which is placed centrally in a vessel, and containing a hook on the sensor housing with which the device can be retrieved.
Figure 15B:
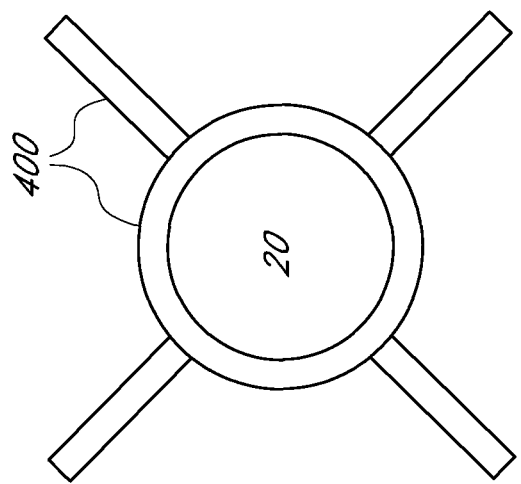
FIG. 15B is an end view diagram of an expanded anchoring platform with an embedded sensor, which is placed centrally in a vessel, and containing a hook on the sensor housing with which the device can be retrieved.

Now referring to FIGS. 15A and 15B, in an alternative embodiment, both the sensor and its anchoring platform could be designed to be retrievable for an indefinite period. In this case, the sensor 20 is centrally mounted in an anchoring platform 400. The sensor housing may be bonded to the platform by positioning the two components in close proximity during the formation of a hermetic seal, using glass, metal, or epoxy, as described above for FIG. 14A. Additionally, if the sensor is hermetically sealed in a metal case, the sensor and anchoring platform could be laser-welded together. Another means of connecting the two components would be by mechanical interfit. The anchoring platform 400 contains side struts 410 which extend axially within the vessel. The anchoring platform 400 is preferably made of a self-expanding material such as nitinol. This anchoring platform 400 centers the sensor 20 in the middle of the flowstream, so that the proximal (upstream) tip of the sensor is again kept free of thrombus or other fouling tissue because of the high flow velocity. The side struts 410 also help to keep the sensor centered in the bloodstream. These side struts 410 may have a length ranging from 1 to 100 mm, with longer struts providing improved ability to prevent the sensor from tipping away from the center of the vessel, and shorter struts making the entire device easier to introduce into the vasculature, and also being easier to retrieve. A preferred length range for the side struts 410 is from 5 to 30 mm. The side struts 410 may contain radially outwardly directed hooks (not shown) to prevent the device from migrating. These migration-resistant hooks could be placed at any position along the side struts, and are oriented in a direction to prevent migration of the device towards the heart or lungs. As described in U.S. Pat. No. 6,258,026, to Ravenscroft et al., issued Jul. 10, 2001, the hooks could be made small enough so that they prevent sensor migration, but can be easily deformed during retrieval, allowing the device to be withdrawn from the vessel. The proximal tip of the sensor is preferably in a streamlined configuration, such as a parabola or a cone, to minimize the risk of thrombus formation. A hook 250, knob, or other easily snareable feature is placed at the distal (downstream) end of the sensor. The entire device can then be removed in a catheterization procedure by using a snare as previously described to catch the hook 250 and draw the anchoring platform into the distal end of a tubular retrieval catheter. Because the parallel struts 410 of the anchoring platform 400 are open-ended, they will not become mechanically interlocked by neointimal tissue, and therefore the entire device will be retrievable for an indefinite period. The retrieval process would be much like withdrawing a hypodermic needle from under the skin.

Figure 23:
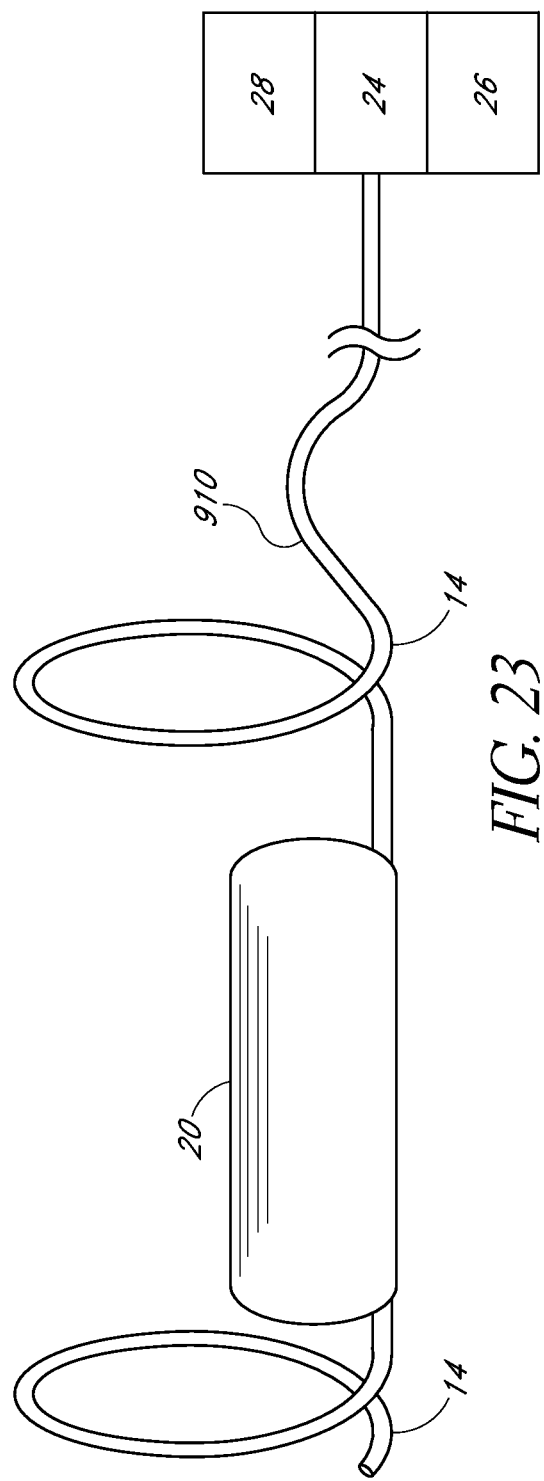
FIG. 23 is a diagram of an expanded anchoring platform or stent with an embedded sensor housing on its luminal side, and containing a tether with which the device can be retrieved.

As shown in FIG. 23, in a further aspect of an embodiment of this invention, the sensor may be inside a housing 20 that has stabilizing anchors 14 at both the proximal and distal ends, and may additionally include a tether 910 that is designed for retrieval of the sensor. The tether 910 may be connected directly to the sensor housing 20, or to the support anchors 14. The tether may be connected by means of an adhesive, such as an epoxy, or may be welded or tied to the sensor housing 20 or support anchors 14. The tether may be made of a polymeric material, such as a polyurethane, silicone rubber, PTFE, polyethylene, polypropylene, or a metal, such as stainless steel or nitinol, or numerous other biocompatible materials. In addition, tether 910 may incorporate electrical leads (not shown), and may extend outside of the patient to a device which contains a power source 28, and which detects the analyte concentration using sensing circuit 24 and uses signal processing circuit 26 to convert the electrical signal from the sensor. Alternatively, the sensor may contain the sensing circuit 24 and the signal processing circuit 26, and transmit the data to an external monitor via electrical leads or an RF link. The tether may be relatively rigid at its distal end, where the sensor is mounted, in order to prevent flow disturbances due to the tether. The tether may further be coated with anti-thrombotic coatings as described herein, and may also have anti-microbial coatings, such as Repelacoat (AST Products, Inc., Billerica, Mass.) or other commercially available coating, to reduce the risk of infection.

Figure 20A:
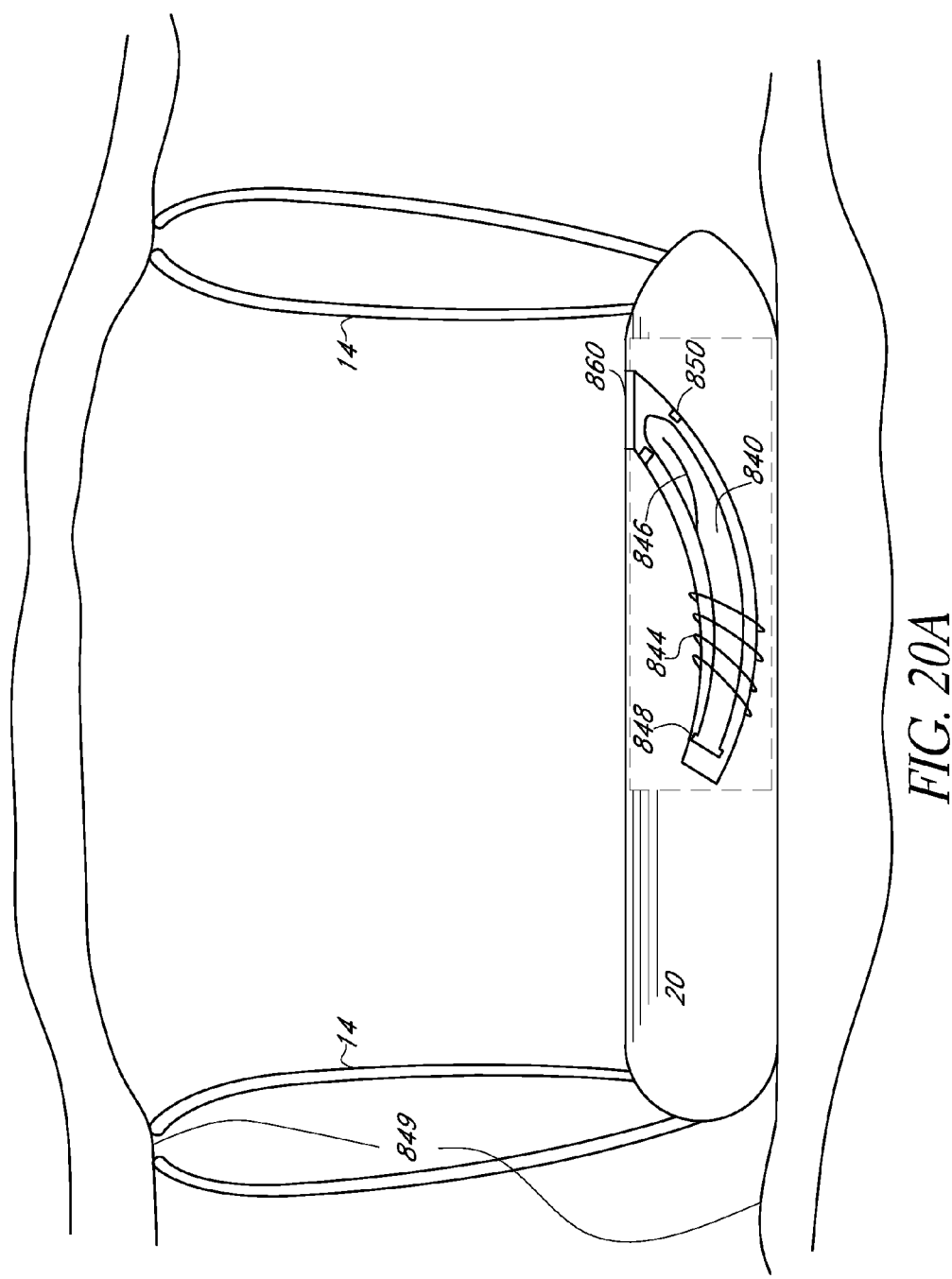
FIG. 20A is a side view of a sensor with a retrieval hook which can be moved into position for retrieval on demand.
Figure 20B:
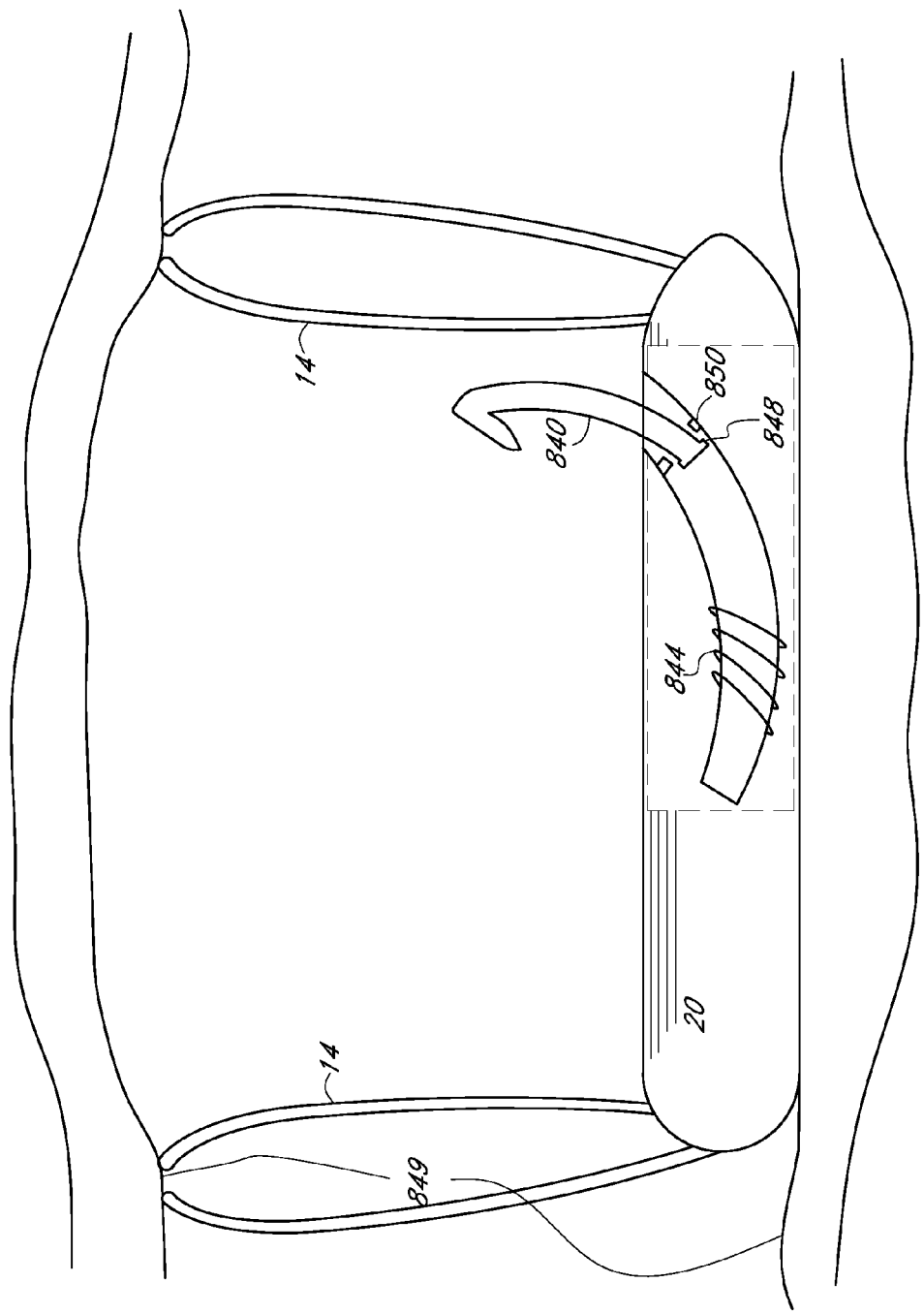
FIG. 20B is a side view of a sensor with a retrieval hook which has been moved into position for retrieval on demand.

An implantable sensor of an embodiment of the present invention may also include a retrieval hook which only moves into a retrieval position to allow retrieval when desired. This may be accomplished by incorporating an activator with the retrieval hook. In one embodiment, as shown in FIG. 20A, a sensor 20 with an anchoring platform 14 is lodged in blood vessel 849. The anchoring platform 14 may be designed so that it does not form a completely closed ring, and therefore the two halves of anchoring platform 14 can separate and slide out from any surrounding tissue when a sufficient tensile force is applied, such as by the use of a snare to retrieve the sensor 20 and its anchoring platform. The sensor 20 can also be made to separate from the anchoring platform 14. The sensor 20 may be attached to an anchoring platform 14 using degradable materials such as PLGA, PCL, or other degradable polymer as an adhesive, and is lodged in blood vessel 849. The sensor 20 can be separated from the anchoring platform 14 following degradation of the adhesive. A hook 840 within sensor 20 may be initially positioned within a solenoid 844, and may be placed under a membrane 860 in the sensor housing, which is near the non-fouling sensing surface. The membrane 860 may be made from a polymeric material, such as Parylene or polyurethane, with a thickness of 0.5-100 microns. When it is desired to retrieve the sensor 20, the solenoid 844 is electrically activated, and the hook 840 is displaced from its original position, through membrane 860, to a new position near the center of the blood vessel 849. The hook 840 may be made from a shape-memory material such as Phynox, Elgiloy, or nitinol. The hook may have a length of 3-10 mm, a diameter of about 0.005" to 0.100", and have a radius of curvature that allows it to move in a curved channel. In addition, a slot 846 with a length of 0.5-9.5 mm is cut in the hook near one end, which is shape-set to open when the hook moves out of its channel, as shown in FIG. 20B. The tip of the hook 840 may come to a point that allows it to penetrate membrane 860 more easily when the hook is activated, and hook 840 may be displaced by the solenoid with sufficient force to penetrate any overlying tissue layer. As shown in FIG. 20B, upon actuation, the hook base 848 moves until it encounters a mechanical stop 850, which prevents the hook from being removed without the sensor. Thus, the hook is present in the center of the lumen when an activating electrical signal is applied. This has the advantage of allowing the sensor to be removed at any time following implantation.

In the illustrated embodiment, the solenoid is used to advance the hook 840 along an arcuate path, between the retracted and the deployed configurations. Alternatively, the hook 840 may be biased in the distal direction of its travel, such as by the use of a spring, and restrained by a solenoid or other mechanical interfit structure within the housing. Application of an electrical or mechanical signal to the lock, depending upon the nature of the locking mechanism, disengages the lock from the hook 840, and the hook 840 thereafter advances into the deployed configuration.

Figure 20C:
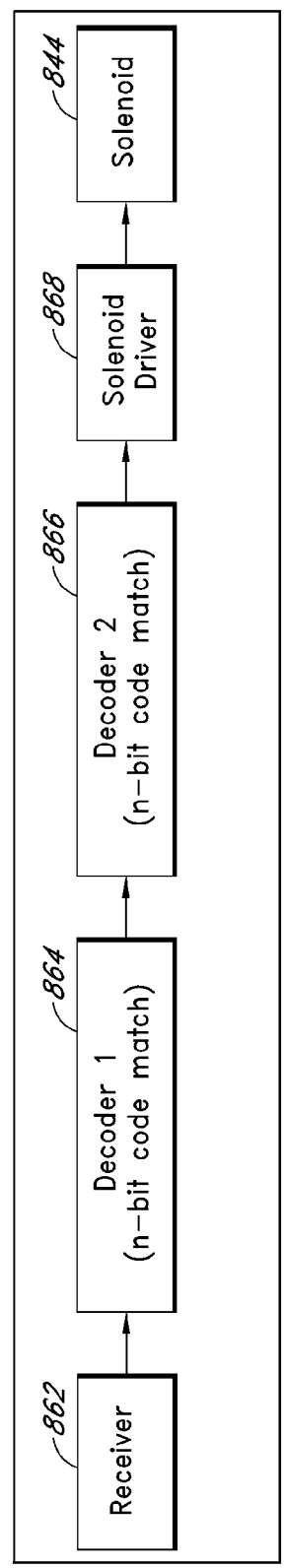
FIG. 20C is a block diagram of the circuitry for activation of sensor retrieval mechanism.

In the illustrated embodiment, the hook 840 is moveable between its retracted and deployed orientations by movement along its own axis. As an alternative, the hook 840 may be deployed by inclining laterally away from the sensor housing, such as by rotating through a predetermined angular range about a pivot point. In one implementation of the invention, an axially extending recess is provided on the surface of the housing. A hook 840 is positioned within the recess, and pivotably attached at a first end to the housing. The hook 840 is moveable between a first orientation within the recess, and generally parallel to a longitudinal axis of the housing, and a second, deployed orientation in which it is inclined outwardly from the housing for engagement by a retrieval device. The hook 840 may be advanced from the first position to the second position by spring bias, upon release of a retention lock as discussed above. Alternatively, the hook 840 may be advanced from the first position to the second position by an electromechanical force, such as a solenoid. Referring now to FIG. 20C, an electro-mechanical system is used to activate a retrieval hook so that the sensor 20 may be retrieved, for example, in the event of sensor failure. A signal is sent to the sensor 20 via a RF link from an RF source (not shown) which is then decoded. If a match occurs, the solenoid 844 will be activated to release the retrieval hook 840. FIG. 20C shows one type of interlock mechanism electronics—a dual-level interlocking scheme—that can be used to prevent any extraneous signals (such as from x-ray, MRI, microwave ovens, and cellphones) from interfering with the signal of interest. Receiver 862 receives a signal sent by, for example, an RF link. Decoder 1 864 receives the serial bit stream from the receiver 862. Specifically, Receiver 862 sends the n-bit code, for example with n>128, serially to the Decoder 1 864. Decoder 1 864 functions as a gate that requires that the n-bit code be received and matched with a stored, internal n-bit code before passing the serial data transparently to the next stage, Decoder 2 866. If Decoder 1 864 received and matched the n-bit code, Decoder 1 864 then sends the n-bit code to Decoder 2 866. Once the second n-bit code is received by Decoder 2 866, Decoder 2 866 matches the code with a stored, internal n-bit code and then sends a signal to the solenoid driver 868. The solenoid driver 868 then activates the solenoid 844 which, in turn, activates the retrieval hook 840. A parallel interlock scheme could also be used where decoder 1 864 and decoder 2 866 are both fed data. If the outputs match, then the solenoid driver 868 would be activated.

In a further aspect of an embodiment of the present invention, it is possible to remove both the sensor and its anchoring platform, using a snare in a follow-up catheterization procedure. As is well known to those skilled in the art, the snare would be introduced into the vasculature using the same Seldinger techniques (or similar technique) that are used to implant a stent. Under fluoroscopic guidance, the physician would first select an appropriate vascular access site, and then would insert a guiding catheter of sufficient diameter so as to be able to accommodate the retrieved sensor and its anchoring platform. Next, the physician would insert a snare, such as the GooseNeck Snare (Microvena Corp.) through the guiding catheter, and approach the sensor hook with the snare. Once the physician grasps the sensor hook with the snare, and proximally retracts the snare, the sensor would collapse into the retrieval catheter, and the sensor and guiding catheter could be simultaneously withdrawn from the patient's body.

Figure 17A:
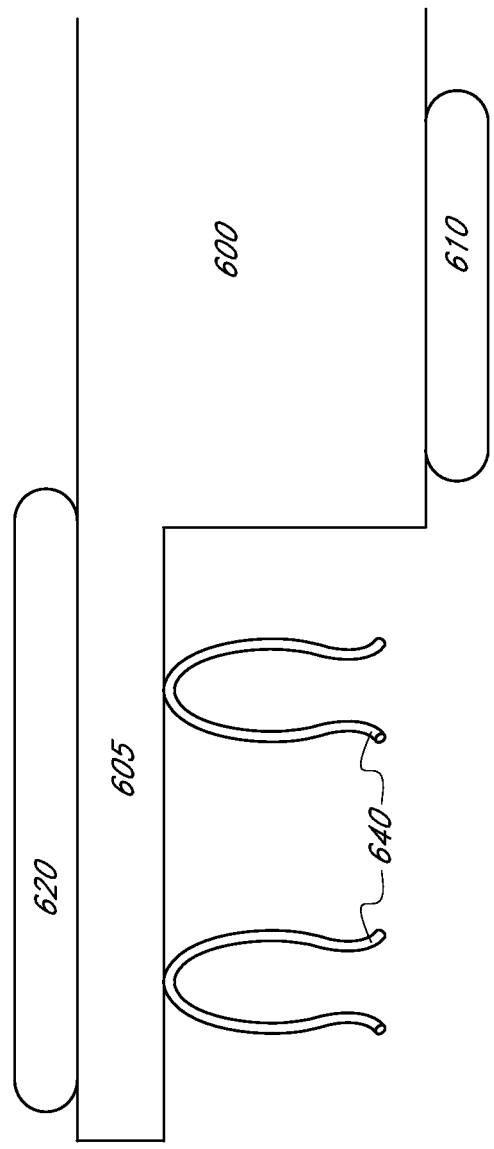
FIG. 17A is a side view of a retrieval catheter designed for removing a sensor at the end of its life.
Figure 17B:
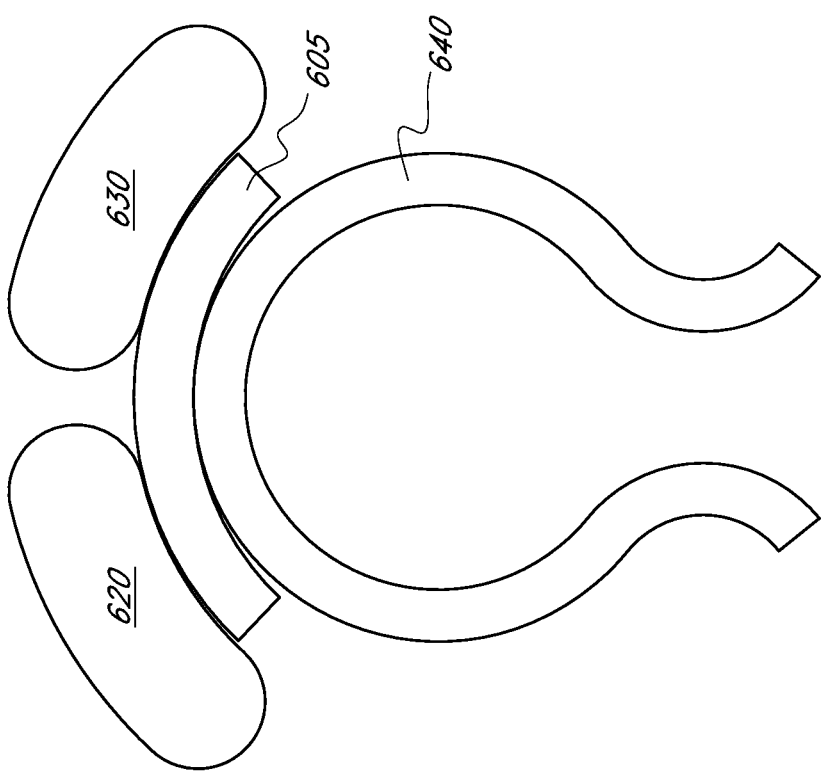
FIG. 17B is an end view of a retrieval catheter designed for removing a sensor at the end of its life.

In an alternative embodiment, it is possible to retrieve the sensor without the presence of a hook on the sensor or anchoring platform. Preferably, this is done using a sensor housing that is bonded to the anchoring platform using a degradable material, and this procedure is performed after the bonds have degraded. Also, this procedure is preferably performed using a distal protection device, such as the Angioguard (Cordis Corp.). Because the sensor is not covered by a layer of neointimal tissue, it is possible to remove the sensor using the retrieval system shown in FIGS. 17A and 17B. A catheter 600 with a set of clips 640 is shown. The catheter 600 includes a tip 605 that includes a pair of balloons 620, 630 placed on the side of the catheter tip 605 opposite the clips. The catheter is maneuvered into position under fluoroscopic guidance, so that the clips 640 are adjacent to the sensor. Next, balloons 620 and 630 are inflated either sequentially or simultaneously, as appropriate for the individual case, so that the clips are forced around or otherwise caused to engage the sensor housing. Next, balloons 620 and 630 are deflated. FIG. 17C shows the retrieval catheter in position next to a sensor 20, which is to be removed. The sensor 20 is attached to an anchoring platform 14 and is lodged in blood vessel 849. The sensor 20 can be separated from the anchoring platform 14 as previously described with reference to FIG. 20A. As balloon 620 is being inflated, the clips 640 are positioned around sensor 20. Finally, the sensor 20 that is being removed, and the catheter tip are separated from the wall of the vessel by inflating balloon 610. Balloon 610 is then deflated, and the entire system is removed from the patient, along with the sensor.

Monitoring Various Arterial Blood Gases

In another aspect of an embodiment of the present invention, the sensor is configured to monitor arterial blood gases. There are at least two types of sensors which are used in monitoring arterial blood gas (ABG) values, and which may be modified in order to practice this embodiment of the invention. The first type is a Clark-type electrode, in which an electrochemical reaction, such as the reduction of $O_2$, occurs at an electrode, and an electrical current is monitored. Early oxygen electrodes required initial calibration against a simultaneous ABG sample, and sensor drift necessitated frequent recalibrations. Thrombosis was also a critical issue for this type of intravascular sensor, and so the oxygen electrode was not widely accepted. (Mahutte, 1998). In addition, electrochemical pH and $pCO_2$ monitors are not available.

The other major category of IABG's is optodes, which measure blood gases optically, and with modifications described herein, are suitable for practicing the present invention. These sensors are based on fiberoptics that are coupled with a reagent. Interaction between the reagent and an analyte of interest results in a change in the optical properties of the reagent, which is detected through the fiber-optic. Optical sensors such as these do not require the use of a reference electrode. There are three main types of optodes, based on either absorbance, fluorescence, or quenching (W. R. Seitz, "Chemical Sensors Based on Fiber Optics", Anal. Chem. 56(1):16A-34A (1984) and C. K. Mahutte, "On-line Arterial Blood Gas Analysis with Optodes: Current Status," Clin. Biochem 1998; 31:119-130). When light of a certain wavelength passes through a reagent, and there is a reduction in intensity of the light, that is termed absorbance. Fluorescence optodes work because the reagent absorbs light at one frequency, and re-emits light at a second frequency. The intensity of light at both frequencies can be measured, providing a correlation with the concentration of the analyte of interest (L. A. Saari and W. R. Seitz, "pH sensor based on immobilized fluoresceinamine", Anal. Chem. 1982; 54:821-23). Fluorescence quenching is also used for detection of analytes such as oxygen. Oxygen can reduce the amount of fluorescence of certain organic compounds, and therefore the reduction in the intensity of re-emitted light can be used as the basis for measurement of oxygen concentration (J. I. Peterson et al., "Fiber-Optic Probe for In Vivo Measurement of Oxygen Partial Pressure", Anal. Chem. (1984) 56:62-67)).

The reagent phase of an optode can be positioned at any point along the fiber-optic, either at the end, or along the sides, allowing for different geometric configurations to be used (Mahutte 1998).

There have been a number of ABG sensors that have reached commercialization at various times, and with modifications described herein, would be suitable for practicing the present invention. These include the Paratrend 7 (Pfizer/Biomedical Sensors, Malvern, Pa.) (I K Weiss, et al, "Continuous arterial gas monitoring: Initial experience with the Paratrend 7 in children," Intensive Care Med. (1996) 22:1414-1417), the CDI 1000 (Cardiovascular Devices, Irvine Calif.), Optex Biomedical (TX), and the PB3300 (Puritan-Bennett, Carlsbad, Calif.) (T. Lumsden, et al. "The PB3300 Intraarterial Blood Gas monitoring system," J. Clin. Monit 1994; 10:59-66).

The Paratrend 7 is a combination electrode-optode system, with fiberoptic pH and $pCO_2$ sensors, an amperometric oxygen sensor, and a thermocouple for temperature compensation, and would be suitable for practicing the present invention. The CDI 1000, the Optex sensor, and the PB3300 are pure optode systems. In the PB3300, the reagent is on the external circumference of the sensor. Acceptable levels of accuracy have been reported with the PB3300 system, but the longest reported duration of implantation was 121 hours.

In addition, U.S. Pat. No. 5,326,531 Jul. 5, 1994 to Hahn et al., "$CO_2$ Sensor using a hydrophilic polyurethane matrix and process for manufacturing" describes a $CO_2$ optode, and U.S. Pat. No. 5,378,432 Jan. 3, 1995 to Bankert et al, "Optical Fiber pH microsensor and method of manufacture" describes a pH optode, both of which can be used in the present invention.

The clinical issues identified which prevent the sensors from functioning properly in vivo are known as the "wall-stress effect", and are attributed to hypotension or vasoconstriction. In some instances, the pH, $pCO_2$ and $pO_2$ values are variable due to thrombus formation at the tip of the catheter, while in other instances, the variation was due to the sensor touching the arterial wall, and measuring gas values in the tissue (C. K. Mahutte, "On-line Arterial Blood Gas Analysis with Optodes: Current Status," Clin. Biochem 1998; 31:119-130). Both vasospasm and wrist flexion have been identified as factors which negatively affect the performance of these sensors. The anchoring platform (14) shown in FIG. 16 is designed to address these problems.

In U.S. Pat. No. 6,447,395 (Nov. 5, 2002), Schulman et al. shows a sensor designed to avoid direct contact between the sensing surface and the vessel wall. This sensor is built near the tip of a catheter, and the catheter at the sensing surface is bent in a zig-zag shape. However, there are two major drawbacks with this type of design. First, blood flow stagnation will occur in the region at the inside apex of the zig-zag, and therefore, thrombosis will occur on this sensing surface, and interfere with sensor function, even if the sensor surface does not touch the vessel wall. Second, because most catheters are made from somewhat rigid materials, such as nylon, any catheter with a zig-zag pattern as shown in FIG. 6 of Schulman would not be able to be introduced into a vessel using a catheter sheath introducer, as is standard clinical practice. In addition, such a sensor could not be introduced into a vessel using a trocar or other small diameter tool to allow vessel access.

Now referring to FIG. 16, the anchoring platform 14 is connected to a catheter 500, which contains multiple sensors 20, such as optode sensors, for monitoring pH, $pO_2$, and $pCO_2$, near its distal end. As in other embodiments, the anchors are made of a self-expanding material such as nitinol. As previously described, these anchors help to position the sensor near the wall, with the sensing surface 20 oriented toward the vessel lumen. These anchors may be split rings, which under a compressive load would form closed rings, resisting vessel compression due to vasospasm (Khatri, S. et al., "Stenting for Coronary Artery Spasm," Catheter Cardiovasc Interv., 2002 May 56(1):16-20, and Cheng, T. O., "Percutaneous Coronary Intervention for Variant Angina: Balloon vs. Stent", Catheter Cardiovasc Interv., 2002 May 56(1):21) but would also open up under tension to allow the catheter and sensor to be withdrawn at the end of its useful life. For monitoring of blood gases in the radial artery, which has a typical diameter of 3-4 mm, these anchors should have an expanded diameter of 3.5-5 mm, to allow for slight oversizing of the anchors, which is common practice in stent placement. The catheter and sensor may be withdrawn from the patient using a slightly larger catheter sheath, in order to accommodate the anchors, and protect the vessel from further damage during removal. As an alternative to placing the sensor near the side of the vessel, the catheter and sensor could be centered in the vessel, with one or more struts connecting the sensor to one or more support rings. The support rings serve to maintain the position of the sensor in the center of the vessel, and additionally serve to resist vessel compression due to vasospasm, and may reduce the risk of vessel compression due to joint flexion. In another embodiment, the support rings may have a helical configuration, the helix being joined to the sensor by one or more struts, which help to position the sensor in the center of the bloodstream. The use of a helical support structure which is connected to the catheter at only a single point provides the option of removing the sensor, even after the wound healing process has occurred, and fibrin which deposits on the strut surfaces has transformed into fibro-collagenous tissue. This is because the helix can be unwound, and pulled into the retrieval catheter. Thus, the addition of these support anchors serves to counteract vessel compression, one of the main obstacles that prevents IABG sensors from functioning long-term in an arterial setting. Appropriate positioning of the sensor in the flow field also minimizes the risk that slow flow will cause thrombosis and sensor fouling. Alternatively, the sensors may be placed in an artery that is larger than the radial artery, such as the femoral artery, and the present invention is suitable for numerous intravascular locations.

In a further aspect of an embodiment of the present invention, it is possible to measure a variety of electrolytes using ion-selective electrode (ISE's). Some of these are described by Bakker et al. (Bakker, E., et al., "Carrier-Based Ion-Selective Electrodes and Bulk Optodes. 1. General Characteristics" Chem. Rev. 1997 97:3083-3132). These ion selective sensors, whether optical or electrochemical, are based on lipophilic complexing agents capable of reversibly binding ions, called ionophores. The sensing layer of most ion selective electrodes (ISE's) or optodes is an organic polymeric membrane, of which polyvinyl chloride (PVC) is the most widely used. Other materials such as derivatized PVC, silicone rubber, or polyurethanes can also be used. A requirement for such membranes is that its glass transition temperature needs to be below the operating temperature. This requirement is necessary to allow reasonably rapid diffusion times. Alternatively, plasticizers, such as those used in PVC can be used to achieve the same goal. The plasticizer is typically selected for its compatibility with the ionophore. The ionophore determines the selectivity of the sensor. The final component of the ISE membrane is either a quaternary ammonium salt, to provide cationic sites, or tetraphenylborate salts to provide anionic sites. (R. D. Johnson et al, "Ionophore-based ion-selective potentiometric and optical sensors," Anal. Bioanal. Chem. 2003 June; 376(3):328-41.)

It is possible to alter the surface of these ISE membranes in order to improve their blood compatibility, such as with the use of phosphorylcholine (Berrocal M J, et al, "Improving the blood-compatibility of ion-selective electrodes by employing poly(MPC-co-BMA), a copolymer containing phosphorylcholine, as a membrane coating." Anal. Chem. 2002 Aug. 1; 74(15):3644-8) or with heparin or hirudin, poly(ethylene glycol), or poly(vinyl pyrrolidone), or the ISE membrane may first be covered by a protective membrane such as ePTFE with 0.4 micron porosity, and then surface modifications applied. Among the species that can be monitored using these technologies are calcium, chlorine, potassium, sodium, bicarbonate, phosphate, phosphorous, and magnesium. Other metal ions which can be detected using this technology include lithium, ammonium, rubidium, cesium, beryllium, strontium, barium, molybdenum, iron, copper, silver, zinc, cadmium, mercury, thallium, bismuth, lead, uranium, and samarium. Other inorganic ionic analytes which can be measured using this technology include creatinine, organic ammonium ions, nucleotides, and polyionic analytes such as heparin and protamine. (Buhlmann P, et al, "Carrier-Based Ion-Selective Electrodes and Bulk Optodes. 2. Ionophores for Potentiometric and Optical Sensors," Chem. Rev. 1998 Jun. 18; 98(4):1593-1688). The response of ISE's toward a single analyte ion is described by the Nernst equation.

In a further aspect of the invention, a pressure sensor can be implanted within a blood vessel in order to monitor a patient on a continuous basis. The pressure sensor may be similar to many described in the art, such as potentiometric pressure sensors, inductive pressure sensors, capacitive pressure sensors, piezoelectric pressure sensors, and strain gage pressure sensors. The pressure sensor can also be a micro electromechanical system (MEMS) device such as those made by Honeywell, Sensym, or All Sensors Corp (San Jose, Calif.) that is constructed using microfabrication methods that are well known in the microelectronics industry. Once the pressure signal has been converted into an electrical signal, the signal is then transmitted to an external receiver that may be worn by the patient. The sensor can be configured on the anchoring platform in any of the various configurations previously described in this disclosure, including those in which the sensor itself is retrievable in the case of sensor malfunction.

In a further aspect of an embodiment of the present invention, it is also valuable to monitor the condition of patients who have abdominal aortic aneurysms, which can be treated with endovascular stent-grafts. Sonesson et al. (Sonesson B., et al., "Intra-aneurysm pressure measurements in successfully excluded abdominal aortic aneurysm after endovascular repair" J Vasc Surg 37:733-8 (2003)) describe how monitoring the pressure on both the luminal side and aneurysmal side of such stent-grafts can help a physician to determine when and whether follow-up intervention is required. However, in their study, a follow-up catheterization procedure was required to monitor these pressures. It would clearly be advantageous to be able to obtain this information without having to perform an additional procedure. An implantable pressure sensor as described herein which does not become covered with a layer of fibrocollagenous tissue would provide accurate intra-arterial measurements. If a second sensor were mounted on the aneurysmal side of the stent-graft, its signal would not change substantially, as the healing process within the aneurysmal sack is known to be substantially delayed.

Schmitz-Rode et al. (Schmitz-Rode T, Schnakenberg U, Pfeffer J G, Piroth W, Vom Bogel G, Mokwa W, Gunther R W, "Vascular capsule for telemetric monitoring of blood pressure," Rofo Fortschr Geb Rontgenstr Neuen Bildgeb Verfahr. 2003 February; 175(2):282-6) describe a capsular pressure sensor that is implanted in the arterial system at an arterial branch. Three self-expanding legs were attached to the sensor capsule in order to maintain sensor position and prevent migration as well as occlusion (WO 00/74557, 07 Jun. 2000 to T. Schmitz-Rode, et al.). However, they reported that in 3/6 cases, the devices migrated several centimeters to the next arterial bifurcation, where the device became lodged, and caused an occlusion of one of the branch vessels. The three-leg anchoring system of this device means that it is prone to tilting, and so its exact position with the vessel is not controllable. Further, this device is not easily retrievable in the event of patient need or device failure. In addition, physicians would prefer to use a device whose placement is more accurate. It may also be important to monitor pressures at a location distant from an arterial bifurcation. Hence, an improved anchoring system, as described herein, can provide a significant improvement in this area.

Bullister et al. (Bullister E., et al., "A Blood Pressure Sensor for Long-Term Implantation," Artificial Organs 25(5): 376-379 (2001)) describe a pressure sensor that is mounted within the wall of a titanium tube, and that may be used in line with a left ventricular assist device. However, such a device would require surgical implantation, which may not be appropriate for monitoring many patients, especially critical care patients, whose condition may exclude them as surgical candidates. In addition, if such a sensor were anastamosed end-to-end in a vessel, there would be a clear compliance mismatch between the vessel and the sensor. Compliance mismatch is well established as a cause of vascular graft failure.

Pressure sensors that are attached to stents have also been disclosed (U.S. Pat. No. 6,015,387 issued Jan. 18, 2000 to Schwartz et al. and U.S. Pat. No. 6,053,873 issued Apr. 25, 2000 to Govari et al.). Govari describes positioning of a pressure sensor on the outer wall of a stent. However, without proper positioning of the sensor with respect to the stent and the vessel lumen, the sensor surface will be covered with fibrin, which will subsequently transform into fibrous tissue, as part of the natural healing process. The fibrous tissue will create a barrier between the sensor and the blood, and will affect the value of the pressure readings obtained from the sensor. The fibrous tissue itself has elastic properties that will vary over time, and will be dependent on the thickness of the tissue layer that is formed. Thus, such a system may not allow immediate determination of whether the sensor is covered with tissue, or whether patient intervention is required. In addition, the devices described by Schwartz and Govari are not designed to be retrievable in case the sensor fails to function properly.

Ultrasonic flow sensors of the type described in U.S. Pat. No. 6,053,873 to Govari et al., which is hereby incorporated in its entirety, may be mounted in a hermetically sealed sensor housing made from epoxy, glass, ceramic, stainless steel, or the like, and mounted on the luminal surface of a stent, such that the luminal surface of the sensor housing protrudes into the lumen, as previously described. The sensor may alternatively be placed between two or more anchors, in such a manner that the sensor housing is designed to protrude into the lumen of the vessel, with respect to the anchors. The sensors are mounted at spaced-apart locations so that the transit time or Doppler ultrasound methods for determining flow rates described by Govari may be used. Additionally, the sensors may be positioned at an appropriate Doppler angle.

The anchors may consist of self-expansive materials, such as nitinol, or may be made from balloon expandable materials such as 316L stainless steel. In addition the anchors may be made from elements that are not closed curves, and which do not become interlocked with fibrous tissue over time. The open hoop structures shown in FIG. 16 are one type of anchor that may be suitable for practicing this invention. There may optionally be provided a retrieval hook at the downstream end of the sensor for removing the sensor at the end of its useful life. The sensor itself may be powered using an inductive link, or an implantable battery, and the sensor responses may be analyzed using an application-specific integrated circuit.

In a further aspect of an embodiment of the present invention, an implantable sensor may be used to determine flowrates. A thermal sensor for measuring flowrates is disclosed which consists of a thermal source, such as a resistive heating element, and at least one sensing unit, such as a thermistor or thermocouple. Both the heating element and the sensor are placed in the sensor housing, which protrudes into the lumen of the vessel in order to minimize tissue overgrowth. The heating element is placed upstream from the first thermocouple, and a small (<2.5° C.) temperature increase is applied to the bloodstream near the heating element. A second thermocouple is positioned immediately distal to the heating element to insure that the local temperature rise is small. The time for the temperature increase to be sensed by the downstream thermocouple is measured, and the flowrate may be determined from this information using standard thermodilution calculations.

Additionally, the Fick method for determination of cardiac output could be performed, using oxygen sensors described herein, placed in both the arterial circulation, and in the pulmonary artery. The Fick method for determining cardiac output is based on the principle that consumption of a substance (oxygen in this case) must equal blood flow to the organ multiplied by the difference between the arterial and venous concentrations of the substance. For this method, the formula for cardiac output is as follows:

$$CO = \frac{\text{oxygen consumption per minute (VO2)}}{\text{(arterial oxygen content} - \text{venous oxygen content)}}$$

where oxygen content is calculated as: (1.34×[Hb]×oxygen saturation)/100. [Hb] is the hemoglobin concentration, which can be periodically assessed by a hemotology laboratory. In this case, the oxygen consumption can either be estimated or directly measured using standard techniques, or using the implantable sensors described herein. Arterial oxygen saturation is usually determined by arterial blood gas analysis (or using an implantable oxygen sensor described herein), while venous oxygen saturation is determined by mixed venous (pulmonary arterial) blood gas analysis (or using an implantable oxygen sensor described herein).

An implantable sensor of an embodiment of the present invention can also be designed to sense cerebral ischemia. Monitoring for cerebral ischemia may be useful in other areas besides stroke. For example, monitoring of cerebral ischemia could be very important in the field of traumatic brain injury (TBI). Each year in the United States, an estimated 1.4 million people sustain a TBI. Of those, 230,000 are hospitalized and survive, which is more than 20 times the number of hospitalizations for spinal cord injury, another key disabling injury. In addition, 50,000 people die from a TBI, and 80,000 to 90,000 people experience the onset of long-term or lifelong disability associated with a TBI (Centers for Disease Control, Traumatic Brain Injury Fact Sheet May 2004). Monitoring of such patients could be performed during hospitalization.

Concussion, which is often referred to as mild TBI (mTBI), has recently been recognized as a significant health problem with up to 3.8 million concussions per year. There is significant interest in sports-related concussions, although most occur during falls (37%) or motor vehicle accidents (17%). Repeated concussions within a week (or longer) can cause severe brain injury due to secondary impact syndrome (Tavazzi B, et al, "Temporal window of metabolic brain vulnerability to concussions: oxidative and nitrosative stresses—part II", Neurosurgery. 2007 August; 61(2):390-5). Patients often don't recognize that they have suffered a concussion (J S Delaney et al, "Recognition and characteristics of concussions in the emergency department population", J Emerg Med. 2005 August; 29(2):189-97). Physicians need better tools for acute diagnosis of concussion, as well as the ability to follow the injury over time to decide when the patient should return to normal activities. Blood biomarkers would be a powerful tool for physicians. Unfortunately, biomechanics of impact (e.g., forces, acceleration) do not correlate with concussions in football. (Broglio S P, et al., "Post-concussion cognitive declines and symptomatology are not related to concussion biomechanics in high school football players", J Neurotrauma, 2011 October; 28(10):2061-8.) Imaging techniques such as MRI—do not allow a real-time diagnosis, such as at the sideline of a sports event. These techniques are therefore unable to help physicians diagnose concussion in a timely manner. NO levels in animals are dramatically elevated for a short period after brain impact injury, and thus may serve as a biomarker for acute concussion (Cheman L, et al, "Brain Nitric Oxide Changes after Controlled Cortical Impact Injury in Rats," J. Neurophysiol, 83:2171-2178, 2000).

Similarly, patients with a type of stroke called subarachnoid hemorrhage (SAH) could also be monitored for cerebral ischemia. Approximately 5-7 days following hemorrhage, vasospasm of intracranial vessels frequently occurs, resulting in cerebral ischemia. Approximately 20-30% of the neurological injury following SAH is due to vasospasm alone, so these patients could also benefit from this type of monitoring.

In addition, patients with mild stroke, or transient ischemic attack (TIA) could benefit from monitoring for cerebral ischemia. There are roughly 300,000 to 500,000 cases of TIA each year, and the risk of stroke within 90 days following a TIA is approximately 20-30% (S. Claiborne Johnston, MD, PhD; J. Donald Easton, MD, "Are Patients With Acutely Recovered Cerebral Ischemia More Unstable?" *Stroke.* 2003; 34:2446-2452.)

Because NO has a short half-life (2-30 s), it is difficult to measure authentic NO. It rapidly decomposes to nitrate and nitrite, which may accumulate in the sample. There are different methods of determining NO. It is possible to measure NO by using a bioassay, an oxyhemoglobin assay, electron paramagnetic resonance, chemiluminescence, HPLC, the Griess reaction, or different electrochemical electrodes. In addition, electrodes for NO detection are commercially available (WPI, (Sarasota, Fla.), Innovative Instruments, (Tampa, Fla.), Diamond General (Ann Arbor, Mich.), and Inter Medical Co., Ltd., (Nagoya, Japan)).

The electrochemical reaction occurs at a working electrode at an applied voltage of 900 mV vs. Ag/AgCl electrode. The reaction is given below:

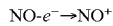

$$NO - e^- \rightarrow NO^+$$

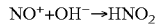

$$NO^+ + OH^- \rightarrow HNO_2$$

The redox current flowing between the working and reference electrodes is proportional to the concentration of NO, and is measured amperometrically (Zhang, X, et al., "Amperometric Detection of Nitric Oxide", Mod. Asp. Immunobiol. 1(4), 160-65, 2000).

An implantable sensor of an embodiment of the present invention can also be designed to sense myocardial infarction. NO and its metabolites may provide a signal for myocardial infarction (MI). The mechanisms of NO release in response to MI appear to be similar to that for stroke. For instance, eNOS is cardioprotective against ischemia/reperfusion injury in mice (Xiao-Ping Yang, et al, "Endothelial Nitric Oxide Gene Knockout Mice Cardiac Phenotypes and the Effect of Angiotensin-Converting Enzyme Inhibitor on Myocardial Ischemia/Reperfusion Injury" *Hypertension.* 1999; 34:24-30.) As with stroke, iNOS appears to exacerbate ischemia/reperfusion injury (Judith S. Hochman, "Cardiogenic Shock Complicating Acute Myocardial Infarction: Expanding the Paradigm", *Circulation.* 2003; 107:2998-3002.) Therefore, detection of MI may be accomplished with similar NO monitoring systems as described for stroke.

In a further aspect of an embodiment of the present invention, an implantable sensor is described for monitoring nitric oxide, nitrites, or nitrates. Sensors have been described that, with modifications described herein, may be suitable for practicing embodiments of present invention of intravascular monitoring of nitrites. These sensors involve the deposition of an electroactive coating or ion-selective membrane onto a substrate of a particular geometry, such as a glassy carbon electrode, or a platinum wire. For use in the embodiments of present invention, the geometry of the sensor is streamlined or gradually sloped as previously described. The coatings or membranes should be applied so that they will be exposed to the blood-contacting interface of the sensor, such as circumferentially along an axis, rather than at an end, as frequently described in the art.

In a preferred embodiment, the indwelling sensor described above for measurement of nitric oxide or its metabolites may be a modification of the sensor described by Malinski (U.S. Pat. No. 5,603,820, to Malinski et al., issued Feb. 18, 1997.) This sensor can monitor NO, but excludes $NO_2$ by the use of a Nafion membrane. The substrate to be used as the electrode must have an appropriate geometry with an appropriate method for stabilizing the sensor in a vessel as described in FIG. 1A, 2, 3, 4, 5A, 9A, 10, 11, 14A, 14B, 15A, 15B, 16, 18, 21A, 21B, 22A, 23, 25A, or 27A, 27B, 27C. Once the substrate geometry is selected, the sensor electronics will be hermetically sealed using either a glass, ceramic, epoxy, or metal housing in order to prevent corrosion, with the electrode portion crossing the hermetic seal. The electrode is comprised of a carbon fiber or platinum wire or tin-indium oxide layered on glass substrate. Next, the electrode is coated with several layers of p-type semiconducting polymeric porphyrin. The thin layer of polymeric porphyrin film can be electrochemically deposited, as described by Malinski. A precursor (e.g., monomer, dimer, or oligomer) used to form the electrochemically active polymeric coating can be electrolytically polymerized onto a surface of the electrode by immersing the substrate in a solution containing the precursor, a supporting electrolyte, and a solvent. The electrochemically active polymeric coating may be comprised of the metallized polymeric porphyrin compounds of tetramethylpyridine pyrrole and dimethyl ester porphyrin, or tetramethylpyridine pyrrole (TMPP) and dimethyl ester porphyrin (DME) metallized with nickel, cobalt, and iron, especially nickel(II) tetrakis (3-methoxy-4-hydroxyphenyl)porphyrin (Ni (II) THMPP). A semi-permeable membrane may then be added which allows the analyte of interest, in this case NO or $NO_2$, to freely contact the sensor, while restricting the passage of other blood components. The semi-permeable membrane may comprise ePTFE, Dacron®, polyurethane, silicone rubber, poly(lactide-co-glycolide) (PLGA), poly(caprolactone) (PCL), poly(ethylene glycol) (PEG), collagen, polypropylene, cellulose acetate, poly(vinylidene fluoride) (PVDF), polyamides, polycarbonate-ethers, regenerated celluloses and polyacrylonitriles (PAN) or other biocompatible materials. The molecular weight cutoff of this membrane should be less than 30,000 daltons. In addition to the semi-permeable membrane, a thromboresistant coating may be added, such as an anticoagulant (like heparin or hirudin), a thromboresistant material such as phosphoryl choline, a hydrogel (such as poly (ethylene glycol), poly(N-vinyl pyrrolidone), poly(hydroxyl ethylmethacrylate), polyacrylamide, polyacrylic acid, cross-linked collagen, sulfonated polyurethane or other sulfonated polymer, or other thromboresistant materials as are known in the art. In addition, this thromboresistant layer may release a pharmacological agent that inhibits cell proliferation or migration. In addition, in the present invention, it may be desirable to monitor both NO and $NO_2$ simultaneously, so the Nafion membrane described by Malinski can be removed. This sensor has a fast response time (around 10 ms) and is therefore suitable for practicing the present invention.

In a preferred embodiment, an outer coating of heparin or hirudin is applied to a layer of poly(ethylene glycol) (PEG), poly(vinylpyrrilidone) (PVP), or other hydrogel, or phosphoryl choline, in order to minimize thrombosis or fouling. The hydrogel is applied to a bioprotective layer of ePTFE, which prevents attack by macrophages. The hydrogel may be bonded to the ePTFE by cross-linking within the pores of the ePTFE, or by plasma activation of the ePTFE surface. A polymer such as poly(dimethylsiloxane) or a polyester membrane such as Sympatex (Azko Nobel, Wuppertal, Germany) which is permeable to NO is employed. (Wang C, Deen, W M, "Nitric oxide delivery system for cell culture studies", Ann Biomed Eng. 2003 January; 31(1):65-79.) The ePTFE surrounds the NO-permeable membrane, and the NO-permeable membrane surrounds the electrode. A porphyrinic sensor may be constructed by coating a carbon-fiber electrode with a solution of nickel (II) tetrakis (3-methoxy-4-hydroxyphenyl) porphyrin (Tschudi, M R et al, "Direct In Situ Measurement of Nitric Oxide in Mesenteric Resistance Arteries", Hypertension 1996; 27:32-35), and then applying the outer membranes. Additionally, a layer of drug-releasing polymer, as described below, may be placed between the ePTFE membrane and the NO-permeable membrane, or may be placed only in certain areas between the ePTFE and NO-permeable membranes, such that there is direct contact between these two membranes. The coating or layer chosen to minimize thrombosis or fouling should have porosity large enough to allow the analyte of interest to reach the sensing surface. In certain applications, radial inward displacement of the sensing surface may be reduced and longevity of the sensor still exist.

While it is anticipated that hemodynamic effects will significantly reduce biological fouling, in the case of NO detection, it may additionally be desirable to further insure the prevention of endothelial growth by the elution of certain pharmacologic agents to prevent endothelial coverage of the sensor surface. Such anti-angiogenic agents include: paclitaxel (Belotti D, et al., "The microtubule-affecting drug paclitaxel has antiangiogenic activity", Clin Cancer Res. 1996 November; 2(11):1843-9.), rapamycin (Novak, K., "Swinging the vote for rapamycin" Nature Reviews Cancer 2002 2:75.) docetaxel (Guo, X L, et al., "Inhibitory effects of docetaxel on expression of VEGF, bFGF and MMPs of LS174T cell" World J Gastroenterol 2003; 9 (9): 1995-1998.) TNP-470 (Yeh, J R J, et al, "The antiangiogenic agent TNP-470 requires p53 and p21CIPyWAF for endothelial cell growth arrest", PNAS, 2000 97(23):12782-12787), carboxyamidotriazole (CAI), thalidomide, or interleukin-12 (Masiero, L, et al. "New anti-angiogenesis agents: review of clinical experience with carboxyamido-triazole (CAI), thalidomide, TNP-470, and interleukin-12" Angiogenesis 1997; 1(1):23-35.). These may be released from a degradable matrix, such as PLGA, or from a non-degradable matrix, such as ethylene vinyl acetate (EVA). This drug-releasing layer may be incorporated within the sensor housing inside the outer bioprotective layers.

In an alternative embodiment, the indwelling nitrite sensor described above may be modified to incorporate the ion selective electrode membrane described by Ganjali, et al., (Anal Sci April 2003; 19:1127-1131), which is capable of measuring nitrite concentrations as low as 0.1 micromolar. This sensor may be prepared by mixing PVC with the ionophore CS and hexadecyltrimethylammonium bromide, and then adding o-nitrophenyloctyl ether, dibutylphthalate, dioctylphthalate, and benzyl acetate as plasticizers in THF. This solution is then partially evaporated and coated onto a substrate such as glass, carbon fiber, platinum wire or tin-indium oxide layered on glass substrate. The filling solution used with this electrode is $NaNO_2$.

In an alternative embodiment, the intravascular nitrite sensor described above may be modified to incorporate the ion selective electrode membrane described by Zen et al. that is based on a ruthenium compound (Jyh-Myng Zen, Annamalai Senthil Kumar and Hsu-Fang Wang, A dual electrochemical sensor for nitrite and nitric oxide, Analyst, 2000, 125, 2169-2172). This membrane is a Nafion/lead-ruthenate pyrochlore (NPyCME) which can be applied to an electrode for use as a dual electrochemical sensor for both $NO_2$ oxidation and NO reduction reactions. A glassy-carbon electrode (GCE) was first prepared by spin-coating 4 μl of 4 wt. % Nafion solution at 3000 rpm onto the GCE. The Nafion-GCE was then ion-exchanged with $Ru^{3+}$ and $Pb^{2+}$ and further reacted in 1.1 M KOH at 53° C. for 24 h with purging of $O_2$. Semi-permeable membranes and/or anti-thrombotic coatings may additionally be applied, as described above.

In an alternative embodiment, the nitrite sensor may use the ion selective membrane technology described by Nezel et al. (Nezel et al., Analytical Sciences 2003 19:551-556). The $NO_2$-selective liquid polymeric membrane incorporates about 0.13 to 2 wt % of aquacyanocobalt (III)-hepta(2-phenylethyl)cobyrinate perchlorate (Fluka), with chromoionophores ([11-[(1-butylphenyl)oxy]-11-oxoundecyl-4-{[9-(dimethylamino)-5H-benzo[a]phenoxazine-5-ylidene]-amino}-benzenate]} and 2',4',5',7'-tetraiodofluorescein octadecyl ester in a concentration of about 100 to 400 mol % with respect to the cobalt compound. Polyvinylchloride (PVC) and bis(2-ethylhexyl)sebacate (DOS) (Fluka) as a plasticizer were used as the matrix in a ratio of about 1:2. The PVC-based ion-selective membranes may then be cast onto platinum, glass, glassy-carbon, or other electrode substrate, with an appropriate geometry, as described above. Semi-permeable membranes and/or anti-thrombotic coatings may additionally be applied, as described above.

In an alternative embodiment, the implantable sensor described above may be modified to incorporate the ion selective electrode membrane described by Johnson et al. (Johnson, R D, et al, Anal Bioanal Chem (2003) 376: 328-341 and Bakker, E, Chem. Rev. 1997, 97, 3083-3132). In addition, ion-selective membranes used for monitoring nitrate and nitrite ions are commercially available (Vernier Software & Technology 13979 S.W. Millikan Way, Beaverton, Oreg. 97005 or Techne® Inc., 3 Terri Lane, Suite 10, Burlington, N.J. 08016). In addition, it is possible to measure nitrite ion concentrations by electrochemical oxidation of nitrite to nitrate, which occurs at a similar potential to the oxidation of nitric oxide to nitrite. Therefore, in another preferred embodiment, measurement of nitric oxide and nitrite and nitrate ions are performed simultaneously, by the use of nitric oxide and nitrite electrodes and nitrate and nitrate ion-selective electrodes. Semi-permeable membranes and/or anti-thrombotic coatings may additionally be applied, as described above.

In an alternative embodiment, the indwelling sensor described above for measurement of nitric oxide or its metabolites may be a modification of the sensors described by Berkels or Kilinc (Berkels, R. et al. A new method to measure nitrate/nitrite with a NO-sensitive electrode. *J Appl Physiol* 90: 317-320, 2001, Kilinc E, et al, J Pharm Biomed Anal. 2002 Apr. 15; 28(2):345-54). These investigators describe the use of a bi-polymer modified, platinum-iridium amperometric microelectrode. Most common biological interferences such as ascorbic acid, uric acid and glucose were eliminated via bi-polymer coatings of four layers of Nafion and a layer of 50 mM o-phenylenediamine (OPD). Semi-permeable membranes and/or anti-thrombotic coatings may additionally be applied, as described above.

An alternative system for measuring NO, involves the use of a microchip sensor (Zhang, X, et al., "A Novel Microchip Nitric Oxide Sensor with sub-nM Detection Limit", Electroanalysis 2002; 14(10):697-703. This system is also commercially available and may be modified for use in the current invention. An alternative microchip sensor for NO detection which is suitable for use in the present invention has been reported by Naware et al. (M. Naware, A. Rege, R. Genov, _M. Stanacevic, G. Cauwenberghs and N. Thakor "Integrated Multi-Electrode Fluidic Nitric-Oxide Sensor and VLSI Potentiostat Array" Circuits and Systems, 2004. ISCAS '04. Proceedings of the 2004 International Symposium on, Volume: 4, 23-26 May 2004 pp:IV-25-8.) The geometry of these microchips may be changed from about 5 mm×5 mm, to something more suitable for an indwelling monitor, such as approximately 1 mm×10 mm. As before, semi-permeable and/or thromboresistant coatings are applied, as described above.

In an alternative embodiment, the indwelling sensor described above for measurement of nitric oxide or its metabolites may be a modification of the sensor described by Itoh Y, et al (Anal Biochem. 2000 Dec. 15; 287(2):203-9). In this embodiment, diaminofluorescein DAF-FM and its diacetate (DAF-FM T) are used for fluorescent detection of NO. DAF-FM is converted via an NO-specific mechanism to an intensely fluorescent triazole derivative (DAF-FM T). In the presence of 1 μM DAF-FM, the concentration of NOR-1, an NO donor, in the range of 2-200 nM was linearly related to the fluorescence intensity. However, this reaction is slower than the use of an NO electrode, having a maximal response at about 30 minutes. This fluorescence reaction for monitoring NO may be monitored by the use of optodes, as described above for arterial blood gas monitoring, or by the immunosensor, described above. An excitation light source at a wavelength of 500 nm is passed through the fiberoptic and reacts with the DAF-FM. The emission wavelength is at 515 nm. A photodiode detects the fluorescence intensity, and sends a signal via the radiotransmitter to an external alarm device worn by the patient. Alternatively, the alarm system can be set to contact someone besides the patient via telephony, such as a relative or physician, to notify them that immediate action needs to be taken.

Figure 26:
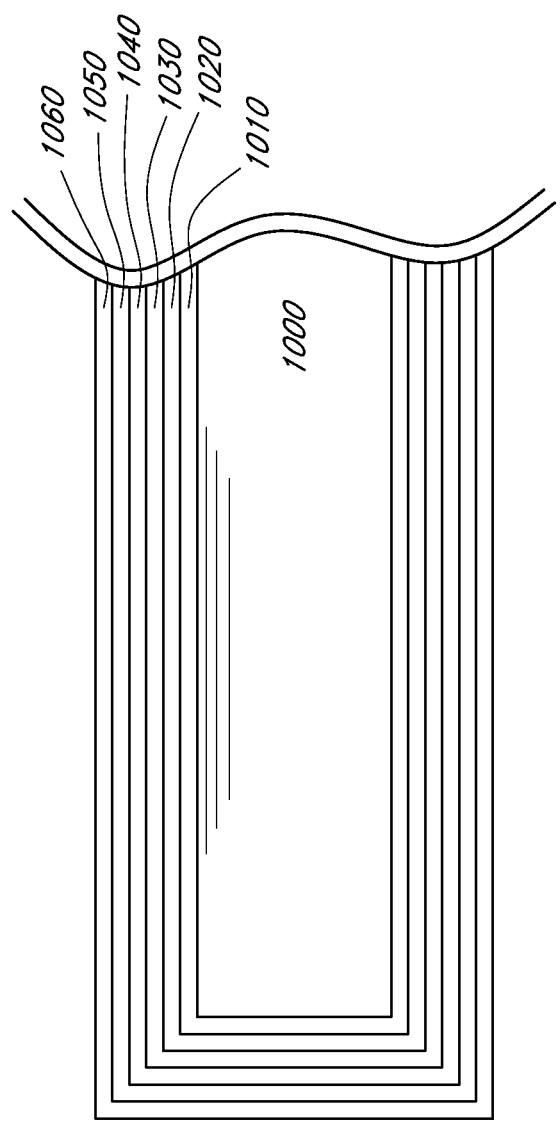
FIG. 26 is a side view of a nitrite sensor tip, with a series of membranes to allow the diffusion of nitrite from the patient to be reacted with acid and iodide to form nitric oxide, and a sensor for monitoring nitric oxide.

In an alternative embodiment, the indwelling sensor described above for measurement of nitric oxide or its metabolites may be a modification of an existing NO sensor, allowing its use as an $NO_2$ sensor. It is known that $NO_2$ can be converted stoichiometrically into NO in the presence of KI and $H_2SO_4$. Referring to FIG. 26, a sensor is shown which includes as its innermost layer, a commercially available NO sensor 1000, such as those available from WPI, (Sarasota, Fla.), Innovative Instruments, (Tampa, Fla.), Diamond General (Ann Arbor, Mich.), or Inter Medical Co., Ltd., (Nagoya, Japan). This NO sensor 1000 is modified by coating it with an acidic polymeric membrane 1010, such as poly(acrylic acid) (PAA), which provides an acidic catalyst for the conversion of $NO_2$ to NO. The PAA may be applied directly to the NO sensor 1000 surface by precipitation, dip coating or spray coating. The concentration and molecular weight of the PAA solution may also be varied from approximately 0.01% (w/v) to 80% (w/v) and from 1000 MW to 500,000 MW in order to vary the thickness of the coating layer. Once the PAA is applied, it may be grafted onto the outer membrane of the NO sensor by plasma polymerization, or by e-beam or gamma irradiation or by UV-crosslinking in the presence of benzophenone. In an alternative embodiment, the PAA may be grafted onto the NO sensor 1000 membrane by plasma polymerization of acrylic acid monomer, as described by Winnik et al. (Winnik, F M, et al, "Polyacrylic acid pore-filled microporous membranes and their use in membrane-mediated synthesis of nanocrystalline ferrihydrite," Can. J. Chem. 76(1):10-17 (1998).) The acidic membrane 1010 is surrounded by an isotonic iodide solution 1020. This layer provides a reservoir of iodide for the reduction of $NO_2$ to NO. In addition, the iodide may be present as part of a gel layer (not shown), similar to that described by Schults et al (U.S. Pat. No. 6,001,067, issued Dec. 14, 1999). Outside the gel or solution layer is a degradable, iodide-containing polymer matrix 1030 prepared from poly(lactide-co-glycolide) (PLGA) or poly(caprolactone) (PCL). The PLGA matrix, which may contain pores to allow for the passage of nitrite, is surrounded by a microdialysis membrane 1040 which can allow diffusion of small molecules such as nitrite. The microdialysis membrane 1040 may be made from materials such as cellulose acetate, cellulose ester, poly(vinylidene fluoride) (PVDF), nylon, polyurethane, polyamides, polycarbonate-ethers, regenerated celluloses and polyacrylonitriles (PAN) or other biocompatible materials as known in the art. The molecular weight cutoff for this membrane is preferably less than 30,000 daltons. Surrounding this microdialysis layer is a bioprotective layer 1050 made from ePTFE. Preferably, the bioprotective layer 1050 is constructed of expanded PTFE with a pore size of about 0.2 microns to about 0.5 microns and a thickness of about 15 to about 35 microns. Most preferably, the bioprotective layer is constructed of expanded PTFE with a pore size of 0.4 microns and a thickness of approximately 25 microns (e.g., Millicell CM-Biopore; Millipore). The outermost layer is a thromboresistant and/or antiproliferative coating 1060, as described previously, consisting of either heparin or hirudin, or a hydrogel, such as poly(ethylene glycol) PEG, poly(vinylpyrrolidone) (PVP), an anticoagulant (such as heparin or hirudin), or an antiproliferative agent, such as paclitaxel or sirolimus, or other coatings as described previously. In another alternative embodiment, the PAA may be dispersed within the iodide layer, but not bonded to the hydrophobic membrane. In this manner, the PAA may also provide an acidic environment for reaction of $NO_2$.

The nitric oxide sensor may be factory-calibrated using a nitric-oxide donor compound, such as S-nitroso-N-acetyl-D, L-penicillamine (SNAP), or using a solution of sulfuric acid and potassium iodide, to which a known amount of potassium nitrite is added. In the latter case, the nitrite is converted stoichiometrically to nitric oxide (Zhang, Mod Asp Immunobiol 2000). Additionally, if deemed appropriate for the patient, calibration may be performed following implantation by local administration of a NO-releasing agent, such as nitroglycerin. The system may not require a high degree of accuracy, because there is a large burst of NO during ischemic stroke, and as long as such a rate of change due to the burst was detected, the exact concentration level may not be critical.

Also, the rate of change of NO or $NO_2$ or NO could be monitored. A rate of change in NO concentrations of about 0.1% per second to about 100% per second can be indicative of stroke in some humans. In certain situations, a rate of change of $NO_2$ or NOx of about 0.01% per second to about 10% per second can be indicative of stroke. Alternatively, the amount or level of change in NO or $NO_2$ or NO concentrations can be monitored. A level of change of NO of about 100% to 100,000% can be indicative of a stroke in humans. A level of change of $NO_2$ or NO of about 10% to 1000% can be indicative of a stroke in humans.

Nitric oxide and its metabolites are released in two stages. The first stage of NO/NOx release begins to occur within 1 to 10 minutes of ischemia. The second stage begins to occur within a few hours of ischemia. If the rate or level of change is detected in the first stage, then the patient is more likely to benefit from treatment. If the rate or level of change is detected in the slower, second stage, the physician is made aware that the patient is suffering further injury.

An implantable sensor of an embodiment of the present invention can also be designed to sense cerebral ischemia by monitoring glutamate Like NO, glutamate is also released into blood plasma during the ischemic cascade following stroke, so detection of glutamate levels provides an alternative method for monitoring stroke. Clinical trials have shown a correlation between glutamate concentrations in plasma and cerebrospinal fluids, and the degree of neurological deficit following stroke (Castillo J, Davalos A, Naveiro J, and Noya M, Stroke 1996; 27:1060-1065).

The glutamate sensor is an enzymatic sensor, similar to the enzymatic glucose sensor described herein, with the exception that 1-glutamate oxidase is used instead of glucose oxidase. The chemical reaction is given below:

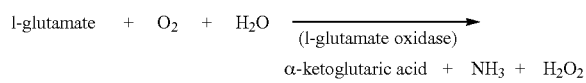

The oxygen or hydrogen peroxide then undergoes a redox reaction at a second electrode to produce an electric current. A two-electrode system is used, in which the first electrode monitors either the consumption of oxygen, or the production of hydrogen peroxide in the presence of the enzyme, and the second electrode makes the same measurement in the absence of the enzyme. The substrate to be used as the electrode must have an appropriate geometry with an appropriate method for stabilizing the sensor in a vessel as shown in FIG. 1A, 2, 3, 4, 5A, 9A, 10, 11, 14A, 14B, 15A, 15B, 16, 18, 21A, 21B, 22A, 23, 25A, or 27A, 27B, 27C of this patent application and related text. Once the substrate geometry is selected, the sensor electronics will be hermetically sealed using either a glass, ceramic, epoxy, or metal housing in order to prevent corrosion, with the electrode portion crossing the hermetic seal. The electrode is comprised of a carbon fiber or platinum wire or tin-indium oxide layered on glass substrate, or other electrode substrates as are known in the art. Next, the electrode is coated with an enzyme-gel layer, such as described, for example, by Burmeister et al (Burmeister J J, Gerhardt G A, Anal Chem 2001 Mar. 1; 73(5):1037-42), and by Niwa et al. (Niwa O, Horiuchi T, Torimitsu K, Biosens Bioelectron 1997; 12(4):311-19.) These enzymatic sensors may be constructed in a manner similar to glucose sensors described herein, substituting glucose oxidase with 1-glutamate oxidase in the enzyme-gel layer. Enzymatic glutamate sensors are commercially available from Pinnacle Technology (Lawrence, Kans.), Applied Enzyme Technology (Gwent, UK), and a fluorescent version is available from Intelligent Optical Systems (Torrance, Calif.). Surrounding the enzyme-gel layer is a microdialysis membrane made from materials such as cellulose acetate, cellulose ester, poly(vinylidene fluoride) (PVDF), nylon, polyurethane, polyamides, polycarbonate-ethers, regenerated celluloses and polyacrylonitriles (PAN) or other biocompatible materials as known in the art. The molecular weight cutoff for this membrane is preferably less than 30,000 daltons. Surrounding this microdialysis layer is a bioprotective layer made from ePTFE, as described above. In addition, a thromboresistant coating may be added, such as an anticoagulant (like heparin or hirudin), a thromboresistant material such as phosphoryl choline, a hydrogel (such as poly (ethylene glycol), poly(N-vinyl pyrrolidone), poly(hydroxyl ethylmethacrylate), polyacrylamide, polyacrylic acid, cross-linked collagen, sulfonated polyurethane or other sulfonated polymer, or other thromboresistant materials as are known in the art. In addition, this thromboresistant layer may release a pharmacological agent that inhibits cell proliferation or migration.

Figure 21A:
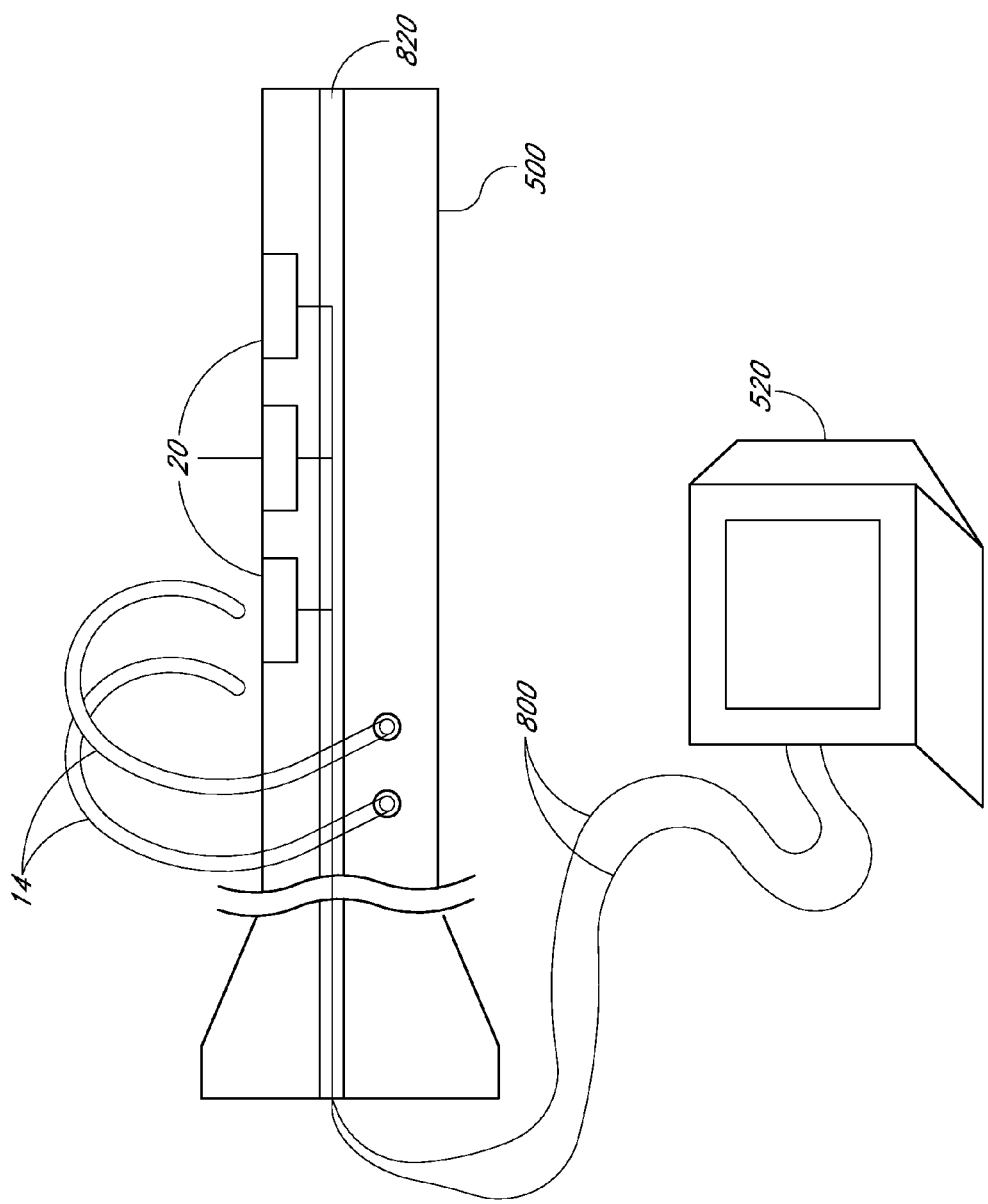
FIG. 21A is a diagram of a catheter with a sensor and an anchoring platform which stabilizes the sensor near the side of a lumen, and an external monitoring system.
Figure 21B:
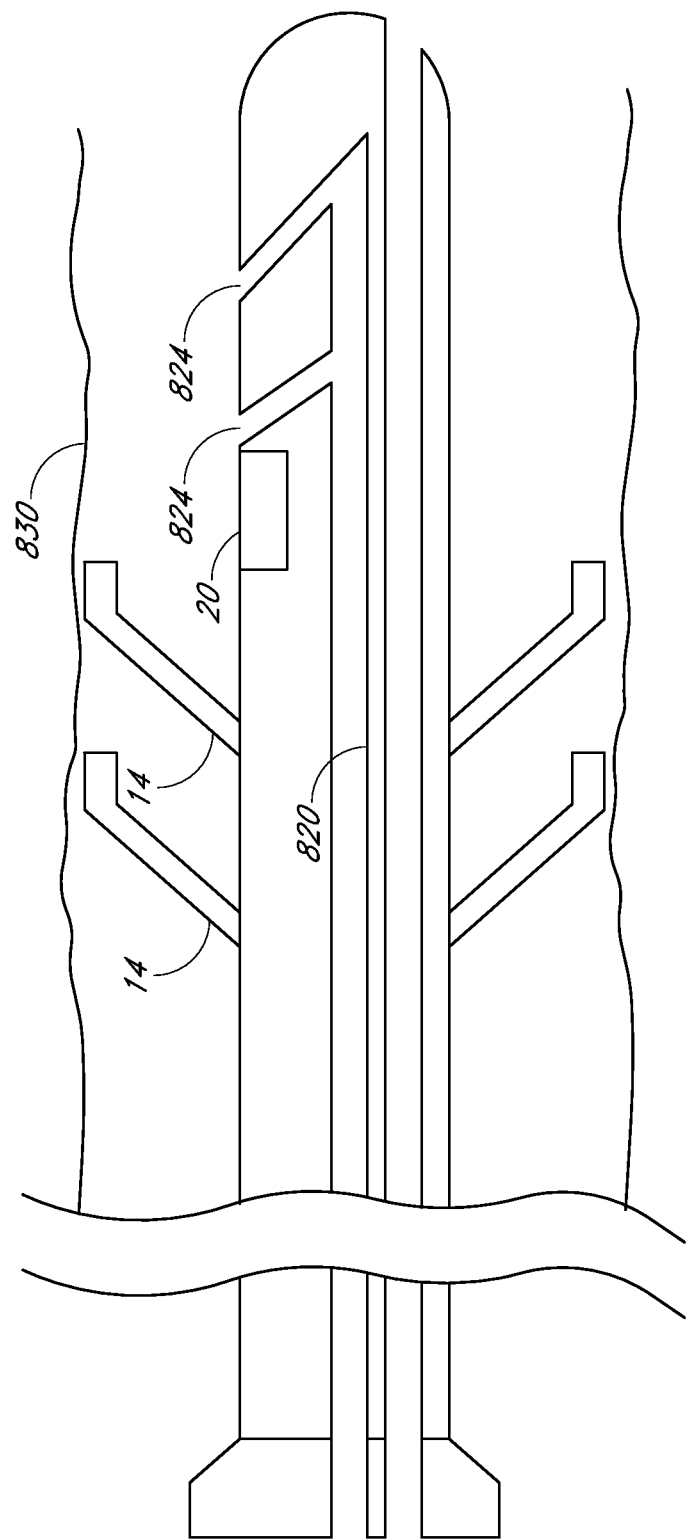
FIG. 21B is a side view of a catheter with a sensor and side holes within the catheter wall for the purpose of flushing the sensor surface, and an anchoring platform which stabilizes the sensor in the middle of a lumen.

Further, the enzymatic sensor is preferably configured to monitor the consumption of oxygen, since in this application, detection of high concentrations of glutamate are more critical than low concentrations. In addition, the glutamate sensor may be further configured as either an implantable sensor described herein, or may be configured for short-term use in combination with a catheter. In both cases, the anchoring platform (as shown in FIG. 21A or 21B for the catheter configuration) would help to minimize each of the problems associated with intra-vascular monitoring. These would act as positioning stabilizers to orient the sensing surface into the vessel lumen, reduce thrombus formation, minimize the wall effect, prevent vasospasm, and prevent sensor movement.

The use of a fluorescent glutamate sensor in combination with a catheter has been described in U.S. Pat. No. 6,738,651 to Jackson, issued May 18, 2004. However, the sensor described by Jackson is one that slides through a catheter, rather than one that is attached and exposed to the exterior of a catheter, as in the present invention, as shown in FIGS. 16, 18, 21A, 21B, 22A, 25A, 27A, 27B, and 27C. As with the intra-arterial blood gas monitors and nitric oxide sensors described herein, it is anticipated that thrombus formation at the tip, measurement of analyte concentrations in the vascular wall instead of the blood stream, vessel compression due to patient movement, vasospasm and catheter movement will limit the effectiveness of this device.

While Jackson et al (U.S. Pat. No. 6,738,651, issued May 18, 2004) recommend monitoring of glutamate concentrations, determination of glutamate concentration alone may not be an accurate method for determining whether a stroke is occurring during surgical procedures. Indeed, it has been shown (James D. Reynolds, David W. Amory, Hilary P. Grocott, William D. White, and Mark F. Newman, "*Change in Plasma Glutamate Concentration During Cardiac Surgery Is a Poor Predictor of Cognitive Outcome*" *J Cardiothoracic Vascular Anesthesia,* 16(4) (August 2002): 431-436) that changes in glutamate levels did not correspond to cerebrovascular accidents (CVA) during a surgical procedure. However, these investigators only made discrete measurements of glutamate concentration at various times during surgery, but it is possible that the rate of change of glutamate concentrations may be indicative of stroke, similar to what is seen with $NO_x$. Such measurements can be made when the sensor monitors the analyte on a continuous basis. The method described by Jackson et al. requires that the sensing probe within a catheter be manipulated by the physician in the event that signal is interrupted, to insure that the sensor is not fouled. This adds complexity to the surgical procedure. In addition, once the patient has been discharged from the hospital, it is impractical for them to perform this task, and therefore such a sensor would not be practical for the post-operative period, when the patient is at high risk for stroke. Therefore, the glutamate sensors described in the current invention can be configured to measure both the concentration and rate of change of glutamate concentration.

An implantable sensor of an embodiment of the present invention can also be designed to sense cerebral ischemia by monitoring amino acids. In addition to the excitatory amino acids glutamate and aspartate, there are amino acids involved in nitric oxide production including arginine, citrulline, and ornithine, which can be monitored in another aspect of this invention. According to Cheman et al., (Cheman L, et al, "Brain Nitric Oxide Changes after Controlled Cortical Impact Injury in Rats," J. Neurophysiol, 83:2171-2178, 2000), both arginine and citrulline are significantly increased following traumatic brain injury. A suitable enzyme electrode for this invention must have a substrate with an appropriate geometry, must be stabilized in a vessel, have hermetically sealed electronics, and be coated with a gel-enzyme layer as described previously. Arginine and citrulline may be monitored by using an enzyme based hydrogen-peroxide electrode, as described above for glucose and glutamate sensors. For arginine, a two enzyme system may be used, in which the first enzyme, arginase, converts arginine to citrulline. For citrulline, the enzyme may be L-amino acid oxidase (Worthington Biochemical, Lakewood N.J.). The gel-enzyme layer is then covered with a semi-permeable membrane with a molecular weight cutoff of 30,000 daltons, which may comprise ePTFE, Dacron®, polyurethane, silicone rubber, poly(lactide-co-glycolide) (PLGA), poly(caprolactone) (PCL), poly(ethylene glycol) (PEG), collagen, polypropylene, cellulose acetate, poly(vinylidene fluoride) (PVDF), or other biocompatible material. In addition to the semi-permeable membrane, a bioprotective membrane, as described above, and a thromboresistant coating may be added, such as an anticoagulant (like heparin or hirudin), a thromboresistant material such as phosphoryl choline, a hydrogel (such as poly(ethylene glycol), poly(N-vinyl pyrrolidone), poly(hydroxyl ethylmethacrylate), polyacrylamide, polyacrylic acid, cross-linked collagen, sulfonated polyurethane or other sulfonated polymer, or other thromboresistant materials as are known in the art. In addition, this thromboresistant layer may release a pharmacological agent that inhibits cell proliferation or migration, as described above.

An implantable sensor of an embodiment of the present invention can also be designed to sense cerebral ischemia by monitoring acetylcholine. Cerebral ischemia may also result in significant changes in acetylcholine levels (Bertrand N, et al, J Cereb Blood Flow Metab. 1993 September; 13(5):789-95 and Beley A, et al, Neurochem Res. 1991 May; 16(5):555-61). Acetylcholine may be detected using an enzyme electrode, similar to that described for glucose, glutamate, arginine and citrulline. This enzyme electrode is made from an appropriate material, have an appropriate geometry, and may have an appropriate method for stabilizing the sensor in a vessel as described above. The sensor electronics will be hermetically sealed as described above. Next, the electrode is coated with an enzyme-gel layer, such as described above for glucose and glutamate electrodes. In this case, the enzymes are acetylcholinesterase and choline oxidase. Similar enzyme electrodes are commercially available from Bioanalytical Systems, Inc. (West Lafayette, Ind.). Surrounding the enzyme-gel layer is a microdialysis membrane, and a bioprotective layer, as described above. A thromboresistant coating may also be added, as described above. In addition, this thromboresistant layer may release a pharmacological agent that inhibits cell proliferation or migration.

An implantable sensor of an embodiment of the present invention can also be designed to sense cerebral ischemia by monitoring dopamine. In addition to NO, nitrite, and glutamate, dopamine may also serve as a potential indicator for stroke, especially in regions of the brain that are subject to "silent infarcts" (Emilia Saulle, et al, "Endogenous Dopamine Amplifies Ischemic Long-Term Potentiation via D1 Receptors", *Stroke*. 2002; 33:2978-2984.) Dopamine can be monitored electrochemically, and the rate of release of dopamine can be determined using either high-speed chronoamperometry or fast-scan cyclic voltammetry (Robinson, D L et al, "Detecting Subsecond Dopamine Release with Fast-Scan Cyclic Voltammetry in Vivo", Clin Chem 49(10):1763-1773). Carbon-fiber, platinum, or other appropriate microelectrodes with appropriate stabilization methods as described above may be used to monitor dopamine. The sensor electronics may be hermetically sealed, and the electrode may be surrounded with a microdialysis membrane, and a bioprotective layer, as described above. A thromboresistant coating may also be added, as described above. In addition, this thromboresistant layer may release a pharmacological agent that inhibits cell proliferation or migration. Dopamine electrodes such as the type commercially available from Cypress Systems (Lawrence, Kans.), may be modified as described above, in order to be used in the present invention.

Figure 24:
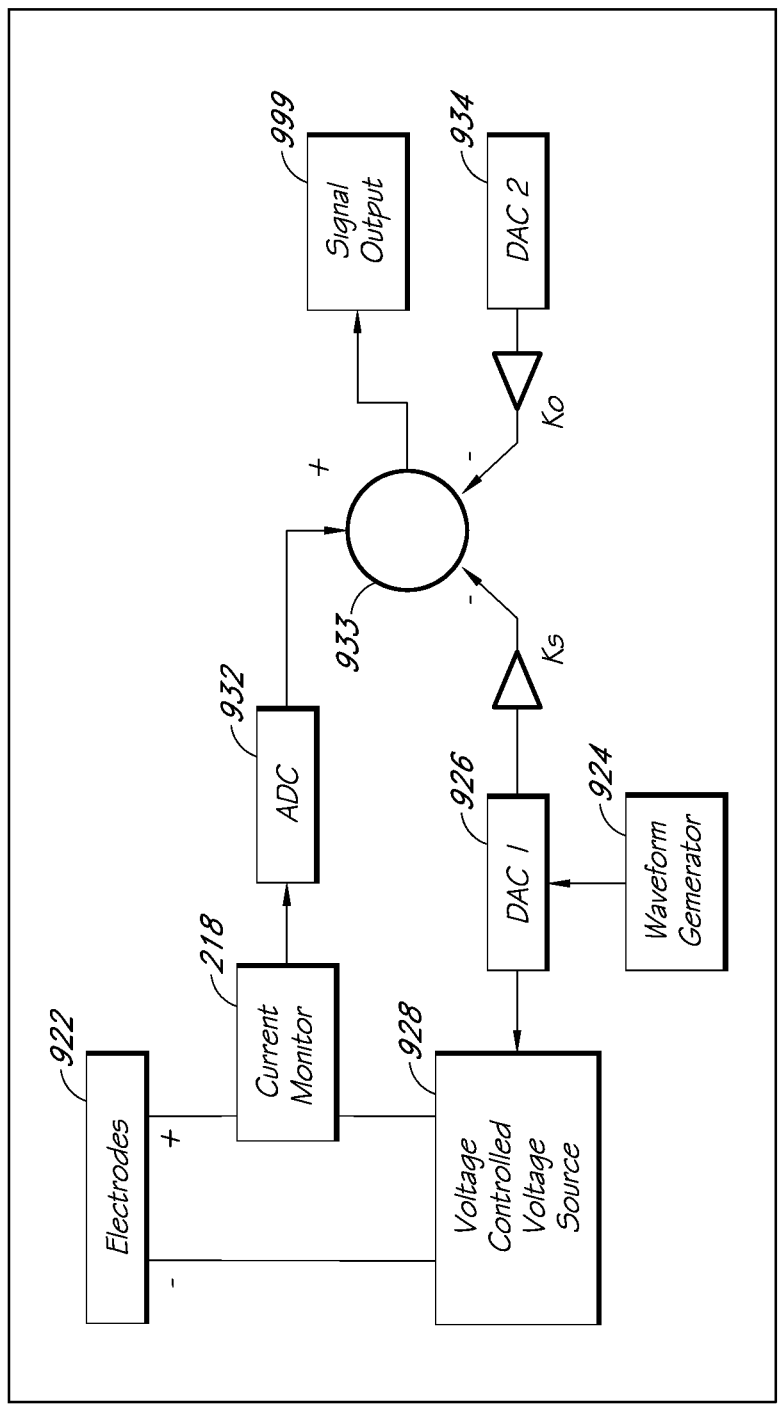
FIG. 24 is a block diagram showing circuitry for fast-scan cyclic voltammetry.

In order to measure dopamine, a fast-scan cyclic voltammetry circuit shown in FIG. 24 can be used. The waveform generator 924 generates pulses whose shape, pulse width, and repetition frequency can all be independently loaded into the device. A digital-to-analog converter (DAC 1) 926 drives a voltage source 928, which in turn drives the electrodes 922 which induces a potential across the two electrodes. This potential results in a current through the solution which is converted to a voltage level by the current monitor 218 which is then measured by the analog-to-digital converter (ADC) 932. Since there is a large background current on the measurement, the DAC value from DAC 1 926 is subtracted from the measured signal at the summing junction 933 obtained from ADC 932, leaving only the residual signal output which is induced by the analyte concentration. There is both a DC (Ko) offset (controlled by DAC 2, 934) and scale (Ks) coefficient that can be set to accommodate the particular electrodes being used. The signal output 999 from the summing junction 933 then becomes the input (for example to sensor 20 or sensor array 870, as shown in FIGS. 19B and 19A, respectively) to further signal processing.

An implantable sensor of an embodiment of the present invention can also be designed to sense cerebral ischemia by monitoring nitrate using the enzyme nitrate reductase. In this case, the enzyme nitrate reductase converts nitrate into nitrite. The nitrite is then electrochemically oxidized back to nitrate, and provides an electrical current that is measured amperometrically. The substrate to be used as the electrode must be made from an appropriate material, with an appropriate geometry and be stabilized in a vessel as described previously. Once the substrate geometry is selected, the sensor electronics will be hermetically sealed. Next, the electrode is coated with an enzyme-gel layer. These enzymatic sensors may be constructed in a manner similar to glucose sensors described herein, substituting glucose oxidase with nitrate reductase in the enzyme-gel layer. The gel-enzyme layer may be surrounded with a microdialysis membrane, and a bioprotective layer, as described above. A thromboresistant coating may also be added, as described above. In addition, this thromboresistant layer may release a pharmacological agent that inhibits cell proliferation or migration.

Figure 19A:
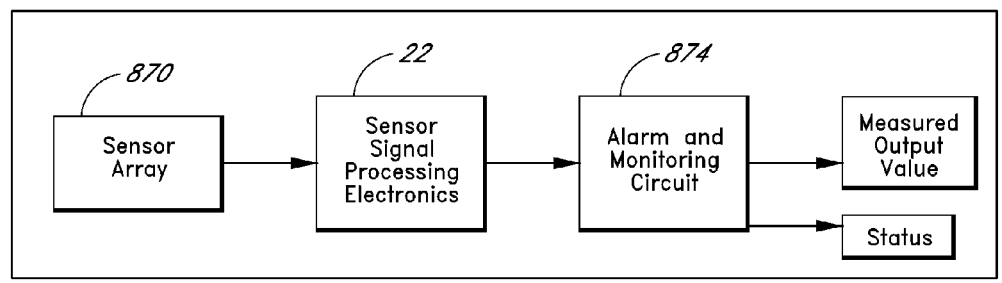
FIG. 19A is a system level block diagram for a sensor.

Referring now to FIG. 19A, the sensor system consists of a sensor array 870, sensor electronics 22, and an alarm and monitoring circuit 874. The sensor array detects the analyte level and provides redundancy in case of failure of any one of the sensors. The signal processing electronics 22 conditions the raw sensor signal by amplifying it and removing any external noise components from the signal. The alarm and monitoring circuit 874 provides a user indication of level or rate of change of measured analyte and outputs sensor status. If a level or rate of change is presented to the circuit that is out of range of pre-determined limits, the status will change from "normal" to "alarm".

Figure 19B:
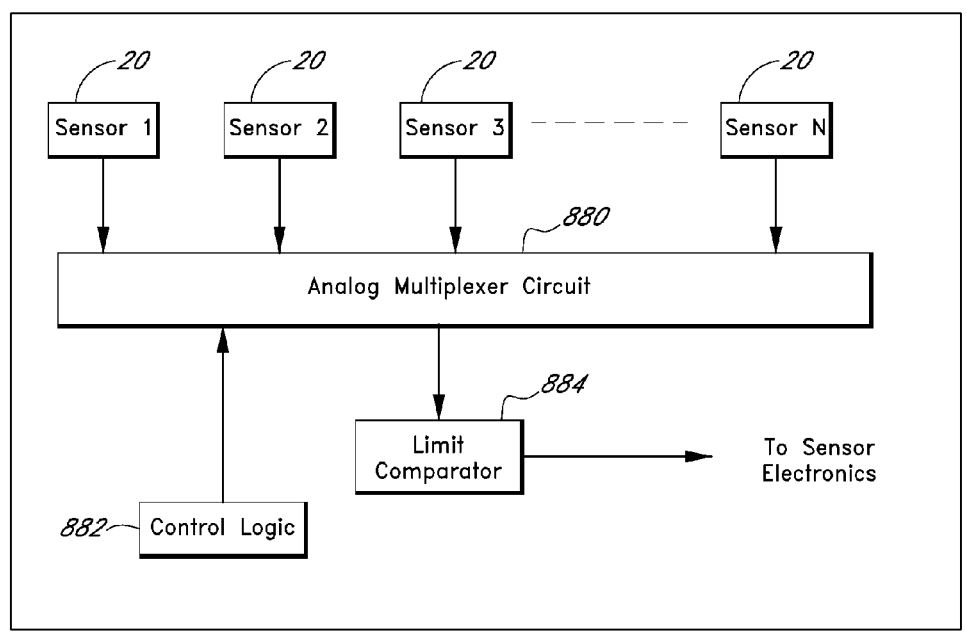
FIG. 19B is a system level block diagram for a sensor array.

In order to provide redundancy for the sensor when used as an intravascular device, the sensor elements used to measure the analyte can be arranged in an array as shown in FIG. 19B. Sensors 1 through N are connected to an analog multiplexer circuit 880. Control logic 882 is used to select one of N sensors 20. If a sensor 20 or connection to that sensor fails, the electrical signal will be outside of preset limits. The limit comparator 884 will detect the out of limit signal and then drive the control logic 882 which will then switch the next available sensor 20 in the array into the circuit.

Figure 19C:
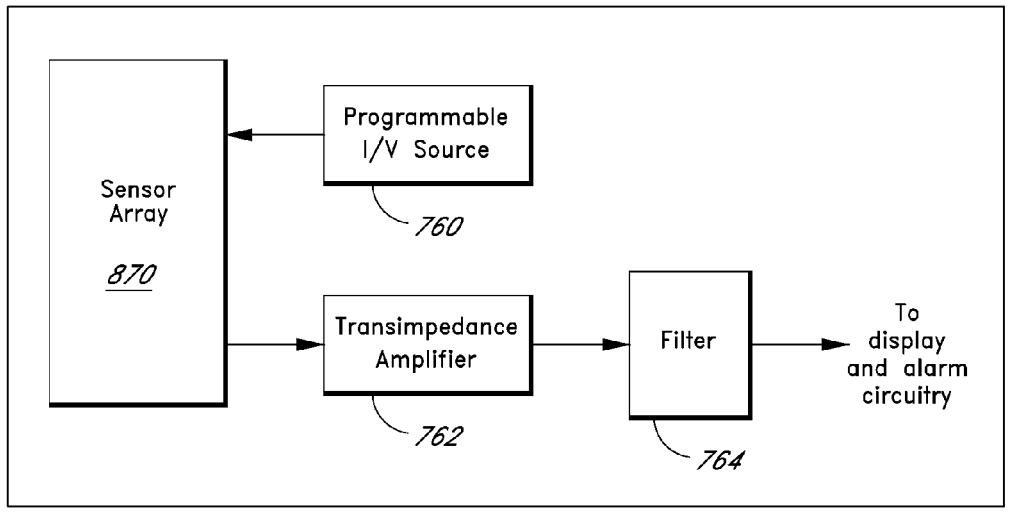
FIG. 19C is a block diagram of the sensor circuitry for measuring nitric oxide or other analyte concentration.
Figure 19D:
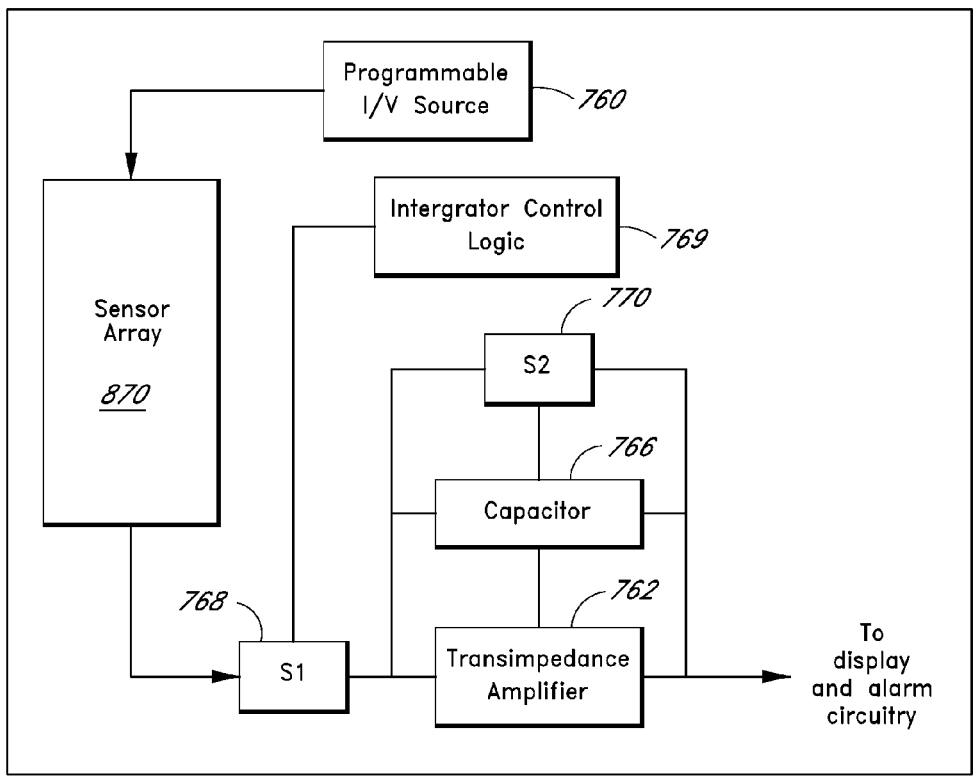
FIG. 19D is a block diagram of the sensor circuitry for measuring nitric oxide or other analyte concentration, when that analyte generates a low current signal.

Two methods of measuring the output of the sensor array are shown in FIGS. 19C and 19D. In both cases, the goal is to provide a voltage output from the raw sensor signal which may be a very small voltage or current. The first method shown in FIG. 19C can be used with a variety of sensors (voltage or current output) and for both types of output, provides a constant voltage output proportional to the sensor signal. The sensor array 870 is driven by either a programmable current or voltage source 760 in order to accommodate various sensor types. The output of the sensor drives a transimpedance amplifier 762 which provides either voltage gain or current-voltage translation, depending again on the type of sensor used. The output voltage is then filtered by filter 764 to remove any noise components in the signal. A notch filter for rejecting 60 Hz line noise may be used as well as a low-pass filter to reject any high-frequency components in the signal. The type of filters used will be determined by the actual analyte being measured. In the case of a low-pass filter, the filter cutoff should be set to a value that is equal to or greater than the bandwidth of the signal from the sensor electronics. For instance, if the rate of change of nitric oxide has a time constant tau, of 10 seconds, and one assumes an exponential rise-time, then the bandwidth of the system in hertz is 1/(2*pi*tau) or 0.0159 Hertz. To reject only noise while still allowing the signal to pass, the cutoff frequency of the low-pass filter should be set about 10-20% higher than the signal or to 0.018 Hz in this case. The final signal is fed to the monitoring/alarm circuitry shown in FIG. 19E. In the case of a current based sensor, a current-voltage conversion is performed. In the case of a voltage based sensor, no conversion is needed.

Figure 19E:
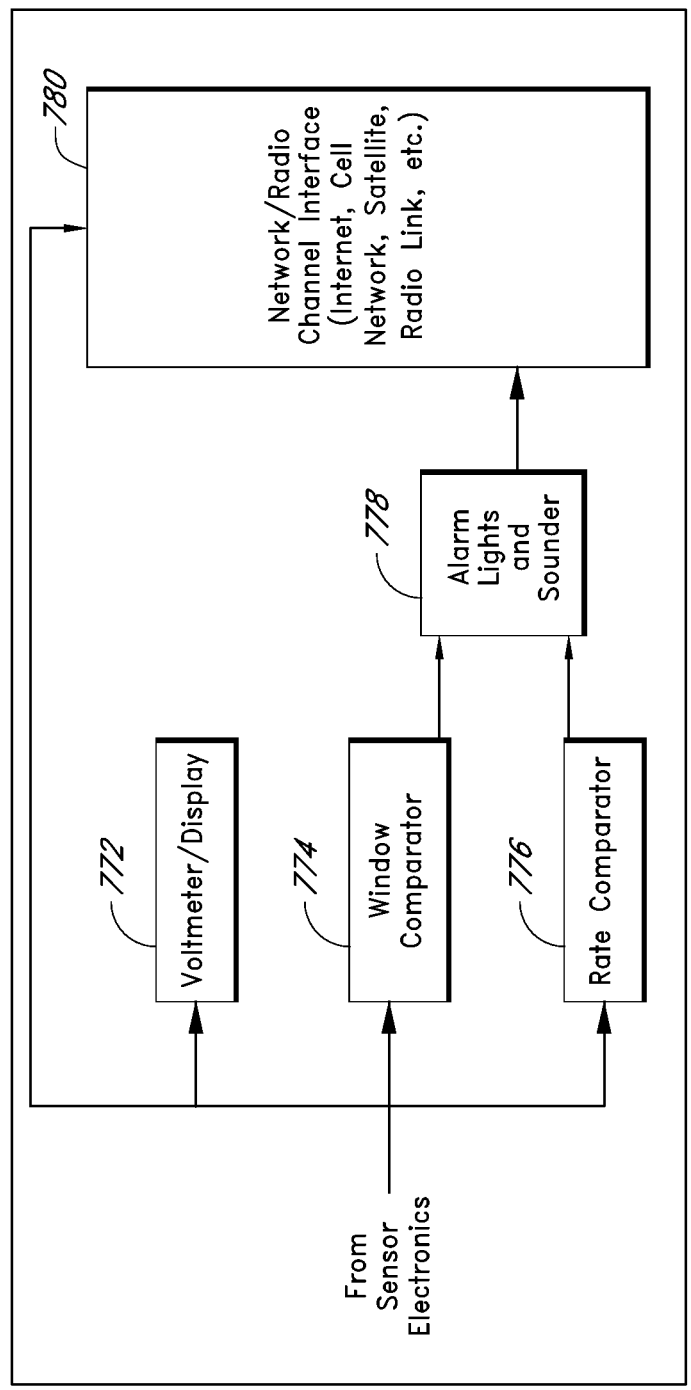
FIG. 19E is a block diagram of the sensor circuitry for signaling an alarm or indicating sensor failure.

Referring to FIG. 19E, the sensor signal is passed to three main circuits; 1) a voltmeter/display 772 to provide a visual display of the signal and/or analyte level with proper units, 2) a window comparator 774 which detects whether the signal is within a pre-determined window defined by low and high limits (i.e. low_limit<x<high limit) and 3) a rate comparator 776 that detects the rate of change of the signal level. The outputs of these three circuits are then sent to circuit 778 that drives lights and an audible alarm to provide user feedback. In addition, the information is passed on to the Network/Radio Channel Interface, 780, so that this information is available at a remote site.

Now referring to FIG. 19D, the second method of measuring a sensor is described that is preferable for sensors with extremely low output currents (1-100 pA). The transimpedance amplifier 762 is configured as an integrator by using a capacitor 766 in the feedback path and two switches S1 768 and S2 770. The switches are low-leakage FET types that are driven by the external control logic shown in FIG. 19D. There are three functional states to the integrator: 1)Integrate, 2) Reset/Dump and 3) Hold. The state of the integrator is determined by the control logic and cycles between reset, Integrate, dump/reset to perform each measurement. This process is repeated indefinitely while measurements are being made.

To make a measurement, the integrator is first reset by the control electronics 769 by closing dump switch S2 770 and opening integrate switch S1 768. Next, the signal is integrated over time by opening S1 768 and closing S2 770 for t seconds where t is the desired integration time. Finally, the integrator enters the hold state by opening S2 770. It is at this point that the voltage present at the output is proportional to the input current to the integrator. For an integrator configured in this manner, $V_{out}$ will be as follows; $V_{out}=-I*T/C$ where −I is the input current, T is the integration time, and C is that value of the feedback capacitor 766 in FIG. 19D. This process is repeated for the next measurement.

FIG. 19E shows the alarm and monitoring circuitry for the system. The processed analyte signal from the sensor electronics is fed to a voltmeter 772 to provide a visual indication of the level of the signal. The signal is also fed to a window comparator 774 and rate comparator 776 circuit. The window comparator provides upper and lower limit alarms that can be used to detect whether or not the sensor is operating normally. The rate detector is used to determine the rate of change of the measured parameter. If the rate limits are exceeded, that status is sent to the alarm panel 778 and network/radio channel interface 780. Limits for the rate and window comparator circuits can be set manually or over the network/radio channel interface 780. The sensor status would show up on the alarm panel 778, or optionally be transmitted over the network or radio channel interface 780 to alert the doctor or patient in the event of an out of limit signal as described above.

Figure 18:
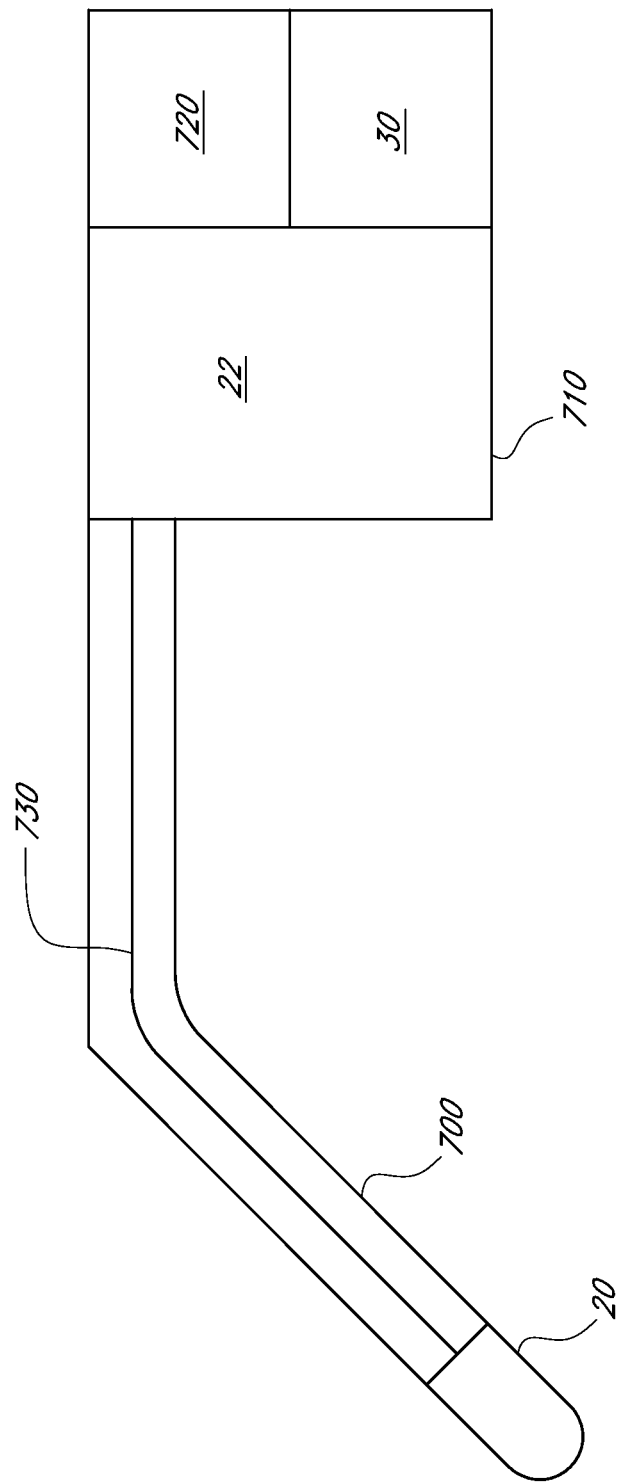
FIG. 18 is a side view of a catheter containing a nitric oxide sensor.

In an alternative embodiment, as shown in FIG. 18, the nitric oxide or nitrite or nitrate sensor 20 may be incorporated into the distal end of a catheter-like tube 700. The proximal end of the catheter-like tube is attached to a hermetically sealed enclosure 710 which contains the antenna 30 and/or battery 720, and the electronic circuitry. Wire leads 730 are then used to connect the sensor 20 with the electronic circuitry. The device is implanted in a patient in a manner similar to transvenous pacemaker insertion which is well known to those of skill in the art. The physician makes a small incision in the skin, and then creates a hole in the vein to insert the distal tip of the catheter containing the sensor using techniques known to those of skill in the art. The hole is preferably smaller than the diameter of the distal tip of the catheter so that the distal tip is forced to stay in place. The distal tip containing the sensor is then advanced into the vein either blind or using ultrasound guidance. The enclosure containing the electronics is then placed subdermally, and the insertion site is closed using standard surgical techniques known to those of skill in the art. The signal indicative of the nitric oxide or nitrite or nitrate present is transmitted to a device worn externally by the patient, as described previously, and can communicate to the patient by an alarm which is either auditory or vibratory, or in the event of a stroke, can transmit information by telephony to either a physician, relative, caregiver, or emergent care provider.

In an alternative embodiment, the implantable catheter described above for measurement of nitric oxide or its metabolites, or other chemical analytes may instead be connected to electronic circuitry that is external to the patient. In this embodiment, shown in FIG. 21A, the catheter 500 contains one or more sensors 20, positioned to face radially inward, and capable of monitoring substances such as NO, NOx, or glutamate, or other physical or chemical signals, with electronic leads 800 extending from the sensor via the catheter to a monitoring system 520 which is external to the patient. The catheter may be made of nylon, polyurethane, PEBAX, silicone rubber, or any of a variety of other materials as known to one skilled in the art, and may contain a braided wire mesh for improved performance. In addition, the catheter may contain one or more lumens 820, such as for guidewire access, flushing or contrast injection, and placement of the electronic leads. In addition, in order to minimize flow disturbances at the sensor interface, it is preferable to position the sensor some distance away from the distal end of the catheter 510. The distance between the distal end of the catheter and the sensor can be about ten times the diameter of the catheter. The sensing surface is exposed to the outside of the catheter. Further, to improve the hemodynamic behavior of the sensor and reduce thrombus formation on the sensor surface, the catheter may possess positioning anchors 14 made of a shape-memory material such as nitinol, elgiloy or phynox, and formed into a curve having a diameter which is approximately 1-10 mm larger than the vessel in which the sensor will be placed such as those shown. For example, an internal jugular vein may have a diameter ranging from 10-20 mm, so the anchors may range from 11-30 mm in diameter. Positional stability aids in detection because it is known that the concentration of NO, NOx or glutamate or other analyte may vary with position. The positioning anchors are placed either proximally to the sensor, or at a distance of about 10 times the diameter of the catheter distally from the sensor, and on one or both sides of the sensor. As shown in FIG. 21B, the positioning anchors 14 may alternatively position the sensor 20 or the catheter containing the sensor in the middle of the vessel 830, using positioning anchors 14, analogous to those shown in FIGS. 15A and 15B. The catheter with positioning anchors may be delivered to the monitoring site through a larger, guide catheter, so that the positioning anchors can be delivered more easily. As shown, multiple sensors may be placed along the length of the catheter, so that in the event that one sensor becomes fouled, the other sensors will still perform properly.

In another embodiment of this invention, shown in FIG. 21B, a flushing lumen 820 may have side-hole ports 824 both proximally and distally to the sensors 20, and the flushing lumen may be configured for continuous delivery of the flushing fluid past the sensor surface, thereby removing any fouling material. Other lumens and catheter features, known to those of skill in the art, have been omitted from FIG. 21B for simplicity.

Figure 21D:
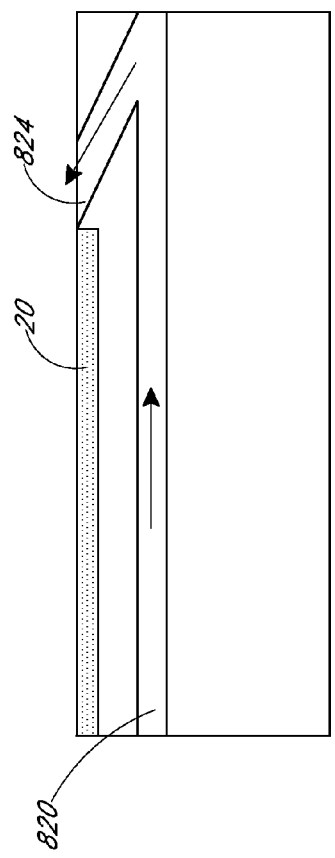
FIG. 21D is a side view of a catheter with a sensor and side holes within the catheter wall for the purpose of flushing the sensor surface.
Figure 21C:
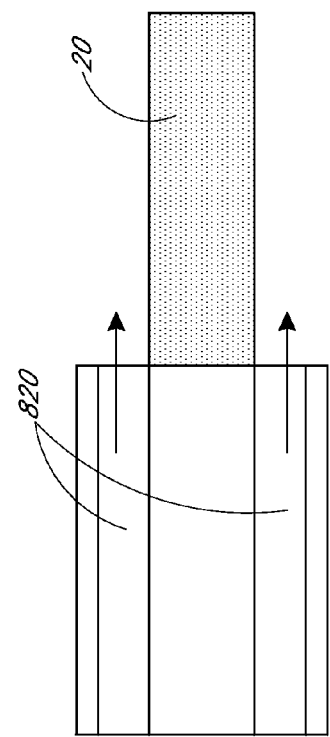
FIG. 21C is a side view of a catheter with a sensor and flushing lumens within the catheter wall for the purpose of flushing the sensor surface.

Referring now to FIG. 21C the potential for thrombus accumulation on the sensor (20) surface is reduced by directing a stream of normal saline or other physiological fluid through a flushing lumen (820) past the surface of the membrane either intermittently or in a continuous fashion, and at flow rates ranging from 0.1 to 100 ml/min. It may also be used to reduce accumulated thrombi. In FIG. 21D, the flushing fluid is directed through sidehole ports 824. The flushing fluid may be directed either towards the tip of the catheter or towards the hub.

Referring now to FIG. 22A, in a further aspect of this invention, it is possible to combine one or more sensors within a single sensor housing. For example, simultaneous detection of nitrite and glutamate concentration changes may improve the accuracy and reliability of an alarm system beyond that for detection of either analyte individually. The catheter 500 contains a nitrite sensor 904, a nitric oxide sensor 906, and a glutamate sensor 908. The catheter contains a lumen 820 through which electrical leads 800 to the sensors are placed, and which connect to an external monitor 520. Other analytes that may be useful for stroke monitoring include a combination of signals, such as from calcium, potassium, or L-aspartate, or glycine, using either ion-selective electrodes, or enzymatic sensors based on L-aspartate oxidase or glycine oxidase, described previously. In a further aspect of this invention, it is possible to couple sensors for monitoring stroke, with a glucose sensor and a thermocouple, since it has been shown that hyperglycemia and hyperthermia can increase neurologic morbidity.

In addition, for monitoring acute myocardial infarction, a combination of nitric oxide or nitrite may be measured using the sensors described above, along with immunosensors described above for biochemical markers such as creatine kinase (CK-MB), serum cardiac troponins (cTnT or cTnI), aspartate aminotransferase (AST), lactate dehydrogenase (LDH), beta-hydroxybutyrate dehydrogenase (HBD), serum myoglobin, glycogen phosphorylase isoenzyme BB (GPBB), fatty acid binding protein (FABP), phosphoglyceric acid mutase isoenzyme MB, enolase isoenzyme alpha beta, S100a0, and annexin V.

Figure 22B:
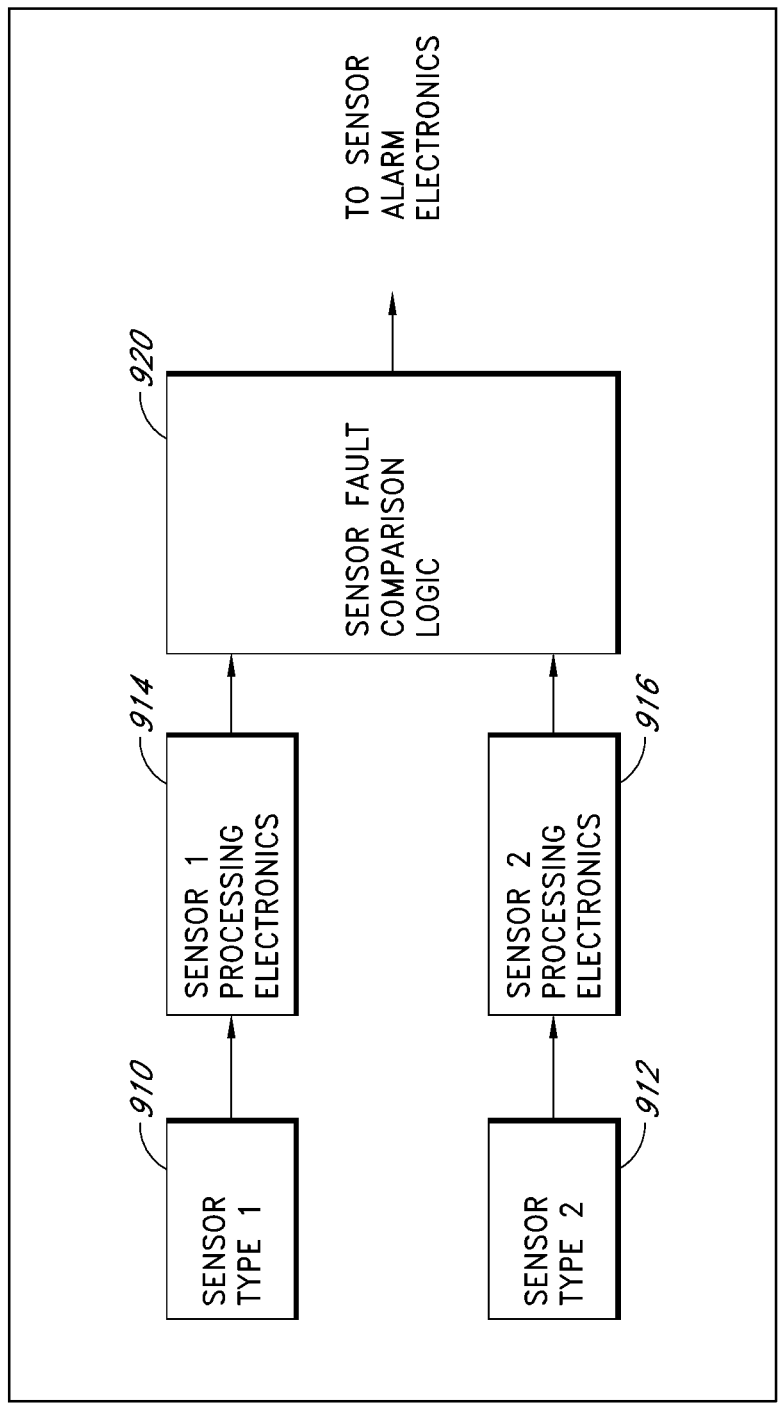
FIG. 22B is a block diagram of the sensor circuitry for evaluating the signals from multiple sensors, and activating an alarm system.

In an alternate embodiment of this invention, more than one type of sensor may be used simultaneously. FIG. 22B shows sensor circuitry that is designed to activate an alarm only when one or more types of sensors detect the predetermined variable level, or the rate of change in variable level. Sensor Type 1 910 and Sensor Type 2 912 are two different types of sensors that respond to different types of chemical analytes or physical stimuli. These can be either individual sensors or a redundant sensor array as shown in FIG. 19B. Two processing electronics sections 914 and 916 are used in order to condition the signals from the respective sensors for the rate or window comparators. This circuitry can be that shown in FIGS. 19C and 19D and should be selected to match the particular sensor used. After being processed by the processing electronics 914 and 916, the two signals are fed to additional logic, such as sensor fault comparison logic 920. This logic 920 requires that both the sensors exhibit a warning condition before the alarm signal is passed on to the rest of the system.

Figure 22C:
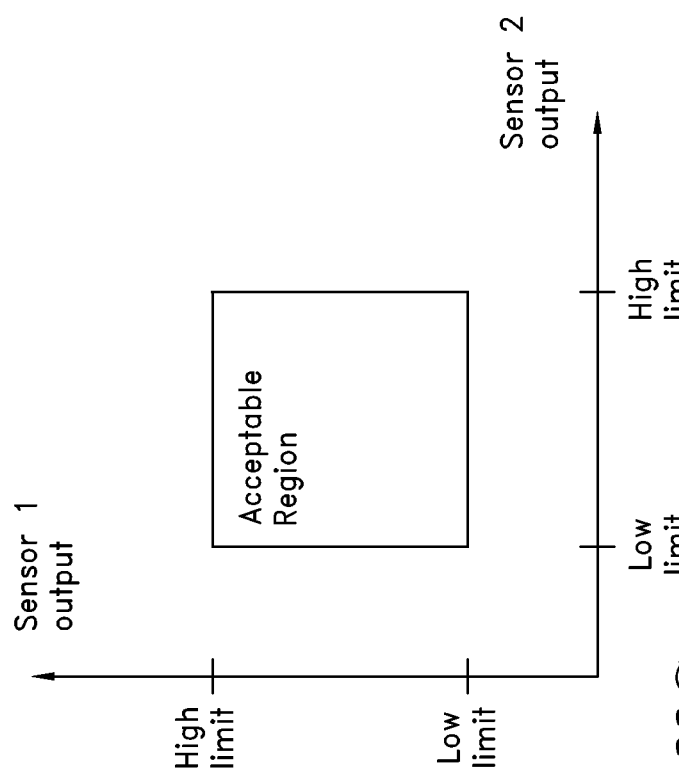
FIG. 22C is a diagram comparing the control logic, which may be used in either a one-dimensional or two dimensional signal space.

Referring now to FIG. 22C, the use of a 2- or more-dimensional signal space as opposed to a one-dimensional space means the decision rules can be much more flexible in allowing the system to be optimized for various conditions, such as level or rate of change, sensor types, etc. For example, the signal from a nitrite sensor may be combined with signals from other detection methods, such as a glutamate sensor in order to maximize the accuracy and reliability of the system. If both the nitrite and glutamate concentrations exceed a certain concentration or rate of release, that may be a more reliable indication of cerebral ischemia than either analyte by itself. Further, it can be seen that it is possible to extend this control logic to multiple sensor arrays, in which two or more analytes are measured, or to sensors that measure a combination of physical variables such as pressure and temperature, or a combination of chemical and physical variables.

In a further aspect of this invention, the sensor may be surgically placed in the cerebral ventricles, in order to monitor analyte concentrations in cerebrospinal fluid (CSF). Placement of the sensor is performed using techniques similar to the placement of a hydrocephalic shunt, as are well known to those skilled in the art. In this instance, the sensor would not be subject to fouling by thrombosis. An anchoring platform as described in an embodiment of the current invention would prevent motion artifacts. Indeed, Castillo et al. have detected both nitric oxide metabolites and glutamate in CSF following stroke.

Figure 25A:
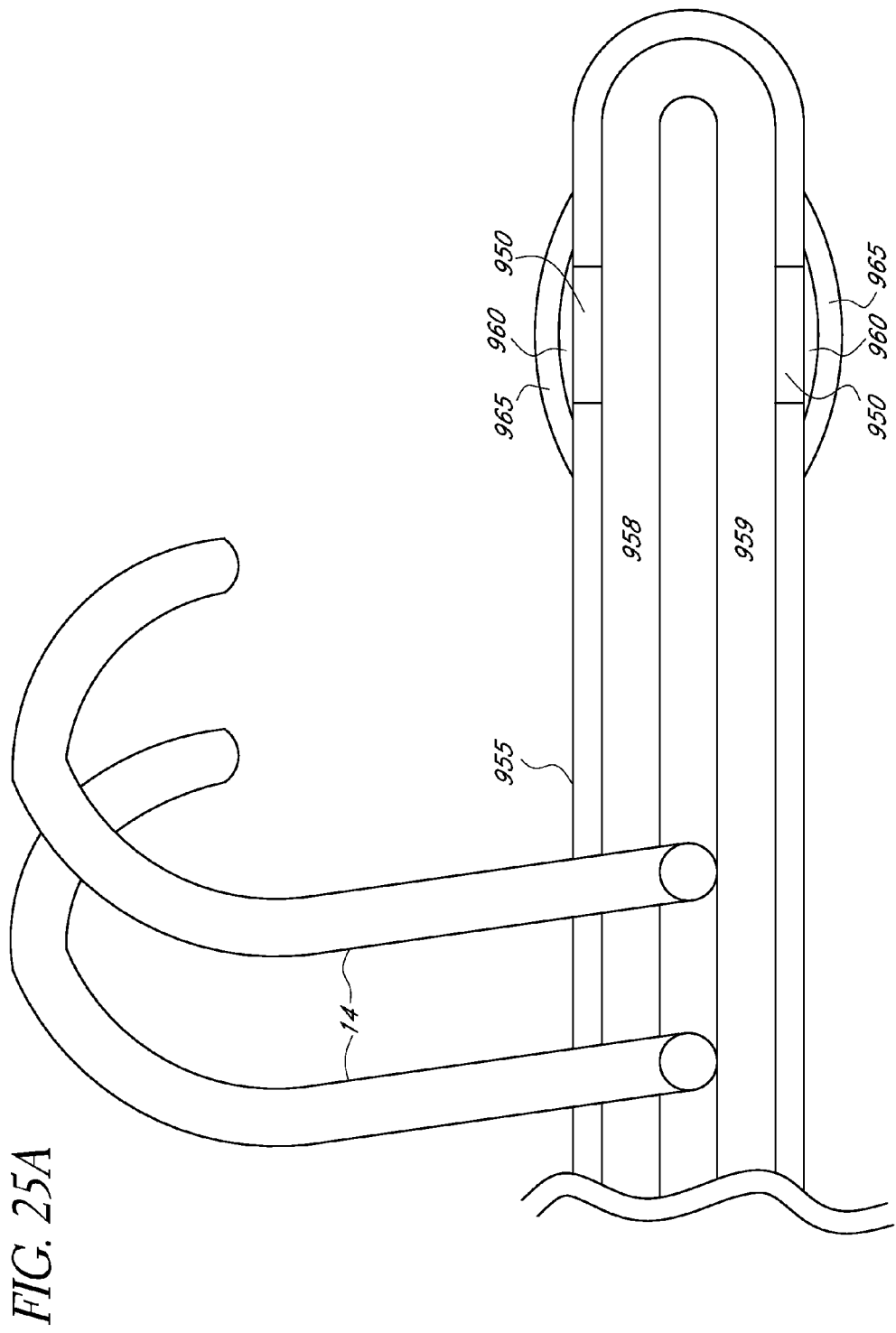
FIG. 25A is a side view of a catheter with positional stabilizers and a microdialysis membrane near its distal end, allowing fluid exchange with the patient.

An indwelling sensor of an embodiment of the present invention can also be designed to measure nitric oxide, nitrites, nitrates or glutamate or other analytes using microdialysis techniques. Referring now to FIG. 25A, in an alternative embodiment, a microdialysis membrane 950 is positioned near the distal end of a catheter 955 and is inserted within the vasculature of the patient using standard Seldinger technique, as is known in the art. The microdialysis membrane 950 has a wall thickness of between 200 and 500 microns, and a molecular weight cut-off of less than 30,000 daltons, and may be made from materials such as ePTFE, Dacron®, polyurethane (e.g. Cuprophane), silicone rubber, poly(lactide-co-glycolide) (PLGA), poly(caprolactone) (PCL), poly(ethylene glycol) (PEG), collagen, polypropylene, cellulose acetate, poly(vinylidene fluoride) (PVDF), polyamides, polycarbonate-ethers, regenerated celluloses and polyacrylonitriles (PAN) or other biocompatible materials. The $NO_2$-permeable microdialysis membrane 950 shown in FIG. 25A extends between the lumen and the outer wall of the catheter 955, and may be formed as a ring, or as a cone at the catheter tip. The lumen of the catheter may also be included as a loop or a concentric or a side-by-side configuration, as known in the art. Microdialysis probes with similar designs are commercially available, for example from Bio-Analytical Systems, Inc. (West Lafayette, Ind.).

However, the problem of thrombus formation and fibrotic encapsulation is known to limit the duration for which these probes can be used. In order to make these probes useful for longer time periods, certain modifications can be made as described below. First, the external surface of the microdialysis membrane may optionally be surrounded by a bioprotective membrane 960, which is preferably constructed of expanded PTFE with a pore size of 0.4 microns and a thickness of approximately 25 microns (e.g., Millicell CM-Biopore; Millipore). Next, a thromboresistant coating 965 may be added, such as an anticoagulant (like heparin or hirudin), a thromboresistant material, such as phosphoryl choline, a hydrogel (such as poly (ethylene glycol), poly(N-vinyl pyrrolidone), poly(hydroxyl ethylmethacrylate), polyacrylamide, polyacrylic acid, cross-linked collagen, sulfonated polyurethane or other sulfonated polymer, or other thromboresistant materials as are known in the art. In addition, a layer of PLGA or ethylene vinyl acetate, (not shown) may release a pharmacological agent such as paclitaxel, rapamycin, docetaxel, TNP-470, carboxyamido-triazole (CAI), thalidomide, or interleukin-12, which inhibits cell proliferation or migration. These pharmacological agents may be released from a degradable matrix, such as PLGA, or from a non-degradable matrix, such as ethylene vinyl acetate (EVA). This drug-releasing layer may be incorporated within the sensor housing inside the outer bioprotective layers.

Now referring to FIG. 25A, the microdialysis catheter 955 is improved by the addition of stabilizers 14, similar to those shown in FIG. 21A and FIG. 22A. These stabilizers 14 orient the sensing surface into the vessel lumen, may reduce thrombus formation, may minimize the wall effect, may prevent vasospasm or external vascular compression, and may prevent microdialysis probe movement. The stabilizing anchors 14 may be made of a shape-memory material such as nitinol, elgiloy or phynox, and may be formed into a curve having a diameter which is approximately 1-10 mm larger than the vessel in which the sensor will be placed. For example, an internal jugular vein may have a diameter ranging from 10-20 mm, so the anchors may range from 11-30 mm in diameter. It is important to achieve positional stability, since it is known that the concentration of NO, NOx or glutamate or other analyte may vary with position. The positioning anchors are placed either proximally to the microdialysis membrane, or at a distance of at least about 10 times the diameter of the catheter distally from the sensor, and on one or both sides of the sensor. The catheter with positioning anchors may be delivered to the monitoring site through a larger, guide catheter, so that the positioning anchors can be delivered more easily. Multiple microdialysis membranes may be placed along the length of the catheter, so that in the event that one membrane becomes fouled, the other membranes will still perform properly.

Figure 25B:
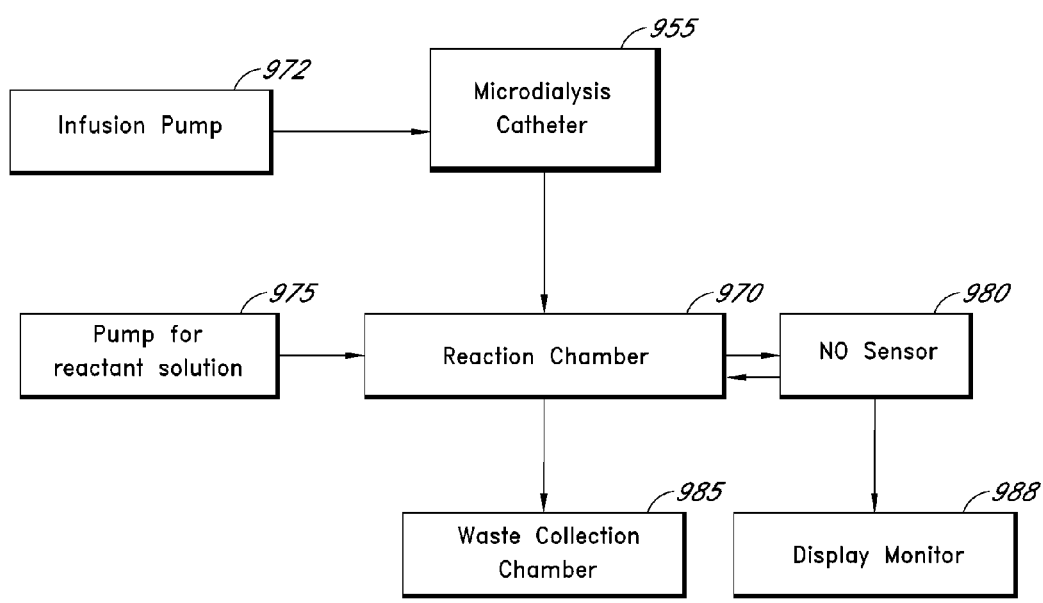
FIG. 25B is a block diagram showing a pump for infusing the catheter with normal saline, a catheter containing a microdialysis membrane, an external pump which provides a reactant solution, a reaction chamber, a sensor for monitoring the reaction, and a waste collection chamber.

FIG. 25B shows a block diagram indicating how the fluid is circulated and how the signal is obtained. The inlet fluid, or perfusate, consists of a physiological fluid such as normal saline, lactated Ringer's saline, perfusion fluid T1 (147 mM $Na^+$, 4 mM $K^+$, 2.3 mM $Ca^{2+}$, and 156 mM $Cl^-$) or perfusion fluid CNS (147 mM NaCl, 2.7 mM KCl, 1.2 mM $CaCl_2$, and 0.85 mM $MgCl_2$) (CMA Microdialysis AB, Sweden) or other physiological replacement fluid. Optionally, the input fluid may contain antithrombotic agents, such as heparin or EDTA, or macromolecules, such as dextran, to avoid ultrafiltration, as is known in the art. The perfusate is pumped via syringe pump 972 through a lumen 958 of the catheter 955. The perfusate is passed through catheter lumen 958 at a flow rate of about 0.5 to 10 μl/min, and $NO_2$ and other electrolytes then diffuse through the membrane 950, and are pumped out of the catheter via a return lumen 959. The fluid exiting the catheter flows into an external reaction chamber 970, which is isolated from the patient by a one-way valve (not shown). A separate syringe pump 975 provides a solution of KI and $H_2SO_4$ at concentrations and flow rates which are in excess of the molar flow rate of $NO_2$. The acid-iodide solution then reacts with the $NO_2$-containing saline solution, producing NO, which then is detected by the NO sensor 980. The dialysate fluid is traditionally analyzed with off-line techniques, such as HPLC.

In the present invention, the dialysate fluid is analyzed using an NO electrode, which allows for continuous, on-line measurements. The NO sensor, which can monitor fluid volumes as little as a few microliters, then provides a signal which is indicative of the concentration of $NO_2$ in circulation, and is sent to an external monitor 988 for analysis, display, and alarm. The reacted solution is then passed into a waste collection chamber 985. The solution is kept isolated from patient contact at all times. Alternatively, acids such as carbonic acid, hydrochloric acid, nitric acid, or acetic acid could be used instead of sulfuric acid. If used for an internal monitor, with potential patient contact, carbonic acid would be the safest, since it would simply decompose into carbon dioxide and water in the event of a system failure or a leak. This type of monitor may be used in order to obtain on-line data from patients with traumatic brain injury, or post-operative patients at high risk for stroke, as examples, in order to reduce the time between secondary brain injury and physician response. This embodiment provides an additional safeguard to the patient, in that the acid remains external to the patient. That way, there is minimal risk to the patient in the event of a leak or other failure.

In an alternative embodiment of this invention, a glutamate sensor is used to monitor the effluent from the microdialysis catheter described in FIG. 25A. The glutamate sensor may be one commercially available from Pinnacle Technology (Lawrence, Kans.), Applied Enzyme Technology (Gwent, UK), or Intelligent Optical Systems (Torrance, Calif.).

Figure 25C:
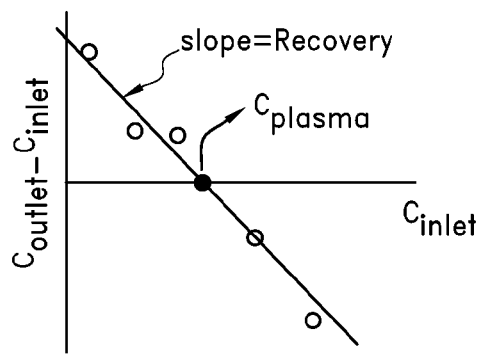
FIG. 25C is a calibration plot of a microdialysis catheter using a "no-net flux" method.
Figure 25D:
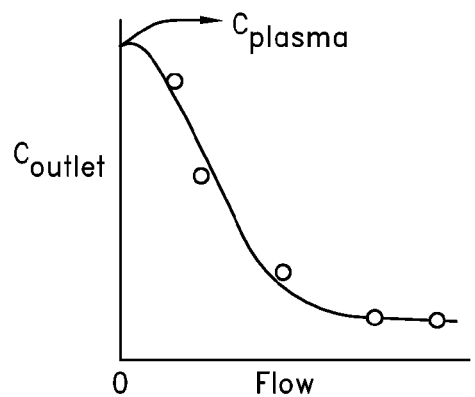
FIG. 25D is a calibration plot of a microdialysis catheter using a "zero-flow" method.
Figure 25E:
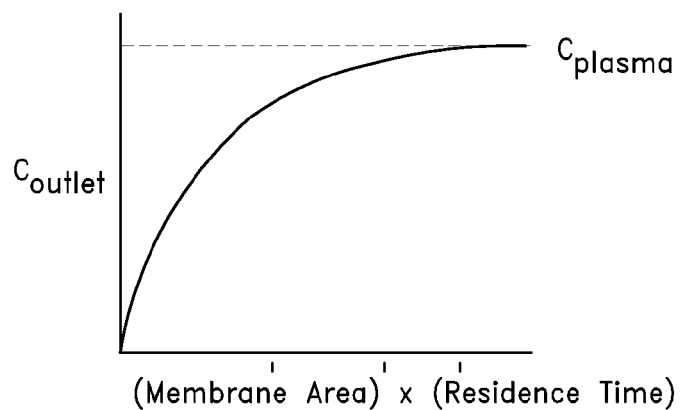
FIG. 25E is a calibration plot of a microdialysis catheter using a "near-equilibrium dialysis" method.

In order to quantify analyte concentrations using microdialysis, a calibration procedure must be performed. Analytes such as NO, nitrite, nitrate or glutamate, diffuse freely in blood plasma to the implanted microdialysis probe. The efficiency of this diffusive process ($E_d$) in microdialysis is called recovery and is defined as:

$$E_d = \text{Recovery} = (C_{outlet} - C_{inlet})/(C_{plasma} - C_{inlet})$$

where $C_{outlet}$ is the concentration of the analyte being measured at the probe outlet, $C_{inlet}$ is the analyte concentration in the perfusion fluid, and $C_{plasma}$ is the concentration of analyte in plasma. There are at least three ways of calibrating a microdialysis sensor. The first method, called the "no-net-flux" method, measures the change in analyte concentration while the same analyte is added to the perfusion solution at several different concentrations. As shown in FIG. 25C, ($C_{outlet}$–$C_{inlet}$) is plotted against $C_{inlet}$ and the slope is equal to the recovery. Linear regression analysis is used to calculate the point where no net diffusion occurs, i.e. when this line crosses the abscissa. A second method, called the "zero-flow method", measures dialysate concentrations at several flow rates as shown in FIG. 25D. Non-linear regression analysis is used to estimate the plasma concentration at zero flow, i.e., at 100% recovery. In the third method, called "near-equilibrium dialysis" the diffusion time is made as long as possible in order to allow equilibration of the concentrations on both sides of the membrane. This requires the use of as low a flow rate as possible and a membrane with as much surface area as possible, providing as long a residence time as possible. Equilibrium becomes established at the outlet of the microdialysis catheter due to the long residence time, so that the measured value is the equilibrium value, as shown in FIG. 25E. These techniques are known to those of skill in the art and may be substituted or modified by other measurement techniques that are equally effective, as is known to those of skill in the art.

Figure 27:
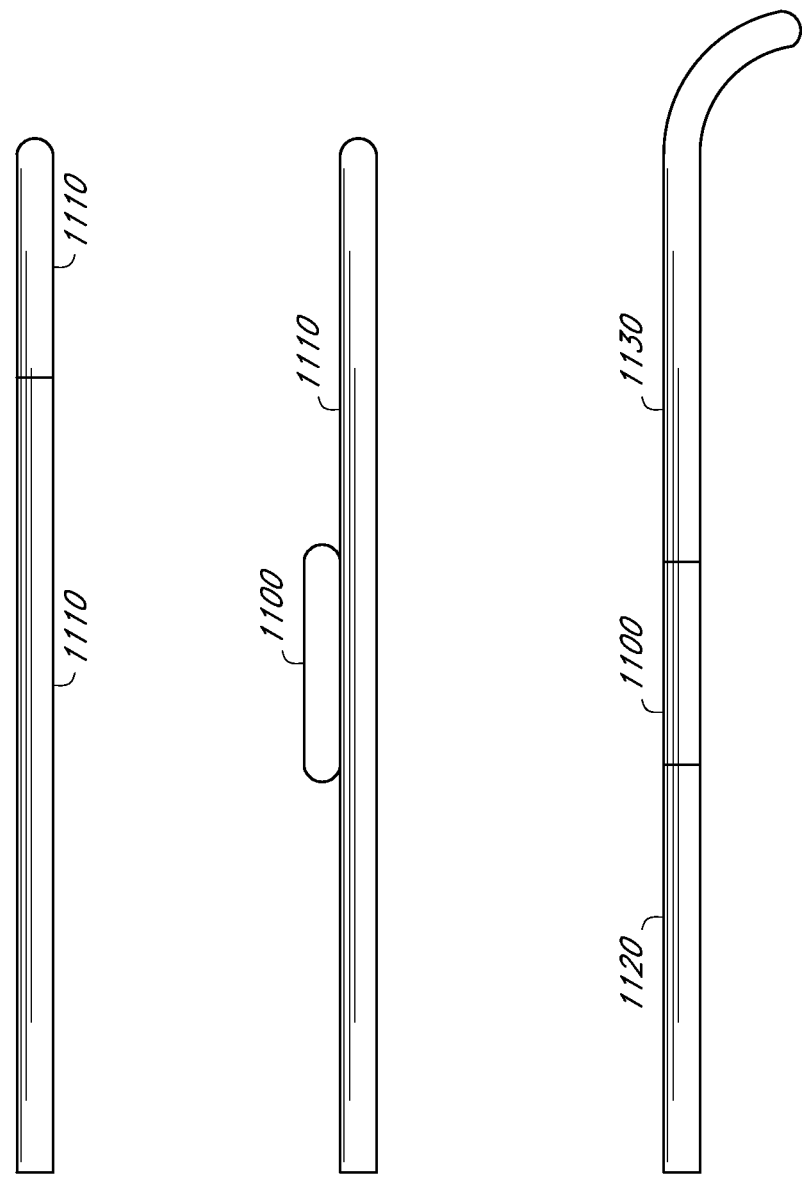
FIG. 27A is a side view of a guidewire with a sensor mounted at its distal tip.
FIG. 27B is a side view of a guidewire with a sensor mounted proximally to the distal tip, on one side of the guidewire.
FIG. 27C is a side view of a guidewire with a sensor positioned coaxially between the proximal and distal end of the guidewire.

In an alternative embodiment, an NO sensor or any of the other sensors described herein can be attached to a guidewire. There are certain advantages to this approach. First, attaching the sensor to a guidewire allows for a very low profile delivery system, allowing the sensor to be used in relatively small blood vessels, such as those found in the cerebrovasculature. The guidewire may have a diameter of 0.035" to 0.010", which is smaller than most catheters. In addition, positioning the sensor on a guidewire allows the sensor to be positioned close to the site which is to be monitored. As seen in FIG. 27A, an NO sensor 1100 is bonded to the distal tip of the guidewire 1110, either by welding, soldering, brazing, mechanical interfit, such as screw threads, or adhesives, such as epoxies, cyanoacrylates, UV-curable adhesives, or a combination thereof, as are known in the art. The shaft of the guidewire may be constructed using materials such as stainless steel or nitinol, and may additionally be coated with Teflon, or with a polymeric jacket containing a radiopaque filler. A polyurethane or other elastomeric material may be used as the jacket material, and may contain barium, bismuth, or tungsten filler in the range of 0-80%, to provide enhanced radiopacity for visualization under fluoroscopy, as is known in the art.

In addition, as shown in FIG. 27B, the sensor 1100 may be mounted on the side of the guidewire 1110 at a position which is proximal to the distal tip, in order that the guidewire may have a smaller diameter at its more flexible distal tip. This provides the advantage of making the device easier to navigate into the desired position. However, in order to minimize the overall profile of the device, as shown in FIG. 27C, the sensor 1100 may be positioned coaxially within the body of the guidewire. In this case, the sensor 1100 is attached to a region of the guidewire 1120 proximal to the distal tip using methods described above, and additionally, a flexible distal tip 1130 is mounted to the opposite end of the sensor, again using the methods described previously. This distal portion may either be straight at its tip, or have a radius of curvature within 2 inches from its tip. It is believed that the guidewire will have a natural tendency to be positioned against a side wall of the vessel. Therefore, it is important that the NO-permeable membrane be positioned circumferentially around the sensor. This will prevent the signal from being lost due to inappropriate radial positioning of the sensor. As discussed previously, the NO sensor may be coated with hydrogels, anticoagulants, or pharmaceutical agents which inhibit cell proliferation or migration. It may be further advantageous to coat at least a portion of the guidewire itself with a hydrogel, in order to improve the lubricity and trackability of the device, as is known in the art.

Electrical leads (not shown) may additionally extend from the sensor and be positioned along the shaft of the guidewire, to the exterior of the patient. The electrical leads may be wound spirally along the shaft of the guidewire in order to minimize mechanical strain on the leads. Near the proximal end of the wire, these electrical leads are then connected to a monitor, in order to measure the response of the patient. Alternatively, the sensor may be coupled with a radiotransmitter as described above, and the power transmitted into the sensor by means of an inductive link, as described above. As an additional alternative, a battery may be placed on the guidewire, coaxially with the sensor, and attached to the guidewire by welding, soldering, brazing, mechanical interfit, such as screw threads, or adhesives, such as epoxies, cyanoacrylates, UV-curable adhesives, or a combination thereof, as are known in the art. The resulting signal may further be transmitted out to an external monitor by means of an inductive link, as described above.

In contrast to microdialysis, in which the driving force is diffusion, the driving force in ultrafiltration or microfiltration is a pressure differential, often a vacuum, which is applied across the membrane. In ultrafiltration, the concentration of the analyte in the tissue is the same as the analyte concentration being removed by the ultrafiltration probe. The limitation of ultrafiltration technique is that fluid can only be removed as quickly as the body can replace it. The concept of in vivo ultrafiltration and the design of probes are covered by U.S. Pat. Nos. 4,777,953, 4,854,322, and 5,002,054 which are incorporated herein by reference.

In the case of an ultrafiltration probe or cross-flow microfiltration probe placed in the bloodstream, this does not represent a significant limitation. In fact, ultrafiltration has been used to treat patients with congestive heart failure who are not responsive to diuretics, and the extraction rate of fluid from blood using ultrafiltration is up to 500 ml/h (8.3 ml/min). (*Ultrafiltration Versus Intravenous Diuretics for Patients Hospitalized for Acute Decompensated Heart Failure* (*UNLOAD*), Maria Rosa Costanzo, Presented at the 2006 American College of Cardiology, Atlanta, Ga. Mar. 11-14, 2006.) This far exceeds the fluid extraction rate required to perform measurements of $NO_x$ or other analyte levels in a patient's bloodstream using the methods described herein.

In the present invention, the ultrafiltration or microfiltration filter preferably have a molecular weight cut-off or pore size which is appropriate to the analyte being measured. In the present example, a membrane made from polysulfone with a 10 kD molecular weight cutoff is preferred, since it is capable of excluding hemoglobin from the ultrafiltrate, and hemoglobin is known to react with nitric oxide, but membranes with molecular weight cutoffs of as low as 5 kD, or pore sizes up to 0.2 µm can be used. The ultrafiltration membrane can be made of polycarbonate, polysulfone, polyethersulfone, polyarylethersulfone, polyurethane (such as Cuprophane), AN-69 polyacrylonitrile, regenerated cellulose, mixed cellulose ester, polyester, Nylon, poly(vinylidene fluoride) (PVDF), polypropylene, polytetrafluoroethylene, or other ultrafiltration membrane material, and may be purchased from numerous vendors, including Pall Corp. (East Hills, N.Y.), Amnicon (Beverly, Mass.), or Millipore (Billerica, Mass.). The membranes may be surface treated in order to produce a positive or negative zeta potential, as is known in the art. The ultrafiltration membrane may also be formed on a porous support structure, as is known in the art.

Different ultrafiltration devices may be used for detection of $NO_2$ and/or $NO_3$ in physiological fluids, such as cerebrospinal fluid or blood. The ultrafiltration device may be a tangential flow separation device, such as those available from Spectrum Laboratories, Inc. (Rancho Dominguez, Calif.). Alternatively, it may be an ultrafiltration unit such as the Aquadex, available from CHF Solutions, Inc. (Brooklyn Park, Minn.), or the Hospal Filtral dialyzer manufactured by Rhone Poulenc Industries (Paris, France). As before, it may be desirable to clean these units to reduce $NO_2$ and $NO_3$ contamination using a cleaning process available from Oxonon, Inc. (Emeryville, Calif.).

Figure 30A:
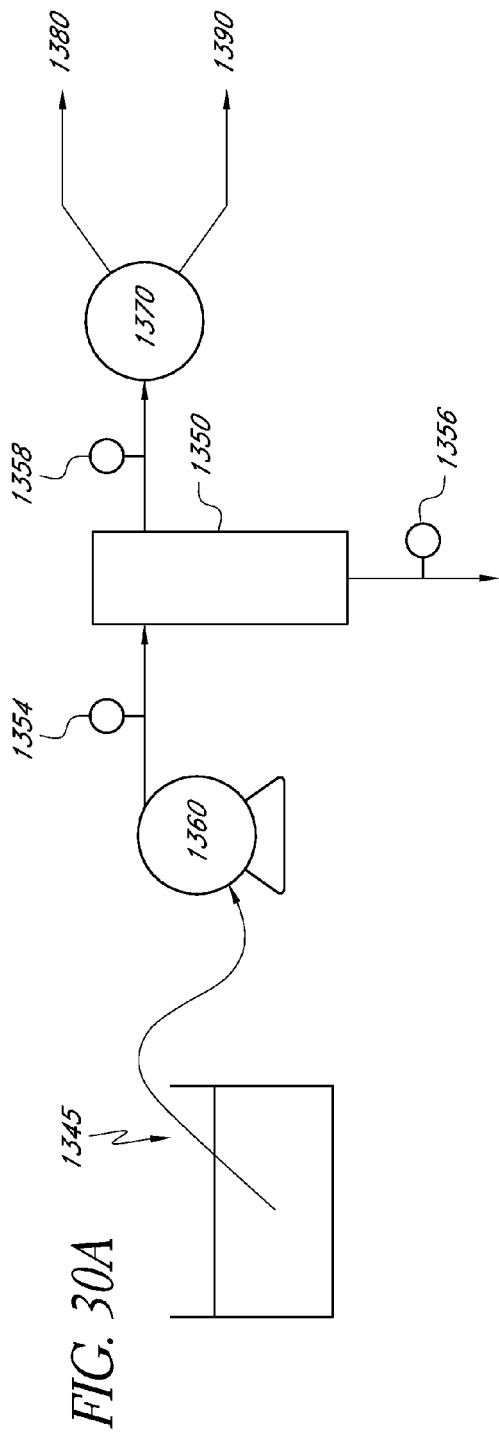
FIG. 30A is a block diagram showing a method of obtaining a sample fluid using an ultrafiltration or microfiltration membrane to obtain fluid streams containing nitrite, nitrate, or the combination.
Figure 30B:
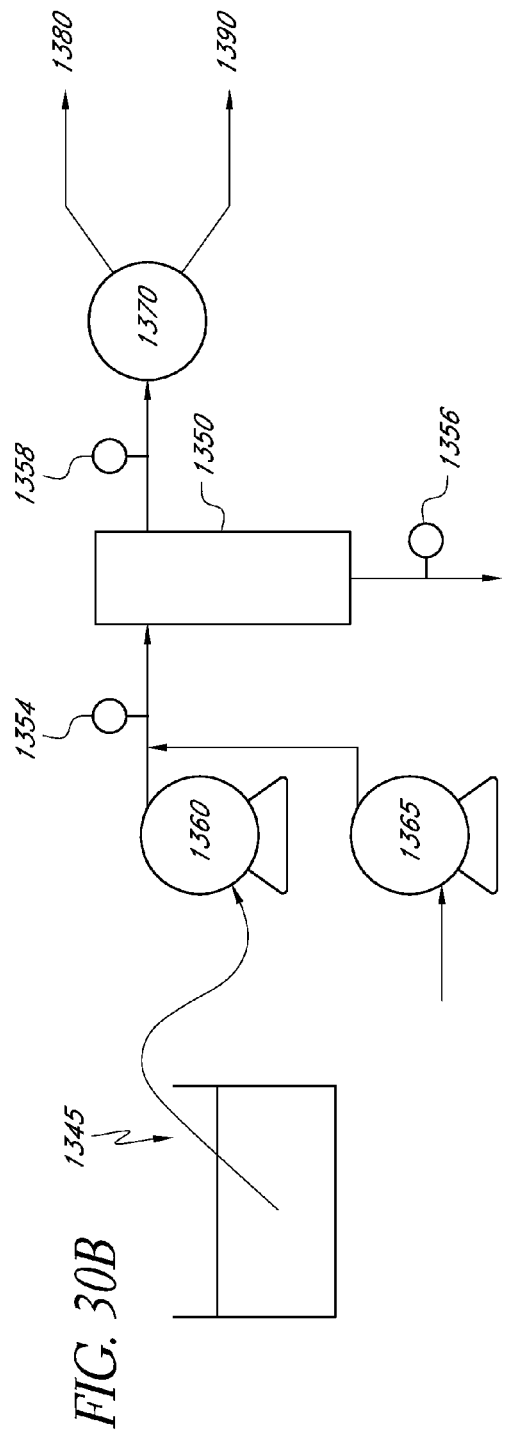
FIG. 30B is a block diagram showing a method of minimizing the amount of sample fluid required using an ultrafiltration or microfiltration membrane to obtain fluid streams containing nitrite, nitrate, or the combination.
Figure 31:
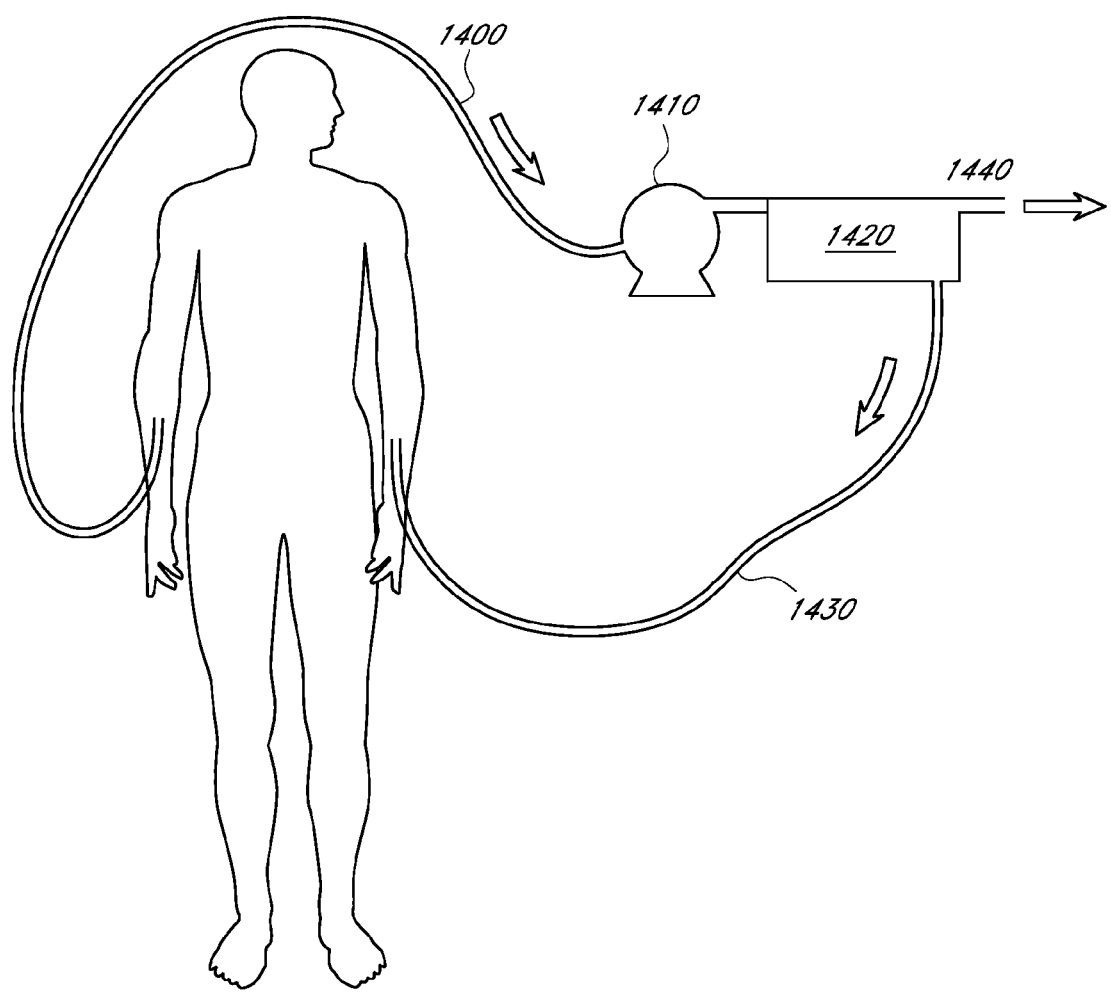
FIG. 31 is a block diagram showing a method of obtaining a fluid sample from a human or an animal, passing the extracted fluid through an ultrafiltration or microfiltration unit, passing the filtrate to a system for analysis, and optionally returning the retentate to the human or animal.

Referring now to FIG. 31, a fluid such as blood may be extracted from an animal or human via a catheter 1400, and then pumped using a pump 1410 through an ultrafiltration unit 1420. The retentate may then optionally be returned to the body via a second catheter 1430, while the ultrafiltrate then becomes the fluid stream containing $NO_2$ and $NO_3$, and can be monitored for either $NO_2$ or $NO_3$, as illustrated in FIG. 30.

Referring now to FIGS. 30A and 30B, in order to operate this system in a physiological fluid, such as blood or cerebrospinal fluid, a sampling system such as an ultrafiltration membrane or cross-flow microfiltration membrane may be used. A physiological solution such as blood containing $NO_2$ and/or $NO_3$ from 1 nM to 1 mM is obtained from a sampling tube 1345, such as a catheter sheath introducer, and pumped through an ultrafiltration filter 1350 such as that available from Spectrum Laboratories. (Rancho Dominguez, Calif.) using a peristaltic pump, syringe pump, or other pump 1360. Optionally, the transmembrane pressure may be monitored using a feed pressure sensor 1354, a concentrate pressure sensor 1356, and a permeate pressure sensor 1358 in order to optimize the rate of filtrate production. The transmembrane pressure may be defined as the arithmetic mean of the feed pressure and the concentrate pressure, minus the permeate pressure. The ultrafiltrate fluid stream containing $NO_2$ and $NO_3$ can be divided to monitor for both analytes. The fluid stream is divided into a first stream, for monitoring $NO_2$, and a second stream, for monitoring the total amount of $NO_2$ and $NO_3$ combined. The filtrate stream is connected to a flow splitter 1370 as shown in FIGS. 30A and 30B. The first outlet stream 1380 from the flow splitter is to be monitored for $NO_2$, and becomes the $NO_2$ input stream in FIG. 28, where the $NO_2$ is further reduced to NO for measurement. The second fluid stream 1390 which contains both $NO_2$ and $NO_3$ becomes the input fluid stream 1300 in FIG. 29, below. In order to quantify the amount of $NO_3$ in the fluid stream, the amount of $NO_2$ in the stream must be subtracted from the total signal that includes both $NO_2$ and $NO_3$. In addition, it is necessary to compensate for time lag. The time lag between the increase in signal from the fluid stream being monitored for $NO_2$, and the increase in signal from the fluid stream containing $NO_2$ plus $NO_3$ stream is measured. The entire curve for $NO_2$ plus $NO_3$ is then shifted by the time lag, and the difference between the two curves can be obtained to provide a signal that is indicative of the concentration of $NO_3$.

Figure 28:
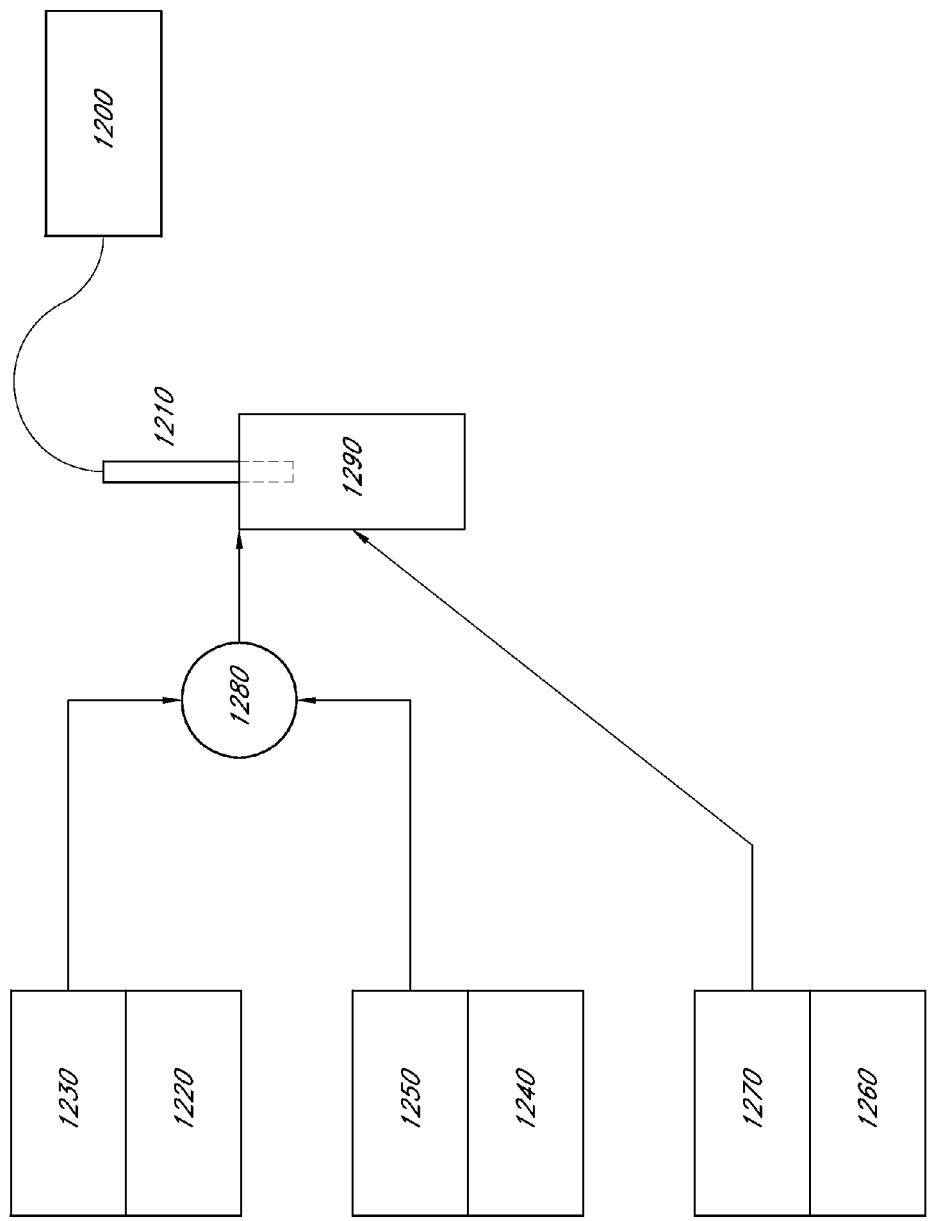
FIG. 28 is a block diagram showing a method of converting a fluid stream of nitrite to nitric oxide, for measurement using a nitric oxide electrode and nitric oxide monitoring system.
Figure 29:
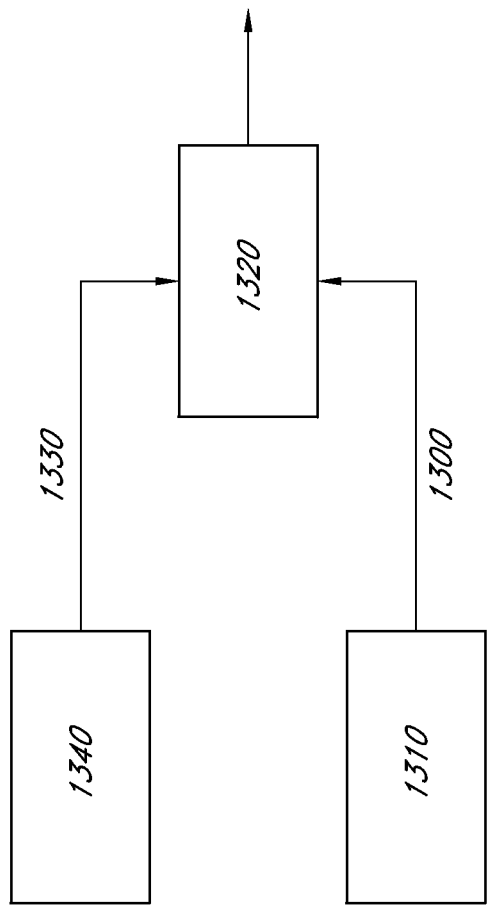
FIG. 29 is a block diagram showing a method of converting a fluid stream of nitrate and/or nitrate plus nitrite to nitrite.

Referring now to FIG. 28, in a preferred embodiment, the level of $NO_2$ in a solution can be measured using a flow system in which a fluid stream containing $NO_2$ reacts with a second fluid stream containing a mixture of acid and iodide. Near the point where the two fluid streams mix in a reaction chamber, they will react to generate nitric oxide which can be measured using a commercially available NO detection system 1200 and NO sensor 1210 such as available from Innovative Instruments (Tampa, Fla.) World Precision Instruments (Sarasota, Fla.) Diamond General (Ann Arbor, Mich.) or Inter Medical Co., Ltd., (Nagoya, Japan). A first syringe pump 1220 such as available from Bioanalytical Systems, Inc. (West Lafayette, Ind.) VWR Scientific, or Fisher Scientific, contains a 1 ml syringe 1230 containing substantially nitrite-free distilled water. Double-distilled water is typically nitrite-free. This syringe is connected by tubing to a liquid switch 1280 (Bioanalytical Systems, Inc., West Lafayette, Ind.) and the liquid switch is initially set to allow this first stream of water to pass through. The outlet of the liquid switch is connected to a flow reaction chamber 1290 by tubing. A second syringe pump 1240 contains a 1 ml syringe 1250 containing a 1:1 mixture of sulfuric acid (0.1 N) and potassium iodide (5% w/v) and it is also connected by tubing to liquid switch 1280 and the liquid switch is initially set not to allow this second acid/iodide stream to pass through. A third pump 1260 advances either a sample solution containing an unknown concentration of nitrite, or a standard solution of 1 nM to 1 mM $NO_2$ and this third pump may be connected to a reaction chamber 1290 by means of tubing, to create a path for flow as shown in FIG. 28. Different volumes of syringes may be used, but the smaller the volume, the more accurate the delivery rate. Some syringe pumps are calibrated for use with a particular size of syringe, such as a 1 ml syringe. Any type of acid, and any iodide solution may be used, as long as there is a molar excess of both acid and iodide in comparison with the concentration of $NO_2$ being detected. In addition, the acid and iodide do not have to be pre-mixed, since this solution is only stable for a few hours, but can be stored in separate reactant reservoirs, pumped into the reaction chamber and mixed simultaneously with the delivery of nitrite to the reaction chamber. The NO sensor is placed in the reaction chamber 1290, and a baseline measurement of water (or other control fluid, such as lactated ringer's saline solution) and acid/iodide solution is obtained at a flow rate of 5 µl/min. The flow rate may be varied from 0.1 to 100 µl/min, but because the sensitivity of the system is dependent upon the rate of analyte flux to the NO sensor, and because of the potential time delay in measurement, higher flowrates are more convenient. After a stable baseline is obtained, the liquid switch 1280 is changed from water or other control solution to the acid/iodide solution. The acid/iodide solution is then pumped into reaction chamber 1290 by means of a pump 1240. Because both the $NO_2$ solution and the acid/iodide solutions are reacted in the flow reactor 1290, the resulting NO concentration can be measured using the NO sensor 1210 and NO measuring system 1200.

Now referring to FIG. 29, a system for measuring $NO_3$ is described, although with a slight time delay with respect to the measurement of $NO_2$. In this system, a fluid stream 1300 containing $NO_3$ at a concentration of 10 nM to 1 mM is pumped using a syringe pump, peristaltic pump or other pump 1310 into a flow reactor 1320. The $NO_3$ solution may also contain $NO_2$. The flow reactor contains a copper-coated cadmium catalyst material, such as a coated wire, or coated beads. A second solution 1330 containing 20 mM carbonate buffer (pH 9.3) and 10 mM EDTA is pumped by a second pump 1340 into the flow reactor 1320. These solutions are pumped at flowrates in the range of 0.1 to 100 µl/min using an appropriate pump or pumps into the flow reactor 1320, at such a flow rate that the residence time (which is the volume of fluid that can be contained in the flow reactor at a single time divided by the flow rate) is sufficient to convert the desired fraction of $NO_3$ to $NO_2$. The longer the residence time, the closer the system will come to achieving 100% conversion of $NO_3$. This must be balanced against the need for minimizing the time delay in obtaining the measurement. Typical residence times are in the range of 1 min to 30 min. In general, the greater the molarity of the carbonate buffer, the faster the reduction of $NO_3$ to $NO_2$, and molarities in the range of 2.5 M to 1 mM will work. In addition, there are other acceptable basic buffers, such as ammonia, glycine, borate, and other buffers as known to one skilled in the art. In addition, the optimal pH for conversion of $NO_3$ to $NO_2$ is about 9, but a pH in the range of 8.5 to 10 will work. However, both the pH and buffer strength must be balanced against the strength of the acid/iodide solution that will convert the $NO_2$ to NO in a secondary flow reactor. A stronger buffer will require the use of a stronger acid for reducing $NO_2$ to NO. The outlet fluid stream from flow reactor 1320 becomes the $NO_2$ containing input fluid stream for the flow system described in FIG. 28, and the $NO_2$ is further reduced to NO, as described in detail above.

One challenge with measurements of $NO_2$ or $NO_3$ in general is that of potential contamination of lab supplies, and ultrafiltration membranes are known to be particularly problematic. However, in the current invention, any error in continuous monitoring of $NO_2$ or $NO_3$ using ultrafiltration can be compensated for by subtracting a background. In addition, the membranes are often stored wet by the manufacturer. The membranes are preferably purchased dry and hydrated using double-distilled water, or other grade of water which has been shown to be substantially free of NO contamination. Alternatively, these devices may be cleaned using a process such as that available from Oxonon, Inc. (Emeryville, Calif.).

To determine the level of background contamination in the system, double-distilled water, physiological saline, or other appropriate control fluid which is substantially free of $NO_x$ contamination may be pumped through the ultrafiltration probe 1350 prior to sampling of the blood, in order to obtain a background measurement. After a stable baseline signal is obtained, the sampling probe 1345 is transferred to a physiological solution containing from 1 nM to 1 mM $NO_2$ and/or $NO_3$ and measurements are obtained using the method described for pure solutions. The flow rates of the pumps in the system may be independently varied between 0.1 and 100 µl/min, as long as the requirement that the acid and iodide must be in molar excess of the nitrite is met.

While filtration of blood is used to separate hemoglobin from free nitrite, there can be problems with hemolysis during pumping or filtration. Roller pumps are known to cause a certain degree of hemolysis. Red blood cells are known to contain a majority of the nitrite in blood, so if hemolysis occurs, errors in the measured level of plasma nitrite level can occur. Alternatively, if desired, the red blood cells can be lysed deliberately, for example with sodium chloride concentrations >0.9%, and the total nitrite level in the blood sample can be measured.

To reduce the degree of hemolysis, it is possible to add a small amount of polyethylene glycol (PEG), polyethylene oxide/polypropylene oxide non-ionic surfactant or polyvinyl pyrrolidone (PVP) (L. A. Goldsmith, Haemolysis Induced by Tyrosine Crystals: Modifiers and Inhibitors. Biochem. J. (1976) 158:17-22). Hemolysis due to mechanical stress can be reduced by adding 0.1% PEG (MW 1000-20,000). (Marina V. Kameneva, Brandon M. Repko, Ellen F. Krasik, Brett C. Perricelli, and Harvey S. Borovetz, Polyethylene Glycol Additives Reduce Hemolysis in Red Blood Cell Suspensions Exposed to Mechanical Stress, *ASAIO Journal* 2003; 49:537-542.) However, higher concentrations of PEG (>0.1%) can affect filtration processes. For the present invention, addition of PEG (MW 300 to 20,000) as low as 0.01% to 0.0001% to samples containing red blood cells can reduce the degree of hemolysis, and therefore improve signal stability.

In addition, other fluids that contain reducing agents for converting nitrite to nitric oxide may be used in place of the acid/iodide stream. For example, $FeSO_4$ may be reacted with nitrite in the presence of acid. Alternatively, nitrite and nitrate may be reduced in the presence of a solid such as $Cr_2O_3$, as shown in the equations below:

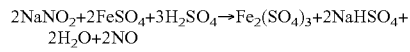

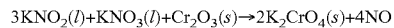

Referring now to FIG. 30B, in cases where it is desirable to minimize the amount of physiological fluid removal, such as blood, interstitial fluid, cerebrospinal fluid, or other bodily fluid, a method related to diafiltration may be used. In this case, a second pump 1365 is used to mix water, physiological saline, or other control fluid with the fluid of interest, such as blood, that is being pumped by the first pump 1360. This can be used to increase the flowrate through the ultrafiltration membrane, and thus increase the transmembrane pressure in order to increase the production rate of the filtrate. However, a dilution factor must be accounted for in the measurement, which is the ratio of the blood flow rate to the sum of the blood and control fluid flow rates. This method also decreases the concentration of nitrite or nitrate being measured, and thus sensitivity requirements should be considered.

Figure 32C:
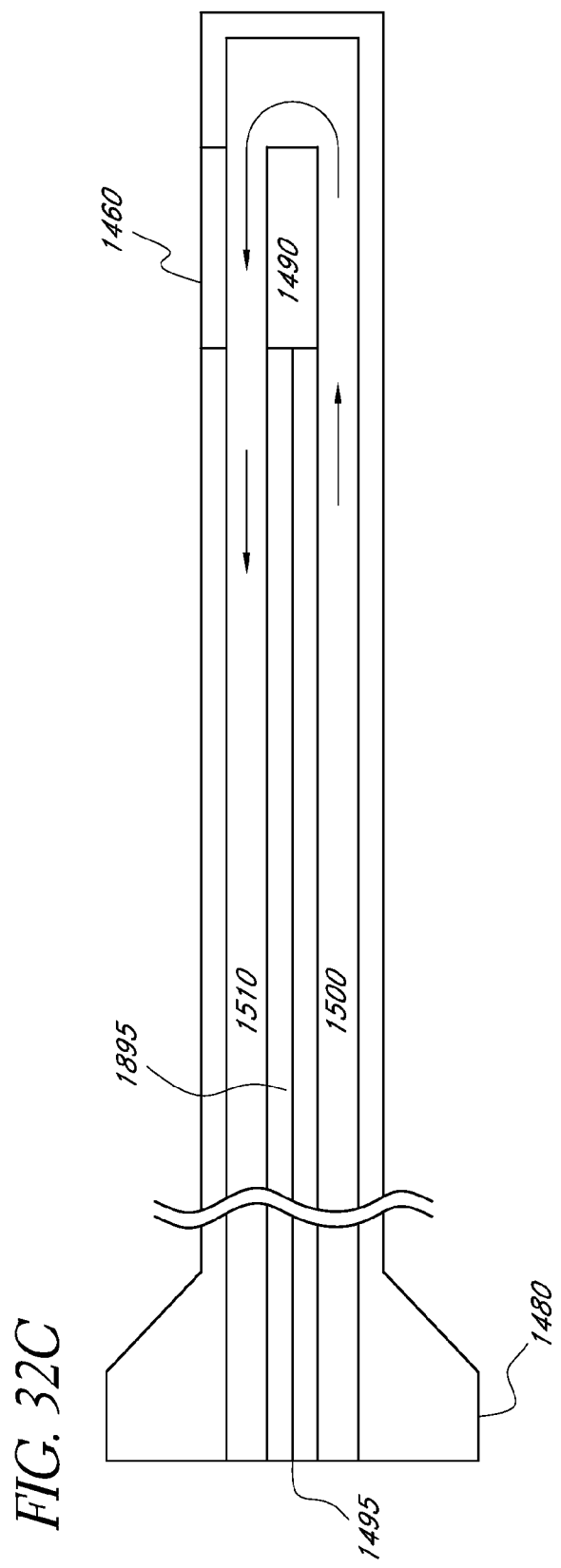
FIG. 32C is a side elevational view of a catheter containing a sensor and an ultrafiltration or microfiltration membrane near its distal tip.

Alternatively, as shown in FIGS. 32A, 32B, and 32C, a catheter 1450 may contain an ultrafiltration membrane 1460 at or near its distal end, or anywhere along its length from the distal tip to the proximal end near the hub. The ultrafiltration membrane may be made of polycarbonate, polysulfone, polyethersulfone, polyarylethersulfone, polyurethane (such as Cuprophane), AN-69 polyacrylonitrile, regenerated cellulose, mixed cellulose ester, polyester, Nylon, poly(vinylidene fluoride) (PVDF), polypropylene, polytetrafluoroethylene, or other ultrafiltration membrane material, as known in the art. The membrane may have a porosity ranging from 5 kD molecular weight cutoff to 0.2 µm. The catheter may contain a window 1470 which extends from the outside diameter of the catheter to at least one inner lumen of the catheter. A pump is connected to the catheter hub 1480 which applies a vacuum that causes the ultrafiltrate to be extracted through the ultrafiltration membrane 1460. The catheter may be primed with a fluid such as heparinized saline. As blood passes across the surface of the membrane, the ultrafiltrate passes through the membrane, into the lumen of the catheter, and from there into a flow reactor, as shown in FIGS. 28, 29, and 30. The input to the flow reactor can be alternated between a calibration fluid, such as water, and the ultrafiltrate from the catheter, so that the levels of $NO_2$ and $NO_3$ can be detected by the flow system described in FIG. 30 above. The membrane 1460 may have a tubular geometry, and may extend along some portion of the catheter's length, it may include the entire distal tip of the catheter, or it may be placed within a window 1470 formed from within the catheter body. The catheter may be made from polyurethane, PEBAX, Nylon, PEEK, polyimide, PTFE, PDMS or other polymeric material, or multiple combinations or layers of such polymeric materials, as is well known in the art. It may also contain a wire braid or coil, as is known in the art. The catheter may have an outside diameter ranging from 1 F to 24 F (0.3 mm to 8 mm), an inside diameter ranging from 0.1 mm to 7.5 mm (smaller diameters will result in shorter measurement delay times), and the length should be appropriate to easily access the monitoring site (30 cm to 150 cm). Shorter lengths will result in shorter delay times. In addition, the catheter hub should have a Luer (or other appropriate) fitting, in order to connect it with a flow system, such as the flow system shown in FIG. 31.

Alternatively, as shown in FIG. 32C, a nitric oxide sensor 1490 with electrical leads 1495 may be positioned within the catheter near the ultrafiltration membrane 1460. A fluid stream containing a solution of acid and iodide is pumped through catheter lumen 1500, and returns past the region containing the ultrafiltrate and the sensor, where the reaction to produce nitric oxide is monitored, and the waste stream is returned through catheter lumen 1510.

In certain aspects of this invention, it is desirable to separate the NOx containing fluid from the physiological fluid prior to removing the fluid from the patient. For example, when monitoring in blood, it is often desirable to leave behind red blood cells and proteins, rather than removing them from the body. Methods for doing this have been described in reference to FIGS. 32A, B, and C.

Figure 33:
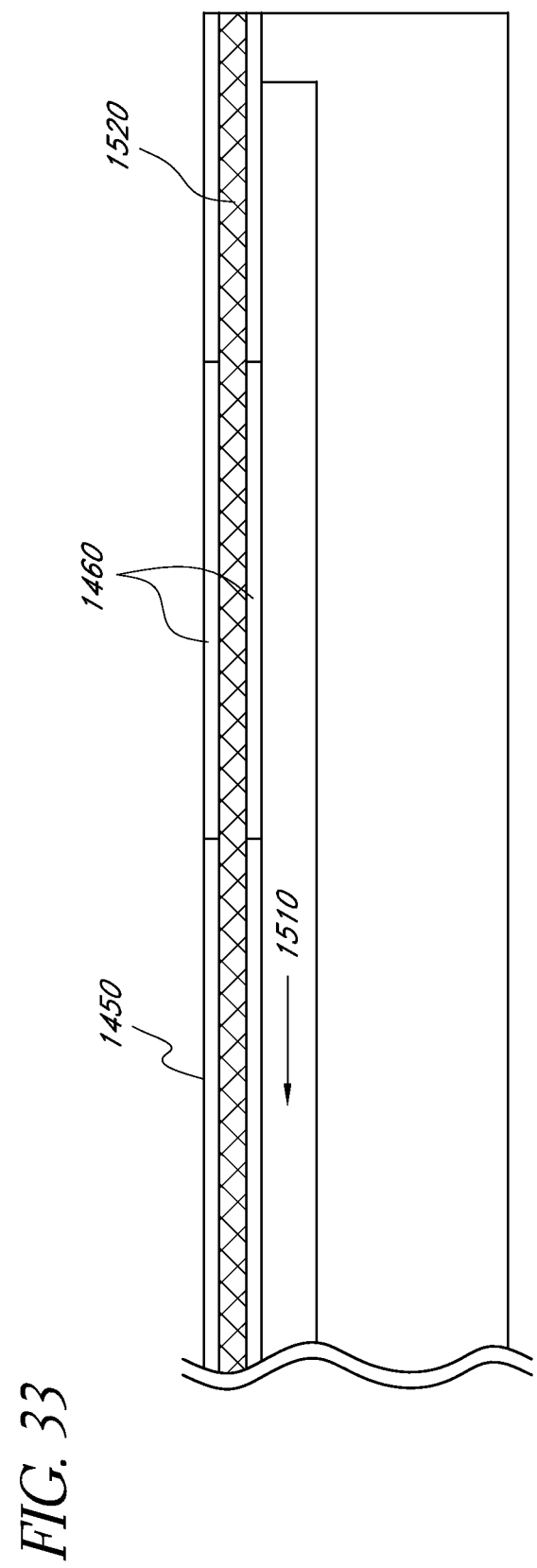
FIG. 33 is a side elevational view of a catheter with a braided member which supports an ultrafiltration membrane.

However, ultrafiltration in viscous fluids such as blood or other bodily fluids may require that the membrane has a support structure, which will prevent the membrane from collapsing. If the blood is withdrawn from the patient for filtration, the ultrafiltration membranes may be supported by an external cartridge, such as commercially available from Spectrum Labs, Inc., (Rancho Dominguez, Calif.). However, if the membrane is part of a catheter or other structure for filtering within the patient, the membrane may be formed by the use of embedded supports or coated supports, as known in the art. For example, a braided wire support 1520 may be used to form a membrane support, and may also serve as a structural component of the catheter, as shown in FIG. 33. The ultrafiltration membrane 1460 is supported by the wire braid 1520, and the filtrate is withdrawn from the catheter 1450 via lumen 1510. Alternatively, the braided wire may be reduced to a small diameter for insertion into the inside of the membrane, and then allowed to expand to support the membrane.

Figure 34:
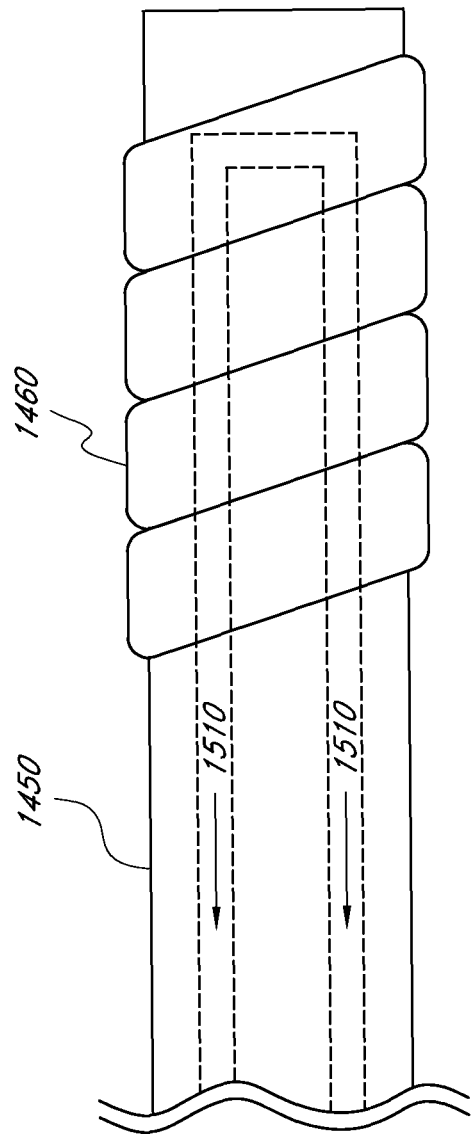
FIG. 34 is a side elevational view of a catheter with an ultrafiltration membrane wound around the exterior of the catheter.

The membrane containing the support structure may also be wrapped around the outside of the catheter in a helical fashion, as shown in FIG. 34. The ultrafiltration membrane 1460 is wound around catheter 1450 in a helical fashion. The filtrate is withdrawn from the catheter via one or more lumens 1510 which are in fluid communication with the membrane 1460. This allows for a significant increase in the surface area of the filter, which improves filtrate flow rates and therefore increases system response times.

Figure 35:
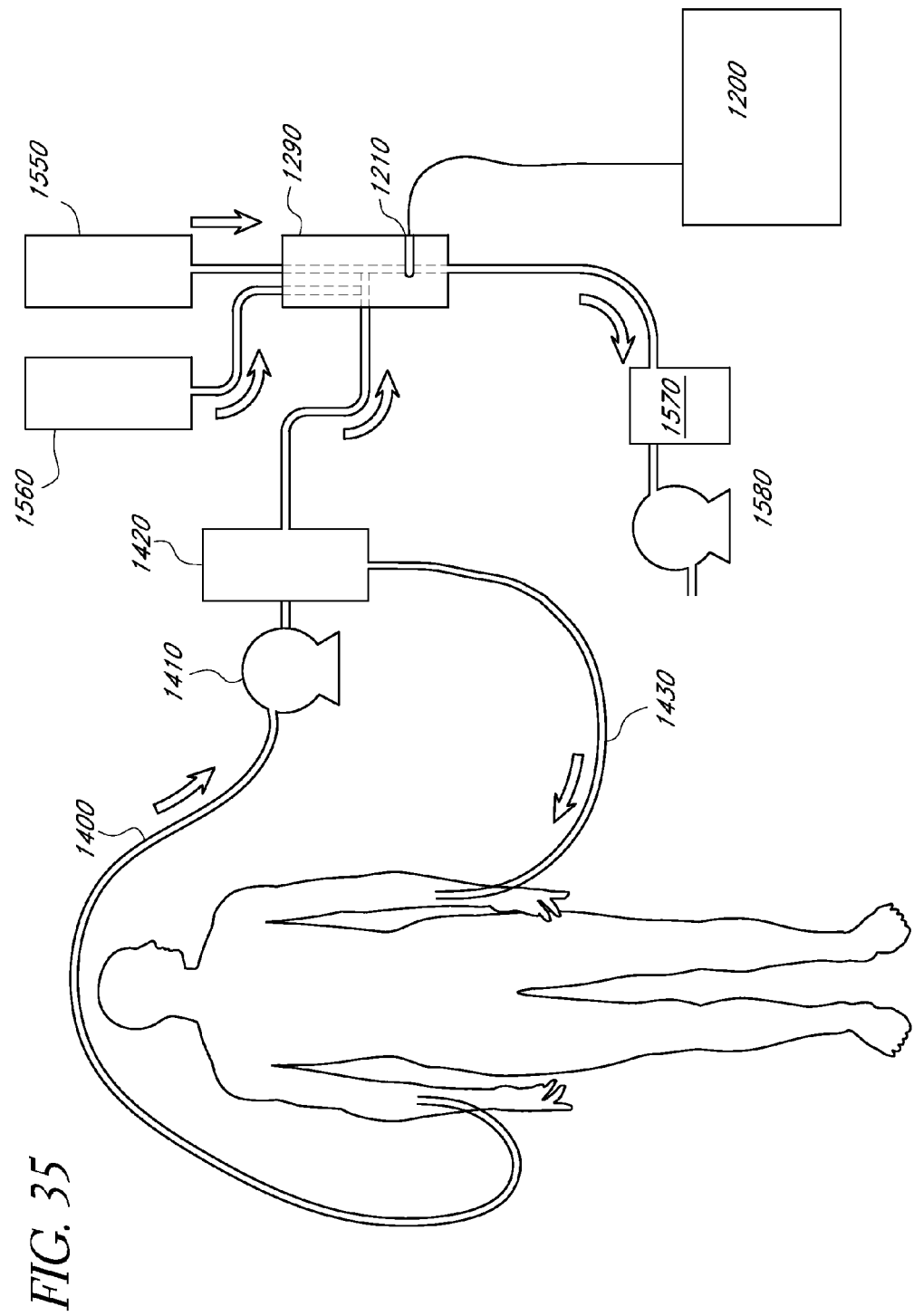
FIG. 35 is a block diagram showing withdrawal of a body fluid from a patient for determination of nitrite levels.

In a further aspect of this invention, the fluids may be advanced through the system using a vacuum pump, or by using hydrostatic pressure. Referring now to FIG. 35, the bodily fluid is withdrawn through catheter 1400, optionally by including a pump 1410, or preferably using a vacuum pump 1580. Arrows indicate the direction of flow. Once the blood is drawn into filter 1420, the filtrate is advanced into the reaction chamber 1290 by means of vacuum pump 1580. The retentate may optionally be returned to the patient via catheter 1430. Reactant solutions such as acid and iodide are stored in reactant reservoirs 1550 and 1560, and advanced into reaction chamber 1290, by means of vacuum pump 1580. The reactants and the filtrate solutions react in reaction chamber 1290 to produce nitric oxide, which is then detected using sensor 1210, and the output is detected by monitor 1200. Waste fluids are then caught in a vacuum trap 1570. An advantage of using the vacuum pump is that pump noise in the output signal is significantly reduced, as compared to using peristaltic pumps as described in FIGS. 28, 29, and 30.

Microfluidics

For certain applications, it will be crucial to minimize the amount of blood volume required. One method for achieving this will be to employ microfluidics technology. While microfluidic measurement of NO has been reported, it is difficult to remove a sample of blood from a patient quickly enough to get a meaningful reading from the sensor. The principals involved in microfluidic measurement are similar to the larger version of the device, that is, separation of plasma nitrite from red blood cells and hemoglobin, followed by conversion of nitrite to nitric oxide for measurement. Microfiltration, as described in the present invention, can be scaled down to small volumes. Microfluidics can be used to separate blood cells from plasma using a filtration membrane, as described by Aota et al. (Arata Aota, Susumu Takahashi, Kazuma Mawatari, Yo Tanaka, Yasuhiko Sugii, and Takehiko Kitamori, "Microchip-Based Plasma Separation From Whole Blood Via Axial Migration Of Blood Cells" Analytical Sci December 2011, Vol. 27 1173-78).

Figure 39:
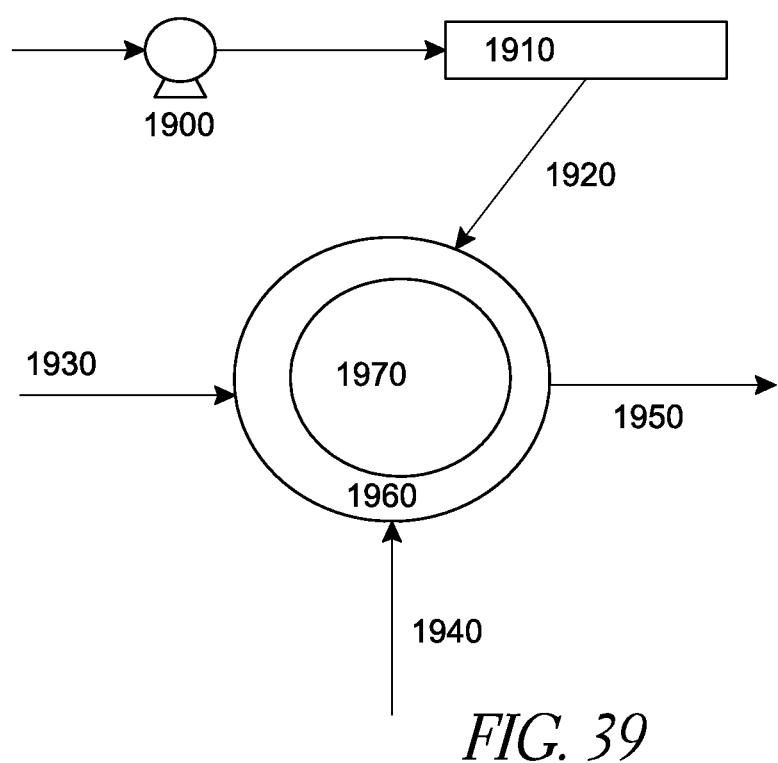
FIG. 39 is a block diagram showing a method of obtaining a fluid sample from a human or an animal, passing the extracted fluid through a microfluidic filtration unit, and sending the filtrate to a reservoir for reduction of nitrite to nitric oxide.

Referring to FIG. 39, the blood sample is advanced either by micropump 1900 [such as described by Laser et al., (DJ Laser and JG Santiago, "A review of micropumps", J. Micromech. Microeng. 14 (2004) R35-R64)], or via capillary action through filter 1910. The filter membrane may be composed of either polysulfone, polyethersulfone, or any other suitable membrane material and have a molecular weight cutoff <60 kD. Once the filtrate is obtained by filtration it can be advanced either using a second micropump or via capillary action through a first channel 1920 into a reservoir 1960, which is in fluid communication with an NO-specific electrode 1970 (e.g., ISO-NOPMC World Precision Instruments (Sarasota, Fla.), or amino-FLAT, Innovative Instruments (Tampa, Fla.)). The reservoir 1960 has 3 inlet channels, and one or more outlet channels. A fixed volume of sample from the first channel 1920 is mixed with acid from a second channel 1930 and iodide from a third channel 1940. Each of these fluids is advanced into the reservoir 1960 either by capillary action, by a micropump, or by a syringe pump (e.g., Harvard Apparatus PhD Ultra). An outlet channel 1950 will allow excess fluid to escape from the reservoir. A fixed volume (typically less than 1 ml) of sample, acid and iodide can reside in the reservoir. The reaction mixture will produce NO by reduction of nitrite over a period of about 1 second to 2 minutes per sample followed by a decay of NO which may be as long as 20 minutes, depending on sensor response time and exact concentrations of nitrite, acid and iodide.

Current Nitrite Measurement Methods:

While there is a significant clinical need for nitrite measurements, there are no techniques that allow direct, real-time measurements of nitrite in the physiological regime (100-300 nM) (J. Silver, (November 2011) "Nitrite and nitric oxide as potential diagnostic markers in acute vascular diseases", J. Neurology & Neurophysiology, dx.doi.org/10.4172/2155-9562.S1-005.) Non-invasive methods such as magnetic resonance imaging, electron spin resonance, and positron emission tomography either lack sensitivity, or require administration of potentially dangerous chemical agents for detection of nitric oxide. The short half-life of nitrite in whole blood, demanding rapid separation of plasma from erythrocytes, is a considerable obstacle for plasma nitrite determination in clinical practice (Dejam A, Hunter C J, Pelletier M M, Hsu L L, Machado R F, et al. (2005) Erythrocytes are the major intravascular storage sites of nitrite in human blood. Blood 106: 734-739.).

Ozone-chemiluminescence, along with other current methods including HPLC, gas chromatography-mass spectroscopy (GC-MS) and capillary electrophoresis requires multiple sample preparation steps that require specimens to be centrifuged, chemically stabilized, frozen and then transported to these instruments for later analysis, with results provided hours or days later, which does not provide a suitable response time for many clinical applications. Methods such as ion-selective nitrite electrodes are insufficiently sensitive to monitor $NO_2^-$ in the physiological regime.

NO-specific electrodes are commercially available, but their potential clinical uses are limited because both oxygenated and deoxygenated hemoglobin compete with the sensor for NO. Recently, Takarada et al. (Takarada S, Imanishi T, Goto M, Mochizuki S, Ikejima H, et al. (2010) First evaluation of real-time nitric oxide changes in the coronary circulation in patients with non-ischaemic dilated cardiomyopathy using a catheter-type sensor. Eur Heart J 31: 2862-2870.) reported the first successful intravascular measurement of NO in humans using an NO electrode mounted onto a catheter, although a large stimulus was required to generate nitric oxide levels at the detection limit of the sensor. The utility of a catheter with an NO sensor could be valuable in circumstances where it can be placed in close proximity to the stimulus. However, while the position of the NO source may be known in animal or in vitro studies, an NO-sensing catheter may not be clinically useful in situations where the location of the NO source is not known in advance or is not safely reachable by the sensor, because NO has a short diffusion distance of ~0.1 µm.

Monitoring exhaled NO is useful for applications involving airway inflammation such as asthma, but not for most other applications where NO from a distant source would convert to nitrite before it reached the lungs. Exhaled NO has a very short half-life in the lung vasculature and should be incapable of distal transport in blood. This is because NO reacts in a nearly diffusion-limited reaction with both oxyhemoglobin (6 to $8 \times 10^7$ mol/L/sec) and deoxyhemoglobin (2 to $6 \times 10^7$ mol/L/sec) to form methemoglobin/nitrate and iron nitrosyl hemoglobin, respectively, which yield a half-life of ~1 µs and a diffusion distance of ~0.1 µm (Dejam A, Hunter C J, Tremonti C, Pluta R M, Hon Y Y, et al. (2007) Nitrite Infusion in Humans and Nonhuman Primates: Endocrine Effects, Pharmacokinetics, and Tolerance Formation. Circulation 116: 1821-1831). Monitoring nitrite using exhaled breath condensate (EBC) is another alternative, but analysis is complicated due to the substantial contribution of nitrite from the oropharyngeal tract during standard collection of EBC (Marteus H, Tornberg D C, Weitzberg E, Schedin U, Alving K (2005) Origin of nitrite and nitrate in nasal and exhaled breath condensate and relation to nitric oxide formation. Thorax 60: 219-225.)

One of the key clinical challenges in the development of nitrite as a diagnostic biomarker is that because nitrite and NO are involved in so many biological pathways, the specificity of the marker will be imperfect. The keys to improved specificity will be concentration, kinetics, and location. (Thomas D, Ridnour L, Isenberg J, Flores-Santana W, Switzer C, et al. (2008) The Chemical Biology of Nitric Oxide. Implications in Cellular Signaling. Free Radic Biol Med 45: 18-31.). Gradients between two different sites can help to determine the origins of any changes that are detected. However, in some clinical settings such as cardiovascular surgery, the organs most at risk will be known, and sensitivity will be a key driver. Interpretation of NO or nitrite readings will require a differential diagnosis by the physician. For example, the rate of increase in NOx levels generated by eNOS and/or nNOS (during ischemia) is from 10 to 50 times faster than the rate of NOx generated by iNOS (during inflammation) (Suzuki M, Tabuchi M, Ikeda M, Tomita T (2002) Concurrent formation of peroxynitrite with the expression of inducible nitric oxide synthase in the brain during middle cerebral artery occlusion and reperfusion in rats. Brain Res 951:113-120 and Brovkovych V, Dobrucki L, Brovkovych S, Dobrucki I, Kalinowski L, (2001) Nitric Oxide Measurements during Endotoxemia. Clinical Chemistry 47: 1068-1074.) This provides one method to distinguish between ischemia and inflammation or infection. Continuous or frequent discrete measurement of NO or an index marker should thus allow distinction between ischemic events superimposed on inflammatory processes. Location-specific measurements will also help to improve marker specificity.

Monitoring Nitrite

While the invention described in FIGS. 31 and 35 is suitable for measuring nitrite levels in blood through the physiological range, it requires removal of blood from the patient, which presents clinical challenges for longer-term monitoring, including the need to return extracted blood to the patient. In order to provide longer-term monitoring without removing blood from the patient, the following embodiments are described.

As described above, nitric oxide sensors can be used in the measurement of nitrite to overcome the challenges posed by the low concentration of nitrite in vivo. Around the vicinity of a sensor or measurement site, a size-exclusion filter can be used to exclude large particles such as hemoglobin and erythrocytes while allowing nitrite to pass through. For example, hemoglobin can have a molecular weight of about 64 kD. Hemoglobin can react with nitrite and cause inaccuracies in the measurement. Erythrocytes include nitrite and can also cause inaccuracies in the measurements. Other particles can also be excluded by size. Once nitrite is in the vicinity around the sensor or at the site of measurement, the nitrite can be converted to nitric oxide using a nitrite reduction agent. In some embodiments, a constant voltage can be applied to convert nitrite to nitric oxide. In some embodiments, a dilute acid can be used to convert nitrite to nitric oxide. Other nitrite reduction agents are also possible. For example, in some embodiments, a bacteria or enzyme (e.g., xanthine oxidoreductase, nitrite reductase, NO synthase, etc.) can be used to reduce nitrite to nitric oxide. After nitrite has been converted to nitric oxide, a nitric oxide sensor can be used to measure the concentration of nitric oxide. For example, an NO-specific electrode can be used. The NO-specific electrode can be an amperometric electrode, which measures current. The NO can diffuse through a membrane of the electrode and react with a compound, such as a porphyrin, for example nickel(II) tetrakis (3-methoxy-4-hydroxyphenyl)porphyrin (Ni (II) THMPP) which coats the electrode. The electrode can be used to measure the current caused by the reaction.

Figure 36:
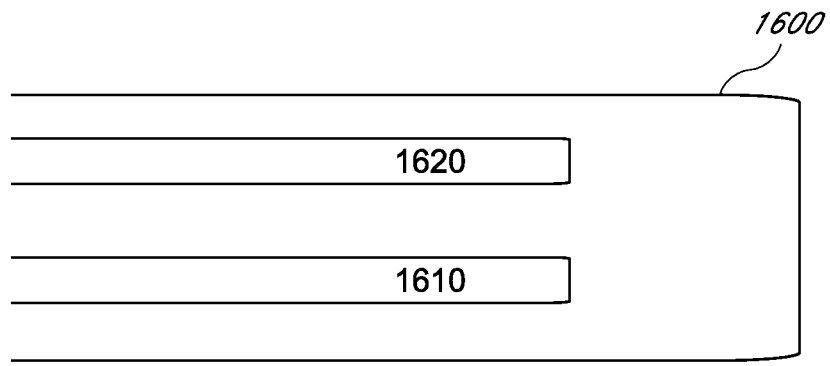
FIG. 36 is a side view of a sensor with an outer size-exclusion membrane which surrounds two electrodes.

In FIG. 36, the end of a needle-type electrode is shown, although the sensor technology is independent of any particular geometry. Surrounding the electrode is an outer size-exclusion membrane 1600. The size-exclusion membrane can have a pore size configured to exclude particles greater than a particular size. For example, the size-exclusion membrane 1600 can have pore sizes providing about a 5-60 kD molecular weight cutoff in order to exclude hemoglobin. In other embodiments, the size-exclusion membrane 1600 can have pore sizes providing about a 5-20 kD molecular weight cutoff. It will be appreciated that not all particles above the cutoff will be excluded. Some particles above the weight cutoff may pass through the filter. The membrane can be made from polycarbonate, polysulfone, polyethersulfone, polyarylethersulfone, polyurethane (such as Cuprophane), AN-69 polyacrylonitrile, regenerated cellulose, mixed cellulose ester, polyester, Nylon, poly(vinylidene fluoride) (PVDF), polypropylene, polytetrafluoroethylene, or other ultrafiltration membrane material, and may be purchased from numerous vendors, including Pall Corp. (East Hills, N.Y.), Amnicon (Beverly, Mass.), or Millipore (Billerica, Mass.). The membrane may be optionally coated with a thromboresistant layer, such as an anticoagulant (like heparin or hirudin), a thromboresistant material such as phosphoryl choline, a hydrogel (such as poly (ethylene glycol), poly(N-vinyl pyrrolidone), poly(hydroxyl ethylmethacrylate), polyacrylamide, polyacrylic acid, or cross-linked collagen) or by a sulfonated polyurethane or other sulfonated polymer, or other thromboresistant materials as described previously. This allows smaller molecules to pass through, while excluding cells, hemoglobin, and other large proteins. A slight vacuum is optionally applied to improve flux past the membrane using a peristaltic pump. There are two electrode-couples inside the outer-membrane. The first electrode-couple 1620 can be a platinum, vanadium, molybdenum and iron, titanium, or chromium cathode to reduce nitrite to nitric oxide by the following reaction:

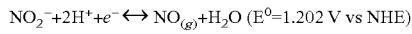

$$NO_2^- + 2H^+ + e^- \leftrightarrow NO_{(g)} + H_2O \quad (E^0 = 1.202 \text{ V vs NHE})$$

The first electrode 1620 is connected to a constant voltage power supply (not shown) in order to create NO from nitrite, rather than being used to directly measure nitrite. For example, if the electrode is held at 1.202 V, then the chemical equilibrium will shift so that the concentration of nitrite is equal to the concentration of nitric oxide. Other voltages can also be used. Multiple chemical species are expected to be reduced at this potential, and thus generation of NO creates a way of specifically measuring nitrite concentrations. The second electrode-couple is an NO-specific electrode 1610 such as commercially available from Innovative Instruments (Tampa, Fla.) or World Precision Instruments (Sarasota, Fla.). The NO-specific electrode detects the nitric oxide which is generated from nitrite by the first electrode-couple. Other NO-sensors are also contemplated.

Figure 37:
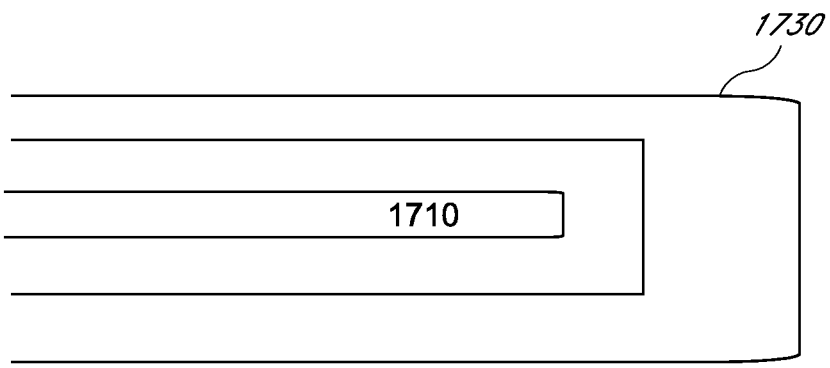
FIG. 37 is a side view of a sensor with an outer size-exclusion membrane, and an inner ion-exchange membrane which surrounds an electrode.

In FIG. 37, the end of a needle-type electrode is shown, again with an outer size-exclusion membrane and thromboresistant coating 1700, similar to that described for FIG. 36. Inside the outer membrane 1700 is an anion-exchange membrane 1730 which allows anions such as nitrite ($NO_2$) to pass through, while impeding the passage of cations, such as $H^+$. A small volume (e.g., <1 ml, <2 ml, <5 ml, etc.) of a dilute acid (e.g., carbonic acid, 0.1 N) can be contained within the anion-exchange membrane. An NO-specific electrode 1710 (as described for FIG. 36) is inside the anion-exchange membrane 1730. Other NO sensors are also contemplated. The anion exchange membrane can be AMI-7001 (Membranes International, Ringwood, N.J.) or AEM Type I (Fujifilm, Tilburg, The Netherlands) or any of a number of commercially available anion-exchange membranes. Thus nitrite can diffuse through both the outer and inner membrane, react with acid inside the anion exchange membrane 1730, where it is reduced to NO, and is then detected by the NO-specific electrode 1710. The anion-exchange membrane allows a small amount of dilute acid to be contained within the inner membrane, without concern that the acid will be released into the patient.

Figure 38:
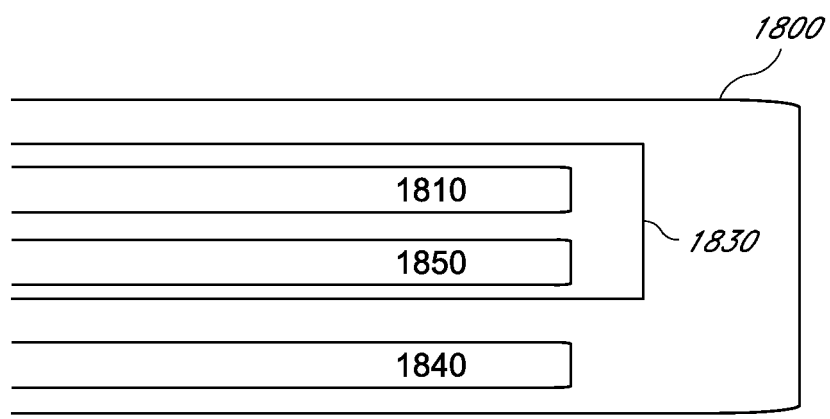
FIG. 38 is a side view of a sensor with an outer size-exclusion membrane which surrounds a half-cell electrode, and an inner ion-exchange membrane which surrounds a second half-cell electrode and a nitric oxide-specific electrode.

In FIG. 38, the end of a needle-type electrode is shown, again with an outer size-exclusion membrane 1800 and thromboresistant coating, similar to that described with respect to FIG. 36, and an inner, anion-exchange membrane 1830, similar to that described with respect to FIG. 37. In this embodiment, a negatively polarized half-cell electrode 1840 is placed between the outer membrane 1800 and the inner membrane 1830. A positively-polarized half-cell electrode 1850 is placed inside the inner anion exchange membrane 1830. This electrode pair is used to provide an electromotive force to increase the flux rate of nitrite past the anion-exchange membrane 1830. This helps to reduce to overall response time of the sensor as compared to simple diffusion.

Nitrite as a Therapeutic Agent:

Recently, an alternative pathway for generation of NO has been discovered (Cosby K, Partovi K, Crawford J, Patel R, Reiter C, et al. (2003) Nitrite reduction to nitric oxide by deoxyhemoglobin vasodilates the human circulation. Nature Medicine 9: 1498-1505.). The anion nitrite was previously considered physiologically inert, a stable end product of nitric oxide (NO) metabolism, and a biomarker for NO activity. Nitrite has been shown to be a circulating storage pool for NO that the body can rapidly activate when needed. (Hill B G, Dranka B P, Bailey S M, Lancaster J R, Darley-Usmar V M (2010) What Part of NO Don't You Understand? Some Answers to the Cardinal Questions in Nitric Oxide Biology. J Biol Chem 285: 19699-19704.) Rapid conversion of nitrite to NO can occur under ischemic conditions (low pH, low partial pressure of oxygen ($pO_2$)) (Gladwin M T, Schechter AN (2004) NO Contest: Nitrite Versus S-Nitroso-Hemoglobin. Circ Res 94: 851-855). There are several enzymes which may act to reduce nitrite to NO, including deoxyhemoglobin, deoxymyoglobin, xanthine oxoreductase (XOR), neuroglobin, eNOS, and components of the mitochondrial electron transport chain (Tiso M, Tejero J, Basu S, Azarov I, Wang X, et al. (2011) Human Neuroglobin Functions as a Redox-regulated Nitrite Reductase. J Biol Chem 286: 18277-18289). The different nitrite reductase "enzyme" systems operate along a range of physiological and pathological hypoxia, with hemoglobin reducing nitrite at an oxygen tension from 60 mm Hg down to 20 mm Hg, myoglobin active below 4 mm Hg, and xanthine oxoreductase and acidic reduction reducing nitrite at zero oxygen and low pH (Shiva S, Sack M N, Greer J J, Duranski M, Ringwood L A, Burwell, et al. (2007) Nitrite augments tolerance to ischemia/reperfusion injury via the modulation of mitochondrial electron transfer. J Exp Med 204: 2089-2102). This allows for graded nitrite reduction to NO along the circulating and metabolic oxygen gradient (Dezfulian C, Raat N, Shiva S, Gladwin M T (2007) Role of the anion nitrite in ischemia-reperfusion cytoprotection and therapeutics. Cardiovascular Research 75: 327-338). In addition, as pH decreases, the rate of the reaction increases. Conversion of nitrite to NO by deoxyhemoglobin can occur in as little as 30 seconds to several minutes (Crawford J H, Isbell T S, Huang Z, Shiva S, Chacko B K, et al. (2006) Hypoxia, red blood cells, and nitrite regulate NO-dependent hypoxic vasodilation. Blood 107: 566-574).

Nitrite therapy has proven to be an effective preconditioning agent for ischemia-reperfusion injury. There are several limitations to the currently used NO-based therapies that preclude their widespread use, but which nitrite might address. Inhaled NO therapy and NO donor therapy have the potential to cause unwanted side effects, since both therapies rely on systemic delivery. For example, NONOates, a class of NO donors, release NO over a period of time depending on the half-life of the drug. Since NO begins to be released as soon as the drug enters the blood stream, there is no way of ensuring that the NO is released only at the site of injury. As a result, higher concentrations of the drug have to be administered to achieve the desirable therapeutic effects. This in turn can result in unwanted systemic side effects, such as hypotension or NO-mediated cytotoxicity. Alternative means to effectively deliver NO to the site of injury are thus necessary to achieve the therapeutic potential of NO-based therapies (Calvert J W, Lefer D J (2010) Clinical translation of nitrite therapy for cardiovascular diseases. Nitric Oxide 22: 91-97).

Nitrite is a relatively stable molecule that can be transported in the circulation and stored in tissues. Nitrite releases NO under conditions that exist in injured tissue (ischemia, hypoxia, or low pH), which allows nitrite to preferentially target injured tissue and reduce the risk of systemic hypotension and other unwanted side effects. This is probably the most important aspect of nitrite therapy. In addition, since nitrite has been used for many years as part of the cyanide antidote kit in humans there is a wealth of clinical data to support the safety of very high doses of sodium nitrite in critically ill patients.

During hypoxia and ischemia, nitrite not only promotes blood flow by conversion to nitric oxide, it also protects the mitochondria (Shiva S (2010) Mitochondria as metabolizers and targets of nitrite. Nitric Oxide 22(2):64-74). Nitrite acts to inhibit mitochondrial respiration by blocking the electron transport chain at both complex I and cytochrome c. Under ischemic conditions, myoglobin reduces nitrite to NO, which can bind reversibly to the catalytic center of cytochrome c oxidase. Nitrite can also inhibit complex I by S-nitrosation (Shiva S, Sack M N, Greer J J, Duranski M, Ringwood L A, Burwell, et al. (2007) Nitrite augments tolerance to ischemia/reperfusion injury via the modulation of mitochondrial electron transfer. J Exp Med 204: 2089-2102.). Partial inhibition of mitochondrial respiration can regulate tissue oxygen gradients and conserve oxygen, particularly in conditions of physiological hypoxia. While reperfusion of the tissue is necessary to restore cellular energetics, reperfusion itself exacerbates mitochondrial damage and tissue injury. Inhibition of complex I by nitrite is thought to contribute to cytoprotection by blocking entry of electrons into the respiratory chain and thus attenuating the burst of reactive oxygen species generation associated with reperfusion. Nitrite has recently been found to confer cytoprotection against IR injury in a number of animal models (Dezfulian C, Raat N, Shiva S, Gladwin M T (2007) Role of the anion nitrite in ischemia reperfusion cytoprotection and therapeutics. Cardiovascular Research 75: 327-338.). Although the mechanisms of this phenomenon are still being characterized, the reproducibility of this effect in multiple animal IR models suggests nitrite as a novel potential therapy for human ischemic diseases.

Acute Myocardial Infarction

The long-term prognosis among patients that survive an acute myocardial infarction is based largely on the amount of myocardium that is infarcted as a result of ischemic injury. Therefore, rapid reperfusion of an occluded coronary artery leading to sustained blood flow optimizes outcomes, whereas a delay in restoring blood flow is associated with adverse effects. Significant advances have been made in therapeutic interventions designed to reperfuse occluded arteries during the past several decades. While timely reperfusion of acute ischemic myocardium is essential for myocardial salvage, reperfusion results in a unique form of myocardial damage. Both myocardial stunning and infarction are seen, as well as functional alterations, including depressed contractile function and decreased coronary flow as well as altered vascular reactivity. It has become increasingly clear that oxidant and oxygen radical formation is greatly increased in the post-ischemic heart and serves as a critical central mechanism of post-ischemic injury (Zweier J L, Hassan Talukder M A (2006) The role of oxidants and free radicals in reperfusion injury. Cardiovascular Research 70: 181-190.). Nitrite therapy in a canine model of coronary artery ischemia limited myocardial infarction and apoptosis. This suggests that infusion of nitrite could be beneficial if initiated prior to percutaneous coronary intervention.

Cardiac Arrest

There are approximately 295,000 cases of out-of-hospital cardiac arrests each year in the US, and an individual's overall chance of surviving until hospital discharge is 7%. The rates of survival to discharge after in-hospital cardiac arrest were 33% among children and 21% among adults (Roger V L, Go A S, Lloyd-Jones D M, Adams R J, Berry J D, et al. (2011) Heart Disease and Stroke Statistics 2011 Update: A Report From the American Heart Association. Circulation 123: e18-e209.). Dezfulian et al. (Dezfulian C, Shiva S, Alekseyenko A, Pendyal A, Beiser D G, et al. (2009) Nitrite Therapy After Cardiac Arrest Reduces Reactive Oxygen Species Generation, Improves Cardiac and Neurological Function, and Enhances Survival via Reversible Inhibition of Mitochondrial Complex I. Circulation 120: 897-905.) showed that global ischemia due to cardiac arrest caused a rapid drop in plasma nitrite levels in mice. They also showed that administration of nitrite solution (as opposed to saline control) at the onset of cardio-pulmonary resuscitation (CPR) following 12 minutes of asystole was cardioprotective. Nitrite therapy significantly improved survival compared with placebo (76% vs. 48%, p=0.033).

The use of nitrite as a therapy for IR injury in humans may have some important limitations. Hypotension due to nitrite mediated vasodilation (Cosby K, Partovi K, Crawford J, Patel R, Reiter C, et al. (2003) Nitrite reduction to nitric oxide by deoxyhemoglobin vasodilates the human circulation. Nature Medicine 9: 1498-1505.) may worsen outcomes in situations where hypoperfusion is already present. In addition, nitrite administration can result in methemoglobinemia, which is potentially lethal. Therefore, the ability to monitor plasma nitrite levels in blood, as per the current invention, has significant clinical potential.

Pediatric Cerebral Ischemia

More than a half million infants in the US were born preterm in 2004. The preterm birth rate has climbed 18 percent since 1990, to one of every eight live-born infants. Of these children, more than 10% will sustain neurological injuries leading to significant learning disabilities, cerebral palsy, or mental retardation, with very low birth weight infants having an even higher incidence of brain injury (Back S, Rivkees S (2004) Emerging concepts in periventricular white matter injury. Semin Perinatol 28: 405-414.). The estimated lifetime costs are expected to total $51.2 billion for persons born in 2000 with mental retardation, and $11.5 billion for persons with cerebral palsy. No effective clinical strategies have yet been developed to counteract this condition (Jensen A, Garnier Y, Middelanis J, Berger R (2003) Perinatal brain damage—from pathophysiology to prevention. Eur J Obstet Gynecol Reprod Biol 110:S70-S79). In addition to preterm infants, the most common birth defect is congenital heart disease (CHD) requiring approximately 36,000 surgeries per year. Improvements in cardiopulmonary bypass (CPB), surgical technique, and intensive care have lowered hospital mortality for most neonatal procedures to <3%. Improvements in survival have stimulated a focus on neurological morbidity, which may approach 70% (McQuillen P S, Barkovich A J, Hamrick S E G, Perez M, Ward P, et al. (2007) Temporal and Anatomic Risk Profile of Brain Injury With Neonatal Repair of Congenital Heart Defects. Stroke 38: 736-741.).

The two most important forms of brain injury in premature infants, which are believed to be primarily responsible for conditions such as mental retardation, cerebral palsy and epilepsy, are germinal matrix-intraventricular hemorrhage (GMH-IVH) (also known as periventricular-intraventricular hemorrhage (PVIVH)) and periventricular leukomalacia (PVL). Postnatally, most hemorrhages occur when the neonate is younger than 72 hours, with 50% of hemorrhages occurring on the first day of life. A large body of experimental and clinical observations indicates that disturbances in cerebral blood flow (CBF) are important in the pathogenesis of PVIVH and PVL. As with adults, nitric oxide is involved in ischemia in this population as well. Hypoxia-induced release of nitric oxide can account for much of the cerebral vasodilatation observed in response to hypoxia in the fetus (Pearce W (2006) Hypoxic regulation of the fetal cerebral circulation. J Appl Physiol 100: 731-738).

Currently there are no methods for continuously monitoring hypoxic-ischemic insults in the neonatal brain. PVL and PVIVH are currently diagnosed using cranial ultrasonography at 7-14 days postnatally, or using MRI, which is more sensitive. However, MRI is not used to assess all infants who may be at risk for PVL. In addition, these methods do not provide continuous monitoring of the patient. A great deal more research is required for near infrared spectroscopy (NIRS) to become a routine clinical tool. Studies estimate a short therapeutic window of 2-6 hours during which interventions may be efficacious in reducing the severity of ultimate brain injury; thus, early identification of a neonate who has sustained a hypoxic-ischemic insult is a paramount objective for optimal management and treatment. Supportive care includes maintenance of adequate ventilation; avoidance of hypotension; maintenance of normal metabolic status including blood glucose, fluid, and nutritional status; control of seizures; and control of brain edema. Recent trials have shown beneficial use of therapeutic hypothermia among infants with hypoxic-ischemic encephalopathy. Blood pressure modification and administration of pharmaceutical agents to decrease oxygen consumption would also be considered (Chao C P, Zaleski C G, Patton A C (2006) Neonatal hypoxic-ischemic encephalopathy: multimodality imaging findings. RadioGraphics 26: S159-S172).

Blood Transfusion

There are nearly 14 million units of blood transfused every year in 4.8 million patients. A Cochrane systematic review of multiple randomized trials found that liberal blood transfusions vs. restrictive strategies are associated with a 20% increase in mortality and a 56% increase in ischemic events. Recent studies have shown that stored blood is depleted in nitric oxide. Stored red blood cells are more likely to have ruptured membranes and therefore release hemoglobin into plasma, consuming nitrite and nitric oxide (Chenell Donadee, et al., "Nitric Oxide Scavenging by Red Blood Cell Microparticles and Cell-Free Hemoglobin as a Mechanism for the Red Cell Storage Lesion", *Circulation.* 2011; 124:465-476.) Thus nitrite therapies may be co-administered along with blood transfusions, but the need to control nitrite levels would require continuous monitoring of nitrite in blood. This is another potential clinical application of the current nitrite monitoring invention.

Organ Transplantation

In the field of organ transplantation, two of the limiting factors are the ischemic window for the organ (i.e., the time between organ donation and organ transplantation into the recipient) and acute organ rejection. The window of opportunity for successful organ transplantation is very short. Organs become ischemic from the moment the heart stops beating. The first phase of ischemia is called warm ischemia since the internal body temperature is warm (normally 98.6 F). Warm ischemia time should not exceed 30 minutes for successful liver transplantation and 60 minutes for kidney and pancreas transplantations. If organs are not transplanted within this narrow time interval, ischemic tissue will become dead tissue and thus unsuitable for transplantation.

Cold storage can delay the deadly effect of prolonged ischemia and give the surgical team the time it needs to perform successful organ transplantation. Once death is pronounced, cold organ-preserving solution is perfused into donor's veins, thus putting the organs in cold storage. This organ-preserving cold storage interval is called cold ischemia time (CIT). It extends from the initiation of cold preservation of donor organs to restoration of warm circulation in the organ recipient. For kidney transplantation, the CIT should be <24 hours; for pancreas transplantation, <18 hours; and for liver transplantation, <8 hours. Even with the benefit of cold storage, the window of opportunity for successful organ transplantation remains short. Indeed, liver ischemia and reperfusion (I/R)-induced hepatocellular damage is thought to be responsible for up to 10% of organ dysfunction in liver transplantation leading to acute and chronic rejection.

Nitrite added to organ preservation solutions has been shown to reduce ischemic injury in animal models of organ transplantation (Wei Li, Zihui, Meng Yuliang Liu, Rakesh P. Patel, and John D. Lang, "The Hepatoprotective Effect of Sodium Nitrite on Cold Ischemia-Reperfusion Injury", J. Transplantation Vol 2012, Article ID 635179, doi:10.1155/2012/635179). However, the possibility of free hemoglobin due to hemolyzed red blood cells from incompletely perfused organs means that the nitrite level in the organ preservation solution may be significantly less than intended. Thus, it could be beneficial to monitor nitrite levels during organ transport up until the time of implantation. The present invention offers a way to achieve that goal.

Acute organ rejection is typically assessed by an invasive needle biopsy procedure. If organ rejection is detected early, there are antibody therapies available for treatment (Dusko Klipa, Nadim Mahmud and Nasimul Ahsan, "Antibody immunosuppressive therapy in solid organ transplant Part II", mAbs 2:6, 607-612; November/December 2010). However, plasma nitrite and nitrate were shown to be significantly elevated in a clinical study of kidney transplantation, and the specificity and sensitivity for acute rejection were 97.7% and 100%, respectively (John K. Bellos, Despina N. Perrea, Eleni Theodoropoulou, Ioannis Vlachos, Antonis Papachristodoulou, Alkiviadis I. Kostakis, Clinical correlation of nitric oxide levels with acute rejection in renal transplantation, Int Urol Nephrol (2011) 43:883-890).

In a further aspect of this invention, multiple devices can be placed in the patient, each at different locations within the body. A single power source and signal processing unit may be used to operate each of the sensors, and that power source can provide energy either by an inductive link, or by multiple leads, between the power source and the sensors.

In another embodiment of the present invention, any of the previously described sensors, whether stent-based, catheter-based, or based upon another support structure, can be in communication with a communication device. The communication device can be carried by a patient. For example, the communication device can be attached to a cord and worn around a patient's neck or the communication device can be attached to the patient by way of a clip or fastener. The communication device can be attached to the patient by any other suitable means well-known to those of skill in the art.

The communication device can be in either fluid communication with the sensor or it can be in wired or wireless communication with the sensor (or both). In the fluid communication configuration, the communication device receives fluid from the sensor and analyzes it, as described in the microdialysis or ultrafiltration embodiments described above. The communication device analyzes that fluid as previously described. A battery pack provides power to the communication device, and may typically comprise conventional batteries, rechargeable batteries any other suitable power means well-known to those of skill in the art.

In either the wired or wireless configuration, the communication device receives information from the sensor. The information may be the concentration of a substance of interest, the rate of change of the concentration of a substance of interest, the baseline concentration of a substance of interest, etc. The alarm may alternatively compose a visual display or tactile feedback. The communication device is capable of sounding an alarm for the patient or nearby healthcare personnel if some predetermined criteria is met. The communication device is also capable of displaying messages regarding the information that it is processing, information about its status, or other useful information.

The communication device can include memory for storing the information determined or received. The memory storage may include RAM, ROM or any other suitable memory storage hardware well known to those of skill in the art. Any stored information can be downloaded to a computer, PDA, or other device. The communication device can include a serial port, USB connection, firewire, or any other suitable downloading hardware and software well-known to those of skill in the art to accomplish the downloading.

The communication device is also capable of relaying the information it determines or receives. The communication device is also capable of sending an alarm to a remote site or user and keeping a time stamp of the occurrence of any alarm or other condition. For example, the communication device can include a radio antenna capable of transmitting data. The antenna can relay information, via telephone lines, a satellite link, a microwave link, or an internet link. The communication device can also include a wireless cell phone or wireless internet connection. Thus, the communication link of the communication device may be any of a variety of well-known techniques.

The communication device can use such a communication link to communicate to a hospital server, hospital personnel, or to a dispatch center. The server can store the information from the communication device in a central data storage hub. A physician or other health care personnel can access this information from a computer, such as a laptop computer or PDA, via a modem link connected to a server. A physician or other health care personnel could also access this data from a cell phone, telephone, or any other device capable of connecting to the server. The server can then access the same information as it arrives from the patient via the communication device. Alternatively, the communication device can allow the wearer to orally communicate with a doctor, healthcare professional or emergency personnel.

The communication device may include an internal global positioning system (GPS). The GPS transceiver is capable of querying a satellite, or satellites, as to its location. It receives the response from the satellite(s) and, translates the site location to, for example, a wireless transceiver for transmitting that information from an antenna. A communication device that includes a cellular phone would be capable of contacting 911, a doctor, or other healthcare profession with information regarding the patient's condition and location. If the patient is unable to speak or otherwise communicate, the communication device could include a number of preset messages to relay to either the 911 operator, healthcare professionals or a doctor. Thus, the communication device is capable of transmitting data and for providing voice communication as well. The communication device may also receive information from a hospital server, hospital personnel or other personnel.

The communication device can also allow the wearer to initiate an emergency locate session. When the user activates a panic button, the locator unit initiates a communication link indicating emergency action is required. The communication device may also be connected to a therapy delivery device. The connection may be wired or wireless. The therapy delivering device may be implanted or wearable by the user. The therapy delivering device is capable of delivering medicine, drugs or other substances to the user. The therapy delivering device may also deliver heat or electrical activity to the user. In response to some information determined by the sensor, or in response from communication from the hospital or other personnel, the communication device may commence a responsive therapy.

Although the present invention has been described in connection with certain preferred embodiments, persons of ordinary skill in the art will understand that many modifications can be made thereto within the scope of the claims which follow. For example, although blood is used as one example of a patient fluid whose properties can be monitored, other patient fluids, such as cerebrospinal fluid, can also be monitored. Also, the rate of change of a substance, or the amount or level of change of a substance, can be monitored in addition to the amount or concentration of a substance.

Accordingly, the scope of the invention is not intended to be limited by the above description but instead is to be determined entirely by reference to the following claims.

What is claimed is:

1. A method of treating a patient with nitrite, the method comprising:
administering nitrite or nitric oxide to the patient;
monitoring a level of nitrite within blood of the patient, the monitoring comprising:
contacting a sensor with the blood of the patient;
excluding particles with a molecular weight greater than 60 kD from a vicinity around the sensor using a size-exclusion filter;
converting nitrite ions included in the vicinity around the sensor to nitric oxide; and
measuring a concentration of nitric oxide using the sensor.

2. The method of claim 1, further comprising using the concentration of nitric oxide to determine a level of nitrite within the blood of the patient.

3. The method of claim 1, further comprising modifying an amount of nitrite or nitric oxide administered to the patient based on the concentration of nitric oxide measured.

4. The method of claim 1, further comprising modifying an amount of nitrite or nitric oxide administered to the patient based on the level of nitrite within the blood of the patient.

5. The method of claim 1, wherein monitoring the level of nitrite within blood of the patient further comprises inserting the sensor within the patient.

6. The method of claim 1, wherein monitoring the level of nitrite occurs as the blood is extracted from the patient.

7. The method of claim 1 wherein excluding particles with a molecular weight greater than 60 kD from the vicinity around the sensor comprises excluding cells and proteins from the vicinity around the sensor.

8. The method of claim 1, wherein converting nitrite ions included in the vicinity around the sensor to nitric oxide comprises applying a constant voltage to the vicinity around the sensor.

9. The method of claim 8, wherein converting nitrite included in the vicinity around the sensor to nitric oxide comprises applying a voltage of about 1.2 V, referenced to a normal hydrogen electrode, to the vicinity around the sensor.

10. The method of claim 1, wherein converting nitrite included in the vicinity around the sensor to nitric oxide comprises reacting nitrite with dilute acid, reducing the nitrite to nitric oxide.

11. The method of claim 10, further comprising containing the dilute acid within the vicinity around the sensor.

12. The method of claim 11, wherein containing the dilute acid within the vicinity around the sensor comprises using an anion-exchange membrane.

13. The method of claim 12, further comprising providing an electromotive force to increase a rate of nitrite diffusing across the anion-exchange membrane.

14. The method of claim 13, wherein providing the electromotive force comprises positioning an anode between the anion-exchange membrane and the size-exclusion filter and positioning a cathode within the anion-exchange membrane and applying a voltage to the anode and cathode.

15. The method of claim 14, wherein applying the voltage to the anode and the cathode comprises applying a constant voltage.

16. The method of claim 14, wherein applying the voltage to the anode and the cathode comprises applying a varying voltage.

17. The method of claim 1, further comprising triggering an alarm if the concentration of nitric oxide is outside a particular range.

18. The method of claim 1, further comprising triggering an alarm if a rate of change of nitric oxide concentration exceeds a particular rate.

19. The method of claim 1, further comprising modifying an amount of nitric or nitric oxide administered to the patient based on a rate of change of nitric oxide concentration.

20. The method of claim 1, further comprising modifying an amount of nitric or nitric oxide administered to the patient based on a rate of change of the level of nitrite.

* * * * *